United States Patent [19]

Takagaki et al.

[11] Patent Number: 5,428,059
[45] Date of Patent: Jun. 27, 1995

[54] BENZOPYRAN DERIVATIVES AND AN ANTI-ALLERGIC AGENT POSSESSING THE SAME AS THE ACTIVE INGREDIENT

[75] Inventors: Hidetsugu Takagaki; Mitsuru Sakai, both of Sakura; Hiromu Takahashi, Matsudo; Kazuhiko Inazawa, Sakura; Masayoshi Abe, Chiba; Nobuyuki Kimura, Sakura, all of Japan

[73] Assignee: Dainippon Ink & Chemicals, Inc., Tokyo, Japan

[21] Appl. No.: 938,132
[22] PCT Filed: Jan. 31, 1992
[86] PCT No.: PCT/JP92/00095
§ 371 Date: Nov. 20, 1992
§ 102(e) Date: Nov. 20, 1992
[87] PCT Pub. No.: WO92/13852
PCT Pub. Date: Aug. 20, 1992

[30] Foreign Application Priority Data

Jan. 31, 1991 [JP] Japan .................................. 3-11276

[51] Int. Cl.⁶ .............................................. A61K 31/35
[52] U.S. Cl. ..................................... 514/457; 549/285
[58] Field of Search ......................... 514/457; 549/285

[56] References Cited

U.S. PATENT DOCUMENTS 4,845,121  7/1989  Witiak et al. ........................ 549/285

FOREIGN PATENT DOCUMENTS 62-246979  10/1987  Japan .
1-165688   6/1989   Japan .
1432809    4/1976   United Kingdom .

OTHER PUBLICATIONS

Nakayama, Journal of Science of the Hiroshima University, Ser. A-II, vol. 33, No. 2, pp. 205-211, Sep. 1969.
Chemical Abstracts, vol. 94, No. 8, 23 Feb. 1981, Columbus, Ohio, US; Abstract No. 52760h.
Chemical Abstracts, vol. 112, No. 9, 26 Feb. 1990, Columbus, Ohio, US; Abstract No. 73872b.
Witiak et al, J. Med. Chem., vol. 31, No. 7, pp. 1437-1445. Jul. 1988.
Ahluwalia et al, Indian Journal of Chemistry, vol. 13, Aug. 1975, pp. 791-794.
Ahluwalia et al, Indian Journal of Chemistry, vol. 14B, Nov. 1976, pp. 85-860.

*Primary Examiner*—C. Warren Ivy
*Assistant Examiner*—A. A. Owens
*Attorney, Agent, or Firm*—Armstrong, Westerman, Hattori, McLeland & Naughton

[57] ABSTRACT

The present invention relates to an extremely effective anti-allergic agent with a low toxicity, which possesses as its active ingredient a benzopyran derivative described by the general formula below (in the formula, $R^1$ and $R^2$ are each respectively a hydrogen atom, an acyl group, an alkyl group having 1~12 carbon atoms, or an alkenyl group having 2~10 carbon atoms; and $R^3$ is a hydroxyl group, an acyloxy group, an alkoxy group having 1~10 carbon atoms, or an alkenyloxy group having 2~10 carbon atoms).

General Formula

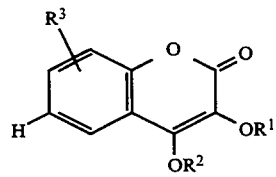

194 Claims, No Drawings

1

BENZOPYRAN DERIVATIVES AND AN ANTI-ALLERGIC AGENT POSSESSING THE SAME AS THE ACTIVE INGREDIENT

BACKGROUND OF THE INVENTION

The present invention relates to a novel benzopyran derivative and its physiologically acceptable salts as well as an anti-allergic agent of low toxicity and superior medical value possessing as its active ingredients a benzopyran derivative and its physiologically acceptable salts.

Relevant Art

A large number of benzopyran derivatives are known from relevant arts, however benzopyran derivative publications such as that of the present invention in which three oxygen atoms are directly linked to the benzopyran derivative skeleton, have been extremely rare.

The benzopyran derivative possessing anti-coagulant action, namely anti-thrombus action, is published in the *British Journal of Pharmocology*, Volume 20, pages 29–35, 1963, by R. B. Arrola, et. al.

As well, a similar derivative possessing anti-thrombus action has been published by Donald T. Witink, et. al. in the *Journal of Medical Chemistry*, Volume 31, pages 1473–1445, 1988, and in U.S. Pat. No. 4,845,121.

A derivative with a methyl group combined with the position-3 oxygen atom has been published by V. K. Ahluwalia, et. al. in the *Indian Journal of Chemistry*, 13B(8), pages 791–794, 1975 and in the *Indian Journal of Chemistry*, Sect. B, 14B(11), pages 858–860, 1976. Additionally, research done by NMR Analysis on a similar compound is noted by Nakayama in *Journal of Science*, Hiroshima University, Ser. A-2, Volume 33(2), pages 205–211, 1969. As a naturally occurring isolated compound, a similar derivative has been published by Wang Ming-Shi in Chung Ts'ao Yao, Volume 11(2), pages 49–54, 1980. Additionally, a similar naturally occurring isolated example has been published by S. Q. Yan in *Yaoxue Xuebao*, Volume 24 (10), pages 744–748, 1989.

However, in these documents, nothing is stated nor even suggested in regards to the benzopyran derivative, the novel compound of the present invention, with anti-allergic action having the formula below (II).

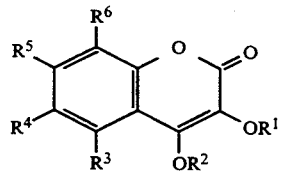

(In the formula $R^1$, $R^2$ are hydrogen atoms, acyl groups, alkyl groups, or alkenyl groups; when one of $R^3$, $R^4$, $R^5$, $R^6$ is a hydroxyl group or a protected hydroxyl group, the remaining groups are hydrogen atoms.)

On one hand, extensive research is being carried out on the development of an anti-allergic agent, and currently various superior anti-allergic agents are being developed. However, Tranilast, a common name for a representative example of an anti-allergic agent currently being sold, has the disadvantages that in spite of the need to administer the drug in comparatively high doses to patients, the acute toxic value ($LD_{50}$) is low, in the range of 680–780 mg/Kg, the difference between the effective concentration and toxic concentration is small, the safety range is narrow, and much care must be exercised during use. Additionally, another anti-allergic agent sold under the common name Disodium Cromoglicate, (DSCG) is satisfactory. In regards to toxicity, can be applied by spray absorption, and when orally administered, is difficult to absorb into the living body. However, from the problems of active time life in the living body and of the ability to easily administer the drug, the development of a drug which can be easily administered orally is desirable.

As a result, recently as anti-allergic agents, a large number of compounds are being published. However, these compounds always possess various problems which are (1) the anti-allergic action being insufficient, (2) the effective and toxic dosage amounts being too close, resulting in the safety of the drug in the living body being poor, or (3) the absorption into the living body being poor, and therefore the administration method is limited.

SUMMARY OF THE INVENTION

The inventors of the present invention have undertaken intensive research of a large number of novel compounds in order to provide a compound possessing low toxicity and anti-allergic action which can be orally administrated. As a result, a benzopyran derivative possessing both low toxic character and superior allergic action which can be orally administrated, has been discovered: a large number of the same type of compound groups have been synthesized, and the safety as well as the anti-allergic reaction have been confirmed, and through the manufacturing of drugs from these compounds, the present invention has been completed.

The present invention uses new benzopyran derivatives and their physiologically acceptable salts (described by general formulae (I) and (II) shown below) as the effective components and supplies an anti-allergic agent possessing low toxicity as well as superior medical effects.

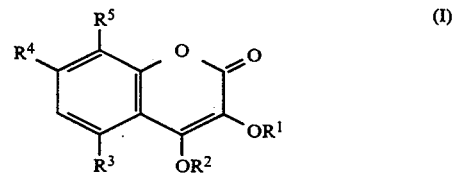

(In the formula, $R^1$ is a hydrogen atom or a straight chained or branched alkyl, acyl, or alkenyl group having 2~12 carbon atoms; $R^2$ is a hydrogen atom, or a straight chained or branched alkyl, acyl, or alkenyl group having 3~12 carbon atoms; when one of $R^3$, $R^4$, $R^5$ is a hydroxyl group or a protected hydroxyl group, the others are hydrogen atoms.)

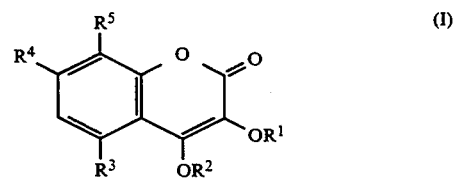

(In the formula, when $R^1$ is a methyl group, $R^2$ is a branched or straight chained alkyl group having 3~12 carbon atoms; when one of $R^3$, $R^4$ $R^5$ is either a hydroxyl group, or a protected hydroxyl group, the others are hydrogen atoms.)

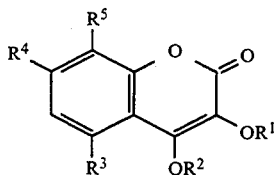

(In the formula, when $R^1$ is a methyl group, $R^2$ is an aroyl group; when one of $R^3$, $R^4$, $R^5$ is either a hydroxyl group or a protected hydroxyl group, the others are hydrogen atoms.)

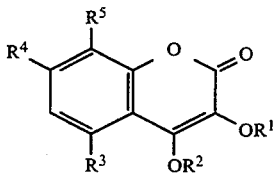

(In the formula, when $R^1$ is a methyl group, $R^2$ is an alkenyl group having 2~10 carbon atoms; when one of $R^3$, $R^4$, $R^5$ is either a hydroxyl group or a protected hydroxyl group, the others are hydrogen atoms.)

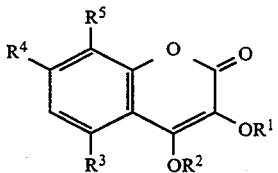

(In the formula, when $R^1$ is a straight chained or branched alkyl group possessing 2-12 carbon atoms, $R^2$ is either a methyl group or an ethyl group; when one of $R^3$, $R^4$, $R^5$ is either a hydroxyl group or a protected hydroxyl group, the others are hydrogen atoms.)

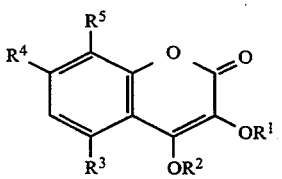

(In the formula, $R^1$ is either an aroyl group or an alkanoyl group; $R^2$ is either a methyl group or an ethyl group; when one of $R^3$, $R^4$, $R^5$ is a hydroxyl group or a protected hydroxyl group, the others are hydrogen atoms.)

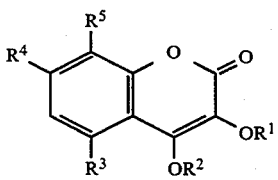

(In the formula, $R^1$ is an alkenyl group possessing 2~10 carbon atoms; $R^2$ is either a methyl group or an ethyl group; when one of $R^3$, $R^4$, $R^5$ is a hydroxyl or a protected hydroxyl group, the others are hydrogen atoms.)

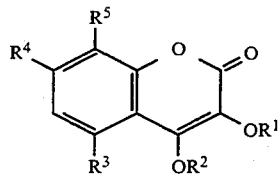

(In the formula, $R^1$ is a methyl group, $R^2$ is a hydrogen atom, $R^3$ is a hydroxyl group, $R^4$ and $R^5$ are also hydrogen atoms.)

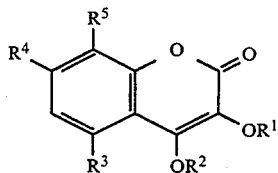

(In the formula, $R^1$ is a methyl group; $R^2$, $R^3$, $R^4$ are hydrogen atoms; $R^5$ is either a hydroxyl group or a protected hydroxyl group.)

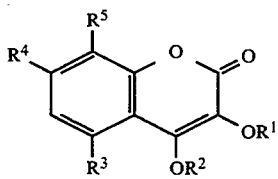

(In the formula, $R^1$ is a methyl group; $R^2$ is an alkanoyl group; $R^3$ is a hydroxyl group; $R^4$ and $R^5$ are hydrogen atoms.)

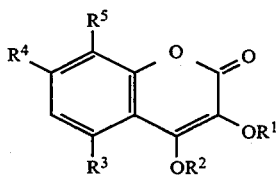

(In the formula, $R^1$ is a methyl group; $R^2$ is an alkanoyl group; $R^3$ and $R^4$ are hydrogen atoms; and $R^5$ is either a hydroxyl group or a protected hydroxyl group.)

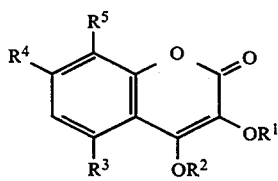

(In the formula, $R^1$ is a hydrogen atom; $R^2$ is a methyl group; $R^3$ is either a hydroxyl group or a protected hydrdoxyl group; $R^4$ and $R^5$ are also hydrogen atoms.)

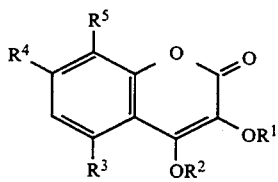

(I)

(In the formula, $R^1$ is a hydrogen atom; $R^2$ is a methyl group; $R^3$ and $R^5$ are hydrogen atoms; and $R^4$ is either a hydroxyl or a protected hydroxyl group.)

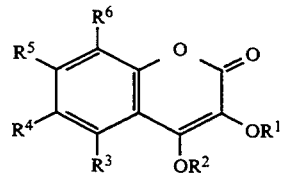

(II)

(In the formula, $R^1$ and $R^2$ are hydrogen atoms, acyl groups, alkyl groups, or alkenyl groups; and when one of $R^3$, $R^4$, $R^5$, $R^6$ is either a hydroxyl or a protected hydroxyl group, the others are hydrogen atoms.)

THE BEST STRUCTURE FOR IMPLEMENTING THE PRESENT INVENTION

In the novel benzopyran derivative shown by general formula (I), provided by means of the present invention, $R^1$ and $R^2$ can be hydrogen atom, acyl group, straight chain or branched alkyl group, or a straight chained or branched alkenyl group. When one of $R^3$, $R^4$, $R^5$ is a hydroxyl or a protected hydroxyl group, the others are hydrogen atoms.

Acyl groups which can be used as $R^1$ and $R^2$ include: alkanoyl groups such as acetyl, propionyl, butyryl, and isobutyryl groups; aroyl groups such as benzoyl, substituted benzoyl groups (for example, p-methoxy benzoyl, p-methyl benzoyl, and p-chloro benzoyl groups), and aryl carbonyl groups, such as substituted naphthyl, phenethyl groups; and acyl groups other than the above-mentioned such as formyl groups, and alkoxy carbonyl groups (for example, methoxycarbonyl, ethoxycarbonyl and propoxycarbonyl groups).

Examples of straight chained or branched alkyl groups include the following groups containing 1412 carbon atoms: methyl groups, ethyl groups, propyl groups, isopropyl groups, n-butyl groups, s-butyl groups, t-butyl groups, n-pentyl groups, 2-methylpentyl groups, octyl groups, decyl groups, and dodecyl groups.

Examples of straight chained or branched alkenyl groups include the following groups containing 2-10 carbon atoms: vinyl groups, propenyl groups, pentenyl groups, hexenyl groups, heptenyl groups, octenyl groups, nonyl groups, decenyl groups, 3-methyl-2-butenyl groups, 3-methyl-3-butenyl groups, and geranyl groups.

Protective groups protecting the hydroxy group of $R^3$, $R^4$, $R^5$ include: acyl groups, straight chained or branched alkyl groups, straight chained or branched alkenyl groups, tetrahydropyranyl groups, sulfonyl groups, and trialkylsilyl groups.

Examples of acyl groups include: alkanoyl groups such as acetyl groups, propionyl groups, butyryl groups, and isobutyryl groups; aroyl groups such as benzoyl groups, substituted benzoyl groups (for example p-methoxybenzoyl groups, p-methylbenzoyl groups, and p-chlorobenzoyl groups), and aryl carbonyl groups such as substituted naphthyl, phenethyl groups; and acyl groups other than those mentioned above, such as formyl groups, and alkoxycarbonyl groups (for example, methoxycarbonyl groups, ethoxy carbonyl groups, and propoxycarbonyl groups).

Examples of straight chained or branched alkyl groups include the following 1-12 carbon groups: methyl groups, ethyl groups, propyl groups, isopropyl groups, n-butyl groups, s-butyl groups, t-butyl groups, n-pentyl groups 2-methylpentyl groups, octyl groups, decyl groups, and dodecyl groups.

Examples of straight chained or branched alkenyl groups include the following 2-10 carbon groups: vinyl groups, propenyl groups, pentenyl groups, hexenyl groups, heptenyl groups, octenyl groups, nonyl groups, decenyl groups, 3-methyl-2-butenyl groups, 3-methyl-3-butenyl groups, and geranyl groups.

Sulfonyl groups include: methane sulfonyl groups, benzene sulfonyl groups, and benzene sulfonyl groups possessing substituents such as p-toluene sulfonyl groups.

In the following an outline of the synthesis method of the benzopyran derivative shown in the aforementioned general formula (I) (In the general formula $R^1$ is a benzoyl group or a hydrogen atom, $R^2$ is a hydrogen atom, one of $R^3 \sim R^5$ is a hydroxyl group and the others are hydrogen atoms) .

After the hydroxyl groups of 2',3'; or 2',4'; or 2',6'-dihydroxyl acetophenone (a) are protected by benzyl groups, the structure (b) is formed. Following this, by using dimethyl carbonate, the number of carbon atoms is increased and a diketone body (c) is formed, and after reacting this structure with dibenzoyl peroxide, (d) is formed. After this takes place, the benzyl group, as the protective group of the hydroxyl group, is de-protected by means of a catalytic reduction, and by treatment with acid a benzoyloxy body (e) (In the general formula $R^1$ is a benzoyl group, $R^2$ is a hydrogen atom, and one of $R^3 \sim R^5$ is a hydroxyl group while the others are hydrogen atoms) is achieved. This benzoyloxy body (e) is then put in a non-aqueous solution and the benzoyl group is removed by means of using a metal alkoxide, and the benzopyran derivative (f) (In the formala $R^1$, $R^2$ are hydrogen atoms, and one of $R^3 \sim R^5$ is a hydroxyl group while the others are hydrogen atoms) is synthesized.

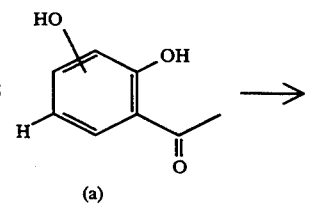

(a)

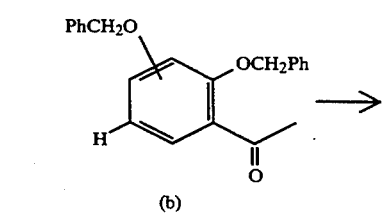

(b)

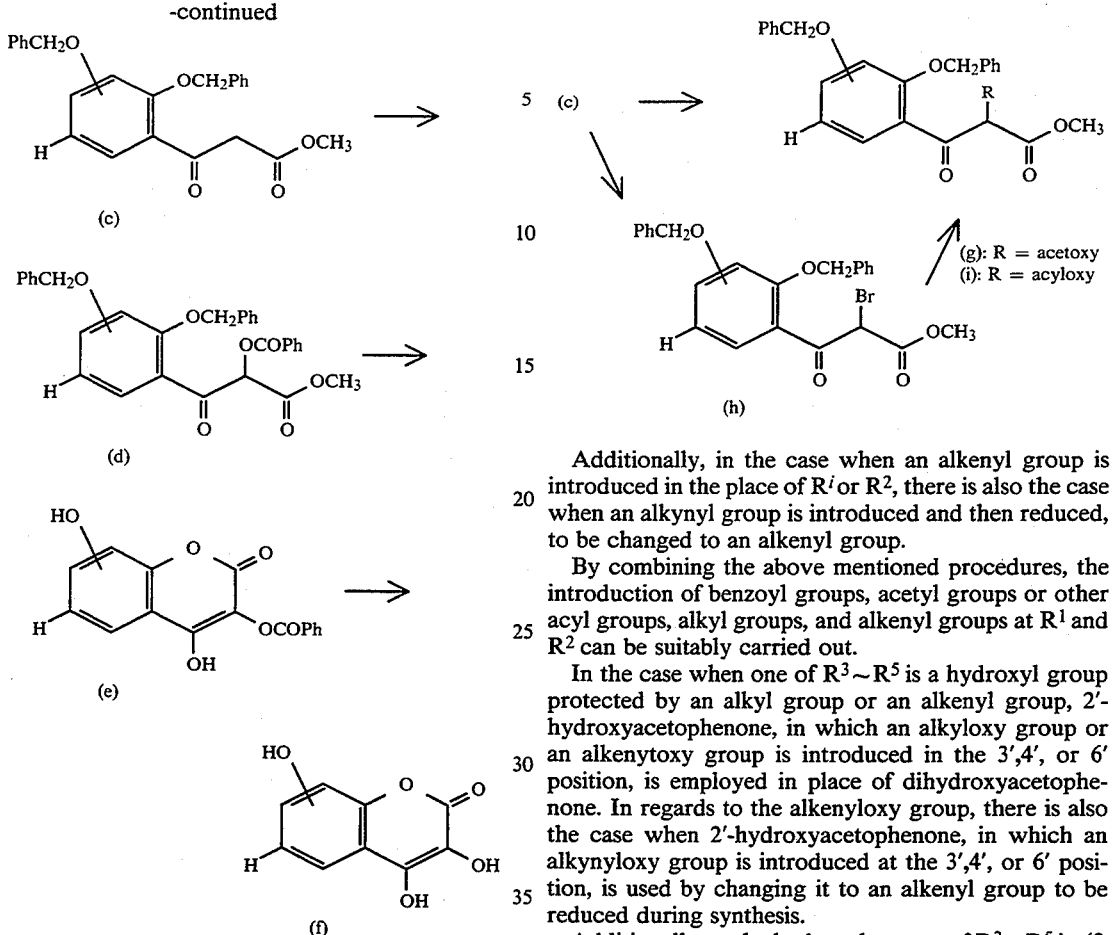

In the following an explanation outlining a synthesis method for a derivative other than that mentioned above will be given.

In the case when R¹ is an acetyl group or another acyl group: and R² is a hydrogen atom, to the diketone body (c), (1) for example to lead tetracetate, introduction of an acetyloxy group (g), or (2) halogenation (h) using copper halogen, followed by introduction of an acyloxy group (i). Following this, a reaction is carried out after using (g), (i) in place of (d) in the above mentioned synthesis method; or, a protective group is introduced selectively in the position of the hydrogen atom of R² in (f), and after an acyl group is introduced in the position of the hydrogen atom of R¹ deprotection of R² is carried out In the case when R¹ equals an alkyl group, or an alkenyl group: and R² equals a hydrogen atom, a protective group is introduced selectively in the position of the hydrogen atom of R² in (f), and then an alkyl group or an alkenyl group is selectively introduced in the position of the hydrogen atom of R¹, after which the de-protection of R¹ is carried out.

Additionally, in the case when an alkenyl group is introduced in the place of R$^i$ or R², there is also the case when an alkynyl group is introduced and then reduced, to be changed to an alkenyl group.

By combining the above mentioned procedures, the introduction of benzoyl groups, acetyl groups or other acyl groups, alkyl groups, and alkenyl groups at R¹ and R² can be suitably carried out.

In the case when one of R³~R⁵ is a hydroxyl group protected by an alkyl group or an alkenyl group, 2'-hydroxyacetophenone, in which an alkyloxy group or an alkenytoxy group is introduced in the 3',4', or 6' position, is employed in place of dihydroxyacetophenone. In regards to the alkenyloxy group, there is also the case when 2'-hydroxyacetophenone, in which an alkynyloxy group is introduced at the 3',4', or 6' position, is used by changing it to an alkenyl group to be reduced during synthesis.

Additionally, at the hydroxyl groups of R³~R⁵ in (f), acyl groups, straight chained or branched alkyl groups, straight chained or branched alkenyl groups, tetrahydropyranyl groups, sulfonyl groups and the like are selectively introduced. Otherwise, after a protective group has been selectively introduced at the position of the hydrogen atom of R¹, R², an acyl groups, straight chained or branched alkyl groups, straight chained or branched alkenyl groups, tetrahydropyranyl groups, or sulfonyl groups are introduced for the hydroxyl groups of R³~R⁵, after which the de-protection of R¹, R² is carried out.

By means of combining the above mentioned procedures for introducing substituents for R¹~R⁵, as the concretely synthesized compound, the following compounds can be listed:

3,4,7-(trihydroxy)-2H-1-benzopyran-2-one
3-(acetoxy)-4,7-(dihydroxy)-2H-1-benzopyran-2-one
3-(benzoyloxy)-4,7-(dihydroxy)-2H-1-benzopyran-2-one
3-(isopropoxy)-4,7-(dihydroxy)-2H-1-benzopyran-2-one
3-(decyloxy)-4,7-(dihydroxy)-2H-1-benzopyran-2-one
3-(3-hexenytoxy)-4,7-(dihydroxy)-2H-1-benzopyran-2-one
3-(geranyloxy)-4,7-(dihydroxy)-2H-1-benzopyran-2-one
3,7-(dihydroxy)-4-(acetoxy)-2H-1-benzopyran-2-one
3,4-(diacetoxy)-7-hydroxy-2H-1-benzopyran-2-one
3-(benzoyloxy)-4-(acetoxy)-7-hydroxy-2H-1-benzopyran-2-one
3-(methoxy)-4-(acetoxy)-7-hydroxy-2H-1-benzopyran-2-one 3-(isopropoxy)-4-(acetoxy)-7-hydroxy-2H-1-benzopyran-2-one
3-(decyloxy)-4-(acetoxy)-7-hydroxy-2H-1-benzopyran-2-one
3-(3-hexenyloxy)-4-(acetoxy)-7-hydroxy-2H-1-benzopyran-2-one
3-(geranyloxy)-4-(acetoxy)-7-hydroxy-2H-1-benzopyran-2-one
3,7-(dihydroxy)-4-(benzoyloxy)-2H-1-benzopyran-2-one
3-(acetoxy)-4-(benzoyloxy)-7-hydroxy-2H-1-benzopyran-2-one
3,4-(dibenzoyloxy)-7-hydroxy-2H-1-benzopyran-2-one
3-(methoxy)-4-(benzoyloxy)-7-hydroxy-2H-1-benzopyran-2-one
3-(isopropoxy)-4-(benzoyloxy)-7-hydroxy-2H-1-benzopyran-2-one
3-(decyloxy)-4-(benzoyloxy)-7-hydroxy-2H-1-benzopyran-2-one
3-(3-hexenyloxy)-4-(benzoyloxy)-7-hydroxy-2H-1-benzopyran-2-one
3-(geranyloxy)-4-(benzoyloxy)-7-hydroxy-2H-1-benzopyran-2-one
3,7-(dihydroxy)-4-(methoxy)-2H-1-benzopyran-2-one
3-(acetoxy)-4-(methoxy)-7-hydroxy-2H-1-benzopyran-2-one
3-(benzoyloxy)-4-(methoxy)-7-hydroxy-2H-1-benzopyran-2-one
3-(isopropoxy)-4-(methoxy)-7-hydroxy-2H-1-benzopyran-2-one
3-(decyloxy)-4-(methoxy)-7-hydroxy-2H- 1-benzopyran-2-one
3-(3-hexenyloxy)-4-(methoxy)-7-hydroxy-2H-1-benzopyran-2-one
3-(geranyloxy)- 4-(methoxy)-7-hydroxy-2 H- 1-benzopyran-2-one
3,7-(dihydroxy)-4-(isopropoxy)-2H-1-benzopyran-2-one
3-(acetoxy)-4-(isopropoxy)-7-hydroxy-2H-1-benzopyran-2-one
3-(benzoyloxy)-4-(isopropoxy)-7-hydroxy-2H-1-benzopyran-2-one
3-(methoxy)-4-(isopropoxy)-7-hydroxy-2H- 1-benzopyran-2-one
3,4-(diisopropoxy)-7-hydroxy-2H- 1-benzopyran-2-one
3-(decyloxy)-4-(isopropoxy)-7-hydroxy-2H-1-benzopyran-2-one
3-(3-hexenyloxy)-4-(isopropoxy)-7-hydroxy-2H-1-benzopyran-2-one
3-(geranyloxy)-4-(isopropoxy)-7-hydroxy-2H-1-benzopyran-2-one
3,7-(dihydroxy)-4-(decyloxy)-2H-1-benzopyran-2-one
3-(acetoxy)-4-(decyloxy)-7-hydroxy-2H-1-benzopyran-2-one
3-(benzoyloxy)-4-(decyloxy)-7-hydroxy-2H-1-benzopyran-2-one
3-(methoxy)-4-(decyloxy)-7-hydroxy-2H-1-benzopyran-2-one
3-(isopropoxy)-4-(decyloxy)-7-hydroxy-2H-1-benzopyran-2one 3,4-(didecyloxy)-7-hydroxy-2H-1-benzopyran-2-one
3-(3-hexenyloxy)-4-(decyloxy)-7-hydroxy-2H-1-benzopyran-2-one
3-(geranyloxy)-4-(decyloxy)-7-hydroxy-2H-1-benzopyran-2-one
3,7-(dihydroxy)-4-(3-hexenyloxy)-2H-1-benzopyran-2-one
3-(acetoxy)-4-(3-hexenyloxy)-7-hydroxy-2H-1-benzopyran-2-one
3-(benzoyloxy)-4-(3-hexenyloxy)-7-hydroxy-2H-1-benzopyran-2-one
3-(methoxy)-4-(3-hexenyloxy)-7-hydroxy-2H-1-benzopyran-2-one
3-(isopropoxy)-4-(3-hexenyloxy)-7-hydroxy-2H-1-benzopyran-2-one
3-(decyloxy)-4-(3-hexenyloxy)-V-hydroxy-2H-1-benzopyran-2-one
3,4-(di-3-hexenyloxy)-7-hydroxy-2H-1-benzopyran-2-one
3-(geranyloxy)-4-(3-hexenyloxy)-7-hydroxy-2H-1-benzopyran-2-one
3,7-(dihydroxy)-4-(geranyloxy)-2H-1-benzopyran-2-one
3-(acetoxy)-4-(geranyloxy)-7-hydroxy-2H-1-benzopyran-2-one
3-(benzoyloxy)-4-(geranyloxy)-7-hydroxy-2H-1-benzopyran-2-one
3-(methoxy)-4-(geranyloxy)-7-hydroxy-2H-1-benzopyran-2-one
3-(isopropoxy)-4-(geranyloxy)-7-hydroxy-2H-1-benzopyran-2-one
3-(decyloxy)-4-(geranyloxy)-7-hydroxy-2H-1-benzopyran-2-one
3-(3-hexenyloxy)-4-(geranyloxy)-7-hydroxy-2H-1-benzopyran-2-one
3,4-(digeranyloxy)-7-hydroxy-2H-1-benzopyran-2-one
3,4-(dihydroxy)-7-(acetoxy)-2H-1-benzopyran-2-one
3,7-(diacetoxy)-4-hydroxy-2H-1-benzopyran-2-one
3-(benzoyloxy)-4-hydroxy-7-(acetoxy)-2H-1-benzopyran-2-one
3-(methoxy)-4-hydroxy-7-(acetoxy)-2H-1-benzopyran-2-one
3-(isopropoxy)-4-hydroxy-7-(acetoxy)-2H-1-benzopyran-2-one
3-(decyloxy)-4-hydroxy-7-(acetoxy)-2H-1-benzopyran-2-one
3-(3-hexenyloxy)-4-hydroxy-7-(acetoxy)-2H-1-benzopyran-2-one
3-(geranyloxy)-4-hydroxy-7-(acetoxy)-2H-1-benzopyran-2-one
3-hydroxy-4,7-(diacetoxy)-2H-1-benzopyran-2-one
3,4,7-(triacetoxy)-2H-1-benzopyran-2-one
3-(benzoyloxy)-4,7-(diacetoxy)-2H-1-benzopyran-2-one
3-(isopropoxy)-4,7-(diacetoxy)-2H-1-benzopyran-2-one
3-(decyloxy)-4,7-(diacetoxy)-2H-1-benzopyran-2-one
3-(3-hexenyloxy)-4,7-(diacetoxy)-2H-1-benzopyran-2-one
3-(geranyloxy)-4,7-(diacetoxy)-2H-1-benzopyran-2-one
3-hydroxy-4-(benzoyloxy)-7-(acetoxy)-2H-1-benzopyran-2-one
3,7-(diacetoxy)-4-(benzoyloxy)-2H-1-benzopyran-2-one
3,4-(dibenzoyloxy)-7-(acetoxy)-2H-1-benzopyran-2-one
3-(methoxy)-4-(benzoyloxy)-7-(acetoxy)-2H-1-benzopyran-2-one
3-(isopropoxy)-4-(benzoyloxy)-7-(acetoxy)-2H-1-benzopyran-2-one
3-(decyloxy)-4-(benzoyloxy)-7-(acetoxy)-2H-1-benzopyran-2-one
3-(3-hexenyloxy)-4-(benzoyloxy)-7-(acetoxy)-2H-1-benzopyran-2-one
3-(geranyloxy)-4-(benzoyloxy)-7-(acetoxy)-2H-1-benzopyran-2-one
3-hydroxy-4-(methoxy)-7-(acetoxy)-2H-1-benzopyran-2-one
3,7-(diacetoxy)-4-(methoxy)-2H-1-benzopyran-2-one
3-(benzoyloxy)-4-(methoxy)-7-(acetoxy)-2H-1-benzopyran-2-one 3-(isopropoxy)-4-(methoxy)-7-(acetoxy)-2H-1-benzopyran-2-one
3-(decyloxy)-4-(methoxy)-7-(acetoxy)-2H-1-benzopyran-2-one
3-(3-hexenyloxy)-4-(methoxy)-7-(acetoxy)-2H-1-benzopyran-2-one
3-(geranyloxy)-4-(methoxy)-7-(acetoxy)-2H-1-benzopyran-2-one
3-hydroxy-4-(isopropoxy)-7-(acetoxy)-2H-1-benzopyran-2-one
3,7-(diacetoxy)-4-(isopropoxy)-2H-1-benzopyran-2-one
3-(benzoyloxy)-4-(isopropoxy)-7-(acetoxy)-2H-1-benzopyran-2-one
3-(methoxy)-4-(isopropoxy)-7-(acetoxy)-2H-1-benzopyran-2-one
3,4-(diisopropoxy)-7-(acetoxy)-2H-1-benzopyran-2-one
3-(decyloxy)-4-(isopropoxy)-7-(acetoxy)-2H-1-benzopyran-2-one
3-(3-hexenyloxy)-4-(isopropoxy)-7-(acetoxy)-2H-1-benzopyran-2-one
3-(geranyloxy)-4-(isopropoxy)-7-(acetoxy)-2H-1-benzopyran-2-one
3-hydroxy-4-(decyloxy)-7-(acetoxy)-2H-1-benzopyran-2-one
3,7-(diacetoxy)-4-(decyloxy)-2H-1-benzopyran-2-one
3-(benzoyloxy)-4-(decyloxy)-7-(acetoxy)-2H-1-benzopyran-2-one
3-(methoxy)-4-(decyloxy)-7-(acetoxy)-2H-1-benzopyran-2-one
3-(isopropoxy)-4-(decyloxy)-7-(acetoxy)-2H-1-benzopyran-2-one
3,4-(didecyloxy)-7-(acetoxy)-2H-1-benzopyran-2-one
3-(3-hexenyloxy)-4-(decyloxy)-7-(acetoxy)-2H-1-benzopyran-2-one
3-(geranyloxy)-4-(decyloxy)-7-(acetoxy)-2H-1-benzopyran-2-one
3-hydroxy-4-(3-hexenyloxy)-7-(acetoxy)-2H-1-benzopyran-2-one
3,7-(diacetoxy)-4-(3-hexenyloxy)-2H-1-benzopyran-2-one
3-(benzoyloxy)-4-(3-hexenyloxy)-7-(acetoxy)-2H-1-benzopyran-2-one
3-(methoxy)-4-(3-hexenyloxy)-7-(acetoxy)-2H-1-benzopyran-2-one
3-(isopropoxy)-4-(3-hexenyloxy)-7-(acetoxy)-2H-1-benzopyran-2-one
3-(decyloxy)-4-(3-hexenyloxy)-7-(acetoxy)-2H-1-benzopyran-2-one
3,4-(di-3-hexenyloxy)-7-(acetoxy)-2H-1-benzopyran-2-one
3-(geranyloxy)-4-(3-hexenyloxy)-7-(acetoxy)-2H-1-benzopyran-2-one
3-hydroxy-4-(geranyloxy)-7-(acetoxy)-2H-1-benzopyran-2-one
3,7-(diacetoxy)-4-(geranyloxy)-2H-1-benzopyran-2-one
3-(benzoyloxy)-4-(geranyloxy)-7-(acetoxy)-2H-1-benzopyran-2-one
3-(methoxy)-4-(geranyloxy)-7-(acetoxy)-2H-1-benzopyran-2-one
3-(isopropoxy)-4-(geranyloxy)-7-(acetoxy)-2H-1-benzopyran-2-one
3-(decyloxy)-4-(geranyloxy)-7-(acetoxy)-2H-1-benzopyran-2-one
3-(3-hexenyloxy)-4-(geranyloxy)-7-(acetoxy)-2H-1-benzopyran-2-one
3,4-(digeranyloxy)-7-(acetoxy)-2H-1-benzopyran-2-one
3,4-(dihydroxy)-7-(methoxy)-2H-1-benzopyran-2-one
3-(acetoxy)-4-hydroxy-7-(methoxy)-2H-1-benzopyran-2-one
3-(benzoyloxy)-4-hydroxy-7-(methoxy)-2H-1-benzopyran-2-one
3-(isopropoxy)-4-hydroxy-7-(methoxy)-2H-1-benzopyran-2-one
3-(decyloxy)-4-hydroxy-7-(methoxy)-2H-1-benzopyran-2-one
3-(3-hexenyloxy)-4-hydroxy-7-(methoxy)-2H-1-benzopyran-2-one
3-(geranyloxy)-4-hydroxy-7-(methoxy)-2H-1-benzopyran-2-one
3-hydroxy-4-(acetoxy)-7-(methoxy)-2H-1-benzopyran-2-one
3,4-(diacetoxy)-7-(methoxy)-2H-1-benzopyran-2-one
3-(benzoyloxy)-4-(acetoxy)-7-(methoxy)-2H-1-benzopyran-2-one
3,7-(dimethoxy)-4-(acetoxy)-2H-1-benzopyran-2-one
3-(isopropoxy)-4-(acetoxy)-7-(methoxy)-2H-1-benzopyran-2-one
3-(decyloxy)-4-(acetoxy)-7-(methoxy)-2H-1-benzopyran-2-one
3-(3-hexenyloxy)-4-(acetoxy)-7-(methoxy)-2H-1-benzopyran-2-one
3-(geranyloxy)-4-(acetoxy)-7-(methoxy)-2H-1-benzopyran-2-one
3-hydroxy-4-(benzoyloxy)-7-(methoxy)-2H-1-benzopyran-2-one
3-(acetoxy)-4-(benzoyloxy)-7-(methoxy)-2H-1-benzopyran-2-one
3,4-(dibenzoyloxy)-7-(methoxy)-2H-1-benzopyran-2-one
3,7-(dimethoxy)-4-(benzoyloxy)-2H-1-benzopyran-2-one
3-(isopropoxy)-4-(benzoyloxy)-7-(methoxy)-2H-1-benzopyran-2-one
3-(decyloxy)-4-(benzoyloxy)-7-(methoxy)-2H-1-benzopyran-2-one
3-(3-hexenyloxy)-4-(benzoyloxy)-7-(methoxy)-2H-1-benzopyran-2-one
3-(geranyloxy)-4-(benzoytoxy)-7-(methoxy)-2H-1-benzopyran-2-one
3-hydroxy-4,7-(dimethoxy)-2H-1-benzopyran-2-one
3-(acetoxy)-4,7-(dimethoxy)-2H-1-benzopyran-2-one
3-(benzoyloxy)-4,7-(dimethoxy)-2H-1-benzopyran-2-one
3-(isopropoxy)-4,7-(dimethoxy)-2H-1-benzopyran-2-one
3-(decyloxy)-4, 7-(dimethoxy)-2H-1-benzopyran-2-one
3-(3-hexenyloxy)-4,7-(dimethoxy)-2H-1-benzopyran-2-one
3-(geranyloxy)-4,7-(dimethoxy)-2H-1-benzopyran-2-one
3-hydroxy-4-(isopropoxy)-7-(methoxy)-2H-1-benzopyran-2-one
3-(acetoxy)-4-(isopropoxy)-7-(methoxy)-2H-1-benzopyran-2-one
3-(benzoyloxy)-4-(isopropoxy)-7-(methoxy)-2H-1-benzopyran-2-one
3,7-(dimethoxy)-4-(isopropoxy)-2H-1-benzopyran-2-one
3,4-(diisopropoxy)-7-(methoxy)-2H-1-benzopyran-2-one
3-(decyloxy)-4-(isopropoxy)-7-(methoxy)-2H-1-benzopyran-2-one
3-(3-hexenyloxy)-4-(isopropoxy)-7-(methoxy)-2H-1-benzopyran-2-one 3-(geranyloxy)-4-(isopropoxy)-7-(methoxy)-2H-1-benzopyran-2-one
3-hydroxy-4-(decyloxy)-7-(methoxy)-2H-1-benzopyran-2-one
3-(acetoxy)-4-(decyloxy)-7-(methoxy)-2H-1-benzopyran-2-one
3-(benzoyloxy)-4-(decyloxy)-7-(methoxy)-2H-1-benzopyran-2-one
3,7-(dimethoxy)-4-(decyloxy)-2H-1-benzopyran-2-one
3-(isopropoxy)-4-(decyloxy)-7-(methoxy)-2H-1-benzopyran-2-one
3,4-(didecyloxy)-7-(methoxy)-2H-1-benzopyran-2-one
3-(3-hexenyloxy)-4-(decyloxy)-7-(methoxy)-2H-1-benzopyran-2-one
3-(geranyloxy)-4-(decyloxy)-7-(methoxy)-2H-1-benzopyran-2-one
3-hydroxy-4-(3-hexenyloxy)-7-(methoxy)-2H-1-benzopyran-2-one
3-(acetoxy)-4-(3-hexenyloxy)-7-(methoxy)-2H-1-benzopyran-2-one
3-(benzoyloxy)-4-(3-hexenyloxy)-7-(methoxy)-2H-1-benzopyran-2-one
3,7-(dimethoxy)-4-(3-hexenyloxy)-2H-1-benzopyran-2-one
3-(isopropoxy)-4-(3-hexenyloxy)-7-(methoxy)-2H-1-benzopyran-2-one
3-(decyloxy)-4-(3-hexenyloxy)-7-(methoxy)-2H-1-benzopyran-2-one
3,4-(di-3-hexenyloxy)-7-(methoxy)-2H-1-benzopyran-2-one
3-(geranyloxy)-4-(3-hexenyloxy)-7-(methoxy)-2H-1-benzopyran-2-one
3-hydroxy-4-(geranyloxy)-7-(methoxy)-2H-1-benzopyran-2-one
3-(acetoxy)-4-(geranyloxy)-7-(methoxy)-2H-1-benzopyran-2-one
3-(benzoyloxy)-4-(geranyloxy)-7-(methoxy)-2H-1-benzopyran-2-one
3,7-(dimethoxy)-4-(geranyloxy)-2H-1-benzopyran-2-one
3-(isopropoxy)-4-(geranyloxy)-7-(methoxy)-2H-1-benzopyran-2-one
3-(decyloxy)-4-(geranyloxy)-7-(methoxy)-2H-1-benzopyran-2-one
3-(3-hexenyloxy)-4-(geranyloxy)-7-(methoxy)-2H-1-benzopyran-2-one
3,4-(digeranyloxy)-7-(methoxy)-2H-1-benzopyran-2-one
3,4-(dihydroxy)-7-(isopropoxy)-2H-1-benzopyran-2-one
3-(acetoxy)-4-hydroxy-7-(isopropoxy)-2H-1-benzopyran-2-one
3-(benzoyloxy)-4-hydroxy-7-(isopropoxy)-2H-1-benzopyran-2-one
3,7-(diisopropoxy)-4-hydroxy-2H-1-benzopyran-2-one
3-(decyloxy)-4-hydroxy-7-(isopropoxy)-2H-1-benzopyran-2-one
3-(3-hexenyloxy)-4-hydroxy-7-(isopropoxy)-2H-1-benzopyran-2-one
3-(geranyloxy)-4-hydroxy-7-(isopropoxy)-2H-1-benzopyran-2-one
3-hydroxy-4-(acetoxy)-7-(isopropoxy)-2H-1-benzopyran-2-one
3,4-(diacetoxy)-7-(isopropoxy)-2H-1-benzopyran-2-one
3-(benzoyloxy)-4-(acetoxy)-7-(isopropoxy)-2H-1-benzopyran-2-one
3,7-(diisopropoxy)-4-(acetoxy)-2H-1-benzopyran-2-one
3-(decyloxy)-4-(acetoxy)-7-(isopropoxy)-2H-1-benzopyran-2-one
3-hydroxy-4-(benzoyloxy)-7-(isopropoxy)-2H-1-benzopyran-2-one
3-(acetoxy)-4-(benzoyloxy)-7-(isopropoxy)-2H-1-benzopyran-2-one
3,4-(dibenzoyloxy)-7-(isopropoxy)-2H-1-benzopyran-2-one
3-(methoxy)-4-(benzoyloxy)-7-(isopropoxy)-2H-1-benzopyran-2-one
3,7-(diisopropoxy)-4-(benzoyloxy)-2H-1-benzopyran-2-one
3-(decyloxy)-4-(benzoyloxy)-7-(isopropoxy)-2H-1-benzopyran-2-one
3-(3-hexenyloxy)-4-(benzoyloxy)-7-(isopropoxy)-2H-1-benzopyran-2-one
3-(geranyloxy)-4-(benzoyloxy)-7-(isopropoxy)-2H-1-benzopyran-2-one
3-hydroxy-4-(methoxy)-7-(isopropoxy)-2H-1-benzopyran-2-one
3-(acetoxy)-4-(methoxy)-7-(isopropoxy)-2H-1-benzopyran-2-one
3-(benzoyloxy)-4-(methoxy)-7-(isopropoxy)-2H-1-benzopyran-2-one
3,7-(diisopropoxy)-4-(methoxy)-7-(isopropoxy)-2H-1-benzopyran-2-one
3-(decyloxy)-4-(methoxy)-7-(isopropoxy)-2H-1-benzopyran-2-one
3-(3-hexenyloxy)-4-(methoxy)-7-(isopropoxy)-2H-1-benzopyran-2-one
3-(geranyloxy)-4-(methoxy)-7-(isopropoxy)-2H-1-benzopyran-2-one
3-hydroxy-4,7-(diisopropoxy)-2H-1-benzopyran-2-one
3-(acetoxy)-4,7-(diisopropoxy)-2H-1-benzopyran-2-one
3-(benzoyloxy)-4,7-(diisopropoxy)-2H-1-benzopyran-2-one
3-(methoxy)-4,7-(diisopropoxy)-2H-1-benzopyran-2-one 3,4,7-(triisopropoxy)-2H-1-benzopyran-2-one
3-(decyloxy)-4,7-(diisopropoxy)-2H-1-benzopyran-2-one
3-(3-hexenyloxy)-4,7-(diisopropoxy)-2H-1-benzopyran-2-one
3-(geranyloxy)-4,7-(diisopropoxy)-2H-1-benzopyran-2-one
3-hydroxy-4-(decyloxy)-7-(isopropoxy)-2H-1-benzopyran-2-one
3-(acetoxy)-4-(decyloxy)-7-(isopropoxy)-2H-1-benzopyran-2-one
3-(benzoyloxy)-4-(decyloxy)-7-(isopropoxy)-2H-1-benzopyran-2-one
3-(methoxy)-4-(decyloxy)-7-(isopropoxy)-2H-1-benzopyran-2-one
3,7-(diisopropoxy)-4-(decyloxy)-2H-1-benzopyran-2-one
3,4-(didecyloxy)-7-(isopropoxy)-2H-1-benzopyran-2-one
3-(3-hexenyloxy)-4-(decyloxy)-7-(isopropoxy)-2H-1-benzopyran-2-one
3-(geranyloxy)-4-(decyloxy)-7-(isopropoxy)-2H-1-benzopyran-2-one
3-hydroxy-4-(3-hexenyloxy)-7-(isopropoxy)-2H-1-benzopyran-2-one
3-(acetoxy)-4-(3-hexenyloxy)-7-(isopropoxy)-2H-1-benzopyran-2-one
3-(benzoyloxy)-4-(3-hexenyloxy)-7-(isopropoxy)-2H-1-benzopyran-2-one
3-(methoxy)-4-(3-hexenyloxy)-7-(isopropoxy)-2H-1-benzopyran-2-one
3,7-(diisopropoxy)-4-(3-hexenyloxy)-2H-1-benzopyran-2-one 3-(decyloxy)-4-(3-hexenyloxy)-7-(isopropoxy)-2H-1-benzopyran-2-one
3,4-(di-3-hexenyloxy)-7-(isopropoxy)-2H-1-benzopyran-2-one
3-(geranyloxy)-4-(3-hexenyloxy)-7-(isopropoxy)-2H-1-benzopyran-2-one
3-hydroxy-4-(geranyloxy)-7-(isopropoxy)-2H-1-benzopyran-2-one
3-(acetoxy)-4-(geranyloxy)-7-(isopropoxy)-2H-1-benzopyran-2-one
3-(benzoyloxy)-4-(geranyloxy)-7-(isopropoxy)-2H-1-benzopyran-2-one
3-(methoxy)-4-(geranyloxy)-7-(isopropoxy)-2H-1-benzopyran-2-one
3,7-(diisopropoxy)-4-(geranyloxy)-2H-1-benzopyran-2-one
3-(decyloxy)-4-(geranyloxy)-7-(isopropoxy)-2H-1-benzopyran-2-one
3-(3-hexenyloxy)-4-(geranyloxy)-7-(isopropoxy)-2H-1-benzopyran-2-one
3,4-(digeranyloxy)-7-(isopropoxy)-2H-1-benzopyran-2-one
3,4-(dihydroxy)-7-(t-butoxy)-2H-1-benzopyran-2-one
3-(acetoxy)-4-hydroxy-7-(t-butoxy)-2H-1-benzopyran-2-one
3-(benzoyloxy)-4-hydroxy-7-(t-butoxy)-2H-1-benzopyran-2-one
3-(isopropoxy)-4-hydroxy-7-(t-butoxy)-2H-1-benzopyran-2-one
3-(decyloxy)-4-hydroxy-7-(t-butoxy)-2H-1-benzopyran-2-one
3-(3-hexenyloxy)-4-hydroxy-7-(t-butoxy)-2H-1-benzopyran-2-one
3-(geranyloxy)-4-hydroxy-7-(t-butoxy)-2H-1-benzopyran-2-one
3-hydroxy-4-(acetoxy)-7-(t-butoxy)-2H-1-benzopyran-2-one
3,4-(diacetoxy)-7-(t-butoxy)-2H-1-benzopyran-2-one
3-(benzoyloxy)-4-(acetoxy)-7-(t-butoxy)-2H-1-benzopyran-2-one
3-(isopropoxy)-4-(acetoxy)-7-(t-butoxy)-2H-1-benzopyran-2-one
3-(decyloxy)-4-(acetoxy)-7-(t-butoxy)-2H-1-benzopyran-2-one
3-hydroxy-4-(benzoyloxy)-7-(t-butoxy)-2H-1-benzopyran-2-one
3-(acetoxy)-4-(benzoyloxy)-7-(t-butoxy)-2H-1-benzopyran-2-one
3,4-(dibenzoyloxy)-7-(t-butoxy)-2H-1-benzopyran-2-one
3-(methoxy)-4-(benzoyloxy)-7-(t-butoxy)-2H-1-benzopyran-2-one
3-(isopropoxy)-4-(benzoyloxy)-7-(t-butoxy)-2H-1-benzopyran-2-one
3-(decytoxy)-4-(benzoyloxy)-7-(t-butoxy)-2H-1-benzopyran-2-one
3-(3-hexenyloxy)-4-(benzoyloxy)-7-(t-butoxy)-2H-1-benzopyran-2-one
3-(geranyloxy)-4-(benzoyloxy)-7-(t-butoxy)-2H-1-benzopyran-2-one
3-hydroxy-4-(methoxy)-7-(t-butoxy)-2H-1-benzopyran-2-one
3-(acetoxy)-4-(methoxy)-7-(t-butoxy)-2H-1-benzopyran-2-one
3-(benzoyloxy)-4-(methoxy)-7-(t-butoxy)-2H-1-benzopyran-2-one
3-(isopropoxy)-4-(methoxy)-7-(t-butoxy)-2H-1-benzopyran-2-one
3-(decyloxy)-4-(methoxy)-7-(t-butoxy)-2H-1-benzopyran-2-one
3-(3-hexenyloxy)-4-(methoxy)-7-(t-butoxy)-2H-1-benzopyran-2-one
3-(geranyloxy)-4-(methoxy)-7-(t-butoxy)-2H-1-benzopyran-2-one
3-hydroxy-4-(isopropoxy)-7-(t-butoxy)-2H-1-benzopyran-2-one
3-(acetoxy)-4-(isopropoxy)-7-(t-butoxy)-2H-1-benzopyran-2-one
3-(benzoyloxy)-4-(isopropoxy)-7-(t-butoxy)-2H-1-benzopyran-2-one
3-(methoxy)-4-(isopropoxy)-7-(t-butoxy)-2H-1-benzopyran-2-one
3,4-(diisopropoxy)-7-(t-butoxy)-2H-1-benzopyran-2-one
3-(decyloxy)-4-(isopropoxy)-7-(t-butoxy)-2H-1-benzopyran-2-one
3-(3-hexenyloxy)-4-(isopropoxy)-7-(t-butoxy)-2H-1-benzopyran-2-one
3-(geranyloxy)-4-(isopropoxy)-7-(t-butoxy)-2H-1-benzopyran-2-one
3-hydroxy-4-(decyloxy)-7-(t -butoxy)-2H-1-benzopyran-2-one
3-(acetoxy)-4-(decyloxy)-7-(t-butoxy)-2H-1-benzopyran-2-one
3-(benzoyloxy)-4-(decyloxy)-7-(t-butoxy)-2H-1-benzopyran-2-one
3-(methoxy)-4-(decyloxy)-7-(t-butoxy)-2H-1-benzopyran-2-one
3-(isopropoxy)-4-(decyloxy)-7-(t-butoxy)-2H-1-benzopyran-2-one
3,4-(didecyloxy)-7-(t-butoxy)-2H-1-benzopyran-2-one
3-(3-hexenyloxy)-4-(decyloxy)-7-(t-butoxy)-2H-1-benzopyran-2-one
3-(geranyloxy)-4-(decyloxy)-7-(t-butoxy)-2H-1-benzopyran-2-one
3-hydroxy-4-(3-hexenyloxy)-7-(t-butoxy)-2H-1-benzopyran-2-one
3-(acetoxy)-4-(3-hexenyloxy)-7-(t-butoxy)-2H-1-benzopyran-2-one
3-(benzoyloxy)-4-(3-hexenyloxy)-7-(t-butoxy)-2H-1-benzopyran-2-one
3-(methoxy)-4-(3-hexenyloxy)-7-(t-butoxy)-2H-1-benzopyran-2-one
3-(isopropoxy)-4-(3-hexenyloxy)-7-(t-butoxy)-2H-1-benzopyran-2-one
3-(decyloxy)-4-(3-hexenyloxy)-7-(t-butoxy)-2H-1-benzopyran-2-one
3,4-(di-3-hexenyloxy)-7-(t-butoxy)-2H-1-benzopyran-2-one
3-(geranyloxy)-4-(3-hexenyloxy)-7-(t-butoxy)-2H-1-benzopyran-2-one
3-hydroxy-4-(geranyloxy)-7-(t-butoxy)-2H-1-benzopyran-2-one
3-(acetoxy)-4-(geranyloxy)-7-(t-butoxy)-2H-1-benzopyran-2-one
3-(benzoyloxy)-4-(geranyloxy)-7-(t-butoxy)-2H-1-benzopyran-2-one
3-(methoxy)-4-(geranyloxy)-7-(t-butoxy)-2H-1-benzopyran-2-one
3-(isopropoxy)-4-(geranyloxy)-7-(t-butoxy)-2H-1-benzopyran-2-one
3-(decyloxy)-4-(geranyloxy)-7-(t-butoxy)-2H-1-benzopyran-2-one
3-(3-hexenyloxy)-4-(geranyloxy)-7-(t-butoxy)-2H-1-benzopyran-2-one
3,4-(digeranyloxy)-7-(t-butoxy)-2H-1-benzopyran-2-one
3,4-(dihydroxy)-7-(decyloxy)-2H-1-benzopyran-2-one 3-(acetoxy)-4-hydroxy-7-(decyloxy)-2H-1-benzopyran-2-one
3-(benzoyloxy)-4-hydroxy-7-(decyloxy)-2H-1-benzopyran-2-one
3-(isopropoxy)-4-hydroxy-7-(decyloxy)-2H-1-benzopyran-2-one
3,7-(didecyloxy)-4-hydroxy-2H-1-benzopyran-2-one
3-(3-hexenyloxy)-4-hydroxy-7-(decyloxy)-2H-1-benzopyran-2-one
3-(geranyloxy)-4-hydroxy-7-(decyloxy)-2H-1-benzopyran-2-one
3-hydroxy-4-(acetoxy)-7-(decyloxy)-2H-1-benzopyran-2-one
3,4-(diacetoxy)-7-(decyloxy)-2H-1-benzopyran-2-one
3-(benzoyloxy)-4-(acetoxy)-7-(decyloxy)-2H-1-benzopyran-2-one
3-(isopropoxy)-4-(acetoxy)-7-(decyloxy)-2H-1-benzopyran-2-one
3,7-(didecyloxy)-4-(acetoxy)-7-(decyloxy)-2H-1-benzopyran-2-one
3-(3-hexenyloxy)-4-(acetoxy)-7-(decyloxy)-2H-1-benzopyran-2-one
3-(geranyloxy)-4-(acetoxy)-7-(decyloxy)-2H-1-benzopyran-2-one
3-hydroxy-4-(benzoyloxy)-7-(decyloxy)-2H-1-benzopyran-2-one
3-(acetoxy)-4-(benzoyloxy)-7-(decyloxy)-2H-1-benzopyran-2-one
3,4-(dibenzoyloxy)-7-(decyloxy)-2H-1-benzopyran-2-one
3-(methoxy)-4-(benzoyloxy)-7-(decyloxy)-2H-1-benzopyran-2-one
3-(isopropoxy)-4-(benzoyloxy)-7-(decyloxy)-2H-1-benzopyran-2-one
3,7-(didecyloxy)-4-(benzoyloxy)-2H-1-benzopyran-2-one
3-(3-hexenyloxy)-4-(benzoyloxy)-7-(decyloxy)-2H-1-benzopyran-2-one
3-(geranyloxy)-4-(benzoyloxy)-7-(decyloxy)-2H-1-benzopyran-2-one
3-hydroxy-4-(methoxy)-7-(decyloxy)-2H-1-benzopyran-2-one
3-(acetoxy)-4-(methoxy)-7-(decyloxy)-2H-1-benzopyran-2-one
3-(benzoyloxy)-4-(methoxy)-7-(decyloxy)-2H-1-benzopyran-2-one
3-(isopropoxy)-4-(methoxy)-7-(decyloxy)-2H-1-benzopyran-2-one
3,7-(didecyloxy)-4-(methoxy)-2H-1-benzopyran-2-one
3-(3-hexenyloxy)-4-(methoxy)-7-(decyloxy)-2H-1-benzopyran-2-one
3-(geranyloxy)-4-(methoxy)-7-(decyloxy)-2H-1-benzopyran-2-one
3-hydroxy-4-(isopropoxy)-7-(decyloxy)-2H-1-benzopyran-2-one
3-(acetoxy)-4-(isopropoxy)-7-(decyloxy)-2H-1-benzopyran-2-one
3-(benzoyloxy)-4-(isopropoxy)-7-(decyloxy)-2H-1-benzopyran-2-one
3-(methoxy)-4-(isopropoxy)-7-(decyloxy)-2H-1-benzopyran-2-one
3,4-(diisopropoxy)-7-(t-butoxy)-2H-1-benzopyran-2-one
3,7-(didecyloxy)-4-(isopropoxy)-2H-1-benzopyran-2-one
3-(3-hexenyloxy)-4-(isopropoxy)-7-(decyloxy)-2H-1-benzopyran-2-one
3-(geranyloxy)-4-(isopropoxy)-7-(decyloxy)-2H-1-benzopyran-2-one
3-hydroxy-4,7-(didecyloxy)-2H-1-benzopyran-2-one
3-(acetoxy)-4,7-(didecyloxy)-2H-1-benzopyran-2-one
3-(benzoyloxy)-4,7-(didecyloxy)-2H-1-benzopyran-2-one
3-(methoxy)-4,7-(didecyloxy)-2H-1-benzopyran-2-one
3-(isopropoxy)-4,7-(didecyloxy)-2H-1-benzopyran-2-one
3,4,7-(tridecyloxy)-2H-1-benzopyran-2-one
3-(3-hexenyloxy)-4,7-(didecyloxy)-2H-1-benzopyran-2-one
3-(geranyloxy)-4,7-(didecyloxy)-2H-1-benzopyran-2-one
3-hydroxy-4-(3-hexenyloxy)-7-(decyloxy)-2H-1-benzopyran-2-one
3-(acetoxy)-4-(3-hexenyloxy)-7-(decyloxy)-2H-1-benzopyran-2-one
3-(benzoyloxy)-4-(3-hexenyloxy)-7-(decyloxy)-2H-1-benzopyran-2-one
3-(methoxy)-4-(3-hexenyloxy)-7-(decyloxy)-2H-1-benzopyran-2-one
3-(isopropoxy)-4-(3-hexenyloxy)-7-(decyloxy)-2H-1-benzopyran-2-one
3,7-(didecyloxy)-4-(3-hexenyloxy)-2H-1-benzopyran-2-one
3,4-(di-3-hexenyloxy)-7-(decyloxy)-2H-1-benzopyran-2-one
3-(geranyloxy)-4-(3-hexenyloxy)-7-(decyloxy)-2H-1-benzopyran-2-one
3-hydroxy-4-(geranyloxy)-7-(decyloxy)-2H-1-benzopyran-2-one
3-(acetoxy)-4-(geranyloxy)-7-(decyloxy)-2H-1-benzopyran-2-one
3-(benzoyloxy)-4-(geranyloxy)-7-(decyloxy)-2H-1-benzopyran-2-one
3-(methoxy)-4-(geranyloxy)-7-(decyloxy)-2H-1-benzopyran-2-one
3-(isopropoxy)-4-(geranyloxy)-7-(decyloxy)-2H-1-benzopyran-2-one
3,7-(didecyloxy)-4-(geranyloxy)-2H-1-benzopyran-2-one
3-(3-hexenyloxy)-4-(geranyloxy)-7-(decyloxy)-2H-1-benzopyran-2-one
3,4-(digeranyloxy)-7-(decyloxy)-2H-1-benzopyran-2-one
3,4-(dihydroxy)-7-(3-hexenyloxy)-2H-1-benzopyran-2-one
3-(acetoxy)-4-hydroxy-7-(3-hexenyloxy)-2H-1-benzopyran-2-one
3-(benzoyloxy)-4-hydroxy-7-(3-hexenyloxy)-2H-1-benzopyran-2-one
3-(isopropoxy)-4-hydroxy-7-(3-hexenyloxy)-2H-1-benzopyran-2-one
3-(decyloxy)-4-hydroxy-7-(3-hexenyloxy)-2H-1-benzopyran-2-one
3,7-(di-3-hexenyloxy)-4-hydroxy-2H-1-benzopyran-2-one
3-(geranyloxy)-4-hydroxy-7-(3-hexenyloxy)-2H-1-benzopyran-2-one
3-hydroxy-4-(acetoxy)-7-(3-hexenyloxy)-2H-1-benzopyran-2-one
3,4-(diacetoxy)-7-(3-hexenyloxy)-2H-1-benzopyran-2-one
3-(benzoyloxy)-4-(acetoxy)-7-(3-hexenyloxy)-2H-1-benzopyran-2-one
3-(isopropoxy)-4-(acetoxy)-7-(3-hexenyloxy)-2H-1-benzopyran-2-one
3-(decyloxy)-4-(acetoxy)-7-(3-hexenyloxy)-2H-1-benzopyran-2-one 3,7-(di-3-hexenyloxy)-4-(acetoxy)-2H-1-benzopyran-2-one
3-(geranyloxy)-4-(acetoxy)-7-(3-hexenyloxy)-2H-1-benzopyran-2-one
3-hydroxy-4-(benzoyloxy)-7-(3-hexenyloxy)-2H-1-benzopyran-2-one
3-(acetoxy)-4-(benzoyloxy)-7-(3-hexenyloxy)-2H-1-benzopyran-2-one
3,4-(dibenzoyloxy)-7-(3-hexenyloxy)-2H-1-benzopyran-2-one
3-(methoxy)-4-(benzoyloxy)-7-(3-hexenyloxy)-2H-1-benzopyran-2-one
3-(isopropoxy)-4-(benzoyloxy)-7-(3-hexenyloxy)-2H-1-benzopyran-2-one
3-(decyloxy)-4-(benzoyloxy)-7-(3-hexenyloxy)-2H-1-benzopyran-2-one
3,7-(di-3-hexenyloxy)-4-(benzoyloxy)-2H-1-benzopyran-2-one
3-(geranyloxy)-4-(benzoyloxy)-7-(3-hexenyloxy)-2H-1-benzopyran-2-one
3-hydroxy-4-(methoxy)-7-(3-hexenyloxy)-2H-1-benzopyran-2-one
3-(acetoxy)-4-(methoxy)-7-(3-hexenyloxy)-2H-1-benzopyran-2-one
3-(benzoyloxy)-4-(methoxy)-7-(3-hexenyloxy)-2H-1-benzopyran-2-one
3-(isopropoxy)-4-(methoxy)-7-(3-hexenyloxy)-2H-1-benzopyran-2-one
3-(decyloxy)-4-(methoxy)-7-(3-hexenyloxy)-2H-1-benzopyran-2-one
3,7-(di-3-hexenyloxy)-4-(methoxy)-2H-1-benzopyran-2-one
3-(geranyloxy)-4-(methoxy)-7-(3-hexenyloxy)-2H-1-benzopyran-2-one
3-hydroxy-4-(isopropoxy)-7-(3-hexenyloxy)-2H-1-benzopyran-2-one
3-(acetoxy)-4-(isopropoxy)-7-(3-hexenyloxy)-2H-1-benzopyran-2-one
3-(benzoyloxy)-4-(isopropoxy)-7-(3-hexenyloxy)-2H-1-benzopyran-2-one
3-(methoxy)-4-(isopropoxy)-7-(3-hexenyloxy)-2H-1-benzopyran-2-one
3,4-(diisopropoxy)-7-(3-hexenyloxy)-2H-1-benzopyran-2-one
3-(decyloxy)-4-(isopropoxy)-7-(3-hexenyloxy)-2H-1-benzopyran-2-one
3,7-(di-3-hexenyloxy)-4-(isopropoxy)-2H-1-benzopyran-2-one
3-(geranyloxy)-4-(isopropoxy)-7-(3-hexenyloxy)-2H-1-benzopyran-2-one
3-hydroxy-4-(decyloxy)-7-(3-hexenyloxy)-2H-1-benzopyran-2-one
3-(acetoxy)-4-(decyloxy)-7-(3-hexenyloxy)-2H-1-benzopyran-2-one
3-(benzoyloxy)-4-(decyloxy)-7-(3-hexenyloxy)-2H-1-benzopyran-2-one
3-(methoxy)-4-(decyloxy)-7-(3-hexenyloxy)-2H-1-benzopyran-2-one
3-(isopropoxy)-4-(decyloxy)-7-(3-hexenyloxy)-2H-1-benzopyran-2-one
3,4-(didecyloxy)-7-(3-hexenyloxy)-2H-1-benzopyran-2-one
3-(3-hexenyloxy)-4-(decyloxy)-7-(3-hexenyloxy)-2H-1-benzopyran-2-one
3-(geranyloxy)-4-(decyloxy)-7-(3-hexenyloxy)-2H-1-benzopyran-2-one
3-hydroxy-4,7-(di-3-hexenyloxy)-2H-1-benzopyran-2-one
3-(acetoxy)-4,7-(di-3-hexenyloxy)-2H-1-benzopyran-2-one
3-(benzoyloxy)-4,7-(di-3-hexenyloxy)-2H-1-benzopyran-2-one
3-(methoxy)-4,7-(di-3-hexenyloxy)-2H-1-benzopyran-2-one
3-(isopropoxy)-4,7-(di-3-hexenyloxy)-2H-1-benzopyran-2-one
3-(decyloxy)-4,7-(di-3-hexenyloxy)-2H-1-benzopyran-2-one
3,4,7-(tri-3-hexenyloxy)-2H-1-benzopyran-2-one
3-(geranyloxy)-4, 7-(di-3-hexenyloxy)-2H-1-benzopyran-2-one
3-hydroxy-4-(geranyloxy)-7-(3-hexenyloxy)-2H-1-benzopyran-2-one
3-(acetoxy)-4-(geranyloxy)-7-(3-hexenyloxy)-2H-1-benzopyran-2-one
3-(benzoyloxy)-4-(geranyloxy)-7-(3-hexenyloxy)-2H-1-benzopyran-2-one
3-(methoxy)-4-(geranyloxy)-7-(3-hexenyloxy)-2H-1-benzopyran-2-one
3-(isopropoxy)-4-(geranyloxy)-7-(3-hexenyloxy)-2H-1-benzopyran-2-one
3-(decyloxy)-4-(geranyloxy)-7-(3-hexenyloxy)-2H-1-benzopyran-2-one
3,7-(di-3-hexenyloxy)-4-(geranyloxy)-2H-1-benzopyran-2-one
3,4-(digeranyloxy)-7-(3-hexenyloxy)-2H-1-benzopyran-2-one
3,4-(dihydroxy)-7-(geranyloxy)-2H-1-benzopyran-2-one
3-(acetoxy)-4-hydroxy-7-(geranyloxy)-2H-1-benzopyran-2-one
3-(benzoyloxy)-4-hydroxy-7-(geranyloxy)-2H-1-benzopyran-2-one
3-(isopropoxy)-4-hydroxy-7-(geranyloxy)-2H-1-benzopyran-2-one
3-(decyloxy)-4-hydroxy-7-(geranyloxy)-2H-1-benzopyran-2-one
3-(3-hexenyloxy)-4-hydroxy-7-(geranyloxy)-2H-1-benzopyran-2-one
3,7-(digeranyloxy)-4-hydroxy-2H-1-benzopyran-2-one
3-hydroxy-4-(acetoxy)-7-(geranyloxy)-2H-1-benzopyran-2-one
3,4-(diacetoxy)-7-(geranyloxy)-2H-1-benzopyran-2-one
3-(benzoyloxy)-4-(acetoxy)-7-(geranyloxy)-2H-1-benzopyran-2-one
3-(isopropoxy)-4-(acetoxy)-7-(geranyloxy)-2H-1-benzopyran-2-one
3-(decyloxy)-4-(acetoxy)-7-(geranyloxy)-2H-1-benzopyran-2-one
3-(3-hexenyloxy)-4-(acetoxy)-7-(geranyloxy)-2H-1-benzopyran-2-one
3,7-(digeranyloxy)-4-(acetoxy)-2H-1-benzopyran-2-one
3-hydroxy-4-(benzoyloxy)-7-(geranyloxy)-2H-1-benzopyran-2-one
3-(acetoxy)-4-(benzoyloxy)-7-(geranyloxy)-2H-1-benzopyran-2-one
3,4-(dibenzoyloxy)-7-(geranyloxy)-2H-1-benzopyran-2-one
3-(methoxy)-4-(benzoyloxy)-7-(geranyloxy)-2H-1-benzopyran-2-one
3-(isopropoxy)-4-(benzoyloxy)-7-(geranyloxy)-2H-1-benzopyran-2-one
3-(decyloxy)-4-(benzoyloxy)-7-(geranyloxy)-2H-1-benzopyran-2-one
3-(3-hexenyloxy)-4-(benzoyloxy)-7-(geranyloxy)-2H-1-benzopyran-2-one 3,7-(digeranyloxy)-4-(benzoyloxy)-2H-1-benzopyran-2-one
3-hydroxy-4-(methoxy)-7-(geranyloxy)-2H-1-benzopyran-2-one
3-(acetoxy)-4-(methoxy)-7-(geranyloxy)-2H-1-benzopyran-2-one
3-(benzoyloxy)-4-(methoxy)-7-(geranyloxy)-2H-1-benzopyran-2-one
3-(isopropoxy)-4-(methoxy)-7-(geranyloxy)-2H-1-benzopyran-2-one
3-(decyloxy)-4-(methoxy)-7-(geranyloxy)-2H-1-benzopyran-2-one
3-(3-hexenyloxy)-4-(methoxy)-7-(geranyloxy)-2H-1-benzopyran-2-one
3,7-(digeranyloxy)-4-(methoxy)-2H-1-benzopyran-2-one
3-hydroxy-4-(isopropoxy)-7-(geranyloxy)-2H-1-benzopyran-2-one
3-(acetoxy)-4-(isopropoxy)-7-(geranyloxy)-2H-1-benzopyran-2-one
3-(benzoyloxy)-4-(isopropoxy)-7-(geranyloxy)-2H-1-benzopyran-2-one
3-(methoxy)-4-(isopropoxy)-7-(geranyloxy)-2H-1-benzopyran-2-one
3,4-(diisopropoxy)-7-(geranyloxy)-2H-1-benzopyran-2-one
3-(decyloxy)-4-(isopropoxy)-7-(geranyloxy)-2H-1-benzopyran-2-one
3-(3-hexenyloxy)-4-(isopropoxy)-7-(geranyloxy)-2H-1-benzopyran-2-one
3,7-(digeranyloxy)-4-(isopropoxy)-2H-1-benzopyran-2-one
3-hydroxy-4-(decyloxy)-7-(geranyloxy)-2H-1-benzopyran-2-one
3-(acetoxy)-4-(decyloxy)-7-(geranyloxy)-2H-1-benzopyran-2-one
3-(benzoyloxy)-4-(decyloxy)-7-(geranyloxy)-2H-1-benzopyran-2-one
3-(methoxy)-4-(decyloxy)-7-(geranyloxy)-2H-1-benzopyran-2-one
3-(isopropoxy)-4-(decyloxy)-7-(geranyloxy)-2H-1-benzopyran-2-one
3,4-(didecyloxy)-7-(geranyloxy)-2H-1-benzopyran-2-one
3-(3-hexenyloxy)-4-(decyloxy)-7-(geranyloxy)-2H-1-benzopyran-2-one
3,7-(digeranyloxy)-4-(decyloxy)-2H-1-benzopyran-2-one
3-hydroxy-4-(3-hexenyloxy)-7-(geranyloxy)-2H-1-benzopyran-2-one
3-(acetoxy)-4-(3-hexenyloxy)-7-(geranyloxy)-2H-1-benzopyran-2-one
3-(benzoyloxy)-4-(3-hexenyloxy)-7-(geranyloxy)-2H-1-benzopyran-2-one
3-(methoxy)-4-(3-hexenyloxy)-7-(geranyloxy)-2H-1-benzopyran-2-one
3-(isopropoxy)-4-(3-hexenyloxy)-7-(geranyloxy)-2H-1-benzopyran-2-one
3-(decyloxy)-4-(3-hexenyloxy)-7-(geranyloxy)-2H-1-benzopyran-2-one
3,4-(di-3-hexenyloxy)-7-(geranyloxy)-2H-1-benzopyran-2-one
3,7-(digeranyloxy)-4-(3-hexenyloxy)-2H-1-benzopyran-2-one
3-hydroxy-4,7-(digeranyloxy)-2H-1-benzopyran-2-one
3-(acetoxy)-4,7-(digeranyloxy)-2H-1-benzopyran-2-one
3-(benzoyloxy)-4,7-(digeranyloxy)-2H-1-benzopyran-2-one
3-(methoxy)-4,7-(digeranyloxy)-2H-1-benzopyran-2-one
3-(isopropoxy)-4,7-(digeranyloxy)-2H-1-benzopyran-2-one
3-(decyloxy)-4,7-(digeranyloxy)-2H-1-benzopyran-2-one
3-(3-hexenyloxy)-4,7-(digeranyloxy)-2H-1-benzopyran-2-one
3,4,7-(trigeranyloxy)-2H-1-benzopyran-2-one
3,4,8-(trihydroxy)-2H-1-benzopyran-2-one
3-(acetoxy)-4,8-(dihydroxy)-2H-1-benzopyran-2-one
3-(benzoyloxy)-4,8-(dihydroxy)-2H-1-benzopyran-2-one
3-(methoxy)-4, 8-(dihydroxy)-2H-1-benzopyran-2-one
3-(isopropoxy)-4,8-(dihydroxy)-2H-1-benzopyran-2-one
3-(decyloxy)-4,8-(dihydroxy)-2H-1-benzopyran-2-one
3-(3-hexenyloxy)-4,8-(dihydroxy)-2H-1-benzopyran-2-one
3-(geranyloxy)-4,8-(dihydroxy)-2H-1-benzopyran-2-one
3,8-(dihydroxy)-4-(acetoxy)-2H-1-benzopyran-2-one
3,4-(diacetoxy)-8-hydroxy-2H-1-benzopyran-2-one
3-(benzoyloxy)-4-(acetoxy)-8-hydroxy-2H-1-benzopyran-2-one
3-(methoxy)-4-(acetoxy)-8-hydroxy-2H-1-benzopyran-2-one
3-(isopropoxy)-4-(acetoxy)-8-hydroxy-2H-1-benzopyran-2-one
3-(decyloxy)-4-(acetoxy)-8-hydroxy-2H-1-benzopyran-2-one
3-(3-hexenyloxy)-4-(acetoxy)-8-hydroxy-2H-1-benzopyran-2-one
3-(geranyloxy)-4-(acetoxy)-8-hydroxy-2H-1-benzopyran-2-one
3,8-(dihydroxy)-4-(benzoyloxy)-2H-1-benzopyran-2-one
3-(acetoxy)-4-(benzoyloxy)-8-hydroxy-2H-1-benzopyran-2-one
3,4-(dibenzoyloxy)-8-hydroxy-2H-1-benzopyran-2-one
3-(methoxy)-4-(benzoyloxy)-8-hydroxy-2H-1-benzopyran-2-one
3-(isopropoxy)-4-(benzoyloxy)-8-hydroxy-2H-1-benzopyran-2-one
3-(decyloxy)-4-(benzoyloxy)-8-hydroxy-2H-1-benzopyran-2-one
3-(3-hexenyloxy)-4-(benzoyloxy)-8-hydroxy-2H-1-benzopyran-2-one
3-(geranyloxy)-4-(benzoyloxy)-8-hydroxy-2H-1-benzopyran-2-one
3,8-(dihydroxy)-4-(methoxy)-2H-1-benzopyran-2-one
3-(acetoxy)-4-(methoxy)-8-hydroxy-2H-1-benzopyran-2-one
3-(benzoyloxy)-4-(methoxy)-8-hydroxy-2H-1-benzopyran-2-one
3-(isopropoxy)-4-(methoxy)-8-hydroxy-2H-1-benzopyran-2-one
3-(decyloxy)-4-(methoxy)-8-hydroxy-2H-1-benzopyran-2-one
3-(3-hexenyloxy)-4-(methoxy)-8-hydroxy-2H-1-benzopyran-2-one
3-(geranyloxy)-4-(methoxy)-8-hydroxy-2H-1-benzopyran-2-one
3,8-(dihydroxy)-4-(isopropoxy)-2H-1-benzopyran-2-one
3-(acetoxy)-4-(isopropoxy)-8-hydroxy-2H-1-benzopyran-2-one
3-(benzoyloxy)-4-(isopropoxy)-8-hydroxy-2H-1-benzopyran-2-one 3-(methoxy)-4-(isopropoxy)-8-hydroxy-2H-1-benzopyran-2-one
3,4-(diisopropoxy)-8-hydroxy-2H-1-benzopyran-2-one
3-(decyloxy)-4-(isopropoxy)-8-hydroxy-2H-1-benzopyran-2-one
3-(3-hexenyloxy)-4-(isopropoxy)-8-hydroxy-2H-1-benzopyran-2-one
3-(geranyloxy)-4-(isopropoxy)-8-hydroxy-2H-1-benzopyran-2-one
3,8-(dihydroxy)-4-(decyloxy)-2H-1-benzopyran-2-one
3-(acetoxy)-4-(decyloxy)-8-hydroxy-2H-1-benzopyran-2-one
3-(benzoyloxy)-4-(decyloxy)-8-hydroxy-2H-1-benzopyran-2-one
3-(methoxy)-4-(decyloxy)-8-hydroxy-2H-1-benzopyran-2-one
3-(isopropoxy)-4-(decyloxy)-8-hydroxy-2H-1-benzopyran-2-one
3,4-(didecyloxy)-8-hydroxy-2H-1-benzopyran-2-one
3-(3-hexenyloxy)-4-(decyloxy)-8-hydroxy-2H-1-benzopyran-2-one
3-(geranyloxy)-4-(decyloxy)-8-hydroxy-2H-1-benzopyran-2-one
3,8-(dihydroxy)-4-(3-hexenyloxy)-2H-1-benzopyran-2-one
3-(acetoxy)-4-(3-hexenyloxy)-8-hydroxy-2H-1-benzopyran-2-one
3-(benzoyloxy)-4-(3-hexenyloxy)-8-hydroxy-2H-1-benzopyran-2-one
3-(methoxy)-4-(3-hexenyloxy)-8-hydroxy-2H-1-benzopyran-2-one
3-(isopropoxy)-4-(3-hexenyloxy)-8-hydroxy-2H-1-benzopyran-2-one
3-(decyloxy)-4-(3-hexenyloxy)-8-hydroxy-2H-1-benzopyran-2-one
3,4-(di-3-hexenyloxy)-8-hydroxy-2H-1-benzopyran-2-one
3-(geranyloxy)-4-(3-hexenyloxy)-8-hydroxy-2H-1-benzopyran-2-one
3,8-(dihydroxy)-4-(geranyloxy)-2H-1-benzopyran-2-one
3-(acetoxy)-4-(geranyloxy)-8-hydroxy-2H-1-benzopyran-2-one
3-(benzoyloxy)-4-(geranyloxy)-8-hydroxy-2H-1-benzopyran-2-one
3-(methoxy)-4-(geranyloxy)-8-hydroxy-2H-1-benzopyran-2-one
3-(isopropoxy)-4-(geranyloxy)-8-hydroxy-2H-1-benzopyran-2-one
3-(decyloxy)-4-(geranyloxy)-8-hydroxy-2H-1-benzopyran-2-one
3-(3-hexenyloxy)-4-(geranyloxy)-8-hydroxy-2H-1-benzopyran-2-one
3,4-(digeranyloxy)-8-hydroxy-2H-1-benzopyran-2-one
3,4-(dihydroxy)-8-(acetoxy)-2H-1-benzopyran-2-one
3,8-(diacetoxy)-4-hydroxy-2H-1-benzopyran-2-one
3-(benzoyloxy)-4-hydroxy-8-(acetoxy)-2H-1-benzopyran-2-one
3-(methoxy)-4-hydroxy-8-(acetoxy)-2H-1-benzopyran-2-one
3-(isopropoxy)-4-hydroxy-8-(acetoxy)-2H-1-benzopyran-2-one
3-(decyloxy)-4-hydroxy-8-(acetoxy)-2H-1-benzopyran-2-one
3-(3-hexenyloxy)-4-hydroxy-8-(acetoxy)-2H-1-benzopyran-2-one
3-(geranyloxy)-4-hydroxy-8-(acetoxy)-2H-1-benzopyran-2-one
3-hydroxy-4,8-(diacetoxy)-2H-1-benzopyran-2-one
3,4,8-(triacetoxy)-2H-1-benzopyran-2-one
3-(benzoyloxy)-4,8-(diacetoxy)-2H-1-benzopyran-2-one
3-(methoxy)-4,8-(diacetoxy)-2H-1-benzopyran-2-one
3-(isopropoxy)-4,8-(diacetoxy)-2H-1-benzopyran-2-one
3-(decyloxy)-4,8-(diacetoxy)-2H-1-benzopyran-2-one
3-(3-hexenyloxy)-4,8-(diacetoxy)-2H-1-benzopyran-2-one
3-(geranyloxy)-4,8-(diacetoxy)-2H-1-benzopyran-2-one
3-hydroxy-4-(benzoyloxy)-8-(acetoxy)-2H-1-benzopyran-2-one
3,8-(diacetoxy)-4-(benzoyloxy)-2H-1-benzopyran-2-one
3,4-(dibenzoyloxy)-8-(acetoxy)-2H-1-benzopyran-2-one
3-(methoxy)-4-(benzoyloxy)-8-(acetoxy)-2H-1-benzopyran-2-one
3-(isopropoxy)-4-(benzoyloxy)-8-(acetoxy)-2H-1-benzopyran-2-one
3-(decyloxy)-4-(benzoyloxy)-8-(acetoxy)-2H-1-benzopyran-2-one
3-(3-hexenyloxy)-4-(benzoyloxy)-8-(acetoxy)-2H-1-benzopyran-2-one
3-(geranyloxy)-4-(benzoyloxy)-8-(acetoxy)-2H-1-benzopyran-2-one
3-hydroxy-4-(methoxy)-8-(acetoxy)-2H-1-benzopyran-2-one
3,8-(diacetoxy)-4-(methoxy)-2H-1-benzopyran-2-one
3-(benzoyloxy)-4-(methoxy)-8-(acetoxy)-2H-1-benzopyran-2-one
3-(isopropoxy)-4-(methoxy)-8-(acetoxy)-2H-1-benzopyran-2-one
3-(decyloxy)-4-(methoxy)-8-(acetoxy)-2H-1-benzopyran-2-one
3-(3-hexenyloxy)-4-(methoxy)-8-(acetoxy)-2H-1-benzopyran-2-one
3-(geranyloxy)-4-(methoxy)-8-(acetoxy)-2H-1-benzopyran-2-one
3-hydroxy-4-(isopropoxy)-8-(acetoxy)-2H-1-benzopyran-2-one
3,8-(diacetoxy)-4-(isopropoxy)-2H-1-benzopyran-2-one
3-(benzoyloxy)-4-(isopropoxy)-8-(acetoxy)-2H-1-benzopyran-2-one
3-(methoxy)-4-(isopropoxy)-8-(acetoxy)-2H-1-benzopyran-2-one
3,4-(diisopropoxy)-8-(acetoxy)-2H-1-benzopyran-2-one
3-(decyloxy)-4-(isopropoxy)-8-(acetoxy)-2H-1-benzopyran-2-one
3-(3-hexenyloxy)-4-(isopropoxy)-8-(acetoxy)-2H-1-benzopyran-2-one
3-(geranyloxy)-4-(isopropoxy)-8-(acetoxy)-2H-1-benzopyran-2-one
3-hydroxy-4-(decyloxy)-8-(acetoxy)-2H-1-benzopyran-2-one
3,8-(diacetoxy)-4-(decyloxy)-2H-1-benzopyran-2-one
3-(benzoyloxy)-4-(decyloxy)-8-(acetoxy)-2H-1-benzopyran-2-one
3-(methoxy)-4-(decyloxy)-8-(acetoxy)-2H-1-benzopyran-2-one
3-(isopropoxy)-4-(decyloxy)-8-(acetoxy)-2H-1-benzopyran-2-one
3,4-(didecyloxy)-8-(acetoxy)-2H-1-benzopyran-2-one
3-(3-hexenyloxy)-4-(decyloxy)-8-(acetoxy)-2H-1-benzopyran-2-one
3-(geranyloxy)-4-(decyloxy)-8-(acetoxy)-2H-1-benzopyran-2-one
3-hydroxy-4-(3-hexenyloxy)-8-(acetoxy)-2H-1-benzopyran-2-one
3,8-(diacetoxy)-4-(3-hexenyloxy)-2H-1-benzopyran-2-one 3-(benzoyloxy)-4-(3-hexenyloxy)-8-(acetoxy)-2H-1-benzopyran-2-one
3-(methoxy)-4-(3-hexenyloxy)-8-(acetoxy)-2H-1-benzopyran-2-one
3-(isopropoxy)-4-(3-hexenyloxy)-8-(acetoxy)-2H-1-benzopyran-2-one
3-(decyloxy)-4-(3-hexenyloxy)-8-(acetoxy)-2H-1-benzopyran-2-one
3,4-(di-3-hexenyloxy)-8-(acetoxy)-2H-1-benzopyran-2-one
3-(geranyloxy)-4-(3-hexenyloxy)-8-(acetoxy)-2H-1-benzopyran-2-one
3-hydroxy-4-(geranyloxy)-8-(acetoxy)-2H-1-benzopyran-2-one
3,8-(diacetoxy)-4-(geranyloxy)-2H-1-benzopyran-2-one
3-(benzoyloxy)-4-(geranyloxy)-8-(acetoxy)-2H-1-benzopyran-2-one
3-(methoxy)-4-(geranyloxy)-8-(acetoxy)-2H-1-benzopyran-2-one
3-(isopropoxy)-4-(geranyloxy)-8-(acetoxy)-2H-1-benzopyran-2-one
3-(decyloxy)-4-(geranyloxy)-8-(acetoxy)-2H-1-benzopyran-2-one
3-(3-hexenyloxy)-4-(geranyloxy)-8-(acetoxy)-2H-1-benzopyran-2-one
3,4-(digeranyloxy)-8-(acetoxy)-2H-1-benzopyran-2-one
3,4-(dihydroxy)-8-(methoxy)-2H-1-benzopyran-2-one
3-(acetoxy)-4-hydroxy-8-(methoxy)-2H-1-benzopyran-2-one
3-(benzoyloxy)-4-hydroxy-8-(methoxy)-2H-1-benzopyran-2-one
3,8-(dimethoxy)-4-hydroxy-2H-1-benzopyran-2-one
3-(isopropoxy)-4-hydroxy-8-(methoxy)-2H-1-benzopyran-2-one
3-(decyloxy)-4-hydroxy-8-(methoxy)-2H-1-benzopyran-2-one
3-(3-hexenyloxy)-4-hydroxy-8-(methoxy)-2H-1-benzopyran-2-one
3-(geranyloxy)-4-hydroxy-8-(methoxy)-2H-1-benzopyran-2-one
3-hydroxy-4-(acetoxy)-8-(methoxy)-2H-1-benzopyran-2-one
3,4-(diacetoxy)-8-(methoxy)-2H-1-benzopyran-2-one
3-(benzoyloxy)-4-(acetoxy)-8-(methoxy)-2H-1-benzopyran-2-one
3,8-(dimethoxy)-4-(acetoxy)-2H-1-benzopyran-2-one
3-(isopropoxy)-4-(acetoxy)-8-(methoxy)-2H-1-benzopyran-2-one
3-(decyloxy)-4-(acetoxy)-8-(methoxy)-2H-1-benzopyran-2-one
3-(3-hexenyloxy)-4-(acetoxy)-8-(methoxy)-2H-1-benzopyran-2-one
3-(geranyloxy)-4-(acetoxy)-8-(methoxy)-2H-1-benzopyran-2-one
3-hydroxy-4-(benzoyloxy)-8-(methoxy)-2H-1-benzopyran-2-one
3-(acetoxy)-4-(benzoyloxy)-8-(methoxy)-2H-1-benzopyran-2-one
3,4-(dibenzoyloxy)-8-(methoxy)-2H-1-benzopyran-2-one
3,8-(methoxy)-4-(benzoyloxy)-2H-1-benzopyran-2-one
3-(isopropoxy)-4-(benzoyloxy)-8-(methoxy)-2H-1-benzopyran-2-one
3-(decyloxy)-4-(benzoyloxy)-8-(methoxy)-2H-1-benzopyran-2-one
3-(3-hexenyloxy)-4-(benzoyloxy)-8-(methoxy)-2H-1-benzopyran-2-one
3-(geranyloxy)-4-(benzoyloxy)-8-(methoxy)-2H-1-benzopyran-2-one
3-hydroxy-4,8-(dimethoxy)-2H-1-benzopyran-2-one
3-(acetoxy)-4,8-(dimethoxy)-2H-1-benzopyran-2-one
3-(benzoyloxy)-4,8-(dimethoxy)-2H-1-benzopyran-2-one
3-(isopropoxy)-4,8-(dimethoxy)-2H-1-benzopyran-2-one
3-(decyloxy)-4,8-(dimethoxy)-2H-1-benzopyran-2-one
3-(3-hexenyloxy)-4,8-(dimethoxy)-2H-1-benzopyran-2-one
3-(geranyloxy)-4,8-(dimethoxy)-2H-1-benzopyran-2-one
3-hydroxy-4-(isopropoxy)-8-(methoxy)-2H-1-benzopyran-2-one
3-(acetoxy)-4-(isopropoxy)-8-(methoxy)-2H-1-benzopyran-2-one
3-(benzoyloxy)-4-(isopropoxy)-8-(methoxy)-2H-1-benzopyran-2-one
3,8-(dimethoxy)-4-(isopropoxy)-2H-1-benzopyran-2-one
3,4-(diisopropoxy)-8-(methoxy)-2H-1-benzopyran-2-one
3-(decyloxy)-4-(isopropoxy)-8-(methoxy)-2H-1-benzopyran-2-one
3-(3-hexenyloxy)-4-(isopropoxy)-8-(methoxy)-2H-1-benzopyran-2-one
3-(geranyloxy)-4-(isopropoxy)-8-(methoxy)-2H-1-benzopyran-2-one
3-hydroxy-4-(decyloxy)-8-(methoxy)-2H-1-benzopyran-2-one
3-(acetoxy)-4-(decyloxy)-8-(methoxy)-2H-1-benzopyran-2-one
3-(benzoyloxy)-4-(decyloxy)-8-(methoxy)-2H-1-benzopyran-2-one
3,8-(dimethoxy)-4-(decyloxy)-2H-1-benzopyran-2-one
3-(isopropoxy)-4-(decyloxy)-8-(methoxy)-2H-1-benzopyran-2-one
3,4-(didecyloxy)-8-(methoxy)-2H-1-benzopyran-2-one
3-(3-hexenyloxy)-4-(decyloxy)-8-(methoxy)-2H-1-benzopyran-2-one
3-(geranyloxy)-4-(decyloxy)-8-(methoxy)-2H-1-benzopyran-2-one
3-hydroxy-4-(3-hexenyloxy)-8-(methoxy)-2H-1-benzopyran-2-one
3-(acetoxy)-4-(3-hexenyloxy)-8-(methoxy)-2H-1-benzopyran-2-one
3-(benzoyloxy)-4-(3-hexenyloxy)-8-(methoxy)-2H-1-benzopyran-2-one
3,8-(dimethoxy)-4-(3-hexenyloxy)-2H-1-benzopyran-2-one
3-(isopropoxy)-4-(3-hexenyloxy)-8-(methoxy)-2H-1-benzopyran-2-one
3-(decyloxy)-4-(3-hexenyloxy)-8-(methoxy)-2H-1-benzopyran-2-one
3-(di-3-hexenyloxy)-8-(methoxy)-2H-1-benzopyran-2-one
3-(geranyloxy)-4-(3-hexenyloxy)-8-(methoxy)-2H-1-benzopyran-2-one
3-hydroxy-4-(geranyloxy)-8-(methoxy)-2H-1-benzopyran-2-one
3-(acetoxy)-4-(geranyloxy)-8-(methoxy)-2H-1-benzopyran-2-one
3-(benzoyloxy)-4-(geranyloxy)-8-(methoxy)-2H-1-benzopyran-2-one
3,8-(dimethoxy)-4-(geranyloxy)-2H-1-benzopyran-2-one 3-(isopropoxy)-4-(geranyloxy)-8-(methoxy)-2H-1-benzopyran-2-one
3-(decyloxy)-4-(geranyloxy)-8-(methoxy)-2H-1-benzopyran-2-one
3-(3-hexenyloxy)-4-(geranyloxy)-8-(methoxy)-2H-1-benzopyran-2-one
3,4-(digeranyloxy)-8-(methoxy)-2H-1-benzopyran-2-one
3,4-(dihydroxy)-8-(isopropoxy)-2H-1-benzopyran-2-one
3-(acetoxy)-4-hydroxy-8-(isopropoxy)-2H-1-benzopyran-2-one
3-(benzoyloxy)-4-hydroxy-8-(isopropoxy)-2H-1-benzopyran-2-one
3-(methoxy)-4-hydroxy-8-(isopropoxy)-2H-1-benzopyran-2-one
3,8-(diisopropoxy)-4-hydroxy-2H-1-benzopyran-2-one
3-(decyloxy)-4-hydroxy-8-(isopropoxy)-2H-1-benzopyran-2-one
3-(3-hexenyloxy)-4-hydroxy-8-(isopropoxy)-2H-1-benzopyran-2-one
3-(geranyloxy)-4-hydroxy-8-(isopropoxy)-2H-1-benzopyran-2-one
3-hydroxy-4-(acetoxy)-8-(isopropoxy)-2H-1-benzopyran-2-one
3-,4-(diacetoxy)-8-(isopropoxy)-2H-1-benzopyran-2-one
3-(benzoyloxy)-4-(acetoxy)-8-(isopropoxy)-2H-1-benzopyran-2-one
3-(methoxy)-4-(acetoxy)-8-(isopropoxy)-2H-1-benzopyran-2-one
3,8-(diisopropoxy)-4-(acetoxy)-2H-1-benzopyran-2-one
3-(decyloxy)-4-(acetoxy)-8-(isopropoxy)-2H-1-benzopyran-2-one
3-hydroxy-4-(benzoyloxy)-8-(isopropoxy)-2H-1-benzopyran-2-one
3-(acetoxy)-4-(benzoyloxy)-8-(isopropoxy)-2H-1-benzopyran-2-one
3,4-(dibenzoyloxy)-8-(isopropoxy)-2H-1-benzopyran-2-one
3-(methoxy)-4-(benzoyloxy)-8-(isopropoxy)-2H-1-benzopyran-2-one
3,8-(diisopropyl)-4-(benzoyloxy)-2H-1-benzopyran-2-one
3-(decyloxy)-4-(benzoyloxy)-8-(isopropoxy)-2H-1-benzopyran-2-one
3-(3-hexenyloxy)-4-(benzoyloxy)-8-(isopropoxy)-2H-1-benzopyran-2-one
3-(geranyloxy)-4-(benzoyloxy)-8-(isopropoxy)-2H-1-benzopyran-2-one
3-hydroxy-4-(methoxy)-8-(isopropoxy)-2H-1-benzopyran-2-one
3-(acetoxy)-4-(methoxy)-8-(isopropoxy)-2H-1-benzopyran-2-one
3-(benzoyloxy)-4-(methoxy)-8-(isopropoxy)-2H-1-benzopyran-2-one
3,8-(diisopropoxy)-4-(methoxy)-8-(isopropoxy)-2H-1-benzopyran-2-one
3-(decyloxy)-4-(methoxy)-8-(isopropoxy)-2H-1-benzopyran-2-one
3-(3-hexenyloxy)-4-(methoxy)-8-(isopropoxy)-2H-1-benzopyran-2-one
3-(geranyloxy)-4-(methoxy)-8-(isopropoxy)-2H-1-benzopyran-2-one
3-hydroxy-4,8-(diisopropoxy)-2H-1-benzopyran-2-one
3-(acetoxy)-4,8-(diisopropoxy)-2H-1-benzopyran-2-one
3-(benzoyloxy)-4,8-(diisopropoxy)-2H-1-benzopyran-2-one
3-(methoxy)-4,8-(diisopropoxy)-2H-1-benzopyran-2-one
3,4,8-(triisopropoxy)-2H-1-benzopyran-2-one
3-(decyloxy)-4,8-(diisopropoxy)-2H-1-benzopyran-2-one
3-(3-hexenyloxy)-4,8-(diisopropoxy)-2H-1-benzopyran-2-one
3-(geranyloxy)-4,8-(diisopropoxy)-2H-1-benzopyran-2-one
3-hydroxy-4-(decyloxy)-8-(isopropoxy)-2H-1-benzopyran-2-one
3-(acetoxy)-4-(decyloxy)-8-(isopropoxy)-2H-1-benzopyran-2-one
3-(benzoyloxy)-4-(decyloxy)-8-(isopropoxy)-2H-1-benzopyran-2-one
3-(methoxy)-4-(decyloxy)-8-(isopropoxy)-2H-1-benzopyran-2-one
3,8-(diisopropoxy)-4-(decyloxy)-2H-1-benzopyran-2-one
3,4-(didecyloxy)-8-(isopropoxy)-2H-1-benzopyran-2-one
3-(3-hexenyloxy)-4-(decyloxy)-8-(isopropoxy)-2H-1-benzopyran-2-one
3-(geranyloxy)-4-(decyloxy)-8-(isopropoxy)-2H-1-benzopyran-2-one
3-hydroxy-4-(3-hexenyloxy)-8-(isopropoxy)-2H-1-benzopyran-2-one
3-(acetoxy)-4-(3-hexenyloxy)-8-(isopropoxy)-2H-1-benzopyran-2-one
3-(benzoyloxy)-4-(3-hexenyloxy)-8-(isopropoxy)-2H-1-benzopyran-2-one
3-(methoxy)-4-(3-hexenyloxy)-8-(isopropoxy)-2H-1-benzopyran-2-one
3,8-(diisopropoxy)-4-(3-hexenyloxy)-2H-1-benzopyran-2-one
3-(decyloxy)-4-(3-hexenyloxy)-8-(isopropoxy)-2H-1-benzopyran-2-one
3,4-(di-3-hexenyloxy)-8-(isopropoxy)-2H-1-benzopyran-2-one
3-(geranyloxy)-4-(3-hexenyloxy)-8-(isopropoxy)-2H-1-benzopyran-2-one
3-hydroxy-4-(geranyloxy)-8-(isopropoxy)-2H-1-benzopyran-2-one
3-(acetoxy)-4-(geranyloxy)-8-(isopropoxy)-2H-1-benzopyran-2-one
3-(benzoyloxy)-4-(geranyloxy)-8-(isopropoxy)-2H-1-benzopyran-2-one
3-(methoxy)-4-(geranyloxy)-8-(isopropoxy)-2H-1-benzopyran-2-one
3,8-(diisopropoxy)-4-(geranyloxy)-2H-1-benzopyran-2-one
3-(decyloxy)-4-(geranyloxy)-8-(isopropoxy)-2H-1-benzopyran-2-one
3-(3-hexenyloxy)-4-(geranyloxy)-8-(isopropoxy)-2H-1-benzopyran-2-one
3,4-(digeranyloxy)-8-(isopropoxy)-2H-1-benzopyran-2-one
3,4-(dihydroxy)-8-(t-butoxy)-2H-1-benzopyran-2-one
3-(acetoxy)-4-hydroxy-8-(t-butoxy)-2H-1-benzopyran-2-one
3-(benzoyloxy)-4-hydroxy-8-(t-butoxy)-2H-1-benzopyran-2-one
3-(methoxy)-4-hydroxy-8-(t-butoxy)-2H-1-benzopyran-2-one
3-(isopropoxy)-4-hydroxy-8-(t-butoxy)-2H-1-benzopyran-2-one
3-(decyloxy)-4-hydroxy-8-(t-butoxy)-2H-1-benzopyran-2-one 3-(3-hexenyloxy)-4-hydroxy-8-(t-butoxy)-2H-1-benzopyran-2-one
3-(geranyloxy)-4-hydroxy-8-(t-butoxy)-2H-1-benzopyran-2-one
3-hydroxy-4-(acetoxy)-8-(t-butoxy)-2H-1-benzopyran-2-one
3,4-(diacetoxy)-8-(t-butoxy)-2H-1-benzopyran-2-one
3-(benzoyloxy)-4-(acetoxy)-8-(t-butoxy)-2H-1-benzopyran-2-one
3-(methoxy)-4-(acetoxy)-8-(t-butoxy)-2H-1-benzopyran-2-one
3-(isopropoxy)-4-(acetoxy)-8-(t-butoxy)-2H-1-benzopyran-2-one
3-(decyloxy)-4-(acetoxy)-8-(t-butoxy)-2H-1-benzopyran-2-one
3-hydroxy-4-(benzoyloxy)-8-(t-butoxy)-2H-1-benzopyran-2-one
3-(acetoxy)-4-(benzoyloxy)-8-(t-butoxy)-2H-1-benzopyran-2-one
3,4-(dibenzoyloxy)-8-(t-butoxy)-2H-1-benzopyran-2-one
3-(methoxy)-4-(benzoyloxy)-8-(t-butoxy)-2H-1-benzopyran-2-one
3-(isopropoxy)-4-(benzoyloxy)-8-(t-butoxy)-2H-1-benzopyran-2-one
3-(decyloxy)-4-(benzoyloxy)-8-(t-butoxy)-2H-1-benzopyran-2-one
3-(3-hexenyloxy)-4-(benzoyloxy)-8-(t-butoxy)-2H-1-benzopyran-2-one
3-(geranyloxy)-4-(benzoyloxy)-8-(t-butoxy)-2H-1-benzopyran-2-one
3-hydroxy-4-(methoxy)-8-(t-butoxy)-2H-1-benzopyran-2-one
3-(acetoxy)-4-(methoxy)-8-(t-butoxy)-2H-1-benzopyran-2-one
3-(benzoyloxy)-4-(methoxy)-8-(t-butoxy)-2H-1-benzopyran-2-one
3-(isopropoxy)-4-(methoxy)-8-(t-butoxy)-2H-1-benzopyran-2-one
3-(decyloxy)-4-(methoxy)-8-(t-butoxy)-2H-1-benzopyran-2-one
3-(3-hexenyloxy)-4-(methoxy)-8-(t-butoxy)-2H-1-benzopyran-2-one
3-(geranyloxy)-4-(methoxy)-8-(t-butoxy)-2H-1-benzopyran-2-one
3-hydroxy-4-(isopropoxy)-8-(t-butoxy)-2H-1-benzopyran-2-one
3-(acetoxy)-4-(isopropoxy)-8-(t-butoxy)-2H-1-benzopyran-2-one
3-(benzoyloxy)-4-(isopropoxy)-8-(t-butoxy)-2H-1-benzopyran-2-one
3-(methoxy)-4-(isopropoxy)-8-(t-butoxy)-2H-1-benzopyran-2-one
3,4-(diisopropoxy)-8-(t-butoxy)-2H-1-benzopyran-2-one
3-(decyloxy)-4-(isopropoxy)-8-(t-butoxy)-2H-1-benzopyran-2-one
3-(3-hexenyloxy)-4-(isopropoxy)-8-(t-butoxy)-2H-1-benzopyran-2-one
3-(geranyloxy)-4-(isopropoxy)-8-(t-butoxy)-2H-1-benzopyran-2-one
3-hydroxy-4-(decyloxy)-8-(t-butoxy)-2H-1-benzopyran-2-one
3-(acetoxy)-4-(decyloxy)-8-(t-butoxy)-2H-1-benzopyran-2-one
3-(benzoyloxy)-4-(decyloxy)-8-(t-butoxy)-2H-1-benzopyran-2-one
3-(methoxy)-4-(decyloxy)-8-(t-butoxy)-2H-1-benzopyran-2-one
3-(isopropoxy)-4-(decyloxy)-8-(t-butoxy)-2H-1-benzopyran-2-one
3,4-(didecyloxy)-8-(t-butoxy)-2H-1-benzopyran-2-one
3-(3-hexenyloxy)-4-(decyloxy)-8-(t-butoxy)-2H-1-benzopyran-2-one
3-(geranyloxy)-4-(decyloxy)-8-(t-butoxy)-2H-1-benzopyran-2-one
3-hydroxy-4-(3-hexenyloxy)-8-(t-butoxy)-2H-1-benzopyran-2-one
3-(acetoxy)-4-(3-hexenyloxy)-8-(t-butoxy)-2H-1-benzopyran-2-one
3-(benzoyloxy)-4-(3-hexenyloxy)-8-(t-butoxy)-2H-1-benzopyran-2-one
3-(methoxy)-4-(3-hexenyloxy)-8-(t-butoxy)-2H-1-benzopyran-2-one
3-(isopropoxy)-4-(3-hexenyloxy)-8-(t-butoxy)-2H-1-benzopyran-2-one
3-(decyloxy)-4-(3-hexenyloxy)-8-(t-butoxy)-2H-1-benzopyran-2-one
3,4-(di-3-hexenyloxy)-8-(t-butoxy)-2H-1-benzopyran-2-one
3-(geranyloxy)-4-(3-hexenyloxy)-8-(t-butoxy)-2H-1-benzopyran-2-one
3-hydroxy-4-(geranyloxy)-8-(t-butoxy)-2H-1-benzopyran-2-one
3-(acetoxy)-4-(geranyloxy)-8-(t-butoxy)-2H-1-benzopyran-2-one
3-(benzoyloxy)-4-(geranyloxy)-8-(t-butoxy)-2H-1-benzopyran-2-one
3-(methoxy)-4-(geranyloxy)-8-(t-butoxy)-2H-1-benzopyran-2-one
3-(isopropoxy)-4-(geranyloxy)-8-(t-butoxy)-2H-1-benzopyran-2-one
3-(decyloxy)-4-(geranyloxy)-8-(t-butoxy)-2H-1-benzopyran-2-one
3-(3-hexenyloxy)-4-(geranyloxy)-8-(t-butoxy)-2H-1-benzopyran-2-one
3,4-(digeranyloxy)-8-(t-butoxy)-2H-1-benzopyran-2-one
3,4-(dihydroxy)-8-(decyloxy)-2H-1-benzopyran-2-one
3-(acetoxy)-4-hydroxy-8-(decyloxy)-2H-1-benzopyran-2-one
3-(benzoyloxy)-4-hydroxy-8-(decyloxy)-2H-1-benzopyran-2-one
3-(methoxy)-4-hydroxy-8-(decyloxy)-2H-1-benzopyran-2-one
3-(isopropoxy)-4-hydroxy-8-(decyloxy)-2H-1-benzopyran-2-one
3,8-(didecyloxy)-4-hydroxy-2H-1-benzopyran-2-one
3-(3-hexenyloxy)-4-hydroxy-8-(decyloxy)-2H-1-benzopyran-2-one
3-(geranyloxy)-4-hydroxy-8-(decyloxy)-2H-1-benzopyran-2-one
3-hydroxy-4-(acetoxy)-8-(decyloxy)-2H-1-benzopyran-2-one
3,4-(diacetoxy)-8-(decyloxy)-2H-1-benzopyran-2-one
3-(benzoyloxy)-4-(acetoxy)-8-(decyloxy)-2H-1-benzopyran-2-one
3-(methoxy)-4-(acetoxy)-8-(decyloxy)-2H-1-benzopyran-2-one
3-(isopropoxy)-4-(acetoxy)-8-(decyloxy)-2H-1-benzopyran-2-one
3,8-(didecyloxy)-4-(acetoxy)-8-(decyloxy)-2H-1-benzopyran-2-one
3-(3-hexenyloxy)-4-(acetoxy)-8-(decyloxy)-2H-1-benzopyran-2-one
3-(geranyloxy)-4-(acetoxy)-8-(decyloxy)-2H-1-benzopyran-2-one 3-hydroxy-4-(benzoyloxy)-8-(decyloxy)-2H-1-benzopyran-2-one
3-(acetoxy)-4-(benzoyloxy)-8-(decyloxy)-2H-1-benzopyran-2-one
3,4-(dibenzoyloxy)-8-(decyloxy)-2H-1-benzopyran-2-one
3-(methoxy)-4-(benzoyloxy)-8-(decyloxy-2H-1-benzopyran-2-one
3-(isopropoxy)-4-(benzoyloxy)-8-(decyloxy)-2H-1-benzopyran-2-one
3,8-(didecyloxy)-4-(benzoyloxy)-2H-1-benzopyran-2-one
3-(3-hexenyloxy)-4-(benzoyloxy)-8-(decyloxy)-2H-1-benzopyran-2-one
3-(geranyloxy)-4-(benzoyloxy)-8-(decyloxy)-2H-1-benzopyran-2-one
3-hydroxy-4-(methoxy)-8-(decyloxy)-2H-1-benzopyran-2-one
3-(acetoxy)-4-(methoxy)-8-(decyloxy)-2H-1-benzopyran-2-one
3-(benzoyloxy)-4-(methoxy)-8-(decyloxy)-2H-1-benzopyran-2-one
3-(isopropoxy)-4-(methoxy)-8-(decyloxy)-2H-1-benzopyran-2-one
3,8-(didecyloxy)-4-(methoxy)-2H-1-benzopyran-2-one
3-(3-hexenyloxy)-4-(methoxy)-8-(decyloxy)-2H-1-benzopyran-2-one
3-(geranyloxy)-4-(methoxy)-8-(decyloxy)-2H-1-benzopyran-2-one
3-hydroxy-4-(isopropoxy)-8-(decyloxy)-2H-1-benzopyran-2-one
3-(acetoxy)-4-(isopropoxy)-8-(decyloxy)-2H-1-benzopyran-2-one
3-(benzoyloxy)-4-(isopropoxy)-8-(decyloxy)-2H-1-benzopyran-2-one
3-(methoxy)-4-(isopropoxy)-8-(decyloxy)-2H-1-benzopyran-2-one
3,4-(diisopropoxy)-8-(decyloxy)-2H-1-benzopyran-2-one
3,8-(didecyloxy)-4-(isopropoxy)-2H-1-benzopyran-2-one
3-(3-hexenyloxy)-4-(isopropoxy)-8-(decyloxy)-2H-1-benzopyran-2-one
3-(geranyloxy)-4-(isopropoxy)-8-(decyloxy)-2H-1-benzopyran-2-one
3-hydroxy-4,8-(didecyloxy)-2H-1-benzopyran-2-one
3-(acetoxy)-4,8-(didecyloxy)-2H-1-benzopyran-2-one
3-(benzoyloxy)-4,8-(didecyloxy)-2H-1-benzopyran-2-one
3-(methoxy)-4,8-(didecyloxy)-2H-1-benzopyran-2-one
3-(isopropoxy)-4,8-(didecyloxy)-2H-1-benzopyran-2-one
3,4,8-(tridecyloxy)-2H-1-benzopyran-2-one
3-(3-hexenyloxy)-4,8-(didecyloxy)-2H-1-benzopyran-2-one
3-(geranyloxy)-4,8-(didecyloxy)-2H-1-benzopyran-2-one
3-hydroxy-4-(3-hexenyloxy)-8-(decyloxy)-2H-1-benzopyran-2-one
3-(acetoxy)-4-(3-hexenyloxy)-8-(decyloxy)-2H-1-benzopyran-2-one
3-(benzoyloxy)-4-(3-hexenyloxy)-8-(decyloxy)-2H-1-benzopyran-2-one
3-(methoxy)-4-(3-hexenyloxy)-8-(decyloxy)-2H-1-benzopyran-2-one
3-(isopropoxy)-4-(3-hexenyloxy)-8-(decyloxy)-2H-1-benzopyran-2-one
3,8-(didecyloxy)-4-(3-hexenyloxy)-2H-1-benzopyran-2-one
3,4-(di-3-hexenyloxy)-8-(decyloxy)-2H-1-benzopyran-2-one
3-(geranyloxy)-4-(3-hexenyloxy)-8-(decyloxy)-2H-1-benzopyran-2-one
3-hydroxy-4-(geranyloxy)-8-(decyloxy)-2H-1-benzopyran-2-one
3-(acetoxy)-4-(geranyloxy)-8-(decyloxy)-2H-1-benzopyran-2-one
3-(benzoyloxy)-4-(geranyloxy)-8-(decyloxy)-2H-1-benzopyran-2-one
3-(methoxy)-4-(geranyloxy)-8-(decyloxy)-2H-1-benzopyran-2-one
3-(isopropoxy)-4-(geranyloxy)-8-(decyloxy)-2H-1-benzopyran-2-one
3,8-(didecyloxy)-4-(geranyloxy)-2H-1-benzopyran-2-one
3-(3-hexenyloxy)-4-(geranyloxy)-8-(decyloxy)-2H-1-benzopyran-2-one
3,4-(digeranyloxy)-8-(decyloxy)-2H-1-benzopyran-2-one
3,4-(dihydroxy)-8-(3-hexenyloxy)-2H-1-benzopyran-2-one
3-(acetoxy)-4-hydroxy-8-(3-hexenyloxy)-2H-1-benzopyran-2-one
3-(benzoyloxy)-4-hydroxy-8-(3-hexenyloxy)-2H-1-benzopyran-2-one
3-(methoxy)-4-hydroxy-8-(3-hexenyloxy)-2H-1-benzopyran-2-one
3-(isopropoxy)-4-hydroxy-8-(3-hexenyloxy)-2H-1-benzopyran-2-one
3-(decyloxy)-4-hydroxy-8-(3-hexenyloxy)-2H-1-benzopyran-2-one
3,8-(di-3-hexenyloxy)-4-hydroxy-2H-1-benzopyran-2-one
3-(geranyloxy)-4-hydroxy-8-(3-hexenyloxy)-2H-1-benzopyran-2-one
3-hydroxy-4-(acetoxy)-8-(3-hexenyloxy)-2H-1-benzopyran-2-one
3,4-(diacetoxy)-8-(3-hexenyloxy)-2H-1-benzopyran-2-one
3-(benzoyloxy)-4-(acetoxy)-8-(3-hexenyloxy)-2H-1-benzopyran-2-one
3-(methoxy)-4-(acetoxy)-8-(3-hexenyloxy)-2H-1-benzopyran-2-one
3-(isopropoxy)-4-(acetoxy)-8-(3-hexenyloxy)-2H-1-benzopyran-2-one
3-(decyloxy)-4-(acetoxy)-8-(3-hexenyloxy)-2H-1-benzopyran-2-one
3,8-(di-3-hexenyloxy)-4-(acetoxy)-2H-1-benzopyran-2-one
3-(geranyloxy)-4-(acetoxy)-8-(3-hexenyloxy)-2H-1-benzopyran-2-one
3-hydroxy-4-(benzoyloxy)-8-(3-hexenyloxy)-2H-1-benzopyran-2-one
3-(acetoxy)-4-(benzoyloxy)-8-(3-hexenyloxy)-2H-1-benzopyran-2-one
3,4-(dibenzoyloxy)-8-(3-hexenyloxy)-2H-1-benzopyran-2-one
3-(methoxy)-4-(benzoyloxy)-8-(3-hexenyloxy)-2H-1-benzopyran-2-one
3-(isopropoxy)-4-(benzoyloxy)-8-(3-hexenyloxy)-2H-1-benzopyran-2-one
3-(decyloxy)-4-(benzoyloxy)-8-(3-hexenyloxy)-2H-1-benzopyran-2-one
3,8-(di-3-hexenyloxy)-4-(benzoyloxy)-2H-1-benzopyran-2-one 3-(geranyloxy)-4-(benzoyloxy)-8-(3-hexenyloxy)-2H-1-benzopyran-2-one
3-hydroxy-4-(methoxy)-8-(3-hexenyloxy)-2H-1-benzopyran-2-one
3-(acetoxy)-4-(methoxy)-8-(3-hexenyloxy)-2H-1-benzopyran-2-one
3-(benzoyloxy)-4-(methoxy)-8-(3-hexenyloxy)-2H-1-benzopyran-2-one
3-(isopropoxy)-4-(methoxy)-8-(3-hexenyloxy)-2H-1-benzopyran-2-one
3-(decyloxy)-4-(methoxy)-8-(3-hexenyloxy)-2H-1-benzopyran-2-one
3,8-(di-3-hexenyloxy)-4-(methoxy)-2H-1-benzopyran-2-one
3-(geranyloxy)-4-(methoxy)-8-(3-hexenyloxy)-2H-1-benzopyran-2-one
3-hydroxy-4-(isopropoxy)-8-(3-hexenyloxy)-2H-1-benzopyran-2-one
3-(acetoxy)-4-(isopropoxy)-8-(3-hexenyloxy)-2H-1-benzopyran-2-one
3-(benzoyloxy)-4-(isopropoxy)-8-(3-hexenyloxy)-2H-1-benzopyran-2-one
3-(methoxy)-4-(isopropoxy)-8-(3-hexenyloxy)-2H-1-benzopyran-2-one
3,4-(diisopropoxy)-8-(3-hexenyloxy)-2H-1-benzopyran-2-one
3-(decyloxy)-4-(isopropoxy)-8-(3-hexenyloxy)-2H-1-benzopyran-2-one
3,8-(di-3-hexenyloxy)-4-(isopropoxy)-2H-1-benzopyran-2-one
3-(geranyloxy)-4-(isopropoxy)-8-(3-hexenyloxy)-2H-1-benzopyran-2-one
3-hydroxy-4-(decyloxy)-8-(3-hexenyloxy)-2H-1-benzopyran-2-one
3-(acetoxy)-4-(decyloxy)-8-(3-hexenyloxy)-2H-1-benzopyran-2-one
3-(benzoyloxy)-4-(decyloxy)-8-(3-hexenyloxy)-2H-1-benzopyran-2-one
3-(methoxy)-4-(decyloxy)-8-(3-hexenyloxy)-2H-1-benzopyran-2-one
3-(isopropoxy)-4-(decyloxy)-8-(3-hexenyloxy)-2H-1-benzopyran-2-one
3,4-(didecyloxy)-8-(3-hexenyloxy)-2H-1-benzopyran-2-one
3-(3-hexenyloxy)-4-(decyloxy)-8-(3-hexenyloxy)-2H-1-benzopyran-2-one
3-(geranyloxy)-4-(decyloxy)-8-(3-hexenyloxy)-2H-1-benzopyran-2-one
3-hydroxy-4,8-(di-3-hexenyloxy)-2H-1-benzopyran-2-one
3-(acetoxy)-4,8-(di-3-hexenyloxy)-2H-1-benzopyran-2-one
3-(benzoyloxy)-4,8-(di-3-hexenyloxy)-2H-1-benzopyran-2-one
3-(methoxy)-4,8-(di-3-hexenyloxy)-2H-1-benzopyran-2-one
3-(isopropoxy)-4,8-(di-3-hexenyloxy)-2H-1-benzopyran-2-one
3-(decyloxy)-4,8-(di-3-hexenyloxy)-2H-1-benzopyran-2-one
3,4,8-(tri-3-hexenyloxy)-2H-1-benzopyran-2-one
3-(geranyloxy)-4,8-(di-3-hexenyloxy)-2H-1-benzopyran-2-one
3-hydroxy-4-(geranyloxy)-8-(3-hexenyloxy)-2H-1-benzopyran-2-one
3-(acetoxy)-4-(geranyloxy)-8-(3-hexenyloxy)-2H-1-benzopyran-2-one
3-(benzoyloxy)-4-(geranyloxy)-8-(3-hexenyloxy)-2H-1-benzopyran-2-one
3-(methoxy)-4-(geranyloxy)-8-(3-hexenyloxy)-2H-1-benzopyran-2-one
3-(isopropoxy)-4-(geranyloxy)-8-(3-hexenyloxy)-2H-1-benzopyran-2-one
3-(decyloxy)-4-(geranyloxy)-8-(3-hexenyloxy)-2H-1-benzopyran-2-one
3,8-(di-3-hexenyloxy)-4-(geranyloxy)-2H-1-benzopyran-2-one
3,4-(digeranyloxy)-8-(3-hexenyloxy)-2H-1-benzopyran-2-one
3,4-(dihydroxy)-8-(geranyloxy)-2H-1-benzopyran-2-one
3-(acetoxy)-4-hydroxy-8-(geranyloxy)-2H-1-benzopyran-2-one
3-(benzoyloxy)-4-hydroxy-8-(geranyloxy)-2H-1-benzopyran-2-one
3-(methoxy)-4-hydroxy-8-(geranyloxy)-2H-1-benzopyran-2-one
3-(isopropoxy)-4-hydroxy-8-(geranyloxy)-2H-1-benzopyran-2-one
3-(decyloxy)-4-hydroxy-8-(geranyloxy)-2H-1-benzopyran-2-one
3-(3-hexenyloxy)-4-hydroxy-8-(geranyloxy)-2H-1-benzopyran-2-one
3,8-(digeranyloxy)-4-hydroxy-2H-1-benzopyran-2-one
3-hydroxy-4-(acetoxy)-8-(geranyloxy)-2H-1-benzopyran-2-one
3,4-(diacetoxy)-8-(geranyloxy),-2H-1-benzopyran-2-one
3-(benzoyloxy)-4-(acetoxy)-8-(geranyloxy)-2H-1-benzopyran-2-one
3-(methoxy)-4-(acetoxy)-8-(geranyloxy)-2H-1-benzopyran-2-one
3-(isopropoxy)-4-(acetoxy)-8-(geranyloxy)-2H-1-benzopyran-2-one
3-(decyloxy)-4-(acetoxy)-8-(geranyloxy)-2H-1-benzopyran-2-one
3-(3-hexenyloxy)-4-(acetoxy)-8-(geranyloxy)-2H-1-benzopyran-2-one
3,8-(digeranyloxy)-4-(acetoxy)-2H-1-benzopyran-2-one
3-hydroxy-4-(benzoyloxy)-8-(geranyloxy)-2H-1-benzopyran-2-one
3-(acetoxy)-4-(benzoyloxy)-8-(geranyloxy)-2H-1-benzopyran-2-one
3,4-(dibenzoyloxy)-8-(geranyloxy)-2H-1-benzopyran-2-one
3-(methoxy)-4-(benzoyloxy)-8-(geranyloxy)-2H-1-benzopyran-2-one
3-(isopropoxy)-4-(benzoyloxy)-8-(geranyloxy)-2H-1-benzopyran-2-one
3-(decyloxy)-4-(benzoyloxy)-8-(geranyloxy)-2H-1-benzopyran-2-one
3-(3-hexenyloxy)-4-(benzoyloxy)-8-(geranyloxy)-2H-1-benzopyran-2-one
3,8-(digeranyloxy)-4-(benzoyloxy)-2H-1-benzopyran-2-one
3-hydroxy-4-(methoxy)-8-(geranyloxy)-2H-1-benzopyran-2-one
3-(acetoxy)-4-(methoxy)-8-(geranyloxy)-2H-1-benzopyran-2-one
3-(benzoyloxy)-4-(methoxy)-8-(geranyloxy)-2H-1-benzopyran-2-one
3,4-(dimethoxy)-8-(geranyloxy)-2H-1-benzopyran-2-one
3-(isopropoxy)-4-(methoxy)-8-(geranyloxy)-2H-1-benzopyran-2-one 3-(decyloxy)-4-(methoxy)-8-(geranyloxy)-2H-1-benzopyran-2-one
3-(3-hexenyloxy)-4-(methoxy)-8-(geranyloxy)-2H-1-benzopyran-2-one
3,8-(digeranyloxy)-4-(methoxy)-2H-1-benzopyran-2-one
3-hydroxy-4-(isopropoxy)-8-(geranyloxy)-2H-1-benzopyran-2-one
3-(acetoxy)-4-(isopropoxy)-8-(geranyloxy)-2H-1-benzopyran-2-one
3-(benzoyloxy)-4-(isopropoxy)-8-(geranyloxy)-2H-1-benzopyran-2-one
3-(methoxy)-4-(isopropoxy)-8-(geranyloxy)-2H-1-benzopyran-2-one
3,4-(diisopropoxy)-8-(geranyloxy)-2H-1-benzopyran-2-one
3-(decyloxy)-4-(isopropoxy)-8-(geranyloxy)-2H-1-benzopyran-2-one
3-(3-hexenyloxy)-4-(isopropoxy)-8-(geranyloxy)-2H-1-benzopyran-2-one
3,8-(digeranyloxy)-4-(isopropoxy)-2H-1-benzopyran-2-one
3-hydroxy-4-(decyloxy)-8-(geranyloxy)-2H-1-benzopyran-2-one
3-(acetoxy)-4-(decyloxy)-8-(geranyloxy)-2H-1-benzopyran-2-one
3-(benzoyloxy)-4-(decyloxy)-8-(geranyloxy)-2H-1-benzopyran-2-one
3-(methoxy)-4-(decyloxy)-8-(geranyloxy)-2H-1-benzopyran-2-one
3-(isopropoxy)-4-(decyloxy)-8-(geranyloxy)-2H-1-benzopyran-2-one
3,4-(didecyloxy)-8-(geranyloxy)-2H-1-benzopyran-2-one
3-(3-hexenyloxy)-4-(decyloxy)-8-(geranyloxy)-2H-1-benzopyran-2-one
3,8-(digeranyloxy)-4-(decyloxy)-2H-1-benzopyran-2-one
3-hydroxy-4-(3-hexenyloxy)-8-(geranyloxy)-2H-1-benzopyran-2-one
3-(acetoxy)-4-(3-hexenyloxy)-8-(geranyloxy)-2H-1-benzopyran-2-one
3-(benzoyloxy)-4-(3-hexenyloxy)-8-(geranyloxy)-2H-1-benzopyran-2-one
3-(methoxy)-4-(3-hexenyloxy)-8-(geranyloxy)-2H-1-benzopyran-2-one
3-(isopropoxy)-4-(3-hexenyloxy)-8-(geranyloxy)-2H-1-benzopyran-2-one
3-(decyloxy)-4-(3-hexenyloxy)-8-(geranyloxy)-2H-1-benzopyran-2-one
3,4-(di-3-hexenyloxy)-8-(geranyloxy)-2H-1-benzopyran-2-one
3,8-(digeranyloxy)-4-(3-hexenyloxy)-2H-1-benzopyran-2-one
3-hydroxy-4,8-(digeranyloxy)-2H-1-benzopyran-2-one
3-(acetoxy)-4,8-(digeranyloxy)-2H-1-benzopyran-2-one
3-(benzoyloxy)-4,8-(digeranyloxy)-2H-1-benzopyran-2-one
3-(methoxy)-4,8-(digeranyloxy)-2H-1-benzopyran-2-one
3-(isopropoxy)-4,8-(digeranyloxy)-2H-1-benzopyran-2-one
3-(decyloxy)-4,8-(digeranyloxy)-2H-1-benzopyran-2-one
3-(3-hexenyloxy)-4,8-(digeranyloxy)-2H-1-benzopyran-2-one
3,4,8-(trigeranyloxy)-2H-1-benzopyran-2-one
3,4,5-(trihydroxy)-2H-1-benzopyran-2-one
3-(acetoxy)-4,5-(dihydroxy)-2H-1-benzopyran-2-one
3-(benzoyloxy)-4,5-(dihydroxy)-2H-1-benzopyran-2-one
3-(methoxy)-4,5-(dihydroxy)-2H-1-benzopyran-2-one
3-(isopropoxy)-4,5-(dihydroxy)-2H-1-benzopyran-2-one
3-(decyloxy)-4,5-(dihydroxy)-2H-1-benzopyran-2-one
3-(3-hexenyloxy)-4,5-(dihydroxy)-2H-1-benzopyran-2-one
3-(geranyloxy)-4,5-(dihydroxy)-2H-1-benzopyran-2-one
3,5-(dihydroxy)-4-(acetoxy)-2H-1-benzopyran-2-one
3,4-(diacetoxy)-5-hydroxy-2H-1-benzopyran-2-one
3-(benzoyloxy)-4-(acetoxy)-5-hydroxy-2H-1-benzopyran-2-one
3-(methoxy)-4-(acetoxy)-5-hydroxy-2H-1-benzopyran-2-one
3-(isopropoxy)-4-(acetoxy)-5-hydroxy-2H-1-benzopyran-2-one
3-(decyloxy)-4-(acetoxy)-5-hydroxy-2H-1-benzopyran-2-one
3-(3-hexenyloxy)-4-(acetoxy)-5-hydroxy-2H-1-benzopyran-2-one
3-(geranyloxy)-4-(acetoxy)-5-hydroxy-2H-1-benzopyran-2-one
3,5-(dihydroxy)-4-(benzoyloxy)-2H-1-benzopyran-2-one
3-(acetoxy)-4-(benzoyloxy)-5-hydroxy-2H-1-benzopyran-2-one
3,4-(dibenzoyloxy)-5-hydroxy-2H-1-benzopyran-2-one
3-(methoxy)-4-(benzoyloxy)-5-hydroxy-2H-1-benzopyran-2-one
3-(isopropoxy)-4-(benzoyloxy)-5-hydroxy-2H-1-benzopyran-2-one
3-(decyloxy)-4-(benzoyloxy)-5-hydroxy-2H-1-benzopyran-2-one
3-(3-hexenyloxy)-4-(benzoyloxy)-5-hydroxy-2H-1-benzopyran-2-one
3-(geranyloxy)-4-(benzoyloxy)-5-hydroxy-2H-1-benzopyran-2-one
3,5-(dihydroxy)-4-(methoxy)-2H-1-benzopyran-2-one
3-(acetoxy)-4-(methoxy)-5-hydroxy-2H-1-benzopyran-2-one
3-(benzoyloxy)-4-(methoxy)-5-hydroxy-2H-1-benzopyran-2-one
3-(isopropoxy)-4-(methoxy)-5-hydroxy-2H-1-benzopyran-2-one
3-(decyloxy)-4-(methoxy)-5-hydroxy-2H-1-benzopyran-2-one
3-(3-hexenyloxy)-4-(methoxy)-5-hydroxy-2H-1-benzopyran-2-one
3-(geranyloxy)-4-(methoxy)-5-hydroxy-2H-1-benzopyran-2-one
3,5-(dihydroxy)-4-(isopropoxy)-2H-1-benzopyran-2-one
3-(acetoxy)-4-(isopropoxy)-5-hydroxy-2H-1-benzopyran-2-one
3-(benzoyloxy)-4-(isopropoxy)-5-hydroxy-2H-1-benzopyran-2-one
3-(methoxy)-4-(isopropoxy)-5-hydroxy-2H-1-benzopyran-2-one
3,4-(diisopropoxy)-5-hydroxy-2H-1-benzopyran-2-one
3-(decyloxy)-4-(isopropoxy)-5-hydroxy-2H-1-benzopyran-2-one
3-(3-hexenyloxy)-4-(isopropoxy)-5-hydroxy-2H-1-benzopyran-2-one
3-(geranyloxy)-4-(isopropoxy)-5-hydroxy-2H-1-benzopyran-2-one
3,5-(dihydroxy)-4-(decyloxy)-2H-1-benzopyran-2-one 3-(acetoxy)-4-(decyloxy)-5-hydroxy-2H-1-benzopyran-2-one
3-(benzoyloxy)-4-(decyloxy)-5-hydroxy-2H-1-benzopyran-2-one
3-(methoxy)-4-(decyloxy)-5-hydroxy-2H-1-benzopyran-2-one
3-(isopropoxy)-4-(decyloxy)-5-hydroxy-2H-1-benzopyran-2-one
3,4-(didecyloxy)-5-hydroxy-2H-1-benzopyran-2-one
3-(3-hexenyloxy)-4-(decyloxy)-5-hydroxy-2H-1-benzopyran-2-one
3-(geranyloxy)-4-(decyloxy)-5-hydroxy-2H-1-benzopyran-2-one
3,5-(dihydroxy)-4-(3-hexenyloxy)-2H-1-benzopyran-2-one
3-(acetoxy)-4-(3-hexenyloxy)-5-hydroxy-2H-1-benzopyran-2-one
3-(benzoyloxy)-4-(3-hexenyloxy)-5-hydroxy-2H-1-benzopyran-2-one
3-(methoxy)-4-(3-hexenyloxy)-5-hydroxy-2H-1-benzopyran-2-one
3-(isopropoxy)-4-(3-hexenyloxy)-5-hydroxy-2H-1-benzopyran-2-one
3-(decyloxy)-4-(3-hexenyloxy)-5-hydroxy-2H-1-benzopyran-2-one
3,4-(di-3-hexenyloxy)-5-hydroxy-2H-1-benzopyran-2-one
3-(geranyloxy)-4-(3-hexenyloxy)-5-hydroxy-2H-1-benzopyran-2-one
3,5-(dihydroxy)-4-(geranyloxy)-2H-1-benzopyran-2-one
3-(acetoxy)-4-(geranyloxy)-5-hydroxy-2H-1-benzopyran-2-one
3-(benzoyloxy)-4-(geranyloxy)-5-hydroxy-2H-1-benzopyran-2-one
3-(methoxy)-4-(geranyloxy)-5-hydroxy-2H-1-benzopyran-2-one
3-(isopropoxy)-4-(geranyloxy)-5-hydroxy-2H-1-benzopyran-2-one
3-(decyloxy)-4-(geranyloxy)-5-hydroxy-2H-1-benzopyran-2-one
3-(3-hexenyloxy)-4-(geranyloxy)-5-hydroxy-2H-1-benzopyran-2-one
3,4-(digeranyloxy)-5-hydroxy-2H-1-benzopyran-2-one
3,4-(dihydroxy)-5-(acetoxy)-2H-1-benzopyran-2-one
3,5-(diacetoxy)-4-hydroxy-2H-1-benzopyran-2-one
3-(benzoyloxy)-4-hydroxy-5-(acetoxy)-2H-1-benzopyran-2-one
3-(isopropoxy)-4-hydroxy-5-(acetoxy)-2H-1-benzopyran-2-one
3-(decyloxy)-4-hydroxy-5-(acetoxy)-2H-1-benzopyran-2-one
3-(3-hexenyloxy)-4-hydroxy-5-(acetoxy)-2H-1-benzopyran-2-one
3-(geranyloxy)-4-hydroxy-5-(acetoxy)-2H-1-benzopyran-2-one
3-hydroxy-4,5-(diacetoxy)-2H-1-benzopyran-2-one
3,4,5-(triacetoxy)-2H-1-benzopyran-2-one
3-(benzoyloxy)-4,5-(diacetoxy)-2H-1-benzopyran-2-one
3-(isopropoxy)-4,5-(diacetoxy)-2H-1-benzopyran-2-one
3-(decyloxy)-4,5-(diacetoxy)-2H-1-benzopyran-2-one
3-(3-hexenyloxy)-4,5-(diacetoxy)-2H-1-benzopyran-2-one
3-(geranyloxy)-4,5-(diacetoxy)-2H-1-benzopyran-2-one
3-hydroxy-4-(benzoyloxy)-5-(acetoxy)-2H-1-benzopyran-2-one
3,5-(diacetoxy)-4-(benzoyloxy)-2H-1-benzopyran-2-one
3,4-(dibenzoyloxy)-5-(acetoxy)-2H-1-benzopyran-2-one
3-(methoxy)-4-(benzoyloxy)-5-(acetoxy)-2H-1-benzopyran-2-one
3-(isopropoxy)-4-(benzoyloxy)-5-(acetoxy)-2H-1-benzopyran-2-one
3-(decyloxy)-4-(benzoyloxy)-5-(acetoxy)-2H-1-benzopyran-2-one
3-(3-hexenyloxy)-4-(benzoyloxy)-5-(acetoxy)-2H-1-benzopyran-2-one
3-(geranyloxy)-4-(benzoyloxy)-5-(acetoxy)-2H-1-benzopyran-2-one
3-hydroxy-4-(methoxy)-5-(acetoxy)-2H-1-benzopyran-2-one
3-(acetoxy)-4-(methoxy)-5-(acetoxy)-2H-1-benzopyran-2-one
3-(benzoyloxy)-4-(methoxy)-5-(acetoxy)-2H-1-benzopyran-2-one
3-(isopropoxy)-4-(methoxy)-5-(acetoxy)-2H-1-benzopyran-2-one
3-(decyloxy)-4-(methoxy)-5-(acetoxy)-2H-1-benzopyran-2-one
3-(3-hexenyloxy)-4-(methoxy)-5-(acetoxy)-2H-1-benzopyran-2-one
3-(geranyloxy)-4-(methoxy)-5-(acetoxy)-2H-1-benzopyran-2-one
3-hydroxy-4-(isopropoxy)-5-(acetoxy)-2H-1-benzopyran-2-one
3,5-(diacetoxy)-4-isopropoxy-2H-1-benzopyran-2-one
3-(benzoyloxy)-4-(isopropoxy)-5-(acetoxy)-2H-1-benzopyran-2-one
3-(methoxy)-4-(isopropoxy)-5-(acetoxy)-2H-1-benzopyran-2-one
3,4-(diisopropoxy)-5-(acetoxy)-2H-1-benzopyran-2-one
3-(decyloxy)-4-(isopropoxy)-5-(acetoxy)-2H-1-benzopyran-2-one
3-(3-hexenyloxy)-4-(isopropoxy)-5-(acetoxy)-2H-1-benzopyran-2-one
3-(geranyloxy)-4-(isopropoxy)-5-(acetoxy)-2H-1-benzopyran-2-one
3-hydroxy-4-(decyloxy)-5-(acetoxy)-2H-1-benzopyran-2-one
3,5-(diacetoxy)-4-(decyloxy)-2H-1-benzopyran-2-one
3-(benzoyloxy)-4-(decyloxy)-5-(acetoxy)-2H-1-benzopyran-2-one
3-(methoxy)-4-(decyloxy)-5-(acetoxy)-2H-1-benzopyran-2-one
3-(isopropoxy)-4-(decyloxy)-5-(acetoxy)-2H-1-benzopyran-2-one
3,4-(didecyloxy)-5-(acetoxy)-2H-1-benzopyran-2-one
3-(3-hexenyloxy)-4-(decyloxy)-5-(acetoxy)-2H-1-benzopyran-2-one
3-(geranyloxy)-4-(decyloxy)-5-(acetoxy)-2H-1-benzopyran-2-one
3-hydroxy-4-(3-hexenyloxy)-5-(acetoxy)-2H-1-benzopyran-2-one
3,5-(diacetoxy)-4-(3-hexenyloxy)-2H-1-benzopyran-2-one
3-(benzoyloxy)-4-(3-hexenyloxy!-5-(acetoxy)-2H-1-benzopyran-2-one
3-(methoxy)-4-(3-hexenyloxy)-5-(acetoxy)-2H-1-benzopyran-2-one
3-(isopropoxy)-4-(3-hexenyloxy)-5-(acetoxy)-2H-1-benzopyran-2-one
3-(decyloxy)-4-(3-hexenyloxy)-5-(acetoxy)-2H-1-benzopyran-2-one
3,4-(di-3-hexenyloxy)-5-(acetoxy)-2H-1-benzopyran-2-one
3-(geranyloxy)-4-(3-hexenyloxy)-5-(acetoxy)-2H-1-benzopyran-2-one 3-hydroxy-4-(geranyloxy)-5-(acetoxy)-2H-1-benzopyran-2-one
3,5-(diacetoxy)-4-(geranyloxy)-2H-1-benzopyran-2-one
3-(benzoyloxy)-4-(geranyloxy)-5-(acetoxy)-2H-1-benzopyran-2-one
3-(methoxy)-4-(geranyloxy)-5-(acetoxy)-2H-1-benzopyran-2-one
3-(isopropoxy)-4-(geranyloxy)-5-(acetoxy)-2H-1-benzopyran-2-one
3-(decyloxy)-4-(geranyloxy)-5-(acetoxy)-2H-1-benzopyran-2-one
3-(3-hexenyloxy)-4-(geranyloxy)-5-(acetoxy)-2H-1-benzopyran-2-one
3,4-(digeranyloxy)-5-(acetoxy)-2H-1-benzopyran-2-one
3,4-(dihydroxy)-5-(methoxy)-2H-1-benzopyran-2-one
3-(acetoxy)-4-hydroxy-5-(methoxy)-2H-1-benzopyran-2-one
3-(benzoyloxy)-4-hydroxy-5-(methoxy)-2H-1-benzopyran-2-one
3-(isopropoxy)-4-hydroxy-5-(methoxy)-2H-1-benzopyran-2-one
3-(decyloxy)-4-hydroxy-5-(methoxy)-2H-1-benzopyran-2-one
3-(3-hexenyloxy)-4-hydroxy-5-(methoxy)-2H-1-benzopyran-2-one
3-(geranyloxy)-4-hydroxy-5-(methoxy)-2H-1-benzopyran-2-one
3-hydroxy-4-(acetoxy)-5-(methoxy)-2H-1-benzopyran-2-one
3,4-(diacetoxy)-5-(methoxy)-2H-1-benzopyran-2-one
3-(benzoyloxy)-4-(acetoxy)-5-(methoxy)-2H-1-benzopyran-2-one
3-(isopropoxy)-4-(acetoxy)-5-(methoxy)-2H-1-benzopyran-2-one
3-(decyloxy)-4-(acetoxy)-5-(methoxy)-2H-1-benzopyran-2-one
3-(3-hexenyloxy)-4-(acetoxy)-5-(methoxy)-2H-1-benzopyran-2-one
3-(geranyloxy)-4-(acetoxy)-5-(methoxy)-2H-1-benzopyran-2-one
3-hydroxy-4-(benzoyloxy)-5-(methoxy)-2H-1-benzopyran-2-one
3-(acetoxy)-4-(benzoyloxy)-5-(methoxy)-2H-1-benzopyran-2-one
3,4-(dibenzoyloxy)-5-(methoxy)-2H-1-benzopyran-2-one
3,5-(dimethoxy)-4-(benzoyloxy)-2H-1-benzopyran-2-one
3-(isopropoxy)-4-(benzoyloxy)-5-(methoxy)-2H-1-benzopyran-2-one
3-(decyloxy)-4-(benzoyloxy)-5-(methoxy)-2H-1-benzopyran-2-one
3-(3-hexenyloxy)-4-(benzoyloxy)-5-(methoxy)-2H-1-benzopyran-2-one
3-(geranyloxy)-4-(benzoyloxy)-5-(methoxy)-2H-1-benzopyran-2-one
3-hydroxy-4,5-(dimethoxy)-2H-1-benzopyran-2-one
3-(acetoxy)-4,5-(dimethoxy)-2H-1-benzopyran-2-one
3-(benzoyloxy)-4,5-(dimethoxy)-2H-1-benzopyran-2-one
3,4,5-(trimethoxy)-2H-1-benzopyran-2-one
3-(isopropoxy)-4,5-(dimethoxy)-2H-1-benzopyran-2-one
3-(decyloxy)-4,5-(dimethoxy)-2H-1-benzopyran-2-one
3-(3-hexenyloxy)-4,5-(dimethoxy)-2H-1-benzopyran-2-one
3-(geranyloxy)-4,5-(dimethoxy)-2H-1-benzopyran-2-one
3-hydroxy-4-(isopropoxy)-5-(methoxy)-2H-1-benzopyran-2-one
3-(acetoxy)-4-(isopropoxy)-5-(methoxy)-2H-1-benzopyran-2-one
3-(benzoyloxy)-4-(isopropoxy)-5-(methoxy)-2H-1-benzopyran-2-one
3,5-(dimethoxy)-4-(isopropoxy)-2H-1-benzopyran-2-one
3,4-(diisopropoxy)-5-(acetoxy)-2H-1-benzopyran-2-one
3-(decyloxy)-4-(isopropoxy)-5-(methoxy)-2H-1-benzopyran-2-one
3-(3-hexenyloxy)-4-(isopropoxy)-5-(methoxy)-2H-1-benzopyran-2-one
3-(geranyloxy)-4-(isopropoxy)-5-(methoxy)-2H-1-benzopyran-2-one
3-hydroxy-4-(decyloxy)-5-(methoxy)-2H-1-benzopyran-2-one
3-(acetoxy)-4-(decyloxy)-5-(methoxy)-2H-1-benzopyran-2-one
3-(benzoyloxy)-4-(decyloxy)-5-(methoxy)-2H-1-benzopyran-2-one
3,5-(dimethoxy)-4-(decyloxy)-2H-1-benzopyran-2-one
3-(isopropoxy)-4-(decyloxy)-5-(methoxy)-2H-1-benzopyran-2-one
3,4-(didecyloxy)-5-(methoxy)-2H-1-benzopyran-2-one
3-(3-hexenyloxy)-4-(decyloxy)-5-(methoxy)-2H-1-benzopyran-2-one
3-(geranyloxy)-4-(decyloxy)-5-(methoxy)-2H-1-benzopyran-2-one
3-hydroxy-4-(3-hexenyloxy)-5-(methoxy)-2H-1-benzopyran-2-one
3-(acetoxy)-4-(3-hexenyloxy)-5-(methoxy)-2H-1-benzopyran-2-one
3-(benzoyloxy)-4-(3-hexenyloxy)-5-(methoxy)-2H-1-benzopyran-2-one
3,5-(dimethoxy)-4-(3-hexenyloxy)-2H-1-benzopyran-2-one
3-(isopropoxy)-4-(3-hexenyloxy)-5-(methoxy)-2H-1-benzopyran-2-one
3-(decyloxy)-4-(3-hexenyloxy)-5-(methoxy)-2H-1-benzopyran-2-one
3,4-(di-3-hexenyloxy)-5-(methoxy)-2H-1-benzopyran-2-one
3-(geranyloxy)-4-(3-hexenyloxy)-5-(methoxy)-2H-1-benzopyran-2-one
3-hydroxy-4-(geranyloxy)-5-(methoxy)-2H-1-benzopyran-2-one
3-(acetoxy)-4-(geranyloxy)-5-(methoxy)-2H-1-benzopyran-2-one
3-(benzoyloxy)-4-(geranyloxy)-5-(methoxy)-2H-1-benzopyran-2-one
3,5-(dimethoxy)-4-(geranyloxy)-2H-1-benzopyran-2-one
3-(isopropoxy)-4-(geranyloxy)-5-(methoxy)-2H-1-benzopyran-2-one
3-(decyloxy)-4-(geranyloxy)-5-(methoxy)-2H-1-benzopyran-2-one
3-(3-hexenyloxy)-4-(geranyloxy)-5-(methoxy)-2H-1-benzopyran-2-one
3,4-(digeranyloxy)-5-(methoxy)-2H-1-benzopyran-2-one
3,4-(dihydroxy)-5-(isopropoxy)-2H-1-benzopyran-2-one
3-(acetoxy)-4-hydroxy-5-(isopropoxy)-2H-1-benzopyran-2-one
3-(benzoyloxy)-4-hydroxy-5-(isopropoxy)-2H-1-benzopyran-2-one
3,5-(diisopropoxy)-4-hydroxy-2H-1-benzopyran-2-one 3-(decyloxy)-4-hydroxy-5-(isopropoxy)-2H-1-benzopyran-2-one
3-(3-hexenyloxy)-4-hydroxy-5-(isopropoxy)-2H-1-benzopyran-2-one
3-(geranyloxy)-4-hydroxy-5-(isopropoxy)-2H-1-benzopyran-2-one
3-hydroxy-4-(acetoxy)-5-(isopropoxy)-2H-1-benzopyran-2-one
3,4-(diacetoxy)-5-(isopropoxy)-2H-1-benzopyran-2-one
3-(benzoyloxy)-4-(acetoxy)-5-(isopropoxy)-2H-1-benzopyran-2-one
3,5-(diisopropoxy)-4-(acetoxy)-2H-1-benzopyran-2-one
3-(decyloxy)-4-(acetoxy)-5-(isopropoxy)-2H-1-benzopyran-2-one
3-hydroxy-4-(benzoyloxy)-5-(isopropoxy)-2H-1-benzopyran-2-one
3-(acetoxy)-4-(benzoyloxy)-5-(isopropoxy)-2H-1-benzopyran-2-one
3,4-(dibenzoyloxy)-5-(isopropoxy)-2H-1-benzopyran-2-one
3-(methoxy)-4-(benzoyloxy)-5-(isopropoxy)-2H-1-benzopyran-2-one
3,5-(diisopropoxy)-4-(benzoyloxy)-2H-1-benzopyran-2-one
3-(decyloxy)-4-(benzoyloxy)-5-(isopropoxy)-2H-1-benzopyran-2-one
3-(3-hexenyloxy)-4-(benzoyloxy)-5-(isopropoxy)-2H-1-benzopyran-2-one
3-(geranyloxy)-4-(benzoyloxy)-5-(isopropoxy)-2H-1-benzopyran-2-one
3-hydroxy-4-(methoxy)-5-(isopropoxy)-2H-1-benzopyran-2-one
3-(acetoxy)-4-(methoxy)-5-(isopropoxy)-2H-1-benzopyran-2-one
3-(benzoyloxy)-4-(methoxy)-5-(isopropoxy)-2H-1-benzopyran-2-one
3,5-(diisopropoxy)-4-(methoxy)-2H-1-benzopyran-2-one
3-(decyloxy)-4-(methoxy)-5-(isopropoxy)-2H-1-benzopyran-2-one
3-(3-hexenyloxy)-4-(methoxy)-5-(isopropoxy)-2H-1-benzopyran-2-one
3-(geranyloxy)-4-(methoxy)-5-(isopropoxy)-2H-1-benzopyran-2-one
3-hydroxy-4,5-(diisopropoxy)-2H-1-benzopyran-2-one
3-(acetoxy)-4,5-(diisopropoxy)-2H-1-benzopyran-2-one
3-(benzoyloxy)-4,5-(diisopropoxy)-2H-1-benzopyran-2-one
3-(methoxy)-4,5-(diisopropoxy)-2H-1-benzopyran-2-one
3,4,5-(triisopropoxy)-2H-1-benzopyran-2-one
3-(decyloxy)-4,5-(diisopropoxy)-2H-1-benzopyran-2-one
3-(3-hexenyloxy)-4,5-(diisopropoxy)-2H-1-benzopyran-2-one
3-(geranyloxy)-4,5-(diisopropoxy)-2H-1-benzopyran-2-one
3-hydroxy-4-(decyloxy)-5-(isopropoxy)-2H-1-benzopyran-2-one
3-(acetoxy)-4-(decyloxy)-5-(isopropoxy)-2H-1-benzopyran-2-one
3-(benzoyloxy)-4-(decyloxy)-5-(isopropoxy)-2H-1-benzopyran-2-one
3-(methoxy)-4-(decyloxy)-5-(isopropoxy)-2H-1-benzopyran-2-one
3,5-(diisopropoxy)-4-(decyloxy)-2H-1-benzopyran-2-one
3,4-(didecyloxy)-5-(isopropoxy)-2H-1-benzopyran-2-one
3-(3-hexenyloxy)-4-(decyloxy)-5-(isopropoxy)-2H-1-benzopyran-2-one
3-(geranyloxy)-4-(decyloxy)-5- isopropoxy)-2H-1-benzopyran-2-one
3-hydroxy-4-(3-hexenyloxy)-5-(isopropoxy)-2H-1-benzopyran-2-one
3-(acetoxy)-4-(3-hexenyloxy)-5-(isopropoxy)-2H-1-benzopyran-2-one
3-(benzoyloxy)-4-(3-hexenyloxy)-5-(isopropoxy)-2H-1-benzopyran-2-one
3-(methoxy)-4-(3-hexenyloxy)-5-(isopropoxy)-2H-1-benzopyran-2-one
3,5-(diisopropoxy)-4-(3-hexenyloxy)-2H-1-benzopyran-2-one
3-(decyloxy)-4-(3-hexenyloxy)-5-(isopropoxy)-2H-1-benzopyran-2-one
3,4-(di-3-hexenyloxy)-5-(isopropoxy)-2H-1-benzopyran-2-one
3-(geranyloxy)-4-(3-hexenyloxy)-5-(isopropoxy)-2H-1-benzopyran-2-one
3-hydroxy-4-(geranyloxy)-5-(isopropoxy)-2H-1-benzopyran-2-one
3-(acetoxy)-4-(geranyloxy)-5-(isopropoxy)-2H-1-benzopyran-2-one
3-(benzoyloxy)-4-(geranyloxy)-5-(isopropoxy)-2H-1-benzopyran-2-one
3-(methoxy)-4-(geranyloxy)-5-(isopropoxy)-2H-1-benzopyran-2-one
3,5-(diisopropoxy)-4-(geranyloxy)-2H-1-benzopyran-2-one
3-(decyloxy)-4-(geranyloxy)-5-(isopropoxy)-2H-1-benzopyran-2-one
3-(3-hexenyloxy)-4-(geranyloxy)-5-(isopropoxy)-2H-1-benzopyran-2-one
3,4-(digeranyloxy)-5-(isopropoxy)-2H-1-benzopyran-2-one
3,4-(dihydroxy)-5-(t-butoxy)-2H-1-benzopyran-2-one
3-(acetoxy)-4-hydroxy-5-(t-butoxy)-2H-1-benzopyran-2-one
3-(benzoyloxy)-4-hydroxy-5-(t-butoxy)-2H-1-benzopyran-2-one
3-(isopropoxy)-4-hydroxy-5-(t-butoxy)-2H-1-benzopyran-2-one
3-(decyloxy)-4-hydroxy-5-(t-butoxy)-2H-1-benzopyran-2-one
3-(3-hexenyloxy)-4-hydroxy-5-(t-butoxy)-2H-1-benzopyran-2-one
3-(geranyloxy)-4-hydroxy-5-(t-butoxy)-2H-1-benzopyran-2-one
3-hydroxy-4-(acetoxy)-5-(t -butoxy)-2H-1-benzopyran-2-one
3,4-(diacetoxy)-5-(t-butoxy)-2H-1-benzopyran-2-one
3-(benzoyloxy)-4-(acetoxy)-5-(t-butoxy)-2H-1-benzopyran-2-one
3-(isopropoxy)-4-(acetoxy)-5-(t-butoxy)-2H-1-benzopyran-2-one
3-(decyloxy)-4-(acetoxy)-5-(t-butoxy)-2H-1-benzopyran-2-one
3-hydroxy-4-(benzoyloxy)-5-(t-butoxy)-2H-1-benzopyran-2-one
3-(acetoxy)-4-(benzoyloxy)-5-(t-butoxy)-2H-1-benzopyran-2-one
3,4-(dibenzoyloxy)-5-(t-butoxy)-2H-1-benzopyran-2-one
3-(methoxy)-4-(benzoyloxy)-5-(t-butoxy)-2H-1-benzopyran-2-one 3-(isopropoxy)-4-(benzoyloxy)-5-(t-butoxy)-2H-1-benzopyran-2-one
3-(decyloxy)-4-(benzoyloxy)-5-(t-butoxy)-2H-1-benzopyran-2-one
3-(3-hexenyloxy)-4-(benzoyloxy)-5-(t-butoxy)-2H-1-benzopyran-2-one
3-(geranyloxy)-4-(benzoyloxy)-5-(t-butoxy)-2H-1-benzopyran-2-one
3-hydroxy-4-(methoxy)-5-(t-butoxy)-2H-1-benzopyran-2-one
3-(acetoxy)-4-(methoxy)-5-(t-butoxy)-2H-1-benzopyran-2-one
3-(benzoyloxy)-4-(methoxy)-5-(t-butoxy)-2H-1-benzopyran-2-one
3-(isopropoxy)-4-(methoxy)-5-(t-butoxy)-2H-1-benzopyran-2-one
3-(decyloxy)-4-(methoxy)-5-(t-butoxy)-2H-1-benzopyran-2-one
3-(3-hexenyloxy)-4-(methoxy)-5-(t-butoxy)-2H-1-benzopyran-2-one
3-(geranyloxy)-4-(methoxy)-5-(t-butoxy)-2H-1-benzopyran-2-one
3-hydroxy-4-(isopropoxy)-5-(t-butoxy)-2H-1-benzopyran-2-one
3-(acetoxy)-4-(isopropoxy)-5-(t-butoxy)-2H-1-benzopyran-2-one
3-(benzoyloxy)-4-(isopropoxy)-5-(t-butoxy)-2H-1-benzopyran-2-one
3-(methoxy)-4-(isopropoxy)-5-(t-butoxy)-2H-1-benzopyran-2-one
3,4-(diisopropoxy)-5-(t-butoxy)-2H-1-benzopyran-2-one
3-(decyloxy)-4-(isopropoxy)-5-(t-butoxy)-2H-1-benzopyran-2-one
3-(3-hexenyloxy)-4-(isopropoxy)-5-(t-butoxy)-2H-1-benzopyran-2-one
3-(geranyloxy)-4-(isopropoxy)-5-(t-butoxy)-2H-1-benzopyran-2-one
3-hydroxy-4-(decyloxy)-5-(t-butoxy)-2H-1-benzopyran-2-one
3-(acetoxy)-4-(decyloxy)-5-(t-butoxy)-2H-1-benzopyran-2-one
3-(benzoyloxy)-4-(decyloxy)-5-(t-butoxy)-2H-1-benzopyran-2-one
3-(methoxy)-4-(decyloxy)-5-(t-butoxy)-2H-1-benzopyran-2-one
3-(isopropoxy)-4-(decyloxy)-5-(t-butoxy)-2H-1-benzopyran-2-one
3,4-(didecyloxy)-5-(t-butoxy)-2H-1-benzopyran-2-one
3-(3-hexenyloxy)-4-(decyloxy)-5-(t-butoxy)-2H-1-benzopyran-2-one
3-(geranyloxy)-4-(decyloxy)-5-(t-butoxy)-2H-1-benzopyran-2-one
3-hydroxy-4-(3-hexenyloxy)-5-(t-butoxy)-2H-1-benzopyran-2-one
3-(acetoxy)-4-(3-hexenyloxy)-5-(t-butoxy)-2H-1-benzopyran-2-one
3-(benzoyloxy)-4-(3-hexenyloxy)-5-(t-butoxy)-2H-1-benzopyran-2-one
3-(methoxy)-4-(3-hexenyloxy)-5-(t-butoxy)-2H-1-benzopyran-2-one
3-(isopropoxy)-4-(3-hexenyloxy)-5-(t-butoxy)-2H-1-benzopyran-2-one
3-(decyloxy)-4-(3-hexenyloxy)-5-(t-butoxy)-2H-1-benzopyran-2-one
3,4-(di-3-hexenyloxy)-5-(t-butoxy)-2H-1-benzopyran-2-one
3-(geranyloxy)-4-(3-hexenyloxy)-5-(t-butoxy)-2H-1-benzopyran-2-one
3-hydroxy-4-(geranyloxy)-5-(t-butoxy)-2H-1-benzopyran-2-one
3-(acetoxy)-4-(geranyloxy)-5-(t-butoxy)-2H-1-benzopyran-2-one
3-(benzoyloxy)-4-(geranyloxy)-5-(t-butoxy)-2H-1-benzopyran-2-one
3-(methoxy)-4-(geranyloxy)-5-(t-butoxy)-2H-1-benzopyran-2-one
3-(isopropoxy)-4-(geranyloxy)-5-(t-butoxy)-2H-1-benzopyran-2-one
3-(decyloxy)-4-(geranyloxy)-5-(t-butoxy)-2H-1-benzopyran-2-one
3-(3-hexenyloxy)-4-(geranyloxy)-5-(t-butoxy)-2H-1-benzopyran-2-one
3,4-(digeranyloxy)-5-(t-butoxy)-2H-1-benzopyran-2-one
3,4-(dihydroxy)-5-(decyloxy)-2H-1-benzopyran-2-one
3-(acetoxy)-4-hydroxy-5-(decyloxy)-2H-1-benzopyran-2-one
3-(benzoyloxy)-4-hydroxy-5-(decyloxy)-2H-1-benzopyran-2-one
3-(isopropoxy)-4-hydroxy-5-(decyloxy)-2H-1-benzopyran-2-one
3,5-(didecyloxy)-4-hydroxy-2H-1-benzopyran-2-one
3-(3-hexenyloxy)-4-hydroxy-5-(decyloxy)-2H-1-benzopyran-2-one
3-(geranyloxy)-4-hydroxy-5-(decyloxy)-2H-1-benzopyran-2-one
3-hydroxy-4-(acetoxy)-5-(decyloxy)-2H-1-benzopyran-2-one
3,4-(diacetoxy)-5-(decyloxy)-2H-1-benzopyran-2-one
3-(benzoyloxy)-4-(acetoxy)-5-(decyloxy)-2H-1-benzopyran-2-one
3-(isopropoxy)-4-(acetoxy)-5-(decyloxy)-2H-1-benzopyran-2-one
3,5-(didecyloxy)-4-(acetoxy)-2H-1-benzopyran-2-one
3-(3-hexenyloxy)-4-(acetoxy)-5-(decyloxy)-2H-1-benzopyran-2-one
3-(geranyloxy)-4-(acetoxy)-5-(decyloxy)-2H-1-benzopyran-2-one
3-hydroxy-4-(benzoyloxy)-5-(decyloxy)-2H-1-benzopyran-2-one
3-(acetoxy)-4-(benzoyloxy)-5-(decyloxy)-2H-1-benzopyran-2-one
3,4-(dibenzoyloxy)-5-(decyloxy)-2H-1-benzopyran-2-one
3-(methoxy)-4-(benzoyloxy)-5-(decyloxy)-2H-1-benzopyran-2-one
3-(isopropoxy)-4-(benzoyloxy)-5-(decyloxy)-2H-1-benzopyran-2-one
3,5-(didecyloxy)-4-(benzoyloxy)-2H-1-benzopyran-2-one
3-(3-hexenyloxy)-4-(benzoyloxy)-5-(decyloxy)-2H-1-benzopyran-2-one
3-(geranyloxy)-4-(benzoyloxy)-5-(decyloxy)-2H-1-benzopyran-2-one
3-hydroxy-4-(methoxy)-5-(decyloxy)-2H-1-benzopyran-2-one
3-(acetoxy)-4-(methoxy)-5-(decyloxy)-2H-1-benzopyran-2-one
3-(benzoyloxy)-4-(methoxy)-5-(decyloxy)-2H-1-benzopyran-2-one
3-(isopropoxy)-4-(methoxy)-5-(decyloxy)-2H-1-benzopyran-2-one
3,5-(didecyloxy)-4-(methoxy)-2H-1-benzopyran-2-one
3-(3-hexenyloxy)-4-(methoxy)-5-(decyloxy)-2H-1-benzopyran-2-one
3-(geranyloxy)-4-(methoxy)-5-(decyloxy)-2H-1-benzopyran-2-one 3-hydroxy-4-(isopropoxy)-5-(decyloxy)-2H-1-benzopyran-2-one
3-(acetoxy)-4-(isopropoxy)-5-(decyloxy)-2H-1-benzopyran-2-one
3-(benzoyloxy)-4-(isopropoxy)-5-(decyloxy)-2H-1-benzopyran-2-one
3-(methoxy)-4-(isopropoxy)-5-(decyloxy)-2H-1-benzopyran-2-one
3,4-(diisopropoxy)-5-(decyloxy)-2H-1-benzopyran-2-one
3,5-(didecyloxy)-4-(isopropoxy)-2H-1-benzopyran-2-one
3-(3-hexenyloxy)-4-(isopropoxy)-5-(decyloxy)-2H-1-benzopyran-2-one
3-(geranyloxy)-4-(isopropoxy)-5-(decyloxy)-2H-1-benzopyran-2-one
3-hydroxy-4,5-(didecyloxy)-2H-1-benzopyran-2-one
3-(acetoxy)-4,5-(didecyloxy)-2H-1-benzopyran-2-one
3-(benzoyloxy)-4,5-(didecyloxy)-2H-1-benzopyran-2-one
3-(methoxy)-4,5-(didecyloxy)-2H-1-benzopyran-2-one
3-(isopropoxy)-4,5-(didecyloxy)-2H-1-benzopyran-2-one
3,4,5-(tridecyloxy)-2H-1-benzopyran-2-one
3-(3-hexenyloxy)-4,5-(didecyloxy)-2H-1-benzopyran-2-one
3-(geranyloxy)-4,5-(didecyloxy)-2H-1-benzopyran-2-one
3-hydroxy-4-(3-hexenyloxy)-5-(decyloxy)-2H-1-benzopyran-2-one
3-(acetoxy)-4-(3-hexenyloxy)-5-(decyloxy)-2H-1-benzopyran-2-one
3-(benzoyloxy)-4-(3-hexenyloxy)-5-(decyloxy)-2H-1-benzopyran-2-one
3-(methoxy)-4-(3-hexenyloxy)-5-(decyloxy)-2H-1-benzopyran-2-one
3-(isopropoxy)-4-(3-hexenyloxy)-5-(decyloxy)-2H-1-benzopyran-2-one
3,5-(didecyloxy)-4-(3-hexenyloxy)-2H-1-benzopyran-2-one
3,4-(di-3-hexenyloxy)-5-(decyloxy)-2H-1-benzopyran-2-one
3-(geranyloxy)-4-(3-hexenyloxy)-5-(decyloxy)-2H-1-benzopyran-2-one
3-hydroxy-4-(geranyloxy)-5-(decyloxy)-2H-1-benzopyran-2-one
3-(acetoxy)-4-(geranyloxy)-5-(decyloxy)-2H-1-benzopyran-2-one
3-(benzoyloxy)-4-(geranyloxy)-5-(decyloxy)-2H-1-benzopyran-2-one
3-(methoxy)-4-(geranyloxy)-5-(decyloxy)-2H-1-benzopyran-2-one
3-(isopropoxy)-4-(geranyloxy)-5-(decyloxy)-2H-1-benzopyran-2-one
3,5-(didecyloxy)-4-(geranyloxy)-2H-1-benzopyran-2-one
3-(3-hexenyloxy)-4-(geranyloxy)-5-(decyloxy)-2H-1-benzopyran-2-one
3,4-(digeranyloxy)-5-(decyloxy)-2H-1-benzopyran-2-one
3,4-(dihydroxy)-5-(3-hexenyloxy)-2H-1-benzopyran-2-one
3-(acetoxy)-4-hydroxy-5-(3-hexenyloxy)-2H-1-benzopyran-2-one
3-(benzoyloxy)-4-hydroxy-5-(3-hexenyloxy)-2H-1-benzopyran-2-one
3-(isopropoxy)-4-hydroxy-5-(3-hexenyloxy)-2H-1-benzopyran-2-one
3-(decyloxy)-4-hydroxy-5-(3-hexenyloxy)-2H-1-benzopyran-2-one
3,5-(di-3-hexenyloxy)-4-hydroxy-2H-1-benzopyran-2-one
3-(geranyloxy)-4-hydroxy-5-(3-hexenyloxy)-2H-1-benzopyran-2-one
3-hydroxy-4-(acetoxy)-5-(3-hexenyloxy)-2H-1-benzopyran-2-one
3,4-(diacetoxy)-5-(3-hexenyloxy)-2H-1-benzopyran-2-one
3-(benzoyloxy)-4-(acetoxy)-5-(3-hexenyloxy)-2H-1-benzopyran-2-one
3-(isopropoxy)-4-(acetoxy)-5-(3-hexenyloxy)-2H-1-benzopyran-2-one
3-(decyloxy)-4-(acetoxy)-5-(3-hexenyloxy)-2H-1-benzopyran-2-one
3,5-(di-3-hexenyloxy)-4-(acetoxy)-2H-1-benzopyran-2-one
3-(geranyloxy)-4-(acetoxy)-5-(3-hexenyloxy)-2H-1-benzopyran-2-one
3-hydroxy-4-(benzoyloxy)-5-(3-hexenyloxy)-2H-1-benzopyran-2-one
3-(acetoxy)-4-(benzoyloxy)-5-(3-hexenyloxy)-2H-1-benzopyran-2-one
3,4-(dibenzoyloxy)-5-(3-hexenyloxy)-2H-1-benzopyran-2-one
3-(methoxy)-4-(benzoyloxy)-5-(3-hexenyloxy)-2H-1-benzopyran-2-one
3-(isopropoxy)-4-(benzoyloxy)-5-(3-hexenyloxy)-2H-1-benzopyran-2-one
3-(decyloxy)-4-(benzoyloxy)-5-(3-hexenyloxy)-2H-1-benzopyran-2-one
3,5-(di-3-hexenyloxy)-4-(benzoyloxy)-2H-1-benzopyran-2-one
3-(geranyloxy)-4-(benzoyloxy)-5-(3-hexenyloxy)-2H-1-benzopyran-2-one
3-hydroxy-4-(methoxy)-5-(3-hexenyloxy)-2H-1-benzopyran-2-one
3-(acetoxy)-4-(methoxy)-5-(3-hexenyloxy)-2H-1-benzopyran-2-one
3-(benzoyloxy)-4-(methoxy)-5-(3-hexenyloxy)-2H-1-benzopyran-2-one
3-(isopropoxy)-4-(methoxy)-5-(3-hexenyloxy)-2H-1-benzopyran-2-one
3-(decyloxy)-4-(methoxy)-5-(3-hexenyloxy)-2H-1-benzopyran-2-one
3,5-(di-3-hexenyloxy)-4-(methoxy)-2H-1-benzopyran-2-one
3-(geranyloxy)-4-(methoxy)-5-(3-hexenyloxy)-2H-1-benzopyran-2-one
3-hydroxy-4-(isopropoxy)-5-(3-hexenyloxy)-2H-1-benzopyran-2-one
3-(acetoxy)-4-(isopropoxy)-5-(3-hexenyloxy)-2H-1-benzopyran-2-one
3-(benzoyloxy)-4-(isopropoxy)-5-(3-hexenyloxy)-2H-1-benzopyran-2-one
3-(methoxy)-4-(isopropoxy)-5-(3-hexenyloxy)-2H-1-benzopyran-2-one
3,4-(diisopropoxy)-5-(3-hexenyloxy)-2H-1-benzopyran-2-one
3-(decyloxy)-4-(isopropoxy)-5-(3-hexenyloxy)-2H-1-benzopyran-2-one
3,5-(di-3-hexenyloxy)-4-(isopropoxy)-2H-1-benzopyran-2-one
3-(geranyloxy)-4-(isopropoxy)-5-(3-hexenyloxy)-2H-1-benzopyran-2-one
3-hydroxy-4-(decyloxy)-5-(3-hexenyloxy)-2H-1-benzopyran-2-one 3-(acetoxy)-4-(decyloxy)-5-(3-hexenyloxy)-2H-1-benzopyran-2-one
3-(benzoyloxy)-4-(decyloxy)-5-(3-hexenyloxy)-2H-1-benzopyran-2-one
3-(methoxy)-4-(decyloxy)-5-(3-hexenyloxy)-2H-1-benzopyran-2-one
3-(isopropoxy)-4-(decyloxy)-5-(3-hexenyloxy)-2H-1-benzopyran-2-one
3,4-(didecyloxy)-5-(3-hexenyloxy)-2H-1-benzopyran-2-one
3-(3-hexenyloxy)-4-(decyloxy)-5-(3-hexenyloxy)-2H-1-benzopyran-2-one
3-(geranyloxy)-4-(decyloxy)-5-(3-hexenyloxy)-2H-1-benzopyran-2-one
3-hydroxy-4,5-(di-3-hexenyloxy)-2H-1-benzopyran-2-one
3-(acetoxy)-4,5-(di-3-hexenyloxy)-2H-1-benzopyran-2-one
3-(benzoyloxy)-4,5-(di-3-hexenyloxy)-2H-1-benzopyran-2-one
3-(methoxy)-4,5-(di-3-hexenyloxy)-2H-1-benzopyran-2-one
3-(isopropoxy)-4,5-(di-3-hexenyloxy)-2H-1-benzopyran-2-one
3-(decyloxy)-4,5-(di-3-hexenyloxy)-2H-1-benzopyran-2-one
3,4,5-(tri-3-hexenyloxy)-2H-1-benzopyran-2-one
3-(geranyloxy)-4,5-(di-3-hexenyloxy)-2H-1-benzopyran-2-one
3-hydroxy-4-(geranyloxy)-5-(3-hexenyloxy)-2H-1-benzopyran-2-one
3-(acetoxy)-4-(geranyloxy)-5-(3-hexenyloxy)-2H-1-benzopyran-2-one
3-(benzoyloxy)-4-(geranyloxy)-5-(3-hexenyloxy)-2H-1-benzopyran-2-one
3-(methoxy)-4-(geranyloxy)-5-(3-hexenyloxy)-2H-1-benzopyran-2-one
3-(isopropoxy)-4-(geranyloxy)-5-(3-hexenyloxy)-2H-1-benzopyran-2-one
3-(decyloxy)-4-(geranyloxy)-5-(3-hexenyloxy)-2H-1-benzopyran-2-one
3,5-(di-3-hexenyloxy)-4-(geranyloxy)-2H-1-benzopyran-2-one
3,4-(digeranyloxy)-5-(3-hexenyloxy-2-one
3,4-(dihydroxy)-5-(geranyloxy)-2H-1-benzopyran-2-one
3-(acetoxy)-4-hydroxy-5-(geranyloxy)-2H-1-benzopyran-2-one
3-(benzoyloxy)-4-hydroxy-5-(geranyloxy)-2H-1-benzopyran-2-one
3-(isopropoxy)-4-hydroxy-5-(geranyloxy)-2H-1-benzopyran-2-one
3-(decyloxy)-4-hydroxy-5-(geranyloxy)-2H-1-benzopyran-2-one
3-(3-hexenyloxy)-4-hydroxy-5-(geranyloxy)-2H-1-benzopyran-2-one
3,5-(digeranyloxy)-4-hydroxy-2H-1-benzopyran-2-one
3-hydroxy-4-(acetoxy)-5-(geranyloxy)-2H-1-benzopyran-2-one
3,4-(diacetoxy)-5-(geranyloxy)-2H-1-benzopyran-2-one
3-(benzoyloxy)-4-(acetoxy)-5-(geranyloxy)-2H-1-benzopyran-2-one
3-(isopropoxy)-4-(acetoxy)-5-(geranyloxy)-2H-1-benzopyran-2-one
3-(decyloxy)-4-(acetoxy)-5-(geranyloxy)-2H-1-benzopyran-2-one
3-(3-hexenyloxy)-4-(acetoxy)-5-(geranyloxy)-2H-1-benzopyran-2-one
3,5-(digeranyloxy)-4-(acetoxy)-2H-1-benzopyran-2-one
3-hydroxy-4-(benzoyloxy)-5-(geranyloxy)-2H-1-benzopyran-2-one
3-(acetoxy)-4-(benzoyloxy)-5-(geranyloxy)-2H-1-benzopyran-2-one
3,4-(dibenzoyloxy)-5-(geranyloxy)-2H-1-benzopyran-2-one
3-(methoxy)-4-(benzoyloxy)-5-(geranyloxy)-2H-1-benzopyran-2-one
3-(isopropoxy)-4-(benzoyloxy)-5-(geranyloxy)-2H-1-benzopyran-2-one
3-(decyloxy)-4-(benzoyloxy)-5-(geranyloxy)-2H-1-benzopyran-2-one
3-(3-hexenyloxy)-4-(benzoyloxy)-5-(geranyloxy)-2H-1-benzopyran-2-one
3,5-(digeranyloxy)-4-(benzoyloxy)-2H-1-benzopyran-2-one
3-hydroxy-4-(methoxy)-5-(geranyloxy)-2H-1-benzopyran-2-one
3-(acetoxy)-4-(methoxy)-5-(geranyloxy)-2H-1-benzopyran-2-one
3-(benzoyloxy)-4-(methoxy)-5-(geranyloxy)-2H-1-benzopyran-2-one
3-,4-(dimethoxy)-5-(geranyloxy)-2H-1-benzopyran-2-one
3-(isopropoxy)-4-(methoxy)-5-(geranyloxy)-2H-1-benzopyran-2-one
3-(decyloxy)-4-(methoxy)-5-(geranyloxy)-2H-1-benzopyran-2-one
3-(3-hexenyloxy)-4-(methoxy)-5-(geranyloxy)-2H-1-benzopyran-2-one
3,5-(digeranyloxy)-4-(methoxy)-2H-1-benzopyran-2-one
3-hydroxy-4-(isopropoxy)-5-(geranyloxy)-2H-1-benzopyran-2-one
3-(acetoxy)-4-(isopropoxy)-5-(geranyloxy)-2H-1-benzopyran-2-one
3-(benzoyloxy)-4-(isopropoxy)-5-(geranyloxy)-2H-1-benzopyran-2-one
3-(methoxy)-4-(isopropoxy)-5-(geranyloxy)-2H-1-benzopyran-2-one
3,4-(diisopropoxy)-5-(geranyloxy)-2H-1-benzopyran-2-one
3-(decyloxy)-4-(isopropoxy)-5-(geranyloxy)-2H-1-benzopyran-2-one
3-(3-hexenyloxy)-4-(isopropoxy)-5-(geranyloxy)-2H-1-benzopyran-2-one
3,5-(digeranyloxy)-4-(isopropoxy)-2H-1-benzopyran-2-one
3-hydroxy-4-(decyloxy)-5-(geranyloxy)-2H-1-benzopyran-2-one
3-(acetoxy)-4-(decyloxy)-5-(geranyloxy)-2H-1-benzopyran-2-one
3-(benzoyloxy)-4-(decyloxy)-5-(geranyloxy)-2H-1-benzopyran-2-one
3-(methoxy)-4-(decyloxy)-5-(geranyloxy)-2H-1-benzopyran-2-one
3-(isopropoxy)-4-(decyloxy)-5-(geranyloxy)-2H-1-benzopyran-2-one
3,4-(didecyloxy)-5-(geranyloxy)-2H-1-benzopyran-2-one
3-(3-hexenyloxy)-4-(decyloxy)-5-(geranyloxy)-2H-1-benzopyran-2-one
3,5-(digeranyloxy)-4-(decyloxy)-2H-1-benzopyran-2-one
3-hydroxy-4-(3-hexenyloxy)-5-(geranyloxy)-2H-1-benzopyran-2-one 3-(acetoxy)-4-(3-hexenyloxy)-5-(geranyloxy)-2H-1-benzopyran-2-one
3-(benzoyloxy)-4-(3-hexenyloxy)-5-(geranyloxy)-2H-1-benzopyran-2-one
3-(methoxy)-4-(3-hexenyloxy)-5-(geranyloxy)-2H-1-benzopyran-2-one
3-(isopropoxy)-4-(3-hexenyloxy)-5-(geranyloxy)-2H-1-benzopyran-2-one
3-(decyloxy)-4-(3-hexenyloxy)-5-(geranyloxy)-2H-1-benzopyran-2-one
3,4-(di-3-hexenyloxy)-5-(geranyloxy)-2H-1-benzopyran-2-one
3,5-(digeranyloxy)-4-(3-hexenyloxy)-2H-1-benzopyran-2-one
3-hydroxy-4,5-(digeranyloxy)-2H-1-benzopyran-2-one
3-(acetoxy)-4,5-(digeranyloxy)-2H-1-benzopyran-2-one
3-(benzoyloxy)-4,5-(digeranyloxy)-2H-1-benzopyran-2-one
3-(methoxy)-4,5-(digeranyloxy)-2H-1-benzopyran-2-one
3-(isopropoxy)-4,5-(digeranyloxy)-2H-1-benzopyran-2-one
3-(decyloxy)-4,5-(digeranyloxy)-2H-1-benzopyran-2-one
3-(3-hexenyloxy)-4,5-(digeranyloxy)-2H-1-benzopyran-2-one
3,4,5-(trigeranyloxy)-2H-1-benzopyran-2-one
as well as their physiologically acceptable salts.

The alkali additional salts of the above mentioned compounds can be manufactured using conventional processes, and these include such medically acceptable salts such as sodium salts, potassium salts, magnesium salts, calcium salts, as well as non-toxic amine salts such as ammonium salts. These medically acceptable salts are also included in the present invention.

The anti-allergic agent of the present invention, possessing as its active ingredient novel compounds as well as their physiologically acceptable salts, effectively treats and prevents a number of various allergic diseases.

The "allergic diseases" of the present invention include: a disease which is thought to take part in the antigen-antibody reaction which occurs at the onset of illness; an allergic disease which is caused by an extrinsic antigen stimulus; and an allergic disease generated by means of abnormalities within the immune system of the living body.

The anti-allergic agent of the present invention possessing as its active ingredients novel compounds according to the present invention as well as their physiologically acceptable salts, effectively treats and prevents the following: bronchial asthma, asthma of children, pulmonary emphysema, chronic catarrhal conjunctivitis, spring catarrh, scleritis, allergic rhinitis, hay fever, food allergy, chronic articular rheumatism, secondary arthritis deformans, acute eczema, chronic eczema, atopic dermatitis, contact dermatitis, acute urticaria, chronic urticaria, strophulus infantum, pruritus, drug eruption, autoimmune hemolytic anemia, allergic purpura, allergic agranulocytosis, allergic gastroenteritis, allergic tonsillitis, drug allergy, serum sickness, systemic lupus erythematosus, dermatomyositis, rheumatic fever, periarteritis nodosa, chronic nephritis, and chronic hepatitis.

The anti-allergic agent of the present invention, possessing as its active ingredients novel compounds as well as their physiologically acceptable salts, can be administered orally or non-orally (for example, by transfusion, intravenous administration, absorption, rectal administration, and spray inhalation), and at the time of administration, preparation to the suitable agent form for each administration method can be made.

This drug can be administered in such dosage forms as pills, capsules, granules, fine granules, powder, troches, buccal, suppositories, ointments, injection, emulsions, suspensions, syrups and sprays.

At the time of preparing these dosage forms, non-toxic additives which can be commonly employed in this type of drug include: excipients, bonding agents, disintegrator, lubricants, preservatives, anti-oxidative agents, isotonic agents, buffering agents, coating agents, sweetening agents, dissolving agent, dispersing agents, stabilizing agents, as well as coloring agents. Additionally, by means of conventional processes, formulation can be carried out.

The following is a list of typical examples of non-toxic additives.

As excipients, the following can be listed: starch, and derivatives of starch (such as dextrin, carboxymethyl starch, and the like) cellulose and derivatives of cellulose (such as methylcellulose, hydroxypropyl methylcellulose, and the like), sugars (such as lactose, white sugars, glucose, and the like), silicic acid and silicates (such as naturally occurring aluminum silicate, magnesium silicate and the like), carbonates (such as calcium carbonate, magnesium carbonate, sodium hydrogencarbonate, and the like), aluminum magnesium hydroxide, synthetic hydrotalcite, polyoxyethylene derivatives, glycerin monostearate, and sorbithane mono oleic acid.

As bonding agents, the following can be listed: starch and starch derivatives (such as alpha starches, dextrin, and the like), cellulose and derivatives of cellulose (such as ethyl cellulose, sodium carboxymethyl cellulose, hydroxypropylmethyl cellulose, and the like), gum arabic, traganth, gelatin, sugars (such as glucose, white sugar, and the like), ethanol, and polyvinyl alcohols.

As disintegrator, the following can be listed: starch and starch derivatives (such as carboxymethyl starch, hydroxypropyl starch, and the like), cellulose and cellulose derivatives (such as carboxymethyl cellulose, sodium carboxymethyl cellulose, crystal cellulose, hydroxypropylmethyl cellulose, and the like), carbonates (such as calcium carbonate, calcium hydrocarbonate, and the like), traganth, gelatins, and agar.

As lubricants, the following can be listed: stearic acid, calcium stearate, magnesium stearate, talc, silic acid and its salts (light silicic anhydrides, naturally ocurring aluminum silicates, and the like), titatnium oxide, calcium hydrogen phosphate, dry aluminum hydroxide gel, and macrogol.

As preservatives the following can be listed: paraoxy benzoic acid esters, sulfites (such as sodium sulfites, sodium pyrosulfites, and the like), phosphates (such as sodium phosphates, calcium polyphosphates, sodium polyphosphates, sodium methaphosphates, and the like), alcohols (such as chlorobutanol, benzyl alcohol, and the like), benzal conium chloride, benzethonium, phenol, cresol, chlorocresol, dihydro acetic acid, sodium dihydro acetate, glycerin sorbic acid, sugars and the like.

As anti-oxidative agents, the following can be listed: sulfites (such as sodium sulfite, sodium hydrogen sulfite, and the like), rongalite, erythorbic acid, L-ascorbic acid, cystine, acetyl, thioglycerot, butylhydroxyanisol, dibutylhydroxytoluene, propylgaliic acid, ascorbyl palmitate, dl-α-tocopherol, nordihydroguaiaretic acid, and the like.

As isotonic agents, the following can be listed: sodium chloride, sodium nitrate, potassium nitrate, dextran, glycerin, glucose and the like.

As buffering agents, the following can be listed: sodium carbonate, hydrochloride, boric acid, phosphates (such as sodium hydrophosphate), and the like.

As coating agents, the following can be listed: cellulose derivatives (such as hydroxypropyl cellulose, cellulose acetate phthalate, hydroxypropylmethyl cellulose phthalate, and the like), shellac, polyvinylpyrrolidone, polyvinylpyridines (such as poly-2-vinylpyridine, poly-2-vinyl-5-ethylpyridine and the like), polyvinylacetyl diethylaminoacetate, polyvinyl alcohol phthalate, methacrylate, methacrylate copolymers, and the like.

As sweetening agents, the following can be listed: sugars (such as glucose, white sugars, lactose and the like), sodium saccharin, sugar alcohols and the like.

As dissolving agents the following can be listed: ethylenediamine, nicotinamide, sodium saccharin, citric acid, citrates, sodium benzoic acid, soaps, polyvinylpyrrolidone, polysolvates, sorbitane fatty acids esters, glycerin, propylene glycol, benzyl alcohols, and the like.

As bases, the following can be listed: fats (such as lard and the like), vegetable oils (such as olive oil, sesame oil and the like), animal oil, lanolin acid, petrolatum, paraffin, wax, resins, bentonite, glycerin, glycol oils, higher alcohols (such as stearyl alcohol, cetanol, and the like), cellulose derivatives, and the like.

As dispersing agents, the following can be listed: gum arabic, traganth, cellulose derivatives (such as methyl cellulose and the like), stearic acid polyesters, sorbitan sesquioleate, aluminum monostearate, sodium alginate, polysolvates, sorbitane fatty acid esters, and the like.

Lastly, as stabilizing agents, the following can be listed: sulfites (such as sodium hydrogen sulfite and the like), nitrogen, carbon dioxide, and the like.

Additionally, in this formulation, it is preferred that the concentrations of the novel compounds according to the present invention and their physiologically acceptable salts generally be from 0.1 to 100% by weight, although this may vary according to the formulation.

The administrative amount of the aforementioned formulation according to the present invention can be changed over a wide range, depending on such things as the type of warm-blooded animal concerned (including human beings), the relative importance of the symptoms of illness, as well as the physician's diagnosis. However, generally as the active ingredient, in the case of oral administration, it is preferred that the administration per day per kilogram of body weight be in the range from 0.01-300mg/kg, more preferably within the range from 0.1-100mg/kg; in the case of non-oral administration, it is preferred that the administration per day per kilogram of body weight be in the range from 0.01-250 mg/kg, and more preferably within the range from 0.01-30 mg/kg However, it is possible to change the range of administration depending on the relative importance of the symptoms of illness of the patient as well as the physician's diagnosis. Additionally, the above mentioned administrative amounts can be applied once or divided over several administrations per day.

EXAMPLES

In the following, the present invention will be more concretely described through the use of examples, however, the present invention is not limited to these examples.

Example 1

1-(2',4'-bis(phenylmethoxy)phenyl)ethanone (Compound 1)

15g ($9.86 \times 10^{-2}$ mol) of 2',4'-dihydroxyacetophenone was dissolved in 150 ml of DMF, after which 32.71 g ($2.37 \times 10^{-1}$ mol) of potassium carbonate and 29.96 g ($2.37 \times 10^{-1}$ mol) of benzylchloride was added and the mixture was refluxed for 3 hours.

Following this, water was added, extracted with benzene, and the solvent was removed under reduced pressure. Recrystallization of the residue was then carried out using ethyl acetate/n-hexane, and 29.86 g of the desired compound 1 was obtained (yield=92.5%).

$^1$H-NMR (CDCl$_3$, δ-TMS) 7.85 (d, 1H, J=9.0 Hz), 7.30~7.60 (m, 10H), 6.50~6.70 (m, 2H), 5.09 (s,2H), 5.03 (s,2H), 2.53 (s,3H)

Example 2

Methyl-β-oxo-2', 4'-bis(phenylmethoxy)benzenepropanate (Compound 2)

5.76 g ($1.44 \times 10^{-1}$ mol) of 60% sodium hydride was suspended in 82.17 g ($9.12 \times 10^{-1}$ mol) of dimethyl carbonate, after which 29.86 g ($9.12 \times 10^{-2}$ mol) of 1-(2',4'-bis(phenylmethoxy)phenyl)ethanone was added and the mixture was heated for 1 hour at a temperature of 70°~75° C. After this was completed, water and 6N-hydrochloric acid were added, the mixture was brought to pH 8, and extracted with methyl chloride. The solvent was then removed under reduced pressure, after which the residue was purified by means of silica gel column chromotography, and 32.46 g of the desired compound 2 was obtained (yield=91.1%).

$^1$H-NMR (CDCl$_3$, δ-TMS) 7.80–8.00 (m, 1H), 7.20–7.60 (m, 10H), 6.50–6.80 (m, 2H), 5.09 (s,2H), 5.03 (s,2H), 3.89 (s,2H), 3.55 (s,3H)

Example 3

Methyl-β-oxo-2',4'-bis(phenylmethoxy)-2-(benzoyloxy)benzenepropanate (Compound 3)

3.99 g ($9.97 \times 10^{-2}$ mol) of 60% sodium hydride was suspended in 40 ml of benzene, and the suspension was titrated by a 100 ml solution of 32.46 g ($8.31 \times 10^{-2}$ mol) of methyl-β-oxo-2',4'-bis(phenylmethoxy)benzenepropanate in benzene at room temperature. After this mixture was agitated at room temperature for one hour, it was cooled in an ice bath, tit rated by a 100 ml solution of 20.13 g ($8.31 \times 10^{-2}$ mol) of dibenzoyl peroxide in benzene, and then agitated at room temperature for 3 hours. Water was added and after the benzene layer divided, the water layer was extracted using methylchloride, following which the solvent of the organic layer, combined with the aforementioned benzene layer, was removed under reduced pressure. The residue was then purified by means of silica gel column chromotography, and 39.13 g of the desired compound 3 was obtained (yield=92.2%).

$^1$H-NMR (CDCl$_3$, δ-TMS)
7.80–8.30 (m, 1H), 7.20–7.60 (m, 15H), 6.50–6.80 (m, 2H), 5.09 (s,2H), 5.03 (s,2H), 3.71 (s, 1H), 3.63 (s,3H)

Example 4

3-(benzoyloxy)-4,7-dihydroxy-2H-1-benzopyran-2-one (Compound 4)

300 ml of ethanol was added to 39.13 g ($7.66 \times 10^{-2}$ mol) of methyl-$\beta$-oxo-2',4'-bis(phenylmethoxy)-2-(benzyloxy)benzenepropanate, after which 3.9 g of 10% palladium on activated carbon was added. After this mixture was refluxed for 4 hours under hydrogen atmosphere, the catalyst was filtered, and the filtrate was concentrated under reduced pressure. 150 ml of methanol and 150 ml of 35% hydrochloric acid were added to the residue, and after refluxing for 30 minutes, the methanol was removed under reduced pressure. The crystals which precipitated out were then collected, washed, and dried under reduced pressure and 19.45 g of the desired compound 4 was obtained (yield=85.1%).

$^1$H-NMR (DMSO-$d_6$, $\delta$-TMS)
11.44 (bs, 1H), 10.61 (bs, 1H), 8.10~8.20 (m, 2H), 7.50-7.80 (m, 4H), 6.70~6.90 (m, 2H)
IR (KBr, cm$^{-1}$) 3550, 3200, 1720, 1680, 1630, 1580
Melting point 250°-253° C.
Elemental analysis value: $C_{16}H_{10}O_6$
Theoretical value (%): C 64.43; H 3.38; O 32.19
Actual measured value (%): C 64.40; H 3.39; O 32.21

Example 5

3,4,7-trihydroxy-2H-1-benzopyran-2-one (Compound 5)

160 ml of anhydrous methanol was added to 6.80 g ($2.28 \times 10^{-2}$ mol) of 3-(benzoyloxy)-4,7-dihydroxy-2H-1-benzopyran-2-one under argon atmosphere, after which the mixture was agitated, cooled in an ice bath, then titrated with 43 ml of an anhydrous methanol solution containing 4.31 g ($7.98 \times 10^{-2}$ mol) of sodium methoxide, and then agitated for 2 hours at room temperature. In an ice bath, 21.76 g of Amberlyst 15 was added, and the mixture was agitated for 2 hours at room temperature. After the Amberlyst 15 was filtered, the filtrate was concentrated under reduced pressure, and 3.80 g of a crude product was obtained. Recrystalization was then carried out using tetrahydrofuran/n-hexene, after which 2.71 g of the desired compound 5 was obtained (yield=61.2%).

$^1$H-NMR (DMSO-$d_6$, $\delta$-TMS) 11.00 (bs, 1H), 10.16 (bs, 1H), 8.73 (bs, 1H), 7.58 (d, 1H, J=8.8Hz), 6.70~6.90 (m, 2H)
IR (KBr, cm$^{-1}$) 3400, 3200, 1700, 1670, 1620, 1580
Melting point: 262°~264° C.
Elemental analysis value: $C_9H_6O_5$
Theoretical value (%): C 51.44; H 2.88; O 45.68
Actual measured value (%): C 51.45; H 2.89; O 45.66

Example 6

Methyl-$\beta$-oxo-2',4'-bis(phenylmethoxy)-2-(acetoxy) benzenepropanate (Compound 6)

300 ml of chloroform was added to 30.58 g ($5.99 \times 10^{-2}$ mol) of methyl-$\beta$-oxo-2',4'-bis(phenylmethoxy) benzenepropanate, and agitated. In an ice bath, 26.56 g ($1.20 \times 10^{-1}$ mol) of copper(II)bromide was added, and the mixture was agitated at room temperature for 24 hours. Following this, water was added, extracted with methylene chloride, and the solvent was concentrated under reduced pressure. 150 ml of acetic acid and 9.83 g ($1.20 \times 10^{-1}$ mol) of sodium acetate were added to the residue, and the mixture was refluxed for 3 hours. Water was then added, extracted with methylene chloride, and the solvent was removed under reduced pressure. The residue was then purified by silica gel column chromotography, and 19.42 g of the desired compound was obtained (yield=72.3%).

$^1$H-NMR (CDCl$_3$, $\delta$-TMS) 7.80~8.30 (m, 1H), 7.20-7.60 (m, 10H), 6.50~6.80 (m, 2H), 5.09 (s,2H), 5.03 (s,2H), 3.71 (s, 1H), 3.63 (s,3H), 1.86 (s,3H)

Example 7

3-(acetoxy)-4,7-(dihydroxy)-2H-1-benzopyran-2-one (Compound 7)

In Example 4, 5.13 g ($1.18 \times 10^{-2}$ mol) methyl-$\beta$-oxo-2',4'-bis(phenylmethoxy)-2-(acetoxy) benzenepropanate was used in place of methyl-$\beta$-oxo-2',4'-bis(phenylmethoxy)-2-(benzoyloxy)benzenepropanate, and 2.18 g of the desired compound 7 was obtained (yield=78%)

$^1$H-NMR (DMSO-$d_6$, $\delta$-TMS) 11.44 (bs, 1H), 10.61 (bs, 1H), 7.68 (d, 1H, J=8.8Hz), 6.70~6.90 (m, 2H), 1.79 (s,3H)
IR (KBr, cm$^{-1}$) 3550, 3200, 1720, 1680, 1630, 1580
Elemental analysis value: $C_{11}H_8O_6$
Theoretical value (%): C 55.94; H 3.41; O 40.65
Actual measured value (%): C 55.95; H 3.39; O 40.66

Example 8

4-(benzoyloxy)-3,7-(dihydroxy)-2H-1-benzopyran-2-one (Compound 8)

After 1.26 g ($6.49 \times 10^{-3}$ mol) of 3,4,7-trihydroxy-2H-1-benzopyran-2-one was added and dissolved in 50 ml of DMSO, 0.55 g ($6.49 \times 10^{-3}$ mol) of sodium bicarbonate was added. Following this, in an ice bath, 0.912 g ($6.49 \times 10^{-3}$ mol) of benzoylchloride was added, and the mixture was agitated at room temperature for 5 hours. After the solid was filtered, water was added, extracted with benzene, and removal of the solvent was carried out under reduced pressure. The crude product obtained was purified by recrystallization, and 0.99 g of the desired compound 8 was obtained (yield=51.6%).

$^1$H-NMR (DMSO-D$_6$, $\delta$TMS) 11.44 (bs, 1H), 10.61 (bs, 1H), 8.10~8.20(m, 2H), 7.50-7.80 (m, 4H), 6.70~6.90 (m, 2H)
IR (KBr, cm$^{-1}$) 3400, 3200, 1720, 1680, 1630, 1580
Elemental analysis value: $C_{16}H_{10}O_6$
Theoretical value (%): C 64.43; H 3.38; O 32.19
Actual measured value (%): C 64.55; H 3.39; O 32.06

Example 9

4-(decyloxy)-3,7-(dihydroxy)-2H-1-benzopyran-2-one (Compound 9)

In Example 8, decylbromide was used in place of benzoylchloride, and 3.08 g of the desired compound 9 was obtained from 3.15 g ($1.62 \times 10^{-2}$ mol) of 3,4,7-trihydroxy-2H-1-benzopyran-2-one (yield=53%).

$^1$H-MNR (DMSO-$d_6$, $\delta$-TMS) 11.23 (bs, 1H), 10.16 (bs, 1H), 7.58 (d, 1H, J=8.8 Hz), 6.70~6.90 (m, 2H), 3.32 (t, 2H, J=7.0 Hz), 1.24-1.70 (m, 16H), 0.91 (t, 3H, J=6.0 Hz)
IR (KBr, cm$^{-1}$) 3350, 3200, 1720, 1680, 1630, 1580
Elemental analysis value: $C_{19}H_{26}O_5$
Theoretical value (%): C 68.24; H 7.84; O 23.92
Actual measured value (%): C 68.15; H 7.93; O 23.92

Example 10

3-(acetoxy)-4-(benzoyloxy)-7-hydroxy-2H-1-benzopyran-2-one (Compound 10)

In Example 8, 3.42 g ($1.45 \times 10^{-2}$ mol) of 3-(acetoxy)-4,7-(dihydroxy)-2H-1-benzopyran-2-one was used in place of 3,4,7-trihydroxy-2H-1-benzopyran-2-one, and 2.94 g of the desired compound 10 (yield=57%) was obtained.

$^1$H-NMR (DMSO-d$_6$, δ-TMS) 11.24 (bs, 1H), 8.10~8.20 (m, 2H), 7.50~7.80 (m, 4H), 6.70-6.90 (m, 2H), 1.75 (s, 3H)

IR (KBr, cm$^{-1}$) 3400, 3200, 1720, 1680, 1630, 1580
Elemental analysis value: C$_{18}$H$_{12}$O$_7$
Theoretical value (%): C 63.53; H 3.55; O 32.91
Actual measured value (%): C 63.65; H 3.59; O 32.76

Example 11

3,4,7-(triacetoxy)-2H-1-benzopyran-2-one (Compound 11)

In Example 8, 1.42 g ($6.01 \times 10^{-3}$ mol) of 3-(acetoxy)-4,7-(dihydroxy)-2H-1-benzopyran-2-one was used in place of 3,4,7-trihydroxy-2H-1-benzopyran-2-one, potassium carbonate was used in place of sodium bicarbonate, acetyl chloride was used in place of benzoyl chloride, and 1.10 g of the desired compound 11 was obtained (yield=57%).

$^1$H-NMR (DMSO-d$_6$, δ-TMS) 7.58 (s, 1H, J=8.8 Hz), 6.70-6.90 (m, 2H), 2.01 (s,3H), 1.80 (s,3H), 1.75 (s,3H)

IR (KBr, cm$^{-1}$) 1720, 1680, 1630, 1580
Elemental analysis value: C$_{15}$H$_{12}$O$_8$
Theoretical value (%): C 56.25; H 3.78; O 39.97
Actual measured value (%): C 56.35; H 3.79; O 39.86

Example 12

3-(acetoxy)-4-(decyloxy)-7-hydroxy-2H-1-benzopyran-2-one (Compound 12)

In Example 8, 3.61 g ($1.43 \times 10^{-2}$ mol) of 3-(acetoxy)-4,7-(dihydroxy)-2H-1-benzopyran-2-one was used in place of 3,4,7-trihydroxy-2H-1-benzopyran-2-one, decylbromide was used in place of benzoyl chloride, and 2.69 g of the desired compound 12 (yield=47%) was obtained.

$^1$H-NMR (DMSO-d$_6$, δ-TMS) 11.01 (bs, 1H), 7.68 (d, 1H, J=8.8 Hz), 6.70~6.90(m, 2H), 3.34 (t, 2H, J=7.0 Hz), 1.80 (s,3H), 1.24~1.70 (m, 16H), 0.82 (t, 3H, J=6.0 Hz)

IR (KBr, cm$^{-1}$) 3550, 3200, 1720, 1680, 1630, 1580
Elemental analysis value: C$_{21}$H$_{28}$O$_6$
Theoretical value (%): C 67.00; H 7.50; O 25.50
Actual measured value (%): C 67.12; H 7.48; O 25.40

Example 1

3-(isopropoxy)-4-(benzoyloxy)-7-hydroxy-2H-1-benzopyran-2-one (Compound 13)

In Example 8, 2.53 g ($8.48 \times 10^{-3}$ mol) of 3,7-(dihydroxy)-4-(benzoyloxy)-2H-1-benzopyran-2-one was used in place of 3,4,7-trihydroxy-2H-1-benzopyran-2-one, isopropylbromide was used in place of benzoylchloride, and 1.56 g of the desired compound 13 (yield=54%) was obtained..

$^1$H-NMR (DMSO-d$_6$, δ-TMS) 11.34 (bs,1H), 8.10~8.20 (m, 2H), 7.50~7.80 (m, 4H), 6.70~6.90 (m, 2H), 3.92 (m, 1H), 1.15 (d, 6H, J=6.0 Hz)

IR (KBr, cm$^{-1}$) 3200, 1720, 1680, 1630, 1580
Elemental analysis value: C$_{19}$H$_{16}$O$_6$
Theoretical value (%): C 67.05; H 4.75; O 28.20
Actual measured value (%): C 67.14; H 4.69; O 28.17

Example 14

3-(methoxy)-4,7-(dihydroxy)-2H-1-benzopyran-2-one (Compound 14)

In Example 5, 1.50 g ($6.00 \times 10^{-3}$ mol) of 3-(methoxy)-4-(acetoxy)-7-hydroxy-2H-1-benzopyran-2-one was used in place of 3-(benzoyloxy)-4,7-(dihydroxy)-2H-1-benzopyran-2-one, and 0.75 g of the desired compound 14 (yield=60%) was obtained.

$^1$H-NMR (DMSO-d$_6$, δ-TMS) 11.00 (bs, 1H), 10.16 (bs, 1H), 7.58 (d, 1H, J=8.8 Hz), 6.70-6.90 (m, 2H), 3.72 (s,3H)

IR (KBr, cm$^{-1}$) 3400, 3200, 1720, 1680, 1630, 1580
Elemental analysis value: C$_{10}$H$_8$O$_5$
Theoretical value (%): C 57.69; H 3.87; O 38.43
Actual measured value (%): C 57.60; H 3.92; O 38.48

Example 15

3-(isopropoxy)-4,7-(dihydroxy)-2H-1-benzopyran-2-one (Compound 15)

In Example 5, 1.55 g ($5.57 \times 10^{-3}$ mol) of 3-(isopropoxy)-4-(acetoxy)-7-hydroxy-2H-1-benzopyran-2-one was used in place of 3-(benzoyloxy)-4,7-(dihydroxy)-2H-1-benzopyran-2-one, and 0.76 g (yield=58%) of the desired compound 15 was obtained.

$^1$H-NMR (DMSO-d$_6$, δ-TMS) 11.23 (bs, 1H), 10.16 (bs, 1H), 7.58 (d, 1H, J=8.8 Hz), 6.70-6.90 (m, 2H), 3.95 (m, 1H), 1.16 (d, 6H, J=6.0 Hz)

IR (KBr, cm$^{-1}$) 3300, 3200, 1720, 1680, 1630, 1580
Elemental analysis value: C$_{12}$H$_{12}$O$_5$
Theoretical value (%): C 61.01; H 5.12; O 33.87
Actual measured value (%): C 61.05; H 5.18; O 33.77

Example 16

3-(decyloxy)-4,7-(dihydroxy)-2H-1-benzopyran-2-one (Compound 16)

In Example 5, 1.53 g ($3.82 \times 10^{-3}$ mol) of 3-(decyloxy)-4-(acetoxy)-7-hydroxy-2H-1-benzopyran-2-one was used in place of 3-(benzoyloxy)-4,7-(dihydroxy)-2H-1-benzopyran-2-one, and 0.90 g (yield=66%) of the desired compound 16 was obtained.

$^1$H-NMR (DMSO-d$_6$, δ-TMS) 11.00 (bs, 1H), 10.16 (bs, 1H), 7.58 (d, 1H, J=8.8 Hz), 6.70~6.90 (m, 2H), 3.39 (t, 2H, J=7.0 Hz), 1.24~1.70 (m, 16H), 0.84 (t, 3H, J=6.0 Hz)

IR (KBr, cm$^{-1}$) 3400, 3200, 1720, 1680, 1630, 1580
Elemental analysis value: C$_{19}$H$_{26}$O$_5$
Theoretical value (%): C 68.24; H 7.84; O 23.92
Actual measured value (%): C 68.19; H 7.91; O 23.90

Example 17

3,4-(dimethoxy)-7-hydroxy-2H-1-benzopyran-2-one (Compound

In Example 8, 2.69 g ($1.29 \times 10^{-2}$ mol) of 3,7-(dihydroxy)-4-(methoxy)-2H-1-benzopyran-2-one was used in place of 3,4,7-trihydroxy-2H-1-benzopyran-2-one, methyl iodide was used in place of benzoylchloride, and 1.76 g (yield=61%) of the desired compound 17 was obtained.

$^1$H-NMR (DMSO-d$_6$, δ-TMS) 11.13 (bs, 1H), 7.53 (d, 1H, J=8.8 Hz), 6.70~6.90 (m, 2H), 3.85 (s,3H), 3.75 (s,3H)

IR (KBr, cm$^{-1}$) 3200, 1700, 1670, 1620, 1580

Elemental analysis value: $C_{11}H_{10}O_5$
Theoretical value (%): C 59.46; H 4.54; O 36.01
Actual measured value (%): C 59.55; H 4.49; O 35.96

Example 18

3-(methoxy)-4-(isopropoxy)-7-hydroxy-2H-1-benzopyran-2-one (Compound 18)

In Example 8, 3.50 g ($1.48 \times 10^{-2}$ mol) of 3,7-(dihydroxy)-4-(isopropoxy)-2H-1-benzopyran-2-one was used in place of 3,4,7-trihydroxy-2H-1-benzopyran-2-one, methyliodide was used in place of benzoylchloride, and 2.04 g (yield=55%) of the desired compound 18 was obtained.

$^1$H-NMR (DMSO-d$_6$, δ-TMS) 11.23 (bs, 1H), 7.58 (d, 1H, J=8.8 Hz), 6.70~6.90 (m, 2H), 3.95 (m, 1H), 3.70 (s, 3H), 1.16 (d, 6H, J=6.0 Hz)

IR (KBr, cm$^{-1}$) 3200, 1720, 1680, 1630, 1580
Elemental analysis value: $C_{13}H_{14}O_5$
Theoretical value (%): C 62.39; H 5.64; O 31.97
Actual measured value (%): C 62.31; H 5.69; O 32.00

Example 19

3-(geranyloxy)-4,7-(dihydroxy)-2H-1-benzopyran-2-one (Compound 19)

In Example 5, 1.60 g ($4.30 \times 10^{-3}$ mol) of 3-(geranyloxy)-4-(acetoxy)-7-hydroxy-2H-1-benzopyran-2-one was used in place of 3-(benzoyloxy)-4,7-(dihydroxy)-2H-1-benzopyran-2-one, and 0.85 g (yield=60%) of the desired compound 19 was obtained.

$^1$H-NMR(DMSO-d$_6$, δ-TMS) 11.43 (bs, 1H), 10.80 (bs, 1H), 7.66 (d, 1H, J=8.8 Hz), 6.70~6.90 (m,2H), 5.48 (bt, 1H, J=7.0 Hz), 5.10 (bt, 1H, J=7.0 Hz), 4.01 (d, 2H, J=7.0 Hz), 1.95~2.20 (m, 4H), 1.85 (m, 9H)

IR (KBr, cm$^{-1}$) 3500, 3200, 1720, 1680, 1630, 1580
Elemental analysis value: $C_{19}H_{22}O_5$
Theoretical value (%): C 69.07; H 6.71; O 24.22
Actual measured value (%): C 69.05; H 6.59; O 24.36

Example 20

3,7-(dihydroxy)-4-(geranyloxy)-2H-1-benzopyran-2-one (Compound 20)

In Example 8, geranylbromide was used in place of benzoylchloride, and 2.55 g (yield=63%) of the desired compound 20 was obtained from 2.38 g ($1.2 \times 10^{-2}$ mol) of 3,4,7-trihydroxy-2H-1-benzopyran-2-one.

$^1$H-NMR (DMSO-d$_6$, δ-TMS) 11.42 (bs, 1H), 9.31 (bs, 1H), 7.62 (d, 1H, J=8.8 Hz), 6.70~6.90 (m, 2H), 5.47 (bt, 1H, J=7.0 Hz), 5.12 (bt, 1H, J=7.0 Hz), 4.00 (d, 2H, J=7.0 Hz), 1.9542.20 (m, 4H), 1.55~1.85 (m, 9H)

IR (KBr, cm$^{-1}$) 3550, 3200, 1720, 1680, 1630, 1580
Elemental analysis value: $C_{19}H_{22}O_5$
Theoretical value (%): C 69.07; H 6.71; O 24.22
Actual measured value (%): C 69.13; H 6.72; O 24.15

Example 21

3-(geranyloxy)-4-(acetoxy)-7-hydroxy-2H-1-benzopyran-2-one (Compound 21)

In Example 8, 2.01 g ($6.08 \times 10^{-3}$ mol) of 3-(geranyloxy)-4,7-(dihydroxy)-2H-1-benzopyran-2-one was used in place of 3, 4,7-trihydroxy-2H-1-benzopyran-2-one, acetylchloride was used in place of benzoylchloride and 1.40 g (yield=62%) of the the desired compound 21 was obtained.

$^1$H-NMR (DMSO-d$_6$, δ-TMS) 11.42 (bs,1H), 10.75 (bs, 1H), 7.64 (d, 1H, J=8.8 Hz), 6.70~6.90 (m, 2H), 5.47 (bt, 1H, J=7.0 Hz), 5.13 (bt, 1H, J=7.0 Hz), 4.02 (d, 2H, J=7.0 Hz), 1.95~2.20 (m, 4H), 1.70 (s, 3H), 1.5541.85 (m, 9H)

IR(KBr, cm$^{-1}$) 3500, 3200, 1710, 1660, 1630, 1580
Elemental analysis value: $C_{21}H_{24}O_6$
Theoretical value (%): C 67.73; H 6.50; O 25.78
Actual measured value (%): C 67.69; H 6.55; O 25.76

Example 22

3-(geranyloxy)-4,7-(diacetoxy)-2H-1-benzopyran-2-one (Compound 22)

In Example 8, 2.00 g ($6.08 \times 10^{-3}$ mol) of 3-(geranyloxy)-4,7-(dihydroxy)-2H-1-benzopyran-2-one was used in place of 3,4,7-trihydroxy-2H-1-benzopyran-2-one, acetylchloride was used in place of benzoylchloride, potassium carbonate was used in place of sodium bicarbonate, and 1.80 g (yield=69%) of the desired compound was obtained.

$^1$H-NMR (DMSO-d$_6$, δ-TMS) 7.64 (d, 1H, J=8.8 Hz), 6.70~6.90 (m, 2H), 5.47 (bt, 1H, J=7.0 Hz), 5.13 (bt, 1H, J=7.0 Hz), 4.02 (d, 2H, J=7.0 Hz), 1.95~2.20 (m, 4H), 1.99 (s,3H), 1.73 (s,3H) , 1.70 (s,3H), 1.55~1.85 (m, 9H)

IR (KBr, cm$^{-1}$) 1710, 1660, 1630, 1580
Elemental analysis value: $C_{23}H_{26}O_6$
Theoretical value (%): C 69.33; H 6.58; O 24.09
Actual measured value (%): C 69.49; H 6.55; 24.02

Example 23

3-(benzoyloxy)-4-(geranyloxy)-7-hydroxy-2H-1-benzopyran-2-one (Compound 23)

In Example 8, 1.59 g ($5.33 \times 10^{-3}$ mol) of 3-(benzoyloxy)-4,7-(dihydroxy)-2H-1-benzopyran-2-one was used in place of 3,4,7-trihydroxy-2H-1-benzopyran-2-one, geranylbromide was used in place of benzoylchloride, and 1.34 g (yield=58%) of the desired compound 23 was obtained.

$^1$H-NMR(DMSO-d$_6$, δ-TMS) 11.46 (bs, 1H) , 8.10~8.20 (m, 2H), 7.50~7.80 (m, 4H), 6.70~6.90 (m, 2H), 5. 46 (bt, 1H, J=7.0 Hz), 5.15 (bt, 1H, J=7.0 Hz) , 4.00 (d, 2H, J=7.0 Hz), 1.95~2.20 (m, 4H), 1.55~1.85 (m, 9H)

IR(KBr, cm$^{-1}$) 3200, 1720, 1680, 1630, 1580
Elemental analysis value: $C_{26}H_{26}O_6$
Theoretical value (%): C 71.82; H 6.03; O 22.10
Actual measured value (%): C 71.76; H 6.18; O 22.06

Example 24

3-(geranyloxyl)-4-(methoxy)-7-hydroxy-2H-1-benzopyran-2-one (Compound 24)

In Example 8, 1.86 g ($5.63 \times 10^{-3}$ mol) of 3-(geranyloxy)-4,7-(dihydroxy)-2H-1-benzopyran-2-one was used in place of 3, 4,7-trihydroxy-2H-1-benzopyran-2-one, methyliodide was used in place of benzoylchloride, and 1.36 g (yield=70%) of the desired compound 24 was obtained.

$^1$H-NMR (DMSO-d$_6$, δ-TMS) 11.48 (bs, 1H), 7.68 (d, 1H, J=8.8 Hz), 6.70~6.90 (m, 2H), 5.45 (bt, 1H, J=7.0 Hz), 5.18 (bt, 1H, J=7.0 Hz), 4.03 (d, 2H, J=7.0 Hz), 3.71 (s,3H), 1.95~2.20 (m,4H), 55~1.85 (m, 9H)

IR (KBr, cm$^{-1}$) 3200, 1720, 1690, 1630, 1580, 1550
Elemental analysis value: $C_{20}H_{24}O_5$
Theoretical value (%): C 69.75; H 7.02; O 23.23
Actual measured value (%): C 69.88; H 7.05; O 23.07

Example 25

3-(isopropoxy)-4-(geranyloxy)-7-hydroxy-2H-1-benzopyran-2-one (Compound 25)

In Example 8, 1.78 g ($5.39 \times 10^{-3}$ mol) of 3,7-(dihydroxy)-4-(geranyloxy)-2H-1-benzopyran-2-one was used in place of 3,4,7-trihydroxy-2H-1-benzopyran-2-one, isopropylbromide was used in place of benzoylchloride, and 1.42 g (yield=71%) of the desired compound 25 was obtained.

$^1$H-NMR (DMSO-$d_6$, δ-TMS) 11.48 (bs, 1H), 7.63 (d, 1H, J=8.8 Hz), 6.70~6.90 (m, 2H), 5.48 (bt, 1H, J=7.0 Hz), 5.14 (bt, 1H, J=7.0 Hz), 4.01 (d, 2H, J=7.0 Hz), 3.90 (m, 1H), 1.95~2.20 (m, 4H), 1.55~1.85 (m, 9H), 1.13 (d, 6H, J=6.0 Hz)
IR (KBr, cm$^{-1}$) 3200, 1710, 1690, 1630, 1580, 1550
Elemental analysis value: $C_{22} H_{28} O_5$
Theoretical value (%): C 70.94; H 7.52; O 21.48
Actual measured value (%): C 71.06; H 7.51; O 21.43

Example 26

3,4-(digeranyloxy)-7-hydroxy-2H-1-benzopyran-2-one (Compound 26)

In Example 8, 1.43 g ($4.33 \times 10^{-3}$ mol) of 3-(geranyloxy)-4,7-(dihydroxy)-2H-1-benzopyran-2-one was used in place of 3,4,7-trihydroxy-2H-1-benzopyran-2-one, geranylbromide was used in place of benzoylchloride, and 1.05 g (yield=51%) of the desired compound 26 was obtained.

$^1$H-NMR (DMSO-$d_6$, δ-TMS) 11.49 (bs, 1H), 7.68 (d, 1H, J=8.8 Hz), 6.70~6.90 (m, 2H), 5.10~5.50 (m, 4H), 4.05 (d, 2H, J=7.0 Hz), 4.03 (d, H, J=6.0 Hz), 1.95~2.20 (m, 8H), 1.55~1.85 (m, 18H)
IR (KBr, cm$^{-1}$) 3200, 1720, 1680, 1630, 1580, 1550
Elemental analysis value: $C_{29} H_{38} O_5$
Theoretical value (%): C 74.65; H 8.21; O 17.14
Actual measured value (%): C 74.68; H 8.25; O 17.07

Example 27

3-(benzoyloxy)-4-hydroxy-7-(methoxy)-2H-1-benzopyran-2-one (Compound 27)

In Example 1, 4'-methoxy-2'-hydroxyacetophenone was used in place of 2',4'-dihydroxyacetophenone, after which Examples 2~4 were carried out, and 1.52 g (yield=72%) of the desired compound 27 was obtained from 2.83 g ($6.76 \times 10^{-3}$ mol) of methyl-β-oxo-2'-(phenylmethoxy)-4'-(methoxy)-2-(benzoyloxy) benzenepropanate.

$^1$H-NMR (DMSO-$d_6$, δ-TMS) 10.61 (bs,1H), 8.10~8.20 (m, 2H), 7.50~7.80 (m, 4H), 6.70~6.90 (m, 2H), 3.71 (s,3H)
IR (KBr, cm$^{-1}$) 3350, 1720, 1680, 1630, 1580
Elemental analysis value: $C_{17} H_{12} O_6$
Theoretical value (%): C 65.38; H 3.89; O 30.74
Actual measured value (%): C 65.41; H 3.82; O 30.77

Example 28

3,4-dihydroxy-7-(methoxy)-2H-1-benzopyran-2-one (Compound 28)

In Example 5, 1.59 g ($5.09 \times 10^{-3}$ mol) of 3-(benzoyloxy)-4-hydroxy-7-(methoxy)-2H-1-benzopyran-2-one was used in place of 3-(benzoyloxy)-4,7-dihydroxy-2H-1-benzopyran-2-one, from which 0.84 g (yield=79%) of the desired compound 28 was obtained.

$^1$H-NMR (DMSO-$d_6$, δ-TMS) 10.11 (bs, 1H), 8.73 (bs, 1H), 7.58 (d, 1H, J=8.8 Hz), 6.70~6.90 (m, 2H), 3.79 (s,3H)
IR (KBr, cm$^{-1}$) 3400, 1700, 1670, 1620, 1580
Elemental analysis value: $C_{10} H_8 O_5$
Theoretical value (%): C 57.69; H 3.87; O 38.43
Actual measured value (%): C 57.76; H 3.90; O 38.34

Example 29

3-(acetoxy)-4-hydroxy-7-(methoxy)-2H-1-benzopyran-2-one (Compound 29)

In Example 4, 5.49 g ($1.54 \times 10^{-2}$ mol) of methyl-β-oxo-2'-(phenylmethoxy)-4'-(methoxy)-2-(acetoxy) benzenepropanate was used in place of methyl-β-oxo-2',4'-bis(phenylmethoxy)-2-(benzoyloxy)benzenepropanate, and 3.12 g (yield=81%) of the desired compound 29 was obtained.

$^1$H-NMR (DMSO-$d_6$, δ-TMS) 8.79 (bs, 1H), 7.58 (d, 1H, J=8.8 Hz), 6.70~6.90(m, 2H), 3.75 (s, 3H), 1.81 (s, 3H)
IR(KBr, cm$^{-1}$) 1720, 1680, 1630, 1580
Elemental analysis value: $C_{12} H_{10} O_6$
Theoretical value (%): C 57.60; H 4.03; O 38.37
Actual measured value (%): C 57.75; H 4.09; O 38.16

Example 30

3,7-(dimethoxy)-4-(benzoyloxy)-2H-1-benzopyran-2-one (Compound 30)

In Example 8, 1.56 g ($5.00 \times 10^{-3}$ mol) of 3-hydroxy-4-(benzoyloxy)-7-(methoxy)-2H-1-benzopyran-2-one was used in place of 3,4,7-trihydroxy-2H-1-benzopyran-2-one, methyliodide was used in place of benzoylchloride, and 0.86 g (yield=53%) of the desired compound 30 was obtained.

$^1$H-NMR (DMSO-$d_6$, δ-TMS) 8.10~8.20 (m, 2H), 7.50~7.80 (m, 4H), 6.70~6.90 (m, 2H), 3.85 (s, 3H), 3.71 (s, 3H)
IR (KBr, cm$^{-1}$) 1720, 1680, 1630, 1580
Elemental analysis value: $C_{18} H_{14} O_6$
Theoretical value (%): C 66.25; H 4.32; O 29.42
Actual measured value (%): C 66.14; H 4.39; O 29.47

Example 31

3-hydroxy-4-(acetoxy)-7-(methoxy)-2H-1-benzopyran-2-one (Compound 31)

In Example 8, 2.54 g ($1.22 \times 10^{-2}$ mol) of 3,4-(dihydroxy)-7-(methoxy)-2H-t-benzopyran-2-one was used in place of 3,4,7-trihydroxy-2H-1-benzopyran-2-one, acetylchloride was used in place of benzoylchloride and 1.65 g (yield=54%) of the desired compound 31 was obtained.

$^1$H-NMR (DMSO-$d_6$, δ-TMS) 9.02 (bs, 1H), 7.56 (d, 1H, J=8.8 Hz), 6.70~6.90 (m, 2H), 3.82 (s,3H), 1.81 (s,3H)
IR (KBr, cm$^{-1}$) 1720, 1680, 1630, 1580
Elemental analysis value: $C_{12} H_{10} O_6$
Theoretical value (%): C 57.60; H 4.03; O 38.37
Actual measured value (%): C 57.68; H 4.19; O 38.13

Example 32

3-(acetoxy)-4-(isopropoxy)-7-(methoxy)-2H-1-benzopyran-2-one (Compound 32)

In Example 8, 2.42 g ($9.67 \times 10^{-3}$ mol) of 3-(acetoxy)-4-hydroxy-7-(methoxy)-2H-1-benzopyran-2-one was used in place of 3,4,7-trihydroxy-2H-1-benzopyran- 2-one, isopropylbromide was used in place of benzoylchloride, and 1.59 g (yield=56%) of the desired compound 32 was obtained.

$^1$H-NMR (DMSO-d$_6$, δ-TMS) 7.59 (d, 1H, J=8.8 Hz), 6.70~6.90 (m, 2H), 3.95 (m, 1H), 3.83 (s, 3H), 1.84 (s, 3H), 1.16 (d, 6H, J=6.0 Hz)

IR (KBr, cm$^{-1}$) 1720, 1680, 1630, 1580

Elemental analysis value: C$_{15}$H$_{16}$O$_6$

Theoretical value (%): C 61.64; H 5.52; O 32.85

Actual measured value (%): C 61.72; H 5.47; O 32.81

Example 33

3-hydroxy-4,7-(dimethoxy)-2H-1-benzopyran-2-one (Compound 33)

In Example 8, 3.25 g (1.56×10$^{-2}$ mol) of 3,4-(dihydroxy)-7-(methoxy)-2H-1-benzopyran-2-one was used in place of 3,4,7-trihydroxy-2H-1-benzopyran-2-one, methyliodide was used in place of benzoylchloride, and 1.70 g (yield=49%) of the desired compound 33 was obtained.

$^1$H-NMR (DMSO-d$_6$, δ-TMS) 9.02 (bs, 1H), 7.60 (d, 1H, J=8.8 Hz), 6.70~6.90 (m, 2H), 3.82 (s, 3H), 3.71 (s, 3H)

IR (KBr, cm$^{-1}$) 3200, 1720, 1680, 1630, 1580

Elemental analysis value: C$_{11}$H$_{10}$O$_5$

Theoretical value (%): C 59.46; H 4.54; O 36.01

Actual measured value (%): C 59.39; H 4.59; O 36.02

Example 34

3-(isopropoxy)-4-hydroxy-7-(methoxy)-2H-1-benzopyran-2-one (Compound 34)

In Example 5, 1.42 g (4.86×10$^{-3}$ mol) of 3-(isopropoxy)-4-(acetoxy)-7-(methoxy)-2H-1-benzopyran-2-one was used in place of 3-(benzoyloxy)-4,7-(dihydroxy)-2H-1-benzopyran-2-one, and 0.76 g (yield=56%) of the desired compound 34 was obtained.

$^1$H-NMR (DMSO-d$_6$, δ-TMS) 10.17 (bs, 1H), 7.59 (d, 1H, J=8.8 Hz), 6.70~6.90 (m, 2H), 3.95 (m, 1H), 3.83 (s,3H), 1.16 (d, 6H, J=6.0 Hz)

IR(KBr, cm$^{-1}$) 3200, 1720, 1680, 1630, 1580

Elemental analysis value: C$_{13}$H$_{14}$O$_5$

Theoretical value (%): C 62.39; H 5.64; O 31.97

Actual measured value (%): C 62.50; H 5.67; O 31.83

Example 35

3-(benzoyloxy)-4-(acetoxy)-7-(methoxy)-2H-1-benzopyran-2-one (Compound 35)

In Example 8, 2.22 g (7.12×10$^{-3}$ mol) of 3-(benzoyloxy)-4-hydroxy-7-(methoxy)-2H-1-benzopyran-2-one was used in place of 3,4,7-trihydroxy-2H-1-benzopyran-2-one, acetylchloride was used in place of benzoylchloride, and 1.40 g (yield=53%) of the desired compound 35 was obtained.

$^1$H-NMR (DMSO-d$_6$, δ-TMS) 8.10~8.20 (m, 2H), 7.50~7.80 (m, 4H), 6.70~6.90 (m, 2H), 3.81 (s, 3H), 1.89 (s, 3H)

IR (KBr, cm$^{-1}$) 1720, 1680, 1630, 1580

Elemental analysis value: C$_{19}$H$_{14}$O$_7$

Theoretical value (%): C 64.40; H 3.98; O 31.61

Actual measured value (%): C 64.34; H 3.92; O 31.74

Example 36

3,7-(dimethoxy)-4-(decyloxy)-2H-1-benzopyran-2-one (Compound 36)

In Example 8, 2.55 g (6.85×10$^{-3}$ mol) of 3-hydroxy-4-(decyloxy)-7-(methoxy)-4-hydroxy-2H-1-benzopyran-2-one was used in place of 3,4,7-trihydroxy-2H-1-benzopyran-2-one, methyliodide was used in place of benzoylchloride, and 1.93 g (yield=51%) of the desired compound 36 was obtained.

$^1$H-NMR (DMSO-d$_6$, δ-TMS) 7.61 (d, 1H, J=8.8 Hz), 6.70~6.90 (m, 2H), 3.81 (s, 3H), 3.66 (s, 3H), 3.34 (t, 2H, J=7.0 Hz), 1.24~1.70 (m, 16H), 0.82 (t, 3H, J=6.0 Hz)

IR (KBr, cm$^{-1}$) 1720, 1680, 1630, 1580

Elemental analysis value: C$_{21}$H$_{30}$O$_5$

Theoretical value (%): C 68.54; H 8.63; O 22.83

Actual measured value (%): C 68.65; H 8.59; O 22.76

Example 37

3-(geranyloxy)-4-hydroxy-7-(methoxy)-2H-1-benzopyran-2-one (Compound 37)

In Example 5, 1.68 g (4.34×10$^{-3}$ mol) of 3-(geranyloxy)-4-(acetoxy)-7-(methoxy)-2H-1-benzopyran-2-one was used in place of 3-(benzoyloxy)-4,7-(dihydroxy)-2H-1-benzopyran-2-one, and 1.06 g (yield=70%) of the desired compound 37 was obtained.

$^1$H-NMR(DMSO-d$_6$, δ-TMS) 8.80 (bs, 1H), 7.63 (d, 1H, J=8.8 Hz), 6.70~6.90 (m, 2H), 5.43 (bt, 1H, J=7.0 Hz), 5.07 (bt, 1H, J=7.0 Hz), 4.01 (d, 2H, J=7.0 Hz), 3.82 (s, 3H), 2.00~2.21 (m, 4H), 1.52~1.85 (m, 9H)

IR (KBr, cm$^{-1}$) 3200, 1720, 1680, 1630, 1580

Elemental analysis value: C$_{20}$H$_{24}$O$_5$

Theoretical value (%): C 69.75; H 7.02; O 23.23

Actual measured value (%): C 69.71; H 7.09; O 23.20

Example 38

3-hydroxy-4-(geranyloxy)-7-(methoxy)-2H-1-benzopyran-2-one (Compound 38)

In Example 8, 1.49 g (7.16×10$^{-3}$ mot) of 3,4-(dihydroxy)-7-(methoxy)-2H-1-benzopyran-2-one was used in place of 3,4,7-trihydroxy-2H-1-benzopyran-2-one, geranylbromide was used in place of benzoylchloride, and 1.31 g (yield=53%) of the desired compound 38 was obtained.

$^1$H-NMR (DMSO-d$_6$, δ-TMS) 9.62 (bs, 1H), 7.59 (d, 1H, J=8.8 Hz), 6.70~6.90 (m, 2H), 5.45 (bt, 1H, J=7.0 Hz), 5.02 (bt, 1H, J=7.0 Hz), 4.08 (d, 2H, J=7.0 Hz), 3.84 (s,3H), 2.00~2.21 (m,4H), 1.52~1.85 (m, 9H)

IR (KBr, cm$^{-1}$) 3200, 1730, 1670, 1630, 1580

Elemental analysis value: C$_{20}$H$_{24}$O$_5$

Theoretical value (%): C 69.75; H 7.02; O 23.23

Actual measured value (%): C 69.70; H 7.01; O 23.29

Example 39

3-(geranyloxy)-4-(benzoyloxy)-7-(methoxy)-2H-1-benzopyran-2-one (Compound 39)

In Example 8, 1.73 g (5.54×10$^{-3}$ mol) of 3-hydroxy-4-(benzoyloxy)-7-(methoxy)-2H-1-benzopyran-2-one was used in place of 3,4,7-trihydroxy-2H-1-benzopyran-2-one, geranylbromide was used in place of benzoylchloride, and 1.59 g (yield=64%) of the desired compound 39 was obtained.

$^1$H-NMR (DMSO-d$_6$, δ-TMS) 8.10~8.20 (m, 2H), 7.50~7.80 (m, 4H), 6.70~6.90 (m, 2H), 5.45 (bt, 1H, J=7.0 Hz), 5.03 (bt, 1H, J=7.0 Hz), 4.08 (d, H, J=7.0 Hz), 3.82 (s, 3H), 2.00~2.21 (m, 4H), 1.52~1.85 (m, 9H)

IR (KBr, cm$^{-1}$) 1730, 1670, 1630, 1580, 1520

Elemental analysis value: C$_{27}$H$_{28}$O$_6$

Theoretical value (%): C 72.30; H 6.29; O 21.41

Actual measured value (%): C 72.36; H 6.25; O 21.39

Example 40

3-(acetoxy)-4-(geranyloxy)-7-(methoxy)-2H-1-benzopyran-2-one (Compound 40)

In Example 8, 1.29 g ($5.16 \times 10^{-3}$ mol) of 3-(acetoxy)-4-hydroxy-7-(methoxy)-2H-1-benzopyran-2-one was used in place of 3,4,7-trihydroxy-2H-1-benzopyran-2-one, geranylbromide was used in place of benzoylchloride, and 1.53 g (yield=66%) of the desired compound 40 was obtained.

$^1$H-NMR (DMSO-d$_6$, δ-TMS) 7.58 (d, 1H, J=8.8 Hz), 6.70~6.90 (m, 2H), 5.42 (bt, 1H, J=7.0 Hz), 5.04 (bt, 1H, J=7.0 Hz), 4.09 (d, 2H, J=7.0 Hz), 3.80 (s,3H), 2.00~2.21 (m, 4H), 1.76 (s, 3H), 1.52~1.85 (m, 9H)

IR (KBr, cm$^{-1}$) 1730, 1670, 1630, 1580, 1520

Elemental analysis value: C$_{22}$H$_{26}$O$_6$

Theoretical value (%): C 68.38; H 6.78; O 24.84

Actual measured value (%): C 68.35; H 6.76; O 24.89

Example 41

3-(geranyloxy)-4-(isopropoxy)-7-(methoxy)-2H-1-benzopyran-2-one (Compound 41)

In Example 8, 1.38 g ($5.51 \times 10^{-3}$ mol) of 3-hydroxy-4-(isopropoxy)-7-(methoxy)-2H-t-benzopyran-2-one was used in place of 3,4,7-trihydroxy-2H-1-benzopyran-2-one, geranylbromide was used in place of benzoylchloride, and 1.47 g (yield=69%) of the desired compound 41 was obtained.

$^1$H-NMR (DMSO-d$_6$, δ-TMS) 7.59 (d, 1H, J=8.8 Hz), 6.70~6.90 (m, 2H), 5.40 (bt, H, J=7.0 Hz), 5.04 (bt, 1H, J=7.0 Hz), 4.09 (d, 2H, J=7.0 Hz), 3.92 (m, 1H), 3.83 (s, 3H), 2.00~2.21 (m, 4H), 1.56 (s, 3H), 1.52~1.85 (m, 9H), 1.15 (d, 6H, J=6.0 Hz)

IR (KBr, cm$^{-1}$) 1720, 1680, 1630, 1580, 1550

Elemental analysis value: C$_{22}$H$_{26}$O$_6$

Theoretical value (%): C 68.38; H 6.78; O 24.84

Actual measured value (%): C 68.35; H 6.76; O 24.89

Example 42

3,7-(dimethoxy)-4-(geranyloxy)-2H-1-benzopyran-2-one (Compound 42)

In Example 8, 1.58 g ($7.11 \times 10^{-3}$ mol) of 3,7-(dimethoxy)-4-hydroxy-2H-1-benzopyran-2-one was used in place of 3,4,7-trihydroxy-2H-1-benzopyran-2-one, geranylbromide was used in place of benzoylchloride, and 1.73 g (yield=68%) of the desired compound 42 was obtained. 1H-NMR (DMSO-d$_6$, δ-TMS) 7.60 (d, 1H, J=8.8 Hz), 6.70~6.90 (m, 2H), 5.45 (bt, H, J=7.0 Hz), 5.01 (bt, 1H, J=7.0 Hz), 4.06 (d, 2H, J=7.0 Hz), 3.80 (S, 3H), 3.64 (s, 3H), 2.00~2.21 (m, 4H), 1.52~1.85 (m, 9H)

IR (KBr, cm$^{-1}$) 1730, 1670, 1630, 1580, 1520

Elemental analysis value: C$_{21}$H$_{26}$O$_5$

Theoretical value (%): C 70.37; H 7.31; O 22.32

Actual measured value (%): C 70.31; H 7.34; O 22.35

Example 43

3,4-(digeranyloxy)-7-(methoxy)-2H-1-benzopyran-2-one (Compound 43)

In Example 8, 1.50 g ($4.36 \times 10^{-3}$ mol) of 3-hydroxy-4-(geranyloxy)-7-(methoxy)-2H-1-benzopyran-2-one was used in place of 3,4,7-trihydroxy-2H-1-benzopyran-2-one, geranylbromide was used in place of benzoylchloride, and 1.05 g (yield=50%) of the desired compound 43 was obtained.

$^1$H-NMR (DMSO-d$_6$, δ-TMS) 7.63 (d, 1H, J=8.8 Hz), 6.70~6.90 (m, 2H), 5.10~5.50 (m, 4H), 4.09 (d, 2H, J=7.0 Hz), 4.05 (d, 2H, J=6.0 Hz), 3.83 (s, 3H), 1.95~2.20 (m, 8H), 1.55~1.85 (m, 18H)

IR (KBr, cm$^{-1}$) 1710, 1670, 1630, 1580, 1550

Elemental analysis value: C$_{30}$H$_{38}$O$_5$

Theoretical value (%): C 75.28; H 8.00; O 16.72

Actual measured value (%): C 75.07; H 8.15; O 16.78

Example 44

3-(benzoyloxy)-4-(hydroxy)-7-(isopropoxy)-2H-1-benzopyran-2-one (Compound 44)

In Example 1, 4'-(isopropoxy)-2'-hydroxyacetophenone was used in place of 2',4'-dihydroxyacetophenone, after which Examples 2~4 were carried out, and 2.68 g (yield=75%) of the desired compound 44 was obtained from 69 g ($1.05 \times 10^{-2}$ mol) of methyl-β-oxo-2'-(phenylmethoxy)-4'-(isopropoxy)-2-(benzoyloxy)benzenepropanate.

$^1$H-NMR (DMSO-d$_6$, δ-TMS) 10.60 (bs, 1H), 8.10~8.20 (m, 2H), 7.50~7.80 (m, 4H), 6.70~6.90 (m, 2H), 3.90 (m, 1H), 1.13 (d, 6H, J=6.0 Hz)

IR (KBr, cm$^{-1}$) 3400, 1720, 1680, 1630, 1580

Elemental analysis value: C$_{19}$H$_{16}$O$_6$

Theoretical value (%): C 67.05; H 4.75; O 28.20

Actual measured value (%): C 67.13; H 4.73; O 28.14

Example 45

3,4-dihydroxy-7-(isopropoxy)-2H-1-benzopyran-2-one (Compound 45)

In Example 5, 2.53 g ($7.43 \times 10^{-3}$ mol) of 3-(benzoyloxy)-4-hydroxy-7-(isopropoxy)-2H-1-benzopyran-2-one was used in place of 3-(benzoyloxy)-4,7-dihydroxy-2H-1-benzopyran-2-one, and 1.42 g (yield=81%) of the desired compound 45 was obtained.

$^1$H-NMR (DMSO-d$_6$, δ-TMS) 10.21 (bs,1H), 8.76 (bs, 1H), 7.62 (d, 1H, J=8.8 Hz), 6.70~6.90 (m, 2H), 3.87 (m, 1H), 1.14 (d, 6H, J=6.0 Hz)

IR (KBr, cm$^{-1}$) 3400, 1700, 1670, 1620, 1580

Elemental analysis value: C$_{12}$H$_{12}$O$_5$

Theoretical value (%): C 62.90; H 4.87; O 32.23

Actual measured value (%): C 62.82; H 4.89; O 32.25

Example 46

3-hydroxy-4-(acetoxy)-7-(isopropoxy)-2H-1-benzopyran-2-one (Compound 46)

In Example 8, 2.10 g ($8.89 \times 10^{-3}$ mol) of 3,4-(dihydroxy)-7-(isopropoxy)-2H-1-benzopyran-2-one was used in place of 3,4,7-trihydroxy-2H-1-benzopyran-2-one, acetylchloride was used in place of benzoylchloride, and 1.43 g (yield=58%) of the desired compound 46 was obtained.

$^1$H-NMR (DMSO-d$_6$, δ-TMS) 9.26 (bs, 1H), 8.10~8.20 (m, 2H), 7.50~7.80 (m, 4H), 6.70~6.90 (m, 2H), 3.34 (m, 1H), 1.86 (s,3H), 1.15 (d, 6H, J=6.0 Hz)

IR (KBr, cm$^{-1}$) 3200, 1720, 1680, 1630, 1580

Elemental analysis value: C$_{14}$H$_{14}$O$_6$

Theoretical value (%): C 60.43; H 5.07; O 34.50

Actual measured value (%): C 60.52; H 5.14; O 34.34

Example 47

3,4-(dibenzoyloxy)-7-(isopropoxy)-2H-1-benzopyran-2-one (Compound 47)

In Example 8, 3.52 g ($1.03 \times 10^{-2}$ mol) of 3-(benzoyloxy)-4-hydroxy-7-(isopropoxy)-2H-1-benzopyran-2-one was used in place of 3,4,7-trihydroxy-2H-1-benzopyran-2-one, and 2.06 g (yield=52%) of the desired compound 47 was obtained.

$^1$H-NMR (DMSO-d$_6$, δ-TMS) 8.00~8.20 (m, 4H), 7.20~7.90 (m, 7H), 6.70~6.90 (m, 2H), 3.49 (m, 1H), 1.12 (d, 6H, J=6.0 Hz)

IR (KBr, cm$^{-1}$) 1700, 1670, 1620, 1580
Elemental analysis value: C$_{26}$ H$_{20}$ O$_7$
Theoretical value (%): C 70.26; H 4.54; O 25.20
Actual measured value (%): C 70.28; H 4.39; O 25.33

Example 48

3-(decyloxy)-4-hydroxy-7-(isopropoxy)-2H-1-benzopyran-2-one (Compound 48)

In Example 5, 2.00 g (4.52×10$^{-3}$ mol) of 3-(decyloxy)-4-(acetoxy)-7-(isopropoxy)-2H-1-benzopyran-2-one was used in place of 3-(benzoyloxy)-4,7-(dihydroxy)-2H-1-benzopyran-2-one, and 1.12 g (yield=62%) of the desired compound 48 was obtained.

$^1$H-NMR (DMSO-d$_6$, δ-TMS) 10.61 (bs, 1H), 7.58 (d, 1H, J=8.8 Hz), 6.70~6.90 (m, 2H), 3.46 (m, 1H), 3.34 (t, 2H, J=7.0 Hz), 1.24~1.70 (m, 16H), 1.12 (d, 6H, J=6.0 Hz), 0.83 (t, 3H, J=6.0 Hz)

IR (KBr, cm$^{-1}$) 3400, 1700, 1670, 1620, 1580
Elemental analysis value: C$_{22}$ H$_{32}$ O$_5$
Theoretical value (%): C 70.18; H 8.57; O 21.25
Actual measured value (%): C 70.25; H 8.51; O 21.24

Example 49

3-hydroxy-4-(methoxy)-7-(isopropoxy)-2H-1-benzopyran-2-one (Compound 49)

In Example 8, 2.01 g (8.51×10$^{-3}$ mol) of 3,4-(dihydroxy)-7-(isopropoxy)-2H-1-benzopyran-2-one was used in place of 3,4,7-trihydroxy-2H-1-benzopyran-2-one, methyliodide was used in place of benzoylchloride, and 1.75 g (yield=82%) of the desired compound 49 was obtained.

$^1$H-NMR (DMSO-d$_6$, δ-TMS) 9.23 (bs, 1H), 8.10~8.20 (m, 2H), 7.50~7.80 (m, 4H), 6.70~6.90 (m, 2H), 3.34 (m, 1H), 3.66 (s, 3H), 1.14 (d, 6H, J=6.0 Hz)

IR (KBr, cm$^{-1}$) 3200, 1720, 1680, 1630, 1580
Elemental analysis value: C$_{13}$ H$_{14}$ O$_5$
Theoretical value (%): C 62.39; H 5.64; O 31.97
Actual measured value (%): C 62.50; H 5.58; O 31.92

Example 50

3-(methoxy)-4-(decyloxy)-7-(isopropoxy)-2H-1-benzopyran-2-one (Compound 50)

In Example 8, 2.15 g (5.37×10$^{-3}$ mol) of 3-hydroxy-4-(decyloxy)-7-(isopropoxy)-2H-1-benzopyran-2-one was used in place of 3,4,7-trihydroxy-2H-1-benzopyran-2-one, methyliodide was used in place of benzoylchloride, and 1.80 g (yield=81%) of the desired compound 50 was obtained.

$^1$H-NMR (DMSO-d$_6$, δ-TMS) 7.58 (d, 1H, J=8.8 Hz), 6.70~6.90 (m, 2H), 3.50 (m, 1H,) 3.62 (t, 2H, J=7.0 Hz), 3.28 (s,3H), 1.24~1.70 (m, 16H), 1.12 (d, 6H, J=6.0 Hz), 0.90 (t, 3H, J=6.0 Hz)

IR (KBr, cm$^{-1}$) 1700, 1670, 1620, 1580
Elemental analysis value: C$_{23}$ H$_{34}$ O$_5$
Theoretical value (%): C 70.74; H 8.78; O 20.49
Actual measured value (%): C 70.62; H 8.75; O 20.63

Example 51

3-(acetoxy)-4-(methoxy)-7-(isopropoxy)-2H-1-benzopyran-2-one (Compound 51)

In Example 8, 4.01 g (1.44×10$^{-2}$ mol) of 3-(acetoxy)-4-hydroxy-7-(isopropoxy)-2H-1-benzopyran-2-one was used in place of 3,4,7-trihydroxy-2H-1-benzopyran-2-one, methyliodide was used in place of benzoylchloride, and 3.20 g (yield=76%) of the desired compound 51 was obtained.

$^1$H-NMR (DMSO-d$_6$, δ-TMS) 7.58 (d, 1H, J=8.8 Hz), 6.70~6.90 (m, 2H), 3.86 (s, 3H), 3.34 (m, 1H), 1.83 (s, 3H), 1.12 (d, 6H, J=6.0 Hz)

IR (KBr, cm$^{-1}$) 1720, 1680, 1630, 1580
Elemental analysis value: C$_{15}$ H$_{16}$ O$_6$
Theoretical value (%): C 61.64; H 5.52; O 32.85
Actual measured value (%): C 61.62; H 5.75; O 32.63

Example 52

3,7-(diisopropoxy)-4-(benzoyloxy)-2H-1-benzopyran-2-one (Compound 52)

In Example 8, 2.32 g (6.82×10$^{-3}$ mol) of 3-hydroxy-4-(benzoyloxy)-7-(isopropoxy)-2H-1-benzopyran-2-one was used in place of 3,4,7-trihydroxy-2H-1-benzopyran-2-one, isopropylbromide was used in place of benzoylchloride, and 1.98 g (yield=76%) of the desired compound 52 was obtained.

$^1$H-NMR (DMSO-d$_6$, δ-TMS) 8.10~8.20 (m, 2H), 7.50~7.80 (m, 4H), 6.70~6.90 (m, 2H), 3.45 (m, 1H), 3.34 (m, 1H), 1.18 (d, 6H, J=6.0 Hz), 1.14 (d, 6H, J=6.0 Hz)

IR (KBr, cm$^{-1}$) 1720, 1680, 1630, 1580
Elemental analysis value: C$_{22}$ H$_{22}$ O$_6$
Theoretical value (%): C 69.10; H 5.80; O 25.10
Actual measured value (%): C 69.23; H 5.79; O 24.98

Example 53

3-(geranyloxy)-4-hydroxy-7-(isopropoxy)-2H-1-benzopyran-2-one (Compound 53)

In Example 5, 2.10 g (5.07×10$^{-3}$ mol) of 3-(geranyloxy)-4-(acetoxy)-7-(isopropoxy)-2H-1-benzopyran-2-one was used in place of 3-(benzoyloxy)-4,7-(dihydroxy)-2H-1-benzopyran-2-one, and 1.11 g (yield=59%) of the desired compound 53 was obtained.

$^1$H-NMR (DMSO-d$_6$, δ-TMS) 10.61 (bs, 1H), 7.65 (d, 1H, J=8.8 Hz), 6.70~6.90 (m, 2H), 5.44 (bt, 1H, J=7.0 Hz), 5.07 (bt, 1H, J=7.0 Hz), 4.01 (d, 2H, J=7.0 Hz), 3.52 (m, 1H), 2.00~2.21 (m, 4H), 1.52~1.85 (m, 9H), 1.12 (d, 6H, J=6.0 Hz)

IR (KBr, cm$^{-1}$) 3200, 1720, 1680, 1630, 1580
Elemental analysis value: C$_{22}$ H$_{28}$ O$_5$
Theoretical value (%): C 70.94; H 7.58; O 21.48
Actual measured value (%): C 70.81; H 7.59; O 21.60

Example 54

3-hydroxy-4-(geranyloxy)-7-(isopropoxy)-2H-1-benzopyran-2-one (Compound 54)

In Example 8, 1.57 g (6.65×10$^{-3}$ mol) of 3,4-(dihydroxy)-7-(isopropoxy)-2H-1-benzopyran-2-one was used in place of 3,4,7-trihydroxy-2H-1-benzopyran-2-one, geranylbromide was used in place of benzoylchloride, and 1.43 g (yield=58%) of the desired compound 54 was obtained.

$^1$H-NMR (DMSO-d$_6$, δ-TMS) 8.92 (bs, 1H), 7.59 (d, 1H, J=8.8 Hz), 6.70~6.90 (m, 2H), 5.42 (bt, 1H, J=7.0 Hz), 5.04 (bt, 1H, J=7.0 Hz), 4.03 (d, 2H, J=7.0 Hz), 3.50 (m, 1H), 2.00~2.21 (m, 4H), 1.52~1.85 (m, 9H), 1.13 (d, 6H, J=6.0 Hz)

IR (KBr, cm$^{-1}$) 3200, 1720, 1670, 1630, 1580, 1520

Elemental analysis value: $C_{22}H_{28}O_5$

Theoretical value (%): C 70.94; H 7.58; O 21.48

Actual measured value (%): C 70.99; H 7.62; O 21.39

Example 55

3-(geranyloxy)-4,7-(diisopropoxy)-2H-1-benzopyran-2-one (Compound 55)

In Example 8, 1.61 g (5.79×10$^{-3}$ mol) of 3-hydroxy-4,7-(diisopropoxy)-2H-1-benzopyran-2-one was used in place of 3,4,7-trihydroxy-2H-1-benzopyran-2-one, geranylbromide was used in place of benzoylchloride, and 1.63 g (yield=68%) of the desired compound 55 was obtained.

$^1$H-NMR (DMSO-d$_6$, δ-TMS) 7.56 (d, 1H, J=8.8 Hz), 6.70~6.90 (m, 2H), 5.46 (bt, 1H, J=7.0 Hz), 5.05 (bt, 1H, J=7.0 Hz), 4.03 (d, 2H, J=7.0 Hz), 3.50 (m, 1H), 3.42 (m, 1H), 2.00~2.21 (m, 4H), 1.52~1.85 (m, 9H), 1.13 (d, 6H, J=6.0 Hz), 1.10 (d, 6H, J=6.0 Hz)

IR (KBr, cm$^{-1}$) 1730, 1660, 1630, 1570, 1520

Elemental analysis value: $C_{25}H_{34}O_5$

Theoretical value (%): C 71.61; H 8.51; O 19.88

Actual measured value (%): C 71.59; H 8.54; O 19.87

Example 56

3-(methoxy)-4-(geranyloxy)-7-(isopropoxy)-2H-1-benzopyran-2-one (Compound 56)

In Example 8, 1.32 g (3.54×10$^{-3}$ mol) of 3-hydroxy-4-(geranyloxy)-7-(isopropoxy)-2H-1-benzopyran-2-one was used in place of 3,4,7-trihydroxy-2H-1-benzopyran-2-one, methyliodide was used in place of benzoylchloride, and 0.88 g (yield=64%) of the desired compound 56 was obtained.

$^1$H-NMR (DMSO-d$_6$, δ-TMS) 7.57 (d, 1H, J=8.8 Hz), 6.70~6.90 (m, 2H), 5.46 (bt, 1H, J=7.0 Hz), 5.09 (bt, 1H, J=7.0 Hz), 4.02 (d, 2H, J=7.0 Hz), 3.76 (s,3H), 3.48 (m, 1H), 2.00~2.21 (m, 4H), 1.52~1.85 (m, 9H), 1.13 (d, 6H, J=6.0 Hz)

IR (KBr, cm$^{-1}$) 1730, 1660, 1630, 1570, 1520

Elemental analysis value: $C_{23}H_{30}O_5$

Theoretical value (%): C 71.48; H 7.82; O 20.70

Actual measured value (%): C 71.46; H 7.79; O 20.75

Example 57

3,4-(digeranyloxy)-7-(isopropoxy)-2H-1-benzopyran-2-one (Compound 57)

In Example 8, 1.26 g (3.38×10$^{-3}$ mol) of 3-hydroxy-4-(geranyloxy)-7-(isopropoxy)-2H-1-benzopyran-2-one was used in place of 3,4,7-trihydroxy-2H-1-benzopyran-2-one, geranylbromide was used in place of benzoylchloride, and 0.96 g (yield=56%) of the desired compound 57 was obtained.

$^1$H-NMR (DMSO-d$_6$, δ-TMS) 7.58 (d, 1H, J=8.8 Hz), 6.70~6.90 (m, 2H), 5.10~5.50 (m, 4H), 4.08 (d, 2H, J=7.0 Hz), 4.02 (d, 2H, J=7.0 Hz), 3.42 (m, 1H), 3.26 (s,3H), 1.90~2.20 (m,8H), 1.50~1.90 (m, t8H), 1.12 (d, 6H, J=6.0 Hz)

IR (KBr, cm$^{-1}$) 1720, 1680, 1630, 1570, 1520

Elemental analysis value: $C_{32}H_{44}O_5$

Theoretical value (%): C 75.55; H 8.72; O 15.73

Actual measured value (%): C 75.48; H 8.74; O 15.78

Example 58

3-(benzoyloxy)-4-hydroxy-7-(decyloxy)-2H-1-benzopyran-2-one (Compound 58)

In Example 1, 4'-(decyloxy)-2'-hydroxyacetophenone was used in place of 2',4'-dihydroxyacetophenone, after which Examples 2~4 were carried out, and 2.17 g (yield=63%) of the desired compound 58 was obtained from 4.23 g (7.44×10$^{-3}$ mol) of methyl-β-oxo-2'-(phenylmethoxy)-4'-(decyloxy)-2-(benzoyloxy) benzenepropanate.

$^1$H-NMR (DMSO-d$_6$, δ-TMS) 10.21 (bs, 1H), 8.1.0~8.30 (m, 2H), 7.50~7.90 (m, 4H), 6.70~6.90 (m, 2H), 3.34 (t, 2H, J=7.0 Hz), 1.24~1.70 (m, 16H), 0.83 (t, 3H, J=6.0 Hz)

IR (KBr, cm$^{-1}$) 3200, 1700, 1670, 1620, 1580

Elemental analysis value: $C_{26}H_{30}O_6$

Theoretical value (%): C 71.21; H 6.90; O 21.89

Actual measured value (%): C 71.37; H 6.99; O 21.64

Example 59

3,4-(dihydroxy)-7-(decyloxy)-2H-1-benzopyran-2-one (Compound

In Example 5, 2.34 g (5.06×10$^{-3}$ mol) of 3-(benzoyloxy)-4-hydroxy-7-(decyloxy)-2H-1-benzopyran-2-one was used in place of 3-(benzoyloxy)-4,7-(dihydroxy)-2H-1-benzopyran-2-one, and 1.47 g (yield=81%) of the desired compound 59 was obtained.

$^1$H-NMR (DMSO-d$_6$, δ-TMS) 10.21 (bs, 1H), 8.77 (bs, 1H), 7.52 (d, 1H, J=8.8 Hz), 6.70~6.90 (m, 2H), 3.34 (t, 2H, J=7.0 Hz), 1.24~1.70 (m, 16H), 0.83 (t, 3H, J=6.0 Hz)

IR (KBr, cm$^{-1}$) 3400, 1700, 1670, 1620, 1580

Elemental analysis value: $C_{19}H_{26}O_5$

Theoretical value (%): C 68.24.; H 7.84; O 23.92

Actual measured value (%): C 68.25; H 7.79; O 23.96

Example 60

3-hydroxy-4-(acetoxy)-7-(decyloxy)-2H-1-benzopyran-2-one (Compound 60)

In Example 8, 2.37 g (6.61×10$^{-3}$ mol) of 3,4-(dihydroxy)-7-(decyloxy)-2H-1-benzopyran-2-one was used in place of 3,4,7-trihydroxy-2H-1-benzopyran-2-one, acetylchloride was used in place of benzoylchloride, and 1.59 g (yield=60%) of the desired compound 60 was obtained.

$^1$H-NMR (DMSO-d$_6$, δ-TMS) 9.21 (bs, 1H), 7.54 (d, 1H, J=8.8 Hz), 6.70~6.90 (m, 2H), 3.35 (t, 2H, J=7.0 Hz), 1.85 (s,3H), 1.24~1.70 (m, 16H), 0.83 (t, 3H, J=6.0 Hz)

IR (KBr, cm$^{-1}$) 3200, 1700, 1670, 1620, 1580

Elemental analysis value: $C_{21}H_{28}O_6$

Theoretical value (%): C 67.00; H 7.50; O 25.50

Actual measured value (%): C 67.10; H 7.56; O 25.34

Example 61

3,4-(diacetoxy)-7-(decyloxy)-2H-1-benzopyran-2-one (Compound 61)

In Example 8, 3.17 g (7.92×10$^{-3}$ mol) of 3-(acetoxy)-4-hydroxy-7-(decyloxy)-2H-1-benzopyran-2-one was used in place of 3,4,7-trihydroxy-2H-1-benzopyran-2-one, acetylchloride was used in place of benzoylchloride, and 2.35 g (yield=67%) of the desired compound 61 was obtained.

$^1$H-NMR (DMSO-d$_6$, δ-TMS)

7.53 (d, 1H, J=8.8 Hz), 6.70~6.90 (m, 2H), 3.35 (t, 2H, J=7.0 Hz), 1.85 (s, 3H), 1.83 (s, 3H), 1.24~1.70 (m, 16H), 0.83 (t, 3H, J=6.0 Hz)

IR (KBr, cm$^{-1}$)

1700, 1670, 1620, 1580

Elemental analysis value: $C_{23} H_{30} O_7$

Theoretical value (%): C 66.01; H 7.23; O 26.76

Actual measured value (%): C 65.89; H 7.29; O 26.82

Example 62

3-(methoxy)-4-hydroxy-7-(decyloxy)-2H-1-benzopyran-2-one (Compound 62)

In Example 5, 1.54 g (3.72×10$^{-3}$ mol) of 3-(methoxy)-4-(acetoxy)-7-(decyloxy)-2H-1-benzopyran-2-one was used in place of 3-(benzoyloxy)-4,7-(dihydroxy)-2H-1-benzopyran-2-one, and 0.83 g (yield=60%) of the desired compound 62 was obtained.

$^1$H-NMR (DMSO-d$_6$, δ-TMS)

10.21 (bs, 1H), 7.52 (d, 1H, J=8.8 Hz), 6.70~6.90 (m, 2H), 3.73 (s,3H), 3.34 (t, 2H, J=7.0 Hz), 1.2441.70 (m, 16H), 0.83 (t, 3H, J=6.0 Hz)

IR (KBr, cm$^{-1}$)

3300, 1700, 1670, 1620, 1580

Elemental analysis value: $C_{20} H_{26} O_5$

Theoretical value (%): C 69.34; H 7.57; O 23.09

Actual measured value (%): C 69.28; H 7.62; O 23.10

Example 63

3-hydroxy-4-(isopropoxy)-7-(decyloxy)-2H-1-benzopyran-2-one (Compound 63)

In Example 8, 2.64 g (7.37×10$^{-3}$ mol) of 3,4-(dihydroxy)-7-(decyloxy)-2H-1-benzopyran-2-one was used in place of 3,4,7-trihydroxy-2H-1-benzopyran-2-one, isopropylbromide was used in place of benzoylchloride, and 1.86 g (yield=63%) of the desired compound 63 was obtained.

$^1$H-NMR (DMSO-d$_6$, δ-TMS) 9.01 (bs, 1H), 7.58 (d, 1H, J=8.8 Hz), 6.70~6.90 (m, 2H), 3.86 (m, 1H), 3.35 (t, 2H, J=7.0 Hz), 1.24~1.70 (m, 16H), 1.13 (d, 6H, J=6.0 Hz), 0.83 (t, 3H, J=6.0 Hz)

IR (KBr, cm$^{-1}$) 3200, 1700, 1670, 1620, 1580

Elemental analysis value: $C_{22} H_{32} O_5$

Theoretical value (%): C 70.18; H 8.57; O 21.25

Actual measured value (%): C 70.27; H 8.62; O 21.11

Example 64

3-(methoxy)-4-(isopropoxy)-7-(decyloxy)-2H-1-benzopyran-2-one (Compound 64)

In Example 8, 2.38 g (6.39×10$^{-3}$ mol) of 3-(methoxy)-4-hydroxy-7-(decyloxy)-2H-1-benzopyran-2-one was used in place of 3,4,7-trihydroxy-2H-1-benzopyran-2-one, isopropylbromide was used in place of benzoylchloride, and 1.80 g (yield=68%) of the desired compound 64 was obtained.

$^1$H-NMR (DMSO-d$_6$, δ-TMS) 7.58 (d, 1H, J=8.8 Hz), 6.70~6.90 (m, 2H), 3.86 (m, 1H), 3.69 (s, 3H), 3.35 (t, 2H, J=7.0 Hz), 1.24~1.70 (m, 16H), 1.13 (d, 6H, J=6.0 Hz), 0.83 (t, 3H, J=6.0 Hz)

IR (KBr, cm$^{-1}$) 700, 1670, 1620, 1580

Elemental analysis value: $C_{23} H_{34} O_5$

Theoretical value (%): C 70.74; H 8.72; O 20.49

Actual measured value (%): C 70.79; H 8.67; O 20.54

Example 65

3-(benzoyloxy)-4-(methoxy)-7-(decyloxy)-2H-1-benzopyran-2-one (Compound 65)

In Example 8, 2.55 g (5.51×10$^{-3}$ mol) of 3-(benzoyloxy)-4-hydroxy-7-(decyloxy)-2H-1-benzopyran-2-one was used in place of 3,4,7-trihydroxy-2H-1-benzopyran-2-one, methyliodide was used in place of benzoylchloride, and 1.71 g (yield=65%) of the desired compound 65 was obtained.

$^1$H-NMR (DMSO-d$_6$, δ-TMS) 8.10~8.30 (m, 2H), 7.50~7.90 (m, 4H), 6.70~6.90 (m, 2H), 3.77 (s, 3H), 3.33 (t, 2H, J=7.0 Hz), 1.24~1.70 (m, 16H), 0.86 (t, 3H, J=6.0 Hz)

IR (KBr, cm$^{-1}$) 700, 1670, 1620, 1580

Elemental analysis value: $C_{27} H_{32} O_5$

Theoretical value (%): C 74.28.; H 7.39; O 18.33

Actual measured value (%): C 74.39; H 7.37; O 18.24

Example 66

3-(isopropoxy)-4-(methoxy)-7-(decyloxy)-2H-1-benzopyran-2-one (Compound 66)

In Example 8, 3.22 g (8.65×10$^{-3}$ mol) of 3-hydroxy-4-(methoxy)-7-(decyloxy)-2H-1-benzopyran-2-one was used in place of 3,4,7-trihydroxy-2H-1-benzopyran-2-one, isopropylbromide was used in place of benzoylchloride, and 2.54 g (yield=71%) of the desired compound 66 was obtained.

$^1$H-NMR (DMSO-d$_6$, δ-TMS) 7.58 (d, 1H, J=8.8 Hz), 6.70~6.90 (m, 2H), 3.86 (m, 1H), 3.85 (s,3H), 3.37 (t, 2H, J=7.0 Hz), 1.24~1.70 (m, 16H), 1.18 (d, 6H, J=6.0 Hz), 0.85 (t, 3H, J=6.0 Hz)

IR (KBr, cm$^{-1}$) 1700, 1670, 1620, 1580

Elemental analysis value: $C_{23} H_{34} O_5$

Theoretical value (%): C 70.74; H 8.72; O 20.49

Actual measured value (%): C 70.67; H 8.77; O 20.56

Example 67

3-(geranyloxy)-4-hydroxy-7-(decyloxy)-2H-1-benzopyran-2-one (Compound 67)

In Example 5, 1.50 g (2.79×10$^{-3}$ mol) of 3-(geranyloxy)-4-(acetoxy)-7-(decyloxy)-2H-1-benzopyran-2-one was used in place of 3-(benzoyloxy)-4,7-(dihydroxy)-2H-1-benzopyran-2-one, and 0.79 g (yield=57%) of the desired compound 67 was obtained.

$^1$H-NMR (DMSO-d$_6$, δ-TMS) 10.59 (bs, 1H), 7.63 (d, 1H, J=8.8 Hz), 6.70~6.90 (m, 2H), 5.43 (bt, 1H, J=7.0 Hz), 5.07 (bt, 1H, j=7.0 Hz), 4.01 (d, 2t1, J=7.0 Hz), 3.32 (t, 2H, J=7.0 Hz), 2.00~2.21 (m, 4H), 1.22~1.85 (m, 25H), 0.84 (t, 3H, J=6.0 Hz)

IR (KBr, cm$^{-1}$) 3200, 1720, 1680, 1630, 1580

Elemental analysis value: $C_{29} H_{42} O_5$

Theoretical value (%): C 74.01; H 9.00; O 17.00

Actual measured value (%): C 74.04; H 8.97; O 16.99

Example 68

3-hydroxy-4-(geranyloxy)-7-(decyloxy)-2H-1-benzopyran-2-one (Compound 68)

In Example 8, 1.82 g (5.08×10$^{-3}$ mol) of 3,4-(dihydroxy)-7-(decyloxy)-2H-1-benzopyran-2-one was used in place of 3,4,7-trihydroxy-2H-1-benzopyran-2-one, geranylbromide was used in place of benzoylchloride, and 1.41 g (yield=56%) of the desired compound 68 was obtained.

$^1$H-NMR (DMSO-d$_6$, δ-TMS) 8.94 (bs, 1H), 7.55 (d, 1H, J=8.8 Hz), 6.70~6.90 (m, 2H), 5.42 (bt, 1H, J=7.0

Hz), 5.02 (bt, 1H, J=7.0 Hz), 4.01 (d, 2H, J=7.0 Hz), 3.35 (t, 2H, J=7.0 Hz), 2.00~2.20 (m, 4H), 1.24~1.85 (m, 25H), 0.83 (t, 3H, J=6.0 Hz)

IR (KBr, cm$^{-1}$) 3200, 1700, 1670, 1620, 1580
Elemental analysis value: $C_{22}H_{32}O_5$
Theoretical value (%): C 74.01; H 9.00; O 17.00
Actual measured value (%): C 74.02; H 8.98; O 17.00

Example 69

3-(geranyloxy)-4-(acetoxy)-7-(decyloxy)-2H-1-benzopyran-2-one (Compound 69)

In Example 8, 1.39 g (3.47×10$^{-3}$ mol) of 3-hydroxy-4'-(acetoxy)-7-(decyloxy)-2H-1-benzopyran-2-one was used in place of 3,4,7-trihydroxy-2H-1-benzopyran-2-one, geranylbromide was used in place of benzoylchloride, and 1.14 g (yield=61%) of the desired compound 69 was obtained.

$^1$H-NMR (DMSO-d$_6$, δ-TMS) 7.58 (d, 1H, J=8.8 Hz), 6.70~6.90 (m, 2H), 5.46 (bt, 1H, J=7.0 Hz), 5.01 (bt, 1H, J=7.0 Hz), 4.04 (d, 2H, J=7.0 Hz), 3.35 (t, 2H, J=7.0 Hz), 2.00~2.20 (m, 4H), 1.86 (s, 3H), 1.24~1.85 (m, 25H), 0.81 (t, 3H, J=6.0 Hz)

IR (KBr, cm-1) 1720, 1670, 1630, 1580, 1530
Elemental analysis value: $C_{31}H_{44}O_6$
Theoretical value (%): C 72.62; H 8.65; O 18.73
Actual measured value (%): C 72.65; H 8.58; O 18.77

Example 70

3-(benzoyloxy)-4-(geranyloxy)-7-(decyloxy)-2H-1-benzopyran-2-one (Compound 70)

In Example 8, 1.45 g (3.13×10$^{-3}$ mol) of 3-(benzoyloxy)-4-hydroxy-7-(decyloxy)-2H-1-benzopyran-2-one was used in place of 3,4,7-trihydroxy-2H-1-benzopyran-2-one, geranylbromide was used in place of benzoylchloride, and 1.22 g (yield=65%) of the desired compound 70 was obtained.

$^1$H-NMR (DMSO-d$_6$, δ-TMS) 8.10~8.30 (m, 2H), 7.50~7.90 (m, 4H), 6.70~6.90 (m, 2H), 5.43 (bt, 1H, J=7.0 Hz), 5.02 (bt, 1H, J=7.0 Hz), 4.01 (d, H, J=7.0 Hz), 3.35 (t, 2H, J=7.0 Hz), 2.00~2.20 (m, 4H), 1.24~1.85 (m, 25H), 0.81 (t, 3H, J=6.0 Hz)

IR (KBr, cm$^{-1}$) 1720, 1670, 1650, 1630, 1580, 1530
Elemental analysis value: $C_{36}H_{46}O_6$
Theoretical value (%): C 75.23; H 8.07; O 16.70
Actual measured value (%): C 75.10; H 8.09; O 16.81

Example 71

3-(geranyloxy)-4-(methoxy)-7-(decyloxy)-2H-1-benzopyran-2-one (Compound 71)

In Example 8, 1.85 g (4.97×10$^{-3}$ mol) of 3-hydroxy-4-(methoxy)-7-(decyloxy)-2H-1-benzopyran-2-one was used in place of 3,4,7-trihydroxy-2H-1-benzopyran-2-one, geranylbromide was used in place of benzoylchloride, and 1.57 g (yield=62%) of the desired compound 71 was obtained.

$^1$H-NMR (DMSO-d$_6$, δ-TMS)
7.57 (d, 1H, J=8.8 Hz), 6.70~6.90 (m, 2H), 5.45 (bt, H, J=7.0 Hz), 5.01 (bt, 1H, J=7.0 Hz), 4.02 (d, 2H, J=7.0 Hz), 3.72 (s, 3H), 3.35 (t, 2H, J=7.0 Hz), 2.00~2.20 (m, 4H), 1.24~1.85 (m, 25H), 0.81 (t, 3H, J=6.0 Hz)

IR (KBr, cm$^{-1}$) 1720, 1670, 1630, 1580, 1530
Elemental analysis value: $C_{30}H_{44}O_5$
Theoretical value (%): C 74.34; H 9.15; O 16.51
Actual measured value (%): C 74.28; H 9.28; O 16.44

Example 72

3-(isopropoxy)-4-(geranyloxy)-7-(decyloxy)-2H-1-benzopyran-2-one (Compound 72)

In Example 8, 1.46 g (3.65×10$^{-3}$ mol) of 3-(isopropoxy)-4-hydroxy-7-(decyloxy)-2H-1-benzopyran-2-one was used in place of 3,4,7-trihydroxy-2H-1-benzopyran-2-one, geranylbromide was used in place of benzoylchloride, and 1.17 g (yield=60%) of the desired compound 72 was obtained.

$^1$H-NMR (DMSO-d$_6$, δ-TMS) 7.56 (d, 1H, J=8.8 Hz), 6.70~6.90 (m, 2H), 5.43 (bt, 1H, J=7.0 Hz), 5.02 (bt, 1H, J=7.0 Hz), 4.01 (d, 2H, J=7.0 Hz), 3.50 (m, 1H), 3.32 (t, 2H, J=7.0 Hz), 2.00~2.20 (m, 4H), 1.24~1.85 (m, 25H), 1.12 (d, 6H, J=6.0 Hz), 0.82 (t, 3H, J=6.0 Hz)

IR (KBr, cm$^{-1}$) 1700, 1670, 1620, 1550, 1520
Elemental analysis value: $C_{32}H_{48}O_5$
Theoretical value (%): C 74.96; H 9.44; O 15.60
Actual measured value (%): C 74.95; H 9.49; O 15.56

Example 73

3-4-(digeranyloxy)-7-(decyloxy)-2H-1-benzopyran-2-one (Compound 73)

In Example 8, 1.61 g (3.25×10$^{-3}$ mol) of 3-hydroxy-4-(geranyloxy)-7-(decyloxy)-2H-1-benzopyran-2-one was used in place of 3,4,7-trihydroxy-2H-1-benzopyran-2-one, geranylbromide was used in place of benzoylchloride, and 0.94 g (yield=46%) of the desired compound 73 was obtained.

$^1$H-NMR (DMSO-d$_6$, δ-TMS) 7.59 (d, 1H, J=8.8 Hz), 6.70~6.90 (m, 2H), 5.00~5.50 (m, 4H), 4.03 (d, 2H, J=7.0 Hz), 4.01 (d, 2H, J=7.0 Hz), 3.32 (t, 2H, J=7.0 Hz), 2.00~2.20 (m, 8H), 1.2441.85 (m, 34H), 0.82 (t, 3H, J=6.0 Hz)

IR (KBr, cm$^{-1}$) 1700, 1670, 1620, 1550, 1520
Elemental analysis value: $C_{39}H_{58}O_5$
Theoretical value (%): C 77.18; H 9.63; O 13.18
Actual measured value (%): C 77.18; H 9.59; O 13.23

Example 74

3-(benzoyloxy)-4-hydroxy-7-(geranyloxy)-2H-1-benzopyran-2-one (Compound 74)

In Example 1, 2'-hydroxy-4'-geranyloxyacetophenone was used in place of 2',4'-dihydroxyacetophenone, after which Examples 2~4 were carried out, and 2.08 g (yield=70%) of the desired compound 74 was obtained from 3.69 g (6.82×$^{-3}$ mol) of methyl-β-oxo-2'-(phenylmethoxy)-4'-(geranyloxy)-2-(benzoyloxy) benzenepropanate.

$^1$H-NMR (DMSO-d$_6$, δ-TMS) 10.34 (bs, 1H), 8.10~8.20 (m, 2H), 7.50~7.80 (m, 4H), 6.70~6.90 (m, 2H), 5.45 (bt, 1H, J=7.0 Hz), 5.02 (bt, 1H, J=7.0 Hz), 4.01 (bt, 2H, J=7.0 Hz), 2.00~2.20 (m, 4H), 1.55~1.85 (m, 9H)

IR (KBr, cm$^{-1}$) 3350, 1720, 1680, 1630, 1580, 1520
Elemental analysis value: $C_{26}H_{26}O_6$
Theoretical value (%): C 71.87; H 6.03; O 22.10
Actual measured value (%): C 71.71; H 6.12; O 22.17

Example 75

3,4-(hydroxy)-7-(geranyloxy)-2H-1-benzopyran-2-one (Compound 75)

In Example 5, 5.45 g (1.25×10$^{-2}$ mol) of 3-(benzoyloxy)-4-hydroxy-7-(geranyloxy)-2H-1-benzopyran-2-one was used in place of 3-(benzoyloxy)-4,7-(dihydroxy)-2H-1-benzopyran-2-one, and 2.49 g (yield=60%) of the desired compound 75 was obtained.

$^1$H-NMR (DMSO-d$_6$, δ-TMS) 10.45 (bs,tH), 8.59 (bs,1H), 7.63 (d, 1H, J=8.8 Hz), 6.70~6.90 (m, 2H), 5.43 (bt, 1H, J=7.0 Hz), 5.07 (bt, 1H, J=7.0 Hz), 4.01 (d, 2H, J=7.0 Hz), 2.00~2.21 (m, 4H), 1.55~1.85 (m, 9H)

IR (KBr, cm$^{-1}$) 3200, 1720, 1680, 1630, 1580

Elemental analysis value: C$_{19}$ H$_{22}$ O$_5$

Theoretical value (%): C 69.07; H 6.71; O 24.22

Actual measured value (%): C 69.07; H 6.79; O 24.14

Example 76

3-hydroxy-4 -(acetoxy)-7-(geranyloxy)-2H-1-benzopyran-2-one (Compound 76)

In Example 8, 1.67 g (5.05×10$^{-3}$ mol) of 3,4-(dihydroxy)-7-(geranyloxy)-2H-1-benzopyran-2-one was used in place of 3,4,7-trihydroxy-2H-1-benzopyran-2-one, acetylchloride was used in place of benzoylchloride, and 0.92 g (yield=49%) of the desired compound 76 was obtained.

$^1$H-NMR (DMSO-d$_6$,δ-TMS) 8.68 (bs, 1H), 7.62 (d, 1H, J=8.8 Hz), 6.70~6.90 (m, 2H), 5.46 (bt, 1H, J=7.0 Hz), 5.07 (bt, 1H, J=7.0 Hz), 4.04 (d, 2H, J=7.0 Hz), 2.00~2.21 (m, 4H), 1.90 (s, 3H), 1.55~1.85 (m, 9H)

IR (KBr, cm$^{-1}$) 3550, 3200, 1720, 1680, 1630, 1580

Elemental analysis value: C$_{21}$ H$_{24}$ O$_6$

Theoretical value (%): C 67.73; H 6.50; O 25.78

Actual measured value (%): C 67.66; H 6.54; O 25.80

Example 77

3-(benzoyloxy)-4-(acetoxy)-7-(geranyloxy)-2H-1-benzopyran-2-one (Compound 77)

In Example 8, 1.42 g (3.27×10$^{-3}$ mol) of 3-(benzoyloxy)-4-hydroxy-7-(geranyloxy)-2H-1-benzopyran-2-one was used in place of 3,4,7-trihydroxy-2H-1-benzopyran-2-one, acetylchloride was used in place of benzoylchloride, and 0.83 g (yield=53%) of the desired compound 77 was obtained.

$^1$H-NMR (DMSO-d$_6$, δ-TMS) 8.10~8.20 (m, 2H), 7.50~7.80 (m, 4H), 6.70~6.90 (m, 2H), 5.46 (bt, 1H, J=7.0 Hz), 5.07 (bt, 1H, J=7.0 Hz), 4.04 (d, H, J=7.0 Hz), 2.00~2.21 (m, 4H), 1.75 (s, 3H), 1.55~1.85 (m, 9H)

IR (KBr, cm$^{-1}$) 1720, 1680, 1630, 1580, 1520

Elemental analysis value: C$_{28}$ H$_{28}$ O$_7$

Theoretical value (%): C 70.57; H 5.92; O 23.50

Actual measured value (%): C 70.44; H 6.10; O 23.46

Example 78

3-(methoxy)-4-hydroxy-7-(geranyloxy)-2H-1-benzopyran-2-one (Compound 78)

In Example 5, 1.60 g (4.14×10$^{-3}$ mol) of 3-(methoxy)-4-(acetoxy)-7-(geranyloxy)-2H-1-benzopyran-2-one was used in place of 3-(benzoyloxy)-4,7-(dihydroxy)-2H-1-benzopyran-2-one, and 0.87 g (yield=61%) of the desired compound 78 was obtained.

$^1$H-NMR (DMSO-d$_6$, δ-TMS) 10.61 (bs, 1H), 7.63 (d, 1H, J=8.8 Hz), 6.70~6.90 (m, 2H), 5.46 (bt, 1H, J=7.0 Hz), 5.03 (bt, 1H, J=7.0 Hz), 4.00 (d, 2H, J=7.0 Hz), 3.76 (s,3H), 2.00~2.21 (m, 4H), 1.55~1.85 (m, 9H)

IR (KBr, cm$^{-1}$) 3200, 1720, 1680, 1630, 1580

Elemental analysis value: C$_{20}$ H$_{24}$ O$_5$

Theoretical value (%): C 69.75; H 7.02; O 23.23

Actual measured value (%): C 69.59; H 7.07; O 23.34

Example 79

3-hydroxy-4-(isopropoxy)-7 -(geranyloxy)-2H-1-benzopyran-2-one (Compound 79)

In Example 8, 1.62 g (4.90×10$^{-3}$ mol) of 3,4-(dihydroxy)-7-(geranyloxy)-2H-1-benzopyran-2-one was used in place of 3,4,7-trihydroxy-2H-1-benzopyran-2-one, isopropylbromide was used in place of benzoylchloride, and 0.97 g (yield=53%) of the desired compound 79 was obtained.

$^1$H-NMR (DMSO-d$_6$, δ-TMS) 8.75 (bs, 1H), 7.59 (d, 1H, J=8.8 Hz), 6.70~6.90 (m, 2H), 5.43 (bt, 1H, J=7.0 Hz), 5.07 (bt, 1H, J=7.0 Hz), 4.02 (d, 2H, J=7.0 Hz), 3.45 (m, 1H), 2.00~2.21 (m, 4H), 1.55~1.85 (m, 9H), 1.12 (d, 6H, J=6.0 Hz)

IR (KBr, cm$^{-1}$) 3200, 1720, 1680, 1630, 1580

Elemental analysis value: C$_{22}$ H$_{28}$ O$_5$

Theoretical value (%): C 70.94; H 7.58; O 21.48

Actual measured value (%): C 71.04; H 7.43; O 21.53

Example 80

3-(decyloxy)-4-(isopropoxy)-7-(geranyloxy)-2H-1-benzopyran-2-one (Compound 80)

In Example 8, 1.34 g (3.60×10$^{-3}$ mol) of 3-hydroxy-4-(isopropoxy)-7-(geranyloxy)-2H-1-benzopyran-2-one was used in place of 3,4,7-trihydroxy-2H-1-benzopyran-2-one, decylbromide was used in place of benzoylchloride, and 0.97 g (yield=50%) of the desired compound 80 was obtained.

$^1$H-NMR (DMSO-d$_6$, δ-TMS) 7.57 (d, 1H, J=8.8 Hz), 6.70~6.90 (m, 2H), 5.43 (bt, 1H, J=7.0 Hz), 5.02 (bt, 1H, J=7.0 Hz), 4.00 (d, 2H, J=7.0 Hz), 3.43 (m, 1H), 3.32 (t, 2H, J=7.0 Hz), 2.00~2.21 (m, 4H), 1.22~1.85 (m, 25H), 1.12 (d, 6H, J=6.0 Hz), 0.83 (t, 3H, J=6.0 Hz)

IR (KBr, cm$^{-1}$) 1720, 1680, 1630, 1580, 1530

Elemental analysis value: C$_{32}$ H$_{48}$ O$_5$

Theoretical value (%): C 74.96; H 9.44; O 15.60

Actual measured value (%): C 74.84; H 9.50; O 15.68

Example 81

3-(benzoyloxy)-4-(isopropoxy)-7-(geranyloxy)-2H-1-benzopyran-2-one (Compound 81)

In Example 8, 1.75 g (4.03×10$^{-3}$ mol) of 3-(benzoyloxy)-4-hydroxy-7-(geranyloxy)-2H-1-benzopyran-2-one was used in place of 3,4,7-trihydroxy-2H-1-benzopyran-2-one, isopropylbromide was used in place of benzoylchloride, and 1.07 g (yield=56%) of the desired compound 81 was obtained.

$^1$H-NMR (DMSO-d$_6$, δ-TMS) 10.41 (bs, 1H), 8.10~8.20 (m, 2H), 7.50~7.80 (m, 4H), 6.70~6.90 (m, 2H), 5.43 (bt, 1H, J=7.0 Hz), 5.04 (bt, 1H, J=7.0 Hz), 4.01 (bt, 2H, J=7.0 Hz), 3.47 (m, 1H), 2.00~2.20 (m, 4H), 1.55~1.85 (m, 9H), 1.13 (d, 6H, J=6.0 Hz)

IR (KBr, cm$^{-1}$) 1720, 1680, 1630, 1580, 1520

Elemental analysis value: C$_{29}$ H$_{32}$ O$_6$

Theoretical value (%): C 73.09; H 6.77; O 20.14

Actual measured value (%): C 73.11; H 6.70; O 20.19

Example 82

3-(methoxy)-4-(acetoxy)-7-(geranyloxy)-2H-1-benzopyran-2-one (Compound 82)

In Example 8, 1.58 g (4.24×10$^{-3}$ mol) of 3-hydroxy-4-(acetoxy)-7-(geranyloxy)-2H-1-benzopyran-2-one was used in place of 3,4,7-trihydroxy-2H-1-benzopyran-2-one, methyliodide was used in place of benzoylchloride, and 0.98 g (yield=60%) of the desired compound 82 was obtained.

$^1$H-NMR(DMSO-d$_6$, δ-TMS) 7.59 (d, 1H, J=8.8 Hz), 6.70~6.90 (m, 2H), 5.46 (bt, 1H, J=7.0 Hz), 5.03 (bt, 1H, J=7.0 Hz), 4.00 (d, 2H, J=7.0 Hz), 3.76 (s,3H), 2.00~2.21 (m, 4H), 1.90 (s, 3H), 1.55~1.85 (m, 9H)

IR (KBr, cm$^{-1}$) 1720, 1680, 1630, 1580, 1520

Elemental analysis value: C$_{22}$ H$_{26}$ O$_6$

Theoretical value (%): C 68.38; H 6.78; O 24.84

Actual measured value (%): C 68.38; H 6.70; O 24.91

Example 83

3,7-(digeranyloxy)-4-hydroxy-2H-1-benzopyran-2-one (Compound 83)

In Example 5, 2.03 g (3.99×10$^{-3}$ mol) of 3,7-(digeranyloxy)-4 (acetoxy)-2H-1-benzopyran-2-one, was used in place of 3-(benzoyloxy)-4,7-(dihydroxy)-2H-1-benzopyran-2-one, and 0.95 g (yield=51%) of the desired compound 83 was obtained.

$^1$H-NMR (DMSO-d$_6$, δ-TMS) 10.59 (bs, 1H), 7.63 (d, 1H, J=8.8 Hz), 6.70~6.90 (m, 2H), 5.00~5.50 (m, 4H), 4.03 (d, 2H, J=7.0 Hz), 4.01 (d, 2H, J=7.0 Hz), 2.00~2.21 (m, 8H), 1.55~1.85 (m, 18H)

IR (KBr, cm$^{-1}$) 3200, 1720, 1680, 1630, 1580

Elemental analysis value: C$_{29}$ H$_{38}$ O$_5$

Theoretical value (%): C 74.65; H 8.21; O 17.14

Actual measured value (%): C 74.56; H 8.24; O 17.20

Example 84

3-hydroxy-4,7-(digeranyloxy)-2H-1-benzopyran-2-one (Compound 84)

In Example 8, 1.59 g (4.81×10$^{-3}$ mol) of 3,4-(dihydroxy)-7-(geranyloxy)-2H-1-benzopyran-2'one was used in place of 3,4,7-trihydroxy-2H-1-benzopyran-2-one, geranylbromide was used in place of benzoylchloride, and 1.21 g (yield=53%) of the desired compound 84 was obtained.

$^1$H-NMR (DMSO-d$_6$, δ-TMS) 9.04 (bs, 1H), 7.56 (d, 1H, J=8.8 Hz), 6.70~6.90 (m, 2H), 5.00~5.50 (m, 4H), 4.01 (d, 2H, J=7.0 Hz), 4.00 (d, 2H, J=7.0 Hz), 2.00~2.20 (m, 8H), 1.55~1.85 (m, 18H)

IR (KBr, cm$^{-1}$) 3200, 1700, 1670, 1620, 1580

Elemental analysis value: C$_{29}$ H$_{38}$ O$_5$

Theoretical value (%): C 74.65; H 8.21; O 17.14

Actual measured value (%): C 74.78; H 8.16:O 17.06

Example 85

3,7-(digeranyloxy)-4-(acetoxy)-2H-1-benzopyran-2-one (Compound 85)

In Example 8, 1.57 g (3.36×10~3 mol) of 3,7-(digeranyloxy)-4-hydroxy-2H-1-benzopyran-2-one was used in place of 3,4,7-trihydroxy-2H-1-benzopyran-2-one, acetylchloride was used in place of benzoylchloride, and 1.01 g (yield=59%) of the desired compound 85 was obtained.

$^1$H-NMR (DMSO-d$_6$, δ-TMS) 7.58 (d, 1H, J=8.8 Hz), 6.70~6.90 (m, 2}t), 5.00~5.50 (m, 4H), 4.04 (d, 2H, J=7.0 Hz), 4.01 (d, 2H, J=7.0 Hz), 2.00~2.20 (m, 8H), 1.86 (s, 3H), 1.55~1.85 (m, 18H)

IR(KBr, cm$^{-1}$) 1720, 1670, 1630, 1580, 1530

Elemental analysis value: C$_{31}$ H$_{40}$ O$_6$

Theoretical value (%): C 73.20; H 7.93; O 18.87

Actual measured value (%): C 73.23; H 8.02; O 18.75

Example 86

3-(benzoyloxy)-4,7-(digeranyloxy)-2H-1-benzopyran-2-one (Compound 86)

In Example 8, 1.45 g (3.13×10$^{-3}$ mol) of 3-(benzoyloxy)-4-hydroxy-7-(geranyloxy)-2H-1-benzopyran-2-one was used in place of 3,4,7-trihydroxy-2H-1-benzopyran-2-one, geranylbromide was used in place of benzoylchloride, and 0.95 g (yield=53%) of the desired compound 86 was obtained.

$^1$H-NMR (DMSO-d$_6$, δ-TMS) 8.10~8.30 (m, 2H), 7.50~7.90 (m, 4H), 6.70~6.90 (m, 2H), 5.00~5.50 (m, 4H), 4.01 (d, 2H, J=7.0 Hz), 4.00 (d, 2H, J=7.0 Hz), 2.00~2.20 (m, 8H), 1.55~1.85 (m, 18H)

IR (KBr, cm$^{-1}$) 1720, 1670, 1650, 1630, 1580, 1530

Elemental analysis value: C$_{36}$ H$_{42}$ O$_6$

Theoretical value (%): C 75.76; H 7.42; O 16.82

Actual measured value (%): C 75.80; H 7.39; O 16.81

Example 87

3,7-(digeranyloxy)-4-(methoxy)-2H-1-benzopyran-2-one (Compound 87)

In Example 8, 1.48 g (4.30×10$^{-3}$ mol) of 3-hydroxy-4-(methoxy)-7-(geranyloxy)-2H-1-benzopyran-2-one was used in place of 3,4,7-trihydroxy-2H-1-benzopyran-2-one, geranylbromide was used in place of benzoylchloride, and 1.22 g (yield=59%) of the desired compound 87 was obtained.

$^1$H-NMR (DMSO-d$_6$, δ-TMS) 7.59 (d, 1H, J=8.8 Hz), 6.70~6.90 (m, 2H), 5.00~5.50 (m, 4H), 4.03 (d, 2H, J=7.0 Hz), 4.02 (d, 2H, J=7.0 Hz), 3.71 (s,3H), 2.00~2.20 (m, 8H), 1.55~1.85 (m, 18H)

IR (KBr, cm$^{-1}$) 1720, 1670, 1630, 1580, 1530

Elemental analysis value: C$_{30}$ H$_{40}$ O$_5$

Theoretical value (%): C 74.97; H 8.39; O 16.65

Actual measured value (%): C 75.17; H 8.30; O 16.53

Example 88

3-(isopropoxy)-4,7-(digeranyloxy)-2H-1-benzopyran-2-one (Compound 88)

In Example 8, 1.46 g (3.13×10$^{-3}$ mol) of 3-hydroxy-4,7-(digeranyloxy)-2H-1-benzopyran-2-one was used in place of 3,4,7-trihydroxy-2H-1-benzopyran-2-one, isopropylbromide was used in place of benzoylchloride, and 0.96 g (yield=60%) of the desired compound 88 was obtained.

$^1$H-NMR (DMSO-d$_6$, δ-TMS) 7.55 (d, 1H, J=8.8 Hz), 6.70~6.90 (m, 2H), 5.00~5.50 (m, 4H), 4.02 (d, 2H, J=7.0 Hz), 4.01 (d, 2H, J=7.0 Hz), 3.50 (m, 1H), 3.32 (t, 2H, J=7.0 Hz), 2.00~2.20 (m, 8H), 1.55~1.85 (m, 18H), 1.12 (d, 6H, J=6.0 Hz)

IR (KBr, cm$^{-1}$) 1700, 1670, 1620, 1550, 1520

Elemental analysis value: C$_{32}$ H$_{44}$ O$_5$

Theoretical value (%): C 75.55; H 8.72; O 15.73

Actual measured value (%): C 75.43; H 8.90; O 15.67

Example 89

1-[2′,3′-bis(phenylmethoxy)phenyl]ethanone (Compound 89)

In Example 1, 25.0 g (1.64×10$^{-1}$ mol) of 2′,3′-dihydroxyacetophenone was used in place of 2′,4′-dihydroxyacetophenone, and 49.32 g (yield=91%) of the desired compound 89 was obtained.

1H-NMR (CDCl$_3$, δ-TMS)

6.60~7.90 (m, 13H), 5.10 (s,2H), 5.01 (s,2H), 2.58 (s, 3H)

Example 90

Methyl-β-oxo-2',3'-bis(phenylmethoxy) benzenepropanate (Compound 90)

In Example 2, 1- [2',4'-bis(phenylmethoxy)phenyl]ethanone was replaced by 48.98 g ($1.50 \times 10^{-1}$ mol) of 1-[2',3'-bis(phenylmethoxy)phenyl]ethanone, and 48.02 g (yield=82%) of the desired compound 90 was obtained.

$^1$H-NMR (CDCl$_3$, δ-TMS) 6.60~7.90 (m, 13H), 5.10 (s,2H), 5.01 (s,2H), 3.80 (s, 2H), 3.50 (s, 3H)

Example 91

Methyl-β-oxo-2',3'-bis(phenylmethoxy)-2-(benzoyloxy) benzenepropanate (Compound 91)

In Example 3, 48.02 g ($1.23 \times 10^{-1}$ mol) of methyl-β-oxo-2',3'-bis(phenylmethoxy)benzenepropanate was used in place of methyl-β-oxo-2',4'-bis(phenylmethoxy)benzenepropanate, and 56.47 g (yield=90%) of the desired compound 91 was obtained.

$^1$H-NMR (CDCl$_3$, δ-TMS) 6.80~8.20 (m, 18H), 5.10 (s,2H), 5.01 (s,2H), 3.69 (s, 1H), 3.62 (s, 3}t)

Example 92

3-(benzoyloxy)- 4,8-dihydroxy-2H- 1 -benzopyran-2-one (Compound 92)

In Example 4, 28.16 g ($5.52 \times 10^{-2}$ mol) of methyl-β-oxo-2',3'-bis(phenylmethoxy)-2-(benzoyloxy)benzenepropanate was used in place of methyl-β-oxo-2',4'-bis(phenylmethoxy)-2 -(benzoyloxy)benzenepropanate, and 14.41 g (yield=88%) of the desired compound 92 was obtained.

$^1$H-NMR (DMSO-d$_6$, δ-TMS) 11.30 (bs,1H), 10.21 (bs,1H), 6.90~8.20 (m, 8H)

IR (KBr, cm$^{-1}$) 3500, 3200, 1710, 1690, 1630, 1590

Melting point 254°~256° C.

Elemental analysis value: C$_{16}$ H$_{10}$ O$_6$

Theoretical value (%): C 64.43; H 3.38; O 32.19

Actual measured value (%): C 64.48; H 3.27; O 32.25

Example 93

3,4,8-trihydroxy-2H-1-benzopyran-2-one (Compound 93)

In Example 5, 5.00 g ($1.68 \times 10^{-2}$ mol) of 3-(benzoyloxy)-4,8-dihydroxy-2H-1-benzopyran-2-one was used in place of 3-(benzoyloxy)-4,7-(dihydroxy)-2H-1-benzopyran-2-one, and 2.12 g (yield=65%) of the desired compound 93 was obtained.

$^1$H-NMR (DMSO-d$_6$, δ-TMS) 10.91 (bs, 1H), 10.02 (bs, 1H), 8.70 (bs, 1H), 6.80~7.50 (m, 3H)

IR (KBr, cm$^{-1}$) 3400, 3200, 1710, 1680, 1610, 1590

Melting point 261°~263° C.

Elemental analysis value: C$_9$ H$_6$ O$_5$

Theoretical value (%): C 51.44; H 2.88; O 45.68

Actual measured value (%): C 51.55; H 2.86; O 45.59

Example 94

3,8-(dihydroxy)-4-(acetoxy)-2H-1-benzopyran-2-one (Compound

In Example 8, 2.18 g ($1.12 \times 10^{-2}$ mol) of 3,4,8-(trihydroxy)-2H-1-benzopyran-2-one was used in place of 3,4,7-trihydroxy-2H-1-benzopyran-2-one, acetylchloride was used in place of benzoylchloride, and 1.80 g (yield=68%) of the desired compound 94 was obtained.

$^1$H-NMR (DMSO-d$_6$, δ-TMS) 10.91 (bs, 1H), 9.02 (bs, 1H), 6.80~7.50 (m, 3H), 1.86 (S, 3H)

IR (KBr, cm$^{-1}$) 3200, 1710, 1680, 1610, 1590

Elemental analysis value: C$_{11}$H$_8$ O$_6$

Theoretical value (%): C 55.94; H 3.41; O 40.65

Actual measured value (%): C 55.86; H 3.40; O 40.74

Example 95

3,4,8-(triacetoxy)-2H-1-benzopyran-2-one (Compound 95)

In Example 8, 1.58 g ($8.14 \times 10^{-3}$ mol) of 3,4,8-(trihydroxy)-2H-1-benzopyran-2-one was used in place of 3,4,7 -trihydroxy-2H- 1 -benzopyran -2 -one, acetylchloride was used in place of benzoylchloride, potassium carbonate was used in place of sodium bicarbonate, and 1.52 g (yield=67%) of the desired compound 95 was obtained.

$^1$H-NMR (DMSO-d$_6$, δ-TMS) 6.80~7.50 (m, 3H), 1.96 (s,3H), 1.7.6 (s,3H), 1.72 (s, 3H)

IR (KBr, cm$^{-1}$) 3200, 1710, 1680, 1610, 1590

Elemental analysis value: C$_{15}$ H$_{12}$ O$_8$

Theoretical value (%): C 56.25; H 3.78; O 39.97

Actual measured value (%): C 56.25; H 3.83; O 39.92

Example 96

3-(acetoxy)-4-(benzoyloxy)-8-hydroxy-2H-1-benzopyran-2-one (Compound 96)

In Example 8, 2.61 g ($1.11 \times 10^{-2}$ mol) of 3-(acetoxy)-4,8-(dihydroxy)-2H-1-benzopyran-2-one was used in place of 3,4,7-trihydroxy-2H-1-benzopyran-2-one, and 2.63 g (yield=70%) of the desired compound 96 was obtained.

$^1$H-NMR (DMSO-d$_6$, δ-TMS) 10.80 (bs, 1H), 6.90~8.20 (m, 8H), 1.92 (s, 3H)

IR (KBr, cm$^{-1}$) 3200, 1710, 1690, 1630, 1590

Elemental analysis value: C$_{18}$ H$_{12}$ O$_7$

Theoretical value (%): C 63.53; H 3.55; O 32.91

Actual measured value (%): C 63.70; H 3.37; O 32.93

Example 97

3-(decyloxy)-4,8-(dihydroxy)-2H-1-benzopyran-2-one (Compound 97)

In Example 5, 2.00 g ($4.99 \times 10^{-2}$ mol) of 3-(decyloxy)-4-(acetoxy)-8-hydroxy-2H-1-benzopyran-2-one was used in place of 3-(benzoyloxy)-4,7-(dihydroxy)-2H-1-benzopyran-2-one, and 1.16 g (yield=65%) of the desired compound 97 was obtained.

$^1$H-NMR(DMSO-d$_6$,δ-TMS) 10.89 (bs, 1H), 10.25 (bs, 1H), 6.80~7.50 (m, 3H), 3.40 (t, 2H, J=7.0 Hz), 1.20~1.70 (m, 16H), 0.86 (t, 3H, J=6.0 Hz)

IR(KBr, cm$^{-1}$) 3200, 1710, 1690, 1630, 1590

Elemental analysis value: C$_{19}$ H$_{26}$ O$_5$

Theoretical value (%): C 68.24; H 7.84; O 23.92

Actual measured value (%): C 68.29; H 7.86; O 23.85

Example 98

3-(isopropoxy)-3,8-(dihydroxy)-2H-1-benzopyran-2-one (Compound 98)

In Example 8, 2.69 g ($1.39 \times 10^{-2}$ mol) of 3,4,8-(trihydroxy)-2H-1-benzopyran-2-one was used in place of 3,4,7-trihydroxy-2H-1-benzopyran-2-one, isopropylbromide was used in place of benzoylchloride, and 2.10 g (yield=64%) of the desired compound 98 was obtained.

¹H-NMR (DMSO-d₆, δ-TMS) 10.86 (bs,1H), 8.87 (bs,1H), 6.80~7.50 (m, 3H), 3.88 (m, 1H), 1.15 (d, 6H, J=6.0 Hz)
IR(KBr, cm⁻¹) 3200, 1710, 1680, 1610, 1590
Elemental analysis value: $C_{12}H_{12}O_5$
Theoretical value (%): C 62.90; H 4.87; O 32.23
Actual measured value (%): C 62.78; H 4.89; O 32.33

Example 99

3-(methoxy)-4-(decyloxy)-8-hydroxy-2H-1-benzopyran-2-one (Compound 99)

In Example 8, 2.81 g (7.84×10⁻³ mol) of 3,8-(dihydroxy)-4-(decyloxy)-2H-1-benzopyran-2-one was used in place of 3,4,7-trihydroxy-2H-1-benzopyran-2-one, methyliodide was used in place of benzoylchloride, and 1.99 g (yield=68%) of the desired compound 99 was obtained.

¹H-NMR (DMSO-d₆, δ-TMS) 10.89 (bs, 1H), 6.80~7.50 (m, 3H), 3.77 (s, 3H), 3.45 (t, 2H, J=7.0 Hz), 1.20~1.70 (m, 16H), 0.83 (t, 3H, J=6.0 Hz)
IR (KBr, cm⁻¹) 3200, 1710, 1690, 1630, 1590
Elemental analysis value: $C_{21}H_{30}O_5$
Theoretical value (%): C 68.54; H 8.63; O 22.83
Actual measured value (%): C 68.66; H 8.68; O 22.66

Example 100

3-(acetoxy)-4-(isopropoxy)-8-hydroxy-2H-1-benzopyran-2-one (Compound 100)

In Example 8, 3.53 g (1.49×10⁻² mol) of 3-(acetoxy)-4,8-(dihydroxy)-2H-1-benzopyran-2-one was used in place of 3,4,7-trihydroxy-2H-1-benzopyran-2-one, isopropylbromide was used in place of benzoylchloride, and 3.04 g (yield=71%) of the desired compound 100 was obtained.

¹H-NMR (DMSO-d₆, δ-TMS) 10.81 (bs,1H), 6.80~7.50 (m, 3H), 3.87 (m, 1H), 1.89 (s, 3H), 1.11 (d, 6H, J=6.0 Hz)
IR (KBr, cm⁻¹) 3200, 1710, 1690, 1630, 1590
Elemental analysis value: $C_{14}H_{14}O_6$
Theoretical value (%): C 60.43; H 5.07; O 34.50
Actual measured value (%): C 60.48; H 5.15; O 34.37

Example 101

3-(methoxy)-4-(acetoxy)-8-hydroxy-2H-1-benzopyran-2-one (Compound 101)

In Example 8, 2.59 g (1.10×10⁻² mol) of 3,8-(dihydroxy)-4-(acetoxy)-2H-1-benzopyran-2-one was used in place of 3,4,7-trihydroxy-2H-1-benzopyran-2-one, methyliodide was used in place of benzoylchloride, and 1.87 g (yield=68%) of the desired compound 101 was obtained.

¹H-NMR (DMSO-d₆, δ-TMS) 10.61 (bs,1H), 6.80~7.50 (m, 3H), 3.72 (s,3H), 1.91 (s, 3H)
IR (KBr, cm⁻¹) 3200, 1710, 1680, 1610, 1590
Elemental analysis value: $C_{12}H_{10}O_6$
Theoretical value (%): C 57.60; H 4.03; O 38.37
Actual measured value (%): C 57.37; H 4.27; O 38.36

Example 102

3-(geranyloxy)-4,8-(dihydroxy)-2H-1-benzopyran-2-one (Compound 102)

In Example 5, 2.01 g (5.40×10⁻³ mol) of 3-(geranyloxy)-4-(acetoxy)-8-hydroxy-2H-1-benzopyran-2-one was used in place of 3-(benzoyloxy)-4,7-(dihydroxy)-2H-1-benzopyran-2-one, and 1.00 g (yield=56%) of the desired compound 102 was obtained.

¹H-NMR (DMSO-d₆, δ-TMS) 10.73 (bs,1H), 10.14 (bs, 1H), 6.80~7.50 (m, 3H), 5.48 (bt, 1H, J=7.0 Hz), 5.09 (bt, 1H, J=7.0 Hz), 4.02 (d, 2H, J=7.0 Hz), 1.95~2.20 (m, 4H), 1.55~1.85 (m, 9H)
IR (KBr, cm⁻¹) 3500, 3200, 1720, 1680, 1630, 1580
Elemental analysis value: $C_{19}H_{22}O_5$
Theoretical value (%): C 69.07; H 6.71; O 24.22
Actual measured value (%): C 69.05; H 6.59; O 24.36

Example 103

3,8-(dihydroxy)-4-(geranyloxy)-2H-1-benzopyran-2-one (Compound 103)

In Example 8, 2.73 g (1.41×10⁻² mol) of 3,4,8-trihydroxy-2H-1-benzopyran-2-one was used in place of 3,4,7-trihydroxy-2H-1-benzopyran-2-one, geranylbromide was used in place of benzoylchloride, and 2.79 g (yield=60%) of the desired compound 103 was obtained.

¹H-NMR (DMSO-d₆, δ-TMS) 10.76 (bs, 1H), 9.21 (bs, 1H), 6.80~7.50 (m, 3H), 5.45 (bt, 1H, J=7.0 Hz), 5.11 (bt, 1H, J=7.0 Hz), 4.00 (d, 2H, J=7.0 Hz), 1.95~2.20 (m, 4H), 1.55~1.85 (m, 9H)
IR (KBr, cm⁻¹) 3200, 1720, 1680, 1630, 1580
Elemental analysis value: $C_{19}H_{22}O_5$
Theoretical value (%): C 69.07; H 6.71; O 24.22
Actual measured value (%): C 69.09; H 6.65; O 24.26

Example 104

3-(geranyloxy)-4-(acetoxy)-8-hydroxy-2H-1-benzopyran-2-one (Compound 104)

In Example 8, 1.71 g (5.16×10⁻³ mol) of 3-(geranyloxy)-4,8-(dihydroxy)-2H-1-benzopyran-2-one was used in place of 3,4,7-trihydroxy-2H-1-benzopyran-2-one, acetylchloride was used in place of benzoylchloride, and 1.21 g (yield=63%) of the desired compound 104 was obtained.

¹H-NMR (DMSO-d₆, δ-TMS) 10.62 (bs,1H), 6.70~7.50 (m, 3H), 5.47 (bt, 1H, J=7.0 Hz), 5.10 (bt, 1H, J=7.0 Hz}, 4.03 (d, 2H, J=7.0 Hz), 1.95~2.20 (m, 4H), 1.70 (s,3H), 1.55~1.85 (m, 9H)
IR (KBr, cm⁻¹) 3500, 3200, 1710, 1660, 1630, 1580
Elemental analysis value: $C_{21}H_{24}O_6$
Theoretical value (%): C 67.73; H 6.50; O 25.78
Actual measured value (%): C 67.78; H 6.43; O 25.79

Example 105

3-(geranyloxy)-4,8-(diacetoxy)-2H-1-benzopyran-2-one (Compound 105)

In Example 8, 1.61 g (4.87×10⁻³ mol) of 3-(geranyloxy)-4,8-(dihydroxy)-2H-1-benzopyran-2-one was use a in place of 3,4,7-trihydroxy-2H-1-benzopyran-2-one, potassium carbonate was used in place of sodium bicarbonate, acetylchloride was used in place of benzoylchloride, and 1.11 g (yield=55%) of the desired compound 105 was obtained.

¹H-NMR (DMSO-d₆, δ-TMS) 6.70~7.50 (m, 3H), 5.47 (bt, 1H, J=7.0 Hz), 5.11 (bt, 1H, J=7.0 Hz), 4.03 (d, 2H, J=7.0 Hz), 1.95~2.20 (m, 4H), 1.95 (s, 3H), 1.70 (s, 3H), 1.55~1.85 (m, 9H)
IR (KBr, cm⁻¹) 3500, 3200, 1710, 1660, 1630, 1580
Elemental analysis value: $C_{23}H_{26}O_7$
Theoretical value (%): C 66.63; H 6.32; O 27.02
Actual measured value (%): C 66.61; H 6.25; O 27.14

Example 106

3-(benzoyloxy)-4-(geranyloxy)-8-hydroxy-2H-1-benzopyran-2-one (Compound 10 6)

In Example 8, 1.53 g (5.13×10⁻³ mol) of 3-(benzoyloxy)-4,8-(dihydroxy)-2H-1-benzopyran-2-one was used in place of 3,4,7-trihydroxy-2H-1-benzopyran-2-one, geranylbromide was used in place of benzoylchloride, and 1.43 g (yield=64%) of the desired compound 106 was obtained.

¹H-NMR (DMSO-d₆, δ-TMS) 10.46 (bs,1H), 8.10~8.20 (m, 2H), 6.80~7.80 (m, 6H), 5.44 (bt, 1H, J=7.0 Hz), 5.15 (bt, 1H, J=7.0 Hz), 4.00 (d, H, J=7.0 Hz), 1.95~2.20 (m, 4H), 1.55~1.85 (m, 9H)

IR (KBr, cm⁻¹) 3200, 1720, 1680, 1630, 1580
Elemental analysis value: C₂₆H₂₆O₆
Theoretical value (%): C 71.82; H 6.03; O 22.10
Actual measured value (%): C 71.85; H 6.14; O 22.01

Example 107

3-(geranyloxy)-4-(methoxy)-8-hydroxy-2H-1-benzopyran-2-one (Compound 107)

In Example 8, 1.53 g (7.35×10⁻³ mol) of 3,8-(dihydroxy)-4-(methoxy)-2H-1-benzopyran-2-one was used in place of 3,4,7-trihydroxy-2H-1-benzopyran-2-one, geranylbromide was used in place of benzoylchloride, and 1.77 g (yield=70%) of the desired compound 107 was obtained.

¹H-NMR (DMSO-d₆, δ-TMS)
10.68 (bs,1H), 6.70~7.60 (m, 3H), 5.45 (bt, 1H, J=7.0 Hz), 5.10 (bt, 1H, J=7.0 Hz), 4.03 (d, 2H, J=7.0 Hz), 3.71 (s, 3H), 1.95~2.20 (m, 4H), 1.55~1.85 (m, 9H)

IR (KBr, cm⁻¹) 3200, 1720, 1690, 1630, 1580, 1550
Elemental analysis value: C₂₀H₂₄O₅
Theoretical value (%): C 69.75; H 7.02; O 23.23
Actual measured value (%): C 69.63; H 7.13; O 23.24

Example 108

3-(isopropoxy)-4-(geranyloxy)-8-hydroxy-2H-1-benzopyran-2-one (Compound 108)

In Example 8, 1.58 g (6.69×10⁻³ mol) of 3-(isopropoxy)-4,8-(dihydroxy)-2H-1-benzopyran-2-one was used in place of 3,4,7-trihydroxy-2H-1-benzopyran-2-one, geranylbromide was used in place of benzoylchloride, and 1.57 g (yield=63%) of the desired compound 108 was obtained.

¹H-NMR (DMSO-d₆, δ-TMS)
10.58 (bs, 1H), 6.70~7.60 (m, 3H), 5.45 (bt, 1H, J=7.0 Hz), 5.11 (bt, 1H, J=7.0 Hz), 4.01 (d, 2H, J=7.0 Hz), 3.89 (m, 1H), 1.95~2.20 (m, 4H), 1.55~1.85 (m, 9H), 1.13 (d, 6H, J=6.0 Hz)

IR (KBr, cm⁻¹) 3200, 1710, 1690, 1630, 1580, 1550
Elemental analysis value: C₂₂H₂₈O₅
Theoretical value (%): C 70.94; H 7.52; O 21.48
Actual measured value (%): C 71.04; H 7.51; O 21.45

Example 109

3,4-(digeranyloxy)-8-hydroxy-2H-1-benzopyran-2-one (Compound 109)

In Example 8, 1.49 g (4.51×10⁻³ mol) of 3,8-(dihydroxy)-4-(geranyloxy)-2H-1-benzopyran-2-one was used in place of 3,4,7-trihydroxy-2H-1-benzopyran-2-one, geranylbromide was used in place of benzoylchloride, and 1.12 g (yield=53%) of the desired compound 109 was obtained.

¹H-NMR (DMSO-d₆,8-TMS) 10.80 (bs, 1H), 6.70~7.60 (m, 3H), 5.10~5.50 (m, 4H), 4.03 (d, 2H, J=7.0 Hz), 4.02 (d, 2H, J=6.0 Hz), 1.95~2.20 (m, 8H), 1.55~1.85 (m, 18H)

IR (KBr, cm⁻¹) 3200, 1720, 1680, 1630, 1580, 1550
Elemental analysis value: C₂₉H₃₈O₅
Theoretical value (%): C 74.65; H 8.21; O 17.14
Actual measured value (%): C 74.74; H 8.17; O 17.09

Example 110

3-(benzoyloxy)-4-hydroxy-8-(methoxy)-2H-1-benzopyran-2-one (Compound 1 t 0)

In Example 1, 2'-hydroxy-3'-methoxyacetophenone was used in place of 2',4'-dihydroxyacetophenone, after which Examples 2~4 were carried out, and 4.87 g (yield=80%) of the desired compound 110 was obtained from 8.16 g (1.95×10⁻² mol) of methyl-β-oxo-2'-(phenylmethoxy)-3'-(methoxy)-2-(benzoyloxy)benzenepropanate.

¹H-NMR (DMSO-d₆, δ-TMS) 10.21 (bs, 1H), 6.90~8.20 (m, 8H), 3.62 (s, 3H)

IR (KBr, cm⁻¹) 3200, 1710, 1690, 1630, 1590
Elemental analysis value: C₁₇H₁₂O₆
Theoretical value (%): C 65.38; H 3.87; O 30.74
Actual measured value (%): C 65.40; H 3.84; O 30.76

Example 111

3,4-(dihydroxy)-8-(methoxy)-2H-1-benzopyran-2-one (Compound 111)

In Example 5, 3.67 g (1.18×10⁻² mol) of 3-(benzoyloxy)-4-hydroxy-8-(methoxy)-2H-1-benzopyran-2-one was used in place of 3-(benzoyloxy)-4,7-(dihydroxy)-2H-1-benzopyran-2-one, and 1,64 9 (yield=67%) of the desired compound 111 was obtained.

¹H-NMR (DMSO-d₆, δ-TMS)
10.22 (bs, 1H), 8.70 (bs, 1H), 6.80~7.50 (m, 3H), 3.48 (s, 3H)

IR (KBr, cm⁻¹)
3400, 1710, 1680, 1610, 1590
Elemental analysis value: C₁₀H₈O₅
Theoretical value (%): C 57.69; H 3.87; O 38.43
Actual measured value (%): C 57.92; H 3.69; O 38.36

Example 112

3-hydroxy-4-(acetoxy)-8-(methoxy)-2H-1-benzopyran-2-one (Compound 112)

In Example 8, 2.49 g (1.20×10⁻² mol) of 3,4-(dihydroxy)-8-(methoxy)-2H-1-benzopyran-2-one was used in place of 3,4,7-trihydroxy-2H-1-benzopyran-2-one, acetylchloride was used in place of benzoylchloride, and 2.07 g (yield=69%) of the desired compound 112 was obtained.

¹H-NMR (DMSO-d₆, δ-TMS)
8.70 (bs, 1H), 6.80~7.50 (m,3H), 3.48 (s,3H), 1.79 (s, 3H)

IR (KBr, cm⁻¹)
3300, 1710, 1680, 1610, 1590
Elemental analysis value: C₁₂H₁₀O₆
Theoretical value (%): C 57.60; H 4.03; O 38.37
Actual measured value (%): C 57.69; H 4.17; O 38.14

Example 113

3,4-(diacetoxy)-8-(methoxy)-2H-1-benzopyran-2-one (Compound 13)

In Example 8, 2.10 g ($1.01 \times 10^{-2}$ mol) of 3,4-(dihydroxy)-8-(methoxy)-2H-1-benzopyran-2-one was used in place of 3,4,7-trihydroxy-2H-1-benzopyran-2-one, potassium carbonate was used in place of sodium bicarbonate, acetylchloride was used in place of benzoylchloride, and 1.92 g (yield=65%) of the desired compound 113 was obtained.

$^1$H-NMR (DMSO-d$_6$, δ-TMS) 8.70 (bs, 1H), 6.80~7.50 (m,3H), 3.48 (s,3H), 1.79 (s, 3H)
IR (KBr, cm$^{-1}$) 3300, 1710, 1680, 1610, 1590
Elemental analysis value: C$_{12}$ H$_{10}$ O$_6$
Theoretical value (%): C 57.60; H 4.03; O 38.37
Actual measured value (%): C 57.69; H 4.17; O 38.14

Example 114

3-(acetoxy)-4-(benzoyloxy)-8-(methoxy)-2H-1-benzopyran-2-one (Compound 114)

In Example 8, 3.64 g ($1.45 \times 10^{-2}$ mol) of 3-(acetoxy)-4-hydroxy-8-(methoxy)-2H-1-benzopyran-2-one was used in place of 3,4,7-trihydroxy-2H-1-benzopyran-2-one, and 3.71 g (yield=72%) of the desired compound 114 was obtained.

$^1$H-NMR (DMSO-d$_6$, δ-TMS) 6.90~8.20 (m, 5H), 3.78 (s,3H), 1.81 (s,3H)
IR (KBr, cm$^{-1}$) 1720, 1680, 1610, 1590
Elemental analysis value: C$_{19}$ H$_{14}$ O$_7$
Theoretical value (%): C 64.40; H 3.98; O 31.61
Actual measured value (%): C 64.40; H 4.07; O 31.53

Example 115

3,8-(dimethoxy)-4-hydroxy-2H-1-benzopyran-2-one (Compound

In Example 5, 2.12 g. ($8.02 \times 10^{-3}$ mol) of 3,8-(dimethoxy)-4-(acetoxy)-2H-1-benzopyran-2-one was used in place of 3-(benzoyloxy)-4,7-(dihydroxy)-2H-1-benzopyran-2-one, and 1.11 g (yield=62%) of the desired compound 115 was obtained.

$^1$H-NMR (DMSO-d$_6$, δ-TMS) 10.22 (bs,1H), 6.80~7.50 (m, 3H), 3.88 (s,3H), 3.61 (s, 3H)
IR (KBr, cm$^{-1}$) 3350, 1710, 1680, 1610, 1590
Elemental analysis value: C$_{11}$H$_{10}$O$_5$
Theoretical value (%): C 59.46; H 4.54; O 36.01
Actual measured value (%): C 59.28; H 4.58; O 36.14

Example 116

3-hydroxy-4-(isopropoxy)-8-(methoxy).2H-1-benzopyran-2-one (Compound 116)

In Example 8, 2.80 g ($1.35 \times 10^{-2}$ mol) of 3,4-(dihydroxy)-8-(methoxy)-2H-1-benzopyran-2-one was used in place of 3,4,7-trihydroxy-2H-1-benzopyran-2-one, isopropylbromide was used in place of benzoylchloride, and 1.99 g (yield=59%) of the desired compound 116 was obtained.

$^1$H-NMR (DMSO-d$_6$, δ-TMS) 8.90 (bs, 1H), 6.80~7.50 (m, 3H), 3.68 (m, 1H), 3.86 (s, 3H), 1.19 (d, 6H, J=6.0Hz)
IR (KBr, cm$^{-1}$) 3200, 1710, 1680, 1610, 1590
Elemental analysis value: C$_{13}$ H$_{14}$ O$_5$
Theoretical value (%): C 62.39; H 5.64; O 31.97
Actual measured value (%): C 62.31; H 5.65; O 32.04

Example 117

3-(decyloxy)-4,8-(dimethoxy)-2H-1-benzopyran-2-one (Compound

In Example 8, 3.01 g ($8.08 \times 10^{-3}$ mol) of 3-(decyloxy)-4-hydroxy-8-(methoxy)-2H-1-benzopyran-2-one was used in place of 3,4,7-trihydroxy-2H-1-benzopyran-2-one, methyliodide was used in place of benzoylchloride, and 1.97 g (yield=63%) of the desired compound 117 was obtained.

$^1$H-NMR (DMSO-d$_6$, δ-TMS) 6.80~7.50 (m, 3H), 3.81 (s,3H), 3.66 (s,3H), 3.26 (t, H, J=7.0Hz), 1.21~1.70 (m, 16H), 0.87 (t, 3H, J=6.0Hz)
IR (KBr, cm$^{-1}$) t710, 1680, 1610, 1590
Elemental analysis value: C$_{21}$ H$_{30}$ O$_5$
Theoretical value (%): C 69.58; H 8.34; O 22.07
Actual measured value (%): C 69.44; H 8.47; O 22.09

Example 118

3-(acetoxy)-4-(decyloxy)-8-(methoxy)-2H-1-benzopyran-2-one (Compound 118)

In Example 8, 2.99 g ($1.20 \times 10^{-2}$ mol) of 3-(acetoxy)-4-hydroxy-8-(methoxy)-2H-1-benzopyran-2-one was used in place of 3,4,7-trihydroxy-2H-1-benzopyran-2-one, decylbromide was used in place of benzoylchloride, and 3.47 g (yield=70%) of the desired compound 118 was obtained.

$^1$H-NMR (DMSO-d$_6$, δ-TMS) 6.80~7.50 (m, 3H), 3.82 (s, 3H), 3.22 (t, 2H, J=7.0Hz), 1.89 (s, 3H), 1.21~1.70 (m, 16H), 0.85 (t, 3H, J=6 , 0Hz)
IR (KBr, cm$^{-1}$) 1710, 1680, 1610, 1590
Elemental analysis value: C$_{22}$ H$_{30}$ O$_6$
Theoretical value (%): C 67.67; H 7.74; O 24.59
Actual measured value (%): C 67.79; H 7.71; O 24.50

Example 119

3-(isopropoxy)-8-(benzoyloxy)-8-(methoxy)-2H-1-benzopyran-2-one (Compound 119)

In Example 8, 2.53 g ($8.10 \times 10^{-3}$ mol) of 3-hydroxy-4-(benzoyloxy)-8-(methoxy)-2H-1-benzopyran-2-one was used in place of 3,4,7-trihydroxy-2H-1-benzopyran-2-one, isopropylbromide was used in place of benzoylchloride, and 1.79 g (yield=65%) of the desired compound 119 was obtained.

$^1$H-NMR (DMSO-d$_6$, δ-TMS) 6.90~8.20 (m, 8H), 3.88 (m, 1H), 3.62 (s, 3H), 1.16 (d, 6H, J=6.0Hz)
IR (KBr, cm$^{-1}$) 1710, 1690, 1630, 1590
Elemental analysis value: C$_{20}$ H$_{18}$ O$_6$
Theoretical value (%): C 67.79; H 5.12; O 27.09
Actual measured value (%): C 67.81; H 5.03; O 27.16

Example 120

3-(geranyloxy)-4-hydroxy-8-(methoxy)-2H-1-benzopyran-2-one (Compound 120)

In Example 5, 1.15 g ($3.93 \times 10^{-3}$ mol) of 3-(geranyloxy)-4-(acetoxy)-8-(methoxy)-2H-1-benzopyran-2-one was used in place of 3-(benzoyloxy)-4,7-(dihydroxy)-2H-1-benzopyran-2-one, and 0.84 g (yield=62%) of the desired compound 120 was obtained.

$^1$H-NMR (DMSO-d$_6$, δ-TMS) 10.20 (bs, 1H), 6.70~7.60 (m, 3H), 5.43 (bt, 1H, J=7.0Hz), 5.03 (bt, 1H, J=7.0Hz), 4.01 (d, 2H, J=7.0Hz), 3.86 (s, 3H), 2.00~2.21 (m, 4H), 1.52~1.85 (m, 9H)
IR (KBr, cm$^{-1}$) 3200, 1720, 1680, 1630, 1580

Elemental analysis value: $C_{20}H_{24}O_5$
Theoretical value (%): C 69.75; H 7.02; O 23.23
Actual measured value (%): C 69.71; H 7.09; O 23.20

Example 121

3-hydroxy-4-(geranyloxy)-8-(methoxy)-2H-1-benzopyran-2-one (Compound 121)

In Example 8, 1.53 g ($7.35 \times 10^{-3}$ mol) of 3,4-(dihydroxy)-8-(methoxy)-2H-1-benzopyran-2-one was used in place of 3,4,7-trihydroxy-2H-1-benzopyran-2-one, geranylbromide was used in place of benzoylchloride, and 1.29 g (yield=51%) of the desired compound 121 was obtained.

$^1$H-NMR (DMSO-$d_6$, δ-TMS) 8.79 (bs, 1H), 6.70~7.60 (m, 3H), 5.45 (bt, 1H, J=7.0Hz), 5.03 (bt, 1H, J=7.0Hz), 4.04 (d, 2H, J=7.0Hz), 3.84 (s,3H), 2.00~2.21 (m, 4H), 1.52~1.85 (m, 9H)

IR (KBr, cm$^{-1}$) 3200, 1730, 1670, 1630, 1580
Elemental analysis value: $C_{20}H_{24}O_5$
Theoretical value (%): C 69.75; H 7.02; O 23.23
Actual measured value (%): C 69.73; H 7.13; O 2.14

Example 122

3-(geranyloxy)-4-(benzoyloxy)-8-(methoxy)-2H-1-benzopyran-2-one (Compound 122)

In Example 8, 1.54 g ($4.47 \times 10^{-3}$ mol) of 3-(geranyloxy)-4-hydroxy-8-(methoxy)-2H-1-benzopyran-2-one was used in place of 3,4,7-trihydroxy-2H-1-benzopyran-2-one, and 1.26 g (yield=63%) of the desired compound 122 was obtained.

$^1$H-NMR (DMSO-$d_6$, δ-TMS) 8.10~8.20 (m, 2H), 6.70~7.80 (m, 6H), 5.45 (bt, 1H, J=7.0Hz), 5.01 (bt, 1H, J=7.0Hz), 4.02 (d, 2H, J=7.0Hz), 3.82 (s, 3H), 2.00~2.21 (m, 4H), 1.52~1.85 (m, 9H)

IR (KBr, cm$^{-1}$) 1730, 1670, 1630, 1580, 1520
Elemental analysis value: $C_{27}H_{28}O_6$
Theoretical value (%): C 72.30; H 6.29; O 21.41
Actual measured value (%): C 72.33; H 6.28; O 21.39

Example 123

3-(acetoxy)-4-(geranyloxy)-8-(methoxy)-2H-1-benzopyran-2-one (Compound 123)

In Example 8, 1.49 g ($5.96 \times 10^{-3}$ mol) of 3-(acetoxy)-4-hydroxy-8-(methoxy)-2H-1-benzopyran-2-one was used in place of 3,4,7-trihydroxy-2H-1-benzopyran-2-one, geranylbromide was used in place of benzoylchloride, and 1.56 g (yield=68%) of the desired compound 123 was obtained. 1H-NMR (DMSO-$d_6$, δ-TMS) 6.70~7.60 (m, 3H), 5.42 (bt, 1H, J=7.0Hz), 5.04 (bt, 1H, J=7.0Hz), 4.01 (d, 2H, J=7.0Hz), 3.81 (s, 3H), 2.00~2.21 (m, 4H), 1.53 (s,3H), 1.52~1.85 (m, 9H)

IR(KBr,cm$^{-1}$) 1730, 1670, 1630, 1580, 1520
Elemental analysis value: $C_{22}H_{26}O_6$
Theoretical value (%): C 68.38; H 6.78; O 24.84
Actual measured value (%): C 68.44; H 6.76; O 24.80

Example 124

3-(geranyloxy)-4-(isopropoxy)-8-(methoxy)-2H-1-benzopyran-2-one (Compound 124)

In Example 8, 1.48 g ($4.30 \times 10^{-3}$ mol) of 3-(geranyloxy)-4-hydroxy-8-(methoxy)-2H-1-benzopyran-2-one was used in place of 3,4,7-trihydroxy-2H-1-benzopyran-2-one, isopropylbromide was used in place of benzoylchloride, and 1.08 g (yield=65%) of the desired compound 124 was obtained. 2. H-NMR (DMSO-$d_6$, δ-TMS) 6.70~7.60 (m, 3H), 5.41 (bt, 1H, J=7.0Hz), 5.04 (bt, 1H, J=7.0Hz), 4.03 (d, 2H, J=7.0Hz), 3.92 (m, 1H), 3.83 (s, 3H), 2.00~2.21 (m, 4H), 1.52~1.85 (m, 9H), 1.11 (d, 6H, J=6.0Hz)

IR (KBr, cm$^{-1}$) 1720, 1680, 1630, 1580, 1550
Elemental analysis value: $C_{22}H_{26}O_6$
Theoretical value (%): C 68.38; H 6.78; O 24.84
Actual measured value (%): C 68.31; H 6.89; O 24.80

Example 125

3,8-(dimethoxy)-4-(geranyloxy)-2H-1-benzopyran-2-one (Compound 125)

In Example 8, 1.55 g ($4.50 \times 10^{-3}$ mol) of 3-hydroxy-4-(geranyloxy)-8-(methoxy)-2 H-1-benzopyran-2-one was used in place of 3,4,7-trihydroxy- 2H-1-benzopyran-2-one, methyliodide was used in place of benzoylchloride, and 1.03 g (yield=64%) of the desired compound 125 was obtained.

$^1$H-NMR (DMSO-$d_6$, δ-TMS) 6.70~7.60 (m, 3H), 5.45 (bt, 1H, J=7.0Hz), 5.01 (bt, 1H, J=7.0Hz), 4.01 (d, 2H, J=7.0Hz), 3.89 (s, 3H), 3.66 (s, 3H), 2.00~2.21 (m, 4H), 1.52~1.85 (m, 9H)

IR (KBr, cm$^{-1}$) 1730, 1670, 1630, 1580, 1520
Elemental analysis value: $C_{21}H_{26}O_5$
Theoretical value (%): C 70.37; H 7.31; O 22.32
Actual measured value (%): C 70.36; H 7.37; O 22.27

Example 126

3,4-(digeranyloxy)-8-(methoxy)-2H-1-benzopyran-2-one (Compound 126)

In Example 8, 1.51 g ($4.38 \times 10^{-3}$ mol) of 3-hydroxy-4-(geranyloxy)-8-(methoxy)-2H-1-benzopyran-2-one was used in place of 3,4,7-trihydroxy-2H-1-benzopyran-2-one, geranylbromide was used in place of benzoylchloride, and 1.26 g (yield=60%) of the desired compound 126 was obtained.

$^1$H-NMR (DMSO-$d_6$, δ-TMS) 6.70~7.60 (m, 3H), 5.10~5.50 (m, 4H), 4.03 (d, 2H, J=7.0Hz), 4.01 (d, 2H, J=6.0Hz), 3.85 (s, 3H), 1.95~2.20 (m, 8H), 1.55~1.85 (m, 18H)

IR (KBr, cm$^{-1}$) 1710, 1670, 1630, 1580, 1550
Elemental analysis value: $C_{30}H_{38}O_5$
Theoretical value (%): C 75.28; H 8.00; O 16.72
Actual measured value (%): C 75.19; H 8.03; O 16.78

Example 127

3-(benzoyloxy)-4-hydroxy-8-(butyloxy)-2H-1-benzopyran-2-one (Compound 127)

In Example 1, 2'-hydroxy-3'-butyloxy-acetophenone was used in place of 2',4'-dihydroxyacetophenone, following which Examples 2, 3, and 4 were carried out, and 4.73 g (yield=81%) of the desired compound 127 was obtained from 7.64 g ($1.69 \times 10^{-2}$ mol) of methyl-β-oxo-2'-(phenylmethoxy)-3'-(butyloxy)-2-(benzoyloxy)-benzenepropanate.

$^1$H-NMR (DMSO-$d_6$, δ-TMS) 10.26 (bs,1H), 6.70~8.20 (m, 8H), 3.21 (t, 2H, J=6.0Hz), 2.98 (s,3H), 1.00~1.70 (m, 4H), 1.25 (s,3H)

IR (KBr, cm$^{-1}$) 3300, 1710, 1690, 1630, 1590
Elemental analysis value: $C_{20}H_{18}O_6$
Theoretical value (%): C 67.79; H 5.12; O 27.09
Actual measured value (%): C 67.63; H 5.23; O 27.14

Example 128

3,4-(dihydroxy)-8-(butyloxy)-2H-1-benzopyran-2-one (Compound

In Example 5, 2.33 g ($6.75 \times 10^{-3}$ mol) of 3-(benzoyloxy)-4-hydroxy-8-(butyloxy)-2H-1-benzopyran-2-one was used in place of 3-(benzoyloxy)-4,7-(dihydroxy)-2H-1-benzopyran-2-one, and 1.11 g (yield=68%) of the desired compound 128 was obtained.

$^1$H-NMR (DMSO-d$_6$, δ-TMS) 10.15 (bs, 1H), 8.75 (bs, 1H), 6.80~7.50 (m, 3H), 3.33 (t, 2H, J=6.0Hz), 1.0~1.7 (m, 4H), 1.36 (s, 3H)

IR (KBr, cm$^{-1}$) 400, 1710, 1680, 1610, 1590

Elemental analysis value: C$_{13}$H$_{14}$O$_5$

Theoretical value (%): C 62.39; H 5.64; O 31.97

Actual measured value (%): C 62.41; H 5.71; O 31.88

Example 129

3-(benzoyloxy)-4-hydroxy-8-(isopropoxy)-2H-1-benzopyran-2-one (Compound 129)

In Example 4, 5.50 g ($1.23 \times 10^{-2}$ mol) of methyl-β-oxo-2'-(phenylmethoxy)-3'-(isopropoxy)-2-(benzoyloxy) benzenepropanate was used in place of methyl-β-oxo-2',4'-bis(phenylmethoxy)-2-(benzoyloxy)benzenepropanate, and 3.49 g (yield=83%) of the desired compound 129 was obtained.

$^1$H-NMR (DMSO-d$_6$, δ-TMS) 10.31 (bs,1H), 8.10~8.20 (m, 2H), 6.70~7.80 (m, 6H), 3.51 (m, 1H), 1.15 (d, 6H, J=6.0Hz)

IR (KBr, cm$^{-1}$) 3200, 1740, 1690, 1630, 1610, 1580

Elemental analysis value: C$_{19}$H$_{16}$O$_6$

Theoretical value (%): C 67.05; H 4.75; O 28.20

Actual measured value (%): C 67.08; H 4.69; O 28.23

Example 130

3,4-(dihydroxy)-8-(isopropoxy)-2H-1-benzopyran-2-one (Compound 130)

In Example 5, 1.89 g ($5.55 \times 10^{-3}$ mol) of 3-(benzoyloxy)-4-hydroxy-5-(isopropoxy)-2H-1-benzopyran-2-one was used in place of 3-(benzoyloxy)-4,7-(dihydroxy)-2H-1-benzopyran-2-one, and 0.81 g (yield=62%) of the desired compound 130 was obtained. 10.36 (bs,1H), 8.89 (bs,1H), 6.70~7.60 (m, 3H), 3.53 (m, H), 1.12 (d, 6H, J=6.0Hz)

IR (KBr, cm$^{-1}$) 3200, 1680, 1650, 1610, 1530

Elemental analysis value: C$_{12}$H$_{12}$O$_5$

Theoretical value (%): C 62.90; H 4.87; O 32.23

Actual measured value (%): C 62.79; H 4.92; O 32.29

Example 131

3-hydroxy-4-(acetoxy)-8-(isopropoxy)-2H-1-benzopyran-2-one (Compound 131)

In Example 8, 1.44 g ($6.10 \times 10^{-3}$ mol) of 3,4-(dihydroxy)-8-(isopropoxy)-2H-1-benzopyran-2-one was used in place of 3,4,7-trihydroxy-2H-1-benzopyran-2-one, acetylchloride was used in place of benzoylchloride, and 1.10 g (yield=65%) of the desired compound 131 was obtained.

$^1$H-NMR (DMSO-d$_6$, δ-TMS) 8.79 (bs, 1H), 6.70~7.60 (m,3H), 3.49 (m, 1H), 1.69 (s, 3H), 1.11 (d, 6H, J=6.0Hz)

IR (KBr, cm$^{-1}$) 3300, 1710, 1680, 1650, 1610

Elemental analysis value: C$_{14}$H$_{14}$O$_6$

Theoretical value (%): C 60.43; H 5.07; O 34.50

Actual measured value (%): C 60.36; H 5.17; O 34.47

Example 132

3,4-(diacetoxy)-8-(isopropoxy)-2H-1-benzopyran-2-one (Compound 132)

In Example 8, 1.61 g ($6.82 \times 10^{-3}$ mol) of 3,4-(dihydroxy)-8-(isopropoxy)-2H-1-benzopyran-2-one was used in place of 3,4,7-trihydroxy-2H-1-benzopyran-2-one, potassium carbonate was used in place of sodium bicarbonate, acetylchloride was used in place of benzoylchloride, and 1.53 g (yield=70%) of the desired compound 132 was obtained.

$^1$H-NMR (DMSO-d$_6$, δ-TMS) 6.70~7.60 (m, 3H), 3.55 (m, 1H), 1.69 (s, 3H), 1.65 (s, 3H), 1.11 (d, 6H, J=6.0Hz)

IR (KBr, cm$^{-1}$) 1750, 1710, 1680, 1650, 1610

Elemental analysis value: C$_{16}$H$_{16}$O$_7$

Theoretical value (%): C 60.00; H 5.04; O 34.96

Actual measured value (%): C 60.12; H 5.01; O 34.87

Example 133

3-(decyloxy)-4-hydroxy-8-(isopropoxy)-2H-1-benzopyran-2-one (Compound 133)

In Example 5, 2.51 g ($5.67 \times 10^{-3}$ mol) of 3-(decyloxy)-4-(acetoxy)-8-(isopropoxy)-2H-1-benzopyran-2-one was used in place of 3-(benzoyloxy)-4,7-(dihydroxy)-2H-1-benzopyran-2-one, and 1.61 g (yield=71%) of the desired compound 133 was obtained.

$^1$H-NMR (DMSO-d$_6$, δ-TMS) 10.19 (bs,1H), 6.70~7.50 (m, 3H), 3.49 (m, 1H), 3.29 (t, 2H, J=7.0Hz), 1.20~1.70 (m, 16H), 1.12 (d, 6H, J=6.0Hz), 0.90 (t, 3H, J=6.0Hz)

IR (KBr, cm$^{-1}$) 3200, 1680, 1650, 1610

Elemental analysis value: C$_{22}$H$_{32}$O$_5$

Theoretical value (%): C 70.18; H 8.57; O 21.25

Actual measured value (%): C 70.12; H 8.59; O 21.29

Example 134

3-hydroxy-4,8-(disopropoxy)-2H-1-benzopyran-2-one (Compound 134)

In Example 8, 1.58 g ($6.69 \times 10^{-3}$ mol) of 3,4-(dihydroxy)-8-(isopropoxy)-2H-1-benzopyran-2-one was used in place of 3,4,7-trihydroxy- 2H-1-benzopyran-2-one, isopropylbromide was used in place of benzoylchloride, and 1.15 g (yield=62%) of the desired compound 134 was obtained.

$^1$H-NMR (DMSO-d$_6$, δ-TMS) 8.98 (bs, 1H), 6.70~7.60 (m, 3H), 3.40~3.60 (m, 2H), 1.13 (d, 6H, J=6.0Hz), 1.11 (d, 6H, J=6.0Hz)

IR (KBr, cm$^{-1}$) 3200, 1680, 1650, 1610

Elemental analysis value: C$_{15}$H$_{18}$O$_5$

Theoretical value (%): C 64.73; H 6.52; O 28.75

Actual measured value (%): C 64.69; H 6.45; O 28.86

Example 135

3-(methoxy)-4-(decyloxy)-8-(isopropoxy)-2H-1-benzoyran-2-one (Compound 135)

In Example 8, 1.64 g ($4.09 \times 10^{-3}$ mol) of 3-hydroxy-4-(decyloxy)-8-(isopropoxy)-2H-1-benzopyran-2-one was used in place of 3,4,7-trihydroxy-2H-1-benzopyran-2-one, methyliodide was used in place of benzoylchloride, and 0.88 g (yield=52%) of the desired compound 135 was obtained.

$^1$H-NMR (DMSO-d$_6$, δ-TMS) 6.70~7.60 (m, 3H), 3.70 (s, 3H), 3.53 (m, 1H), 3.36 (t, H, J=7.0Hz), 1.20~1.70 (m, 16H), 1.18 (d, 6H, J=6.0Hz), 0.88 (t, 3H, J=6.0Hz)

IR (KBr, cm$^{-1}$) 1680, 1650, 1610, 1580, 1550
Elemental analysis value: $C_{23}H_{34}O_5$
Theoretical value (%): C 70.74; H 8.78; O 20.49
Actual measured value (%): C 70.65; H 8.92; O 20.50

Example 136

3-(acetoxy)-4-(decyloxy)-8-(isopropoxy)-2H-1-benzopyran-2-one (Compound 136)

In Example 8, 1.57 g ($5.64 \times 10^{-3}$ mol) of 3-(acetoxy)-4-hydroxy-8-(isopropoxy)-2H-1-benzopyran-2-one was used in place of 3,4,7-trihydroxy-2H-1-benzopyran-2-one, decylbromide was used in place of benzoylchloride, and 1.62 g (yield=65%) of the desired compound 136 was obtained.

$^1$H-NMR (DMSO-d$_6$, δ-TMS) 6.70~7.60 (m, 3H), 3.52 (m, 1H), 3.31 (t, 2H, J=7.0Hz), 1.82 (s, 3H), 1.20~1.70 (m, 16H), 1.11 (d, 6H, J=6.0Hz), 0.90 (t, 3H, J=6.0Hz)

IR (KBr, cm$^{-1}$) 1720, 1680, 1650, 1610, 1570
Elemental analysis value: $C_{24}H_{34}O_6$
Theoretical value (%): C 68.87; H 8.19; O 22.94
Actual measured value (%): C 68.79; H 8.20; O 23.01

Example 137

3-(decyloxy)-4-(benzoyloxy)-8-(isopropoxy)-2H-1-benzopyran-2-one (Compound 137)

In Example 8, 1.63 g ($4.79 \times 10^{-3}$ mol) of 3-hydroxy-4-(benzoyloxy)-8-(isopropoxy)-2H-1-benzopyran-2-one was used in place of 3,4,7-trihydroxy-2H-1-benzopyran-2-one, decylbromide was used in place of benzoylchloride, and 1.67 g (yield=69%) of the desired compound 137 was obtained.

$^1$H-NMR (DMSO-d$_6$, δ-TMS) 8.10~8.20 (m, 2H), 6.70~7.60 (m, 4H), 3.52 (m, 1H), 3.32 (t, 2H, J=7.0Hz), 1.20~1.70 (m, 16H), 1.13 (d, 6H, J=6.0Hz), 0.91 (t, 3H, J=6.0Hz)

IR (KBr, cm$^{-1}$) 1720, 1680, 1650, 1610, 1520
Elemental analysis value: $C_{29}H_{36}O_6$
Theoretical value (%): C 72.47; H 7.55; O 19.98
Actual measured value (%): C 72.41; H 7.59; O 20.00

Example 138

3-(geranyloxy)-4-hydroxy-8-(isopropoxy)-2H-1-benzopyran-2-one (Compound 138)

In Example 5, 2.01 g ($4.83 \times 10^{-3}$ mol) of 3-(geranyloxy)-4-(acetoxy)-8-(isopropoxy)-2H-1-benzopyran-2-one was used in place of 3-(benzoyloxy)-4,7-(dihydroxy)-2H-1-benzopyran-2-one, and 1.19 g (yield=66%) of the desired compound 138 was obtained.

$^1$H-NMR (DMSO-d$_6$, δ-TMS) 10.35 (bs, 1H), 6.70~7.60 (m, 3H), 5.44 (bt, 1H, J=7.0Hz), 5.03 (bt, 1H, J=7.0Hz), 4.01 (d, 2H, J=7.0Hz), 3.51 (m, 1H), 2.00~2.21 (m, 4H), 1.52~1.85 (m, 9H), 1.12 (d, 6H, J=6.0Hz),

IR(KBr, cm$^{-1}$) 3200, 1720, 1680, 1630, 1580
Elemental analysis value: $C_{22}H_{28}O_5$
Theoretical value (%): C 70.94; H 7.58; O 21.48
Actual measured value (%): C 70.86; H 7.53; O 21.61

Example 139

3-hydroxy-4-(geranyloxy)-8-(isopropoxy)-2H-1-benzopyran-2-one (Compound 139)

In Example 8, 1.52 g ($6.43 \times 10^{-3}$ mol) of 3,4-(dihydroxy)-8-(isopropoxy)-2H-1-benzopyran-2-one was used in place of 3,4,7-trihydroxy-2H-1-benzopyran-2-one, geranylbromide was used in place of benzoylchloride, and 1.29 g (yield=54%) of the desired compound 139 was obtained.

$^1$H-NMR (DMSO-d$_6$, δ-TMS) 8.82 (bs, 1H), 6.70~7.60 (m, 3H), 5.42 (bt, 1H, J=7.0Hz), 5.02 (bt, 1H, J=7.0Hz), 4.03 (d, 2H, J=7.0Hz), 3.50 (m, 1H), 2.00~2.21 (m, 4H), 1.52~1.85 (m, 9H), 1.12 (d, 6H, J=6.0Hz)

IR (KBr, cm$^{-1}$) 3200, 1720, 1670, 1630, 1580, 1520
Elemental analysis value: $C_{22}H_{28}O_5$
Theoretical value (%): C 70.94; H 7.58; O 21.48
Actual measured value (%): C 71.02; H 7.52; O 21.46

Example 140

3-(geranyloxy)-4,8-(diisopropoxy)-2H-1-benzopyran-2-one (Compound 140)

In Example 8, 1.57 g ($4.22 \times 10^{-3}$ mol) of 3-(geranyloxy)-4-hydroxy-8-(isopropoxy)-2H-1-benzopyran-2-one was used in place of 3,4,7-trihydroxy-2H-1-benzopyran-2-one, isopropylbromide was used in place of benzoylchloride, and 1.19 g (yield=68%) of the desired compound 140 was obtained.

$^1$H-NMR (DMSO-d$_6$, δ-TMS) 6.70~7.60 (m, 3H), 5.42 (bt, 1H, J=7.0Hz), 5.02 (bt, 1H, J=7.0Hz), 4.03 (d, 2H, J=7.0Hz), 3.40~3.60 (m, 2H), 2.00~2.21 (m, 4H), 1.52~1.85 (m, 9H), 1.13 (d, 6H, J=6.0Hz), 1.10 (d, 6H, J=6.0Hz)

IR (KBr, cm$^{-1}$) 1730, 1660, 1630, 1570, 1520
Elemental analysis value: $C_{25}H_{34}O_5$
Theoretical value (%): C 71.61; H 8.51; O 19.88
Actual measured value (%): C 71.69; H 8.50; O 19.81

Example 141

3-(methoxy)-4-(geranyloxy)-8-(isopropoxy)-2H-1-benzopyran-2-one (Compound 141)

In Example 8, 1.52 g ($4.08 \times 10^{-3}$ mol) of 3-hydroxy-4-(geranyloxy)-8-(isopropoxy)-2H-1-benzopyran-2-one was used in place of 3,4,7-trihydroxy-2H-1-benzopyran-2-one, methyliodide was used in place of benzoylchloride, and 0.95 g (yield=60%) of the desired compound 141 was obtained.

$^1$H-NMR (DMSO-d$_6$, δ-TMS) 6.70~7.60 (m, 3H), 5.43 (bt, 1H, J=7.0Hz), 5.09 (bt, 1H, J=7.0Hz), 4.02 (d, 2H, J=7.0Hz), 3.72 (s, 3H), 3.48 (m, 1H), 2.00~2.21 (m, 4H), 1.52~1.85 (m, 9H), 1.13 (d, 6H, J=6.0Hz)

IR (KBr, cm$^{-1}$) 1730, 1660, 1630, 1570, 1520
Elemental analysis value: $C_{23}H_{30}O_5$
Theoretical value (%): C 71.48; H 7.82; O 20.70
Actual measured value (%): C 71.40; H 7.94; O 20.66

Example 142

3,4-(digeranyloxy)-8-(isopropoxy)-2H-1-benzopyran-2-one (Compound 142)

In Example 8, 1.46 g ($6.18 \times 10^{-3}$ mol) of 3,4-(dihydroxy)-8-(isopropoxy)-2H-1-benzopyran-2-one was used in place of 3,4,7-trihydroxy-2H-1-benzopyran-2-one, potassium carbonate was used in place of sodium bicarbonate, geranylbromide was used in place of benzoylchloride, and 1.63 g (yield=52%) of the desired compound 142 was obtained.

¹H-NMR (DMSO-d₆, δ-TMS) 6.70~7.60 (m, 3H), 5.10~5.50 (m, 4H), 4.08 (d, 2H, J=7.0Hz), 4.02 (d, 2}t, J=7.0Hz), 3.42 (m, 1H), 1.90~2.20 (m, 8H), 1.50~1.90 (m, 18H), 1.12 (d, 6H, J=6.0Hz)

IR (KBr, cm⁻¹) 1720, 1680, 1630, 1570, 1520
Elemental analysis value: C₃₂ H₄₄ O₅
Theoretical value (%): C 75.55; H 8.72; O 15.73
Actual measured value (%): C 75.43; H 8.73; O 15.84

Example 143

3-(benzoyloxy)-4-hydroxy-8-(decyloxy)-2H-1-benzopyran-2-one (Compound 143)

In Example 4, 5.56 g (9.76×10⁻³ mol) of methyl-β-oxo-2'-(phenylmethoxy)-3'-(decyloxy)-2-(benzoyloxy)-benzenepropanate was used in place of of methyl-β-oxo-2',4'-bis(phenylmethoxy)- 2-(benzoyloxy)benzenepropanate, and 3.44 (yield=76%) of the desired compound 143 was obtained.

¹H-NMR (DMSO-d6,8-TMS) 10.35 (bs, 1H), 8.10~8.20 (m, 2H), 6.70~7.60 (m, 6H), 3.32 (m, 2H, J=7.0Hz), 1.20~1.70 (m, 16H), 0.88 (t, 3H, J=6.0Hz)

IR (KBr, cm⁻¹) 3200, 1740, 1690, 1630, 1610, 1580
Elemental analysis value: C₂₆ H₃₀ O₆
Theoretical value (%): C 71.21; H 6.90; O 21.89
Actual measured value (%): C 71.2 9; H 6.80; O 21.91

Example 144

3,4-(dihydroxy)-8-(decyloxy)-2H-1-benzopyran-2-one (Compound

In Example 5, 2.01 g (4.35×10⁻³ mol) of 3-(benzoyloxy)-4-hydroxy-8-(decyloxy)-2H-1-benzopyran-2-one was used in place of 3-(benzoyloxy)-4,7-(dihydroxy)-2H-1-benzopyran-2-one, and 0.93 g (yield=60%) of the desired compound 144 was obtained.

¹H-NMR (DMSO-d6,8-TMS) 10.39 (bs, 1H), 8.79 (bs, 1H), 6.70~7.60 (m, 3H), 3.31 (d, H, J=7.0Hz), 1.21~1.70 (m, 16H), 0.86 (t, 3H, J=6.0Hz)

IR (KBr, cm⁻¹) 3200, 1680, 1650, 1610
Elemental analysis value: C₁₉ H₂₆ O₅
Theoretical value (%): C 68.24; H 7.84; O 23.92
Actual measured value (%): C 68.20; H 7.89; O 23.91

Example 145

3-hydroxy-4-(acetoxy)-8-(decyloxy)-2H-1-benzopyran-2-one (Compound 145)

In Example 8, 1.56 g (4.35×10⁻³ mol) of 3,4-(dihydroxy)-8-(decyloxy)-2H-1-benzopyran-2-one was used in place of 3,4,7-trihydroxy-2H-1-benzopyran-2-one, acetylchloride was used in place of benzoylchloride, and 1.08 g (yield=62%) of the desired compound 145 was obtained.

¹H-NMR (DMSO-d₆, δ-TMS) 8.91 (bs, 1H), 6.70~7.60 (m, 3H), 3.40 (d, 2H, J=7.0Hz), 1.80 (s, 3H), 1.21~1.70 (m, 16H), 0.83 (t, 3H, J=6.0Hz)

IR (KBr, cm⁻¹) 3200, 1680, 1650, 1610
Elemental analysis value: C₂₁ H₂₈ O₆
Theoretical value (%): C 67.00; H 7.50; O 25.50
Actual measured value (%): C 66.91; H 7.52; O 25.57

Example 146

3-(acetoxy)-4-(benzoyloxy)-8-(decyloxy)-2H-1-benzopyran-2-one (Compound 14 6)

In Example 8, 1.65 g (4.12×10⁻³ mol) of 3-(acetoxy)-4-hydroxy-8-(decyloxy)-2H-1-benzopyran-2-one was used in place of 3,4,7-trihydroxy-2H-1-benzopyran-2-one, and 1.37 g (yield=66%) of the desired compound 146 was obtained.

¹H-NMR (DMSO-d₆, δ-TMS) 8.10~8.20 (m, 2H), 6.70~7.70 (m, 6H), 3.35 (m, 2H, J=7.0Hz), 1.79 (s,3H), 1.20~1.70 (m, 16H), 0.90 (t, 3H, J=6.0Hz)

IR(KBr, cm⁻¹) 1740, 1690, 1630, 1610, 1580
Elemental analysis value: C₂₈ H₃₂ O₇
Theoretical value (%): C 69.98; H 6.71; O 23.31
Actual measured value (%): C 69.90; H 6.79; O 23.31

Example 147

3-(isopropoxy)-4-hydroxy-8-(decyloxy)-2H-1-benzopyran-2-one (Compound 147)

In Example 5, 2.67 g (6.03×10⁻³ mol) of 3-(isopropoxy)-4-(acetoxy)-8-(decyloxy)-2H-1-benzopyran-2-one was used in place of 3-(benzoyloxy)-4,7-(dihydroxy)-2H-1-benzopyran-2-one, and 1.69 g (yield=70%) of the desired compound 147 was obtained.

¹H-NMR (DMSO-d₆, δ-TMS) 10.22 (bs,1H), 6.70~7.60 (m,3H), 3.51 (m, 1H), 3.36 (d, H, J=7.0Hz), 1.21~1.70 (m, 16H), 1.12 (d, 6H, J=6.0Hz), 0.85 (t, 3H, J=6.0Hz)

IR (KBr, cm⁻¹) 3200, 1680, 1650, 1610
Elemental analysis value: C₂₂ H₃₂ O₅
Theoretical value (%): C 70.18; H 8.57; O 21.25
Actual measured value (%): C 70.22; H 8.59; O 21.19

Example 148

3-hydroxy-4-(butoxy)-8-(decyloxy)-2H-1-benzopyran-2-one (Compound 148)

In Example 8, 1.57 g (4.38×10⁻³ mol) of 3,4-(dihydroxy)-8-(decyloxy)-2H-1-benzopyran-2-one was used in place of 3,4,7-trihydroxy-2H-1-benzopyran-2-one, butylbromide was used in place of benzoylchloride, and 1.05 g (yield=59%) of the desired compound 148 was obtained.

¹H-NMR (DMSO-d₆, δ-TMS) 8.79 (bs,1H), 6.70~7.70 (m,3H), 3.48 (d, 2H, J=7.0Hz), 3.20 (t, 2H, J=6.0Hz), 1.00~1.70 (m, 20H), 0.96 (t, 3H, J=6.0Hz), 0.81 (t, 3H, J=6.0Hz)

IR (KBr, cm⁻¹) 3200, 1680, 1650, 1610
Elemental analysis value: C₂₃ H₃₄ O₅
Theoretical value (%): C 70.74; H 8.78; O 20.49
Actual measured value (%): C 70.61; H 8.80; O 20.59

Example 149

3-(acetoxy)-4-(isopropoxy)-8-(decyloxy)-2H-1-benzopyran-2-one (Compound 149)

In Example 8, 1.58 g (3.95×10⁻³ mol) of 3-(acetoxy)-4-hydroxy-8-(decyloxy)-2H-1-benzopyran-2-one was used in place of 3,4,7-trihydroxy-2H-1-benzopyran-2-one, isopropylbromide was used in place of benzoylchloride, and 1.22 g (yield=70%) of the desired compound 149 was obtained.

¹H-NMR (DMSO-d₆, δ-TMS) 6.70~7.60 (m, 3H), 3.50 (m, 1H), 3.39 (d, 2H, J=7.0Hz), 1.80 (s, 3H), 1.21~1.70 (m, 16H), 1.12 (d, 6H, J=6.0Hz), 0.84 (t, 3H, J=6.0Hz)

IR (KBr, cm$^{-1}$) 1740, 1680, 1650, 1610
Elemental analysis value: $C_{24}H_{34}O_6$
Theoretical value (%): C 69.21; H 7.74; O 23.05
Actual measured value (%): C 69.33; H 7.70; O 22.97

Example 150

3-(methoxy)-4-(benzoyloxy)-8-(decyloxy)-2H-1-benzopyran-2-one (Compound 150)

In Example 8, 1.54 g ($3.33 \times 10^{-3}$ mol) of 3-hydroxy-4-(benzoyloxy)-8-(decyloxy)-2H-1-benzopyran-2-one was used in place of 3,4,7-trihydroxy-2H-1-benzopyran-2-one, methyliodide was used in place of benzoylchloride, and 0.94 g (yield=59%) of the desired compound 150 was obtained.

$^1$H-NMR (DMSO-d$_6$, δ-TMS) 8.10~8.20 (m, 2H), 6.70~7.60 (m, 6H), 3.68 (s, 3H), 3.33 (m, 2H, J=7.0Hz), 1.20~1.70 (m, 16H), 0.88 (t, 3H, J=6.0Hz)
IR (KBr, cm$^{-1}$) 1740, 1690, 1630, 1610, 1580
Elemental analysis value: $C_{27}H_{32}O_6$
Theoretical value (%): C 71.66; H 7.13; O 21.21
Actual measured value (%): C 71.60; H 7.19; O 21.21

Example 151

3-(geranyloxy)-4-hydroxy-8-(decyloxy)-2H-1-benzopyran-2-one (Compound 151)

In Example 5, 2.76 g ($5.14 \times 10^{-3}$ mol) of 3-(geranyloxy)-4-(acetoxy)-8-(decyloxy)-2H-1-benzopyran-2-one was used in place of 3-(benzoyloxy)-4,7-(dihydroxy)-2H-1-benzopyran-2-one, and 1.53 g (yield=60%) of the desired compound 151 was obtained.

$^1$H-NMR (DMSO-d$_6$, δ-TMS) 8.99 (bs, 1H), 6.70~7.60 (m, 3H), 5.43 (bt, 1H, J=7.0Hz), 5.03 (bt, 1H, J=7.0Hz), 4.01 (d, 2H, J=7.0Hz), 3.34 (t, 2H, J=7.0Hz), 2.00~2.21 (m, 4H), 1.22~1.85 (m, 25H), 0.84 (t, 3H, J=6.0Hz)
IR (KBr, cm$^{-1}$) 200, 1720, 1680, 1630, 1580
Elemental analysis value: $C_{29}H_{42}O_5$
Theoretical value (%): C 74.01; H 9.00; O 17.00
Actual measured value (%): C 74.08; H 8.90; O 17.02

Example 152

3-hydroxy-4-(geranyloxy)-8-(decyloxy)-2H-1-benzopyran-2-one (Compound 152)

In Example 8, 1.52 g ($4.24 \times 10^{-3}$ mol) of 3,4-(dihydroxy)-8-(decyloxy)-2H-1-benzopyran-2-one was used in place of 3,4,7-trihydroxy-2H-1-benzopyran-2-one, geranylbromide was used in place of benzoylchloride, and 1.26 g (yield=60%) of the desired compound 152 was obtained.

$^1$H-NMR (DMSO-d$_6$, δ-TMS) 9.04 (bs, 1H), 6.70~7.60 (m, 3H), 5.42 (bt, 1H, J=7.0Hz), 5.02 (bt, 1H, J=7.0Hz), 4.01 (d, 2H, J=7.0Hz), 3.31 (t, 2H, J=7.0Hz), 2.00~2.20 (m, 4H), 1.24~1.85 (m, 25H), 0.83 (t, 3H, J=6.0Hz)
IR (KBr, cm$^{-1}$) 3200, 1700, 1670, 1620, 1580
Elemental analysis value: $C_{22}H_{32}O_5$
Theoretical value (%): C 74.01; H 9.00; O 17.00
Actual measured value (%): C 74.08; H 8.95; O 16.97

Example 153

3-(geranyloxy)-4-(acetoxy)-8-(decyloxy)-2H-1-benzopyran-2-one (Compound 153)

In Example 8, 1.52 g ($3.07 \times 10^{-3}$ mol) of 3-(geranyloxy)-4-hydroxy-8-(decyloxy)-2H-1-benzopyran-2-one was used in place of 3,4,7-trihydroxy-2H-1-benzopyran-2-one, acetylchloride was used in place of benzoylchloride, and 1.01 (yield=61%) of the desired compound 153 was obtained.

$^1$H-NMR (DMSO-d$_6$, δ-TMS) 6.70~7.60 (m, 3H), 5.46 (bt, 1H, J=7.0Hz), 5.01 (bt, 1H, J=7.0Hz), 4.04 (d, 2H, J-7.0Hz), 3.35 (t, 2H, J=7.0Hz), 2.00~2.20 (m, 4H), 1.86 (s, 3H), 1.24~1.85 (m, 25H), 0.81 (t, H, J=6.0Hz)
IR (KBr, cm$^{-1}$) 1720, 1670, 1630, 1580, 1530
Elemental analysis value: $C_{31}H_{44}O_6$
Theoretical value (%): C 72.62; H 8.65; O 18.73
Actual measured value (%): C 72.65; H 8.69; O 18.66

Example 154

3-(benzoyloxy)-4-(geranyloxy)-8-(decyloxy)-2H-1-benzopyran-2-one (Compound 154)

In Example 8, 1.57 g ($3.39 \times 10^{-3}$ mol) of 3-(benzoyloxy)-4-hydroxy-8-(decyloxy)-2H-1-benzopyran-2-one was used in place of 3,4,7-trihydroxy-2H-1-benzopyran-2-one, geranylbromide was used in place of benzoylchloride, and 1.28 g (yield=63%) of the desired compound 154 was obtained.

$^1$H-NMR (DMSO-d$_6$, δ-TMS) 8.10~8.30 (m,2H), 6.70~7.60 (m, 6H), 5.43 (bt, 1H, J=7.0 Hz), 5.02 (bt, 1H, J=7.0Hz), 4.01 (d, 2H, J=7.0Hz), 3.35 (t, 2H, J=7.0Hz), 2.00~2.20 (m, 4H), 1.24~1.85 (m, 25H), 0.81 (t, 3H, J=6.0Hz)
IR (KBr, cm$^{-1}$) 1720, 1670, 1650, 1630, 1580, 1530
Elemental analysis value: $C_{36}H_{46}O_6$
Theoretical value (%): C 75.23; H 8.07; O 16.70
Actual measured value (%): C 75.15; H 8.00; O 16.85

Example 155

3-(geranyloxy)-4-(methoxy)-8-(decyloxy)-2H-1-benzopyran-2-one (Compound 155)

In Example 8, 1.51 g ($3.05 \times 10^{-3}$ mol) of 3-(geranyloxy)-4-hydroxy-8-(decyloxy)-2H-1-benzopyran-2-one was used in place of 3,4,7-trihydroxy-2H-1-benzopyran-2-one, methyliodide was used in place of benzoylchloride, and 0.92 g (yield=59%) of the desired compound 155 was obtained.

$^1$H-NMR (DMSO-d$_6$, δ-TMS) 6.70~7.60 (m, 3H), 5.42 (bt, 1H, J=7.0Hz), 5.01 (bt, 1H, J=7.0Hz), 4.02 (d, 2H, J=7.0Hz), 3.69 (s, 3H), 3.32 (t, 2H, J=7.0Hz), 2.00~2.20 (m, 4H), 1.24~1.85 (m, 25H), 0.81 (t, 3H, J=6.0Hz)
IR (KBr, cm$^{-1}$) 1720, 1670, 1630, 1580, 1530
Elemental analysis value: $C_{30}H_{44}O_5$
Theoretical value (%): C 74.34; H 9.15; O 16.51
Actual measured value (%): C 74.38; H 9.18; O 16.44

Example 156

3-(isopropoxy)-4-(geranyloxy)-8-(decyloxy)-2H-1-benzopyran-2-one (Compound 156)

In Example 8, 1.46 g ($2.95 \times 10^{-3}$ mol) of 3-hydroxy-4-(geranyloxy)-8-(decyloxy)-2H-1-benzopyran-2-one was used in place of 3,4,7-trihydroxy-2H-1-benzopyran-2-one, isopropylbromide was used in place of benzoylchloride, and 0.95 g (yield=60%) of the desired compound 156 was obtained.

$^1$H-NMR (DMSO-d$_6$, δ-TMS) 6.70~7.60 (m, 3H), 5.42 (bt, 1H, J=7.0Hz), 5.02 (bt, 1H, J=7.0Hz), 4.01 (d, 2H, J=7.0Hz), 3.50 (m, 1H), 3.32 (t, 2H, J=7.0Hz), 2.00~2.20 (m, 4H), 1.24~1.85 (m, 25H), 1.12 (d, 6H, J=6.0Hz), 0.81 (t, 3H, J=6.0Hz)
IR (KBr, cm$^{-1}$) 1720, 1670, 1620, 1550, 1520

Elemental analysis value: $C_{32}H_{48}O_5$
Theoretical value (%): C 74.96; H 9.44; O 15.60
Actual measured value (%): C 74.90; H 9.39; O 15.71

Example 157

3,4-(digeranyloxy)-8-(decyloxy)-2H-1-benzopyran-2-one (Compound 157)

In Example 8, 1.54 g ($4.30 \times 10^{-3}$ mol) of 3,4-(dihydroxy)-8-(decyloxy)-2H-1-benzopyran-2-one was used in place of 3,4,7-trihydroxy-2H-1-benzopyran-2-one, potassium carbonate was used in place of sodium bicarbonate, geranylbromide was used in place of benzoylchloride, and 1.36 g (yield=50%) of the desired compound 157 was obtained.

$^1$H-NMR (DMSO-d$_6$, δ-TMS) 6.70~7.60 (m, 3H), 5.00~5.50 (m, 4H), 4.03 (d, 2H, J=7.0Hz), 4.01 (d, 2H, J=7.0Hz), 3.32 (t, 2H, J=7.0Hz), 2.00~2.20 (m, 8H), 1.24~1.85 (m, 34H), 0.82 (t, 3H, J=6.0Hz)

IR (KBr, cm$^{-1}$) 1700, 1670, 1620, 1550, 1520
Elemental analysis value: $C_{39}H_{58}O_5$
Theoretical value (%): C 77.18; H 9.63; O 13.18
Actual measured value (%): C 77.18; H 9.51; O 13.31

Example 158

3-(benzoyloxy)-4-hydroxy-8-(geranyloxy)-2H-1-benzopyran-2-one (Compound 158)

In Example 4, 3.50 g ($6.47 \times 10^{-3}$ mol) of methyl-β-oxo-2'-(phenylmethoxy)-3'-(geranyloxy)-2-(benzoyloxy)benzenepropanate was used in place of of methyl-β-oxo-2',4'-bis (phenylmethoxy)-2-(benzoyloxy)benzenepropanate, and 1.97 g (yield=70%) of the desired compound 158 was obtained.

$^1$H-NMR (DMSO-d$_6$, δ-TMS) 10.14 (bs, 1H), 8.10~8.20 (m, 2H), 6.70~7.60 (m, 6H), 5.45 (bt, 1H, J=7.0Hz), 5.02 (bt, 1H, J=7.0Hz), 4.01 (bt, 2H, J=7.0Hz), 2.00~2.20 (m, 4H), 1.55~1.85 (m, 9H)

IR (KBr, cm$^{-1}$) 3350, 1720, 1680, 1630, 1580, 1520
Elemental analysis value: $C_{26}H_{26}O_6$
Theoretical value (%): C 71.87; H 6.03; O 22.10
Actual measured value (%): C 71.79; H 6.12; O 22.09

Example 159

3,4-(hydroxy)-8-(geranyloxy)-2H-1-benzopyran-2-one (Compound

In Example 5, 5.00 g ($1.15 \times 10^{-2}$ mol) of 3-(benzoyloxy)-4-hydroxy-8-(geranyloxy)-2H-1-benzopyran-2-one was used in place of 3-(benzoyloxy)-4,7-(dihydroxy)-2H-1-benzopyran-2-one, and 2.28 g (yield=60%) of the desired compound 159 was obtained.

$^1$H-NMR (DMSO-d$_6$, δ-TMS) 10.35 (bs,1H), 8.89 (bs, 1H), 6.70~7.60 (m,3H), 5.43 (bt, 1H, J=7.0Hz), 5.07 (bt, 1H, J=7.0Hz), 4.01 (d, 2H, J=7.0Hz), 2.00~2.21 (m, 4H), 1.55~1.85 (m, 9H)

IR (KBr, cm$^{-1}$) 3550, 3200, 1720, 1680, 1630, 1580
Elemental analysis value: $C_{19}H_{22}O_5$
Theoretical value (%): C 69.07; H 6.71; O 24.22
Actual measured value (%): C 69.13; H 6.75; O 24.12

Example 160

3-hydroxy-4-(acetoxy)-8-(geranyloxy)-2H-1-benzopyran-2-one (Compound 160)

In Example 8, 1.54 g ($4.66 \times 10^{-3}$ mol) of 3,4-(dihydroxy)-8-(geranyloxy)-2H-1-benzopyran-2-one was used in place of 3,4,7-trihydroxy-2H-1-benzopyran-2-one, acetylchloride was used in place of benzoylchloride, and 0.94 g (yield=54%) of the desired compound 160 was obtained.

$^1$H-NMR (DMSO-d$_6$, δ-TMS) 8.78 (bs, 1H), 6.70~7.60 (m, 3H), 5.46 (bt, 1H, J=7.0Hz), 5.07 (bt, 1H, J=7.0Hz), 4.04 (d, 2H, J=7.0Hz), 2.00~2.21 (m, 4H), 1.86 (s,3H), 1.55~1.85 (m, 9H)

IR (KBr, cm$^{-1}$) 550, 3200, 1720, 1680, 1630, 1580
Elemental analysis value: $C_{21}H_{24}O_6$
Theoretical value (%): C 67.73; H 6.50; O 25.78
Actual measured value (%): C 67.76; H 6.59; O 25.65

Example 161

3-(benzoyloxy)-4-(acetoxy)-8-(geranyloxy)-2H-1-benzopyran-2-one (Compound 161)

In Example 8, 1.52 g ($3.50 \times 10^{-3}$ mol) of 3-(benzoyloxy)-4-hydroxy-8-(geranyloxy)-2H-1-benzopyran-2-one was used in place of 3,4,7-trihydroxy-2H-1-benzopyran-2-one, acetylchloride was used in place of benzoylchloride, and 0.98 g (yield=59%) of the desired compound 161 was obtained.

$^1$H-NMR (DMSO-d$_6$, δ-TMS) 8.10~8.20 (m, 2H), 6.70~7.60 (m, 3H), 5.46 (bt, 1H, J=7.0Hz), 5.07 (bt, 1H, J=7.0Hz), 4.04 (d, 2H, J=7.0Hz), 2.00~2.21 (m, 4H), 1.75 (s, 3H), 1.55~1.85 (m, 9H)

IR (KBr, cm$^{-1}$) 1720, 1680, 1630, 1580, 1520
Elemental analysis value: $C_{28}H_{28}O_7$
Theoretical value (%): C 70.57; H 5.92; O 23.50
Actual measured value (%): C 70.50; H 6.10; O 23.40

Example 162

3-(methoxy)-4-hydroxy-8-(geranyloxy)-2H-1-benzopyran-2-one (Compound 162)

In Example 5, 1.67 g ($4.32 \times 10^{-3}$ mol) of 3-(methoxy)-4-(acetoxy)-8-(geranyloxy)-2H-1-benzopyran-2-one was used in place of 3-(benzoyloxy)-4,7-(dihydroxy)-2H-1-benzopyran-2-one, and 0.89 g (yield=60%) of the desired compound 162 was obtained.

$^1$H-NMR (DMSO-d$_6$, δ-TMS) 10.31 (bs, 1H), 6.70~7.60 (m, 3H), 5.46 (bt, 1H, J=7.0Hz), 5.03 (bt, 1H, J=7.0Hz), 4.00 (d, 2H, J=7.0Hz), 3.76 (s, 3H), 2.00~2.21 (m, 4H), 1.55~1.85 (m, 9H)

IR (KBr, cm$^{-1}$) 3200, 1720, 1680, 1630, 1580
Elemental analysis value: $C_{20}H_{24}O_5$
Theoretical value (%): C 69.75; H 7.02; O 23.23
Actual measured value (%): C 69.65; H 7.07; O 23.28

Example 163

3-hydroxy-4-(isopropoxy)-8-(geranyloxy)-2H-1-benzopyran-2-one (Compound 163)

In Example 8, 1.52 g ($4.60 \times 10^{-3}$ mol) of 3,4-(dihydroxy)-8-(geranyloxy)-2H-1-benzopyran-2-one was used in place of 3,4,7-trihydroxy-2H-1-benzopyran-2-one, isopropylbromide was used in place of benzoylchloride, and 0.99 g (yield=58%) of the desired compound 163 was obtained.

$^1$H-NMR (DMSO-d$_6$, δ-TMS) 8.95 (bs, 1H), 6.70~7.60 (m,3H), 5.43 (bt, 1H, J=7.0Hz), 5.07 (bt, 1H, J=7.0Hz), 4.02 (d, 2H, J=7.0Hz), 3.45 (m, 1H), 2.00~2.21 (m, 4H), 1.55~1.85 (m, 9H), 1.12 (d, 6H, J=6.0Hz)

IR (KBr, cm$^{-1}$) 3200, 1720, 1680, 1630, 1580
Elemental analysis value: $C_{22}H_{28}O_5$
Theoretical value (%): C 70.94; H 7.58; O 21.48
Actual measured value (%): C 71.00; H 7.53; O 21.47

Example 164

3-(decyloxy)-4-(isopropoxy)-8-(geranyloxy)-2H-1-benzopyran-2-one (Compound 164)

In Example 8, 1.50 g (3.03×10$^{-3}$ mol) of 3-(decyloxy)-4-hydroxy-8-(geranyloxy)-2H-1-benzopyran-2-one was used in place of 3,4,7-trihydroxy-2H-1-benzopyran-2-one, isopropylbromide was used in place of benzoylchloride, and 0.98 g (yield=60%) of the desired compound 163 was obtained.

$^1$H-NMR (DMSO-d$_6$, δ-TMS) 6.70~7.60 (m, 3H), 5.43 (bt, 1H, J=7.0Hz), 5.02 (bt, 1H,
(d, 2H, J=7.0Hz), 3.43 (m, 1H), 3.33 (t, 2H, J=7.0Hz), 4.00 J=7.0Hz), 2.00~2.20 (m, 4H), 1.22~1.85 (m, 25H), 1.12 (d, 6H, J=6.0Hz), 0.83 (t, 3H, J=6.0Hz)

IR (KBr, cm$^{-1}$) 1720, 1680, 1630, 1580, 1530
Elemental analysis value: C$_{32}$H$_{48}$O$_5$
Theoretical value (%): C 74.96; H 9.44; O 15.60
Actual measured value (%): C 74.88; H 9.49; O 15.63

Example 165

3-(benzoyloxy)-4-(isopropoxy)-8-(geranyloxy)-2H-1-benzopyran-2-one (Compound 165)

In Example 8, 1.55 g (3.57×10$^{-3}$ mol) of 3-(benzoyloxy)-4-hydroxy-8-(geranyloxy)-2H-1-benzopyran-2-one was used in place of 3,4,7-trihydroxy-2H-1-benzopyran-2-one, isopropylbromide was used in place of benzoylchloride, and 0.94 g (yield=59%) of the desired compound 165 was obtained.

$^1$H-NMR (DMSO-d$_6$, δ-TMS) 8.10~8.20 (m, 2H), 6.50~7.80 (m, 6H), 5.43 (bt, 1H, J=7.0Hz), 5.04 (bt, 1H, J=7.0Hz), 4.01 (bt, 2H, J=7.0Hz), 3.47 (m, 1H), 2.00~2.20 (m, 4H), 1.55~1.85 (m, 9H), 1.12 (d, 6H, J=6.0Hz)

IR (KBr, cm$^{-1}$) 1720, 1680, 1630, 1580, 1520
Elemental analysis value: C$_{29}$H$_{32}$O$_6$
Theoretical value (%): C 73.09; H 6.77; O 20.14
Actual measured value (%): C 73.15; H 6.79; O 20.06

Example 166

3-(methoxy)-4-(acetoxy)-8-(geranyloxy)-2H-1-benzopyran-2-one (Compound 166)

In Example 8, 1.51 g (4.05×10$^{-3}$ mol) of 3-hydroxy-4-(acetoxy)-8-(geranyloxy)-2H-1-benzopyran-2-one was used in place of 3,4,7-trihydroxy-2H-1-benzopyran-2-one, methyliodide was used in place of benzoylchloride, and 0.86 g (yield=55%) of the desired compound 166 was obtained.

$^1$H-NMR (DMSO-d$_6$, δ-TMS) 6.70~7.60 (m, 2H), 5.43 (bt, 1H, J=7.0Hz), 5.03 (bt, 1H, J=7.0Hz), 4.01 (d, 2H, J=7.0Hz), 3.75 (s, 3H), 2.00~2.21 (m, 4H), 1.87 (s, 3H), 1.55~1.85 (m, 9H)

IR (KBr, cm$^{-1}$) 1720, 1680, 1630, 1580, 1520
Elemental analysis value: C$_{22}$H$_{26}$O$_6$
Theoretical value (%): C 68.38; H 6.78; O 24.84
Actual measured value (%): C 68.29; H 6.78; O 24.93

Example 167

3,8-(digeranyloxy)-4-hydroxy-2H-1-benzopyran-2-one (Compound

In Example 5, 2.03 g (3.99×10$^{-3}$ mol) of 3,8-(digeranyloxy)-4-(acetoxy)-2H-1-benzopyran-2-one was used in place of 3-(benzoyloxy)-4,7-(dihydroxy)-2H-1-benzopyran-2-one, and 0.93 g (yield=50%) of the desired compound 167 was obtained.

$^1$H-NMR (DMSO-d$_6$, δ-TMS) 10.13 (bs,1H), 6.70~7.60 (m, 3H), 5.00~5.50 (m, 4H), 4.03 (d, 2H, J=7.0Hz), 4.01 (d, 2H, J=7.0Hz), 2.00~2.21 (m, 8H), 1.55~1.85 (m, 18H)

IR (KBr, cm$^{-1}$) 3200, 1720, 1680, 1630, 1580
Elemental analysis value: C$_{29}$H$_{38}$O$_5$
Theoretical value (%): C 74.65; H 8.21; O 17.14
Actual measured value (%): C 74.61; H 8.27; O 17.12

Example 168

3-hydroxy-4,8-(digeranyloxy)-2H-1-benzopyran-2-one (Compound

In Example 8, 1.50 g (4.54×10$^{-3}$ mol) of 3,4-(dihydroxy)-8-(geranyloxy)-2H-1-benzopyran-2-one was used in place of 3,4,7-trihydroxy-2H-1-benzopyran-2-one, geranylbromide was used in place of benzoylchloride, and 1.27 g (yield=60%) of the desired compound 168 was obtained.

$^1$H-NMR (DMSO-d$_6$, δ-TMS)
9.01 (bs, 1H), 6.70~7.60 (m,3H), 5.00~5.50 (m,4H), 4.01 (d, 2H, J=7.0Hz), 4.00 (d, 2H, J=7.0Hz), 2.00~2.20 (m, 8H), 1.55~1.85 (m, 18H)

IR (KBr, cm$^{-1}$) 3550, 3200, 1700, 1670, 1620, 1580
Elemental analysis value: C$_{29}$H$_{38}$O$_5$
Theoretical value (%): C 74.65; H 8.21; O 17.14
Actual measured value (%): C 74.59; H 8.20; O 17.21

Example 169

3,8-(digeranyloxy)-4-(acetoxy)-2H-1-benzopyran-2-one (Compound 169)

In Example 8, 1.55 g (3.32×10$^{-3}$ mol) of 3,8-(digeranyloxy)-4-hydroxy-2H-1-benzopyran-2-one was used in place of 3,4,7-trihydroxy-2H-1-benzopyran-2-one, acetylchloride was used in place of benzoylchloride, and 1.03 g (yield=61%) of the desired compound 169 was obtained.

$^1$H-NMR (DMSO-d$_6$, δ-TMS)
6.70~7.60 (m, 3H), 5.00~5.50 (m, 4H), 4.04 (d, 2H, J=7.0Hz), 4.01 (d, 2H, J=7.0Hz), 2.00~2.20 (m, 8H), 1.86 (s, 3H), 1.55~1.85 (m, 18H)

IR (KBr, cm$^{-1}$) 1720, 1670, 1630, 1580, 1530
Elemental analysis value: C$_{31}$H$_{40}$O$_6$
Theoretical value (%): C 73.20; H 7.93; O 18.87
Actual measured value (%): C 73.26; H 8.00; O 18.74

Example 170

3-(benzoyloxy)-4,8-(digeranyloxy)-2H-1-benzopyran-2-one (Compound 170)

In Example 8, 1.45 g (3.26×10$^{-3}$ mol) of 3-(benzoyloxy)-4-hydroxy-8-(geranyloxy)-2H-1-benzopyran-2-one was used in place of 3,4,7-trihydroxy-2H-1-benzopyran-2-one, geranylbromide was used in place of benzoylchloride, and 1.01 g (yield=53%) of the desired compound 170 was obtained.

$^1$H-NMR (DMSO-d$_6$, δ-TMS) 8.10~8.30 (m, 2H), 6.50~7.70 (m, 6H), 5.00~5.50 (m, 4H), 4.01 (d, 2H, J=7.0Hz), 4.00 (d, 2H, J=7.0Hz), 2.00~2.20 (m, 8H), 1.55~1.85 (m, 18H)

IR (KBr, cm$^{-1}$) 3.720, 1670, 1650, 1630, 1580, 1530
Elemental analysis value: C$_{36}$H$_{42}$O$_6$
Theoretical value (%): C 75.76; H 7.42; O 16.82
Actual measured value (%): C 75.83; H 7.4 9; O 16.68

Example 171

3,8-(digeranyloxy)-4-(methoxy)-2H-1-benzopyran-2-one (Compound 17 1)

In Example 8, 1.53 g ($3.28 \times 10^{-3}$ mol) of 3,8-(digeranyloxy)-4-hydroxy-2H-1-benzopyran-2-one was used in place of 3,4,7-trihydroxy-2H-1-benzopyran-2-one, methyliodide was used in place of benzoylchloride, and 1.01 g (yield=66%) of the desired compound 171 was obtained.

$^1$H-NMR (DMSO-d$_6$, δ-TMS) 6.70~7.60 (m, 3H), 5.00~5.50 (m, 4H), 4.03 (d, 2H, J=7.0Hz), 4.02 (d, 2H, J=7.0Hz), 3.77 (s,3H), 2.00~2.20 (m, 8H), 1.55~1.85 (m, 18H)

IR(KBr, cm$^{-1}$) 1720, 1670, 1630, 1580, 1530
Elemental analysis value: C$_{30}$H$_{40}$O$_5$
Theoretical value (%): C 74.97; H 8.39; O 16.65
Actual measured value (%): C 75.07; H 8.37; O 16.56

Example 172

3-(isopropoxy)-4,8-(digeranyloxy)-2H-1-benzopyran-2-one (Compound 172)

In Example 8, 1.50 g ($3.21 \times 10^{-3}$ mol) of 3-hydroxy-4,8-(digeranyloxy)-2H-1-benzopyran-2-one was used in place of 3,4,7-trihydroxy-2H-1-benzopyran-2-one, isopropylbromide was used in place of benzoylchloride, and 0.98 g (yield=60%) of the desired compound 172 was obtained.

$^1$H-NMR (DMSO-d$_6$, δ-TMS) 6.70~7.60 (m, 3H), 5.00~5.50 (m, 4H), 4.02 (d, 2H, J=7.0Hz), 4.01 (d, 2H, J=7.0Hz), 3.50 (m, 1H), 3.32 (t, 2H, J=7.0Hz), 2.00~2.20 (m, 8H), 1.55~1.85 (m, 18H), 1.12 (d, 6H, J=6.0Hz)

IR (KBr, cm$^{-1}$) 1700, 1670, 1620, 1550, 1520
Elemental analysis value: C$_{32}$H$_{44}$O$_5$
Theoretical value (%): C 75.55; H 8.72; O 15.73
Actual measured value (%): C 75.46; H 8.80; O 15.74

Example 173

1-[2',6'-bis(phenylmethoxy)phenyl]ethanone (Compound 173)

In Example 1, 25 g ($1.64 \times 10^{-1}$ mol) of 2',6'-dihydroxyacetophenone was used in place of 2',4'-dihydroxyacetophenone, and 48.98 g (yield=90%) of the desired compound 173 was obtained.

$^1$H-NMR (CDCl$_3$, δ-TMS) 6.90~7.40 (m, 11H), 6.65 (s, 1H), 6.53 (s, 1H), 4.99 (s, 4H), 2.42 (s, 3H)

Example 174

Methyl-β-oxo-2',6'-bis(phenylmethoxy)benzenepropanate (Compound 174)

In Example 2, 45.12 g ($1.38 \times 10^{-1}$ mol) of 1-[2',6'-bis(phenylmethoxy)phenyl]ethanone was used in place of 1-[2',4'-bis(phenylmethoxy)phenyl]ethanone, and 44 66 g (yield=83%) of the desired compound 174 was obtained.

$^1$H-NMR (DMSO-d6,δ-TMS) 7.10~7.50 (m, 11H), 6.61 (s,1H), 6.50 (s, 1H), 5.03 (s, 4H), 3.81 (s, 2H), 3.55 (s, 3H)

Example 175

Methyl-β-oxo-2',6'-bis(phenylmethoxy)-2-(benzoyloxy)benzenepropanate (Compound 175)

In Example 3, 43.19 g ($1.11 \times 10^{-1}$ mol) of methyl-β-oxo-2',6'-bis(phenylmethoxy)benzenepropanate was used in place of methyl-β-oxo-2',4'-bis(phenylmethoxy) benzenepropanate, and 46.88 g (yield=83%) of the desired compound 175 was obtained.

$^1$H-NMR (CDCl$_3$, δ-TMS) 7.00~8.00 (m, 16H), 6.58 (s,1H), 6.64 (s,1H), 5.01 (s,2H), 5.00 (s,2H), 3.78 (s, 1H), 3.53 (s,3H)

Example 176

3-(benzoyloxy)-4,5-dihydroxy-2H-1-benzopyran-2-one (Compound

In Example 4, 30.45 g ($5.96 \times 10^{-2}$ mol) of methyl-β-oxo-2',6'-bis(phenylmethoxy)-2-(benzoyloxy)benzenepropanate was used in place of methyl-β-oxo-2',4'-bis(phenylmethoxy)-2-(benzoyloxy)benzenepropanate, and 15.65 g (yield=88%) of the desired compound 176 was obtained.

$^1$H-NMR (DMSO-d6,δ-TMS) 9.31 (bs, 2H), 7.40~8.20 (m, 6H), 6.70~6.90 (m,2H)

IR (KBr, cm$^{-1}$) 3050, 1740, 1690, 1630, 1610, 1580
Melting point: 216°~218° C. Elemental analysis value: C$_{16}$H$_{10}$O$_6$
Theoretical value (%): C 64.43; H 3.38; O 32.19
Actual measured value (%): C 64.36; H 3.51; O 32.13

Example 177

3,4,5-trihydroxy-2H-1-benzopyran-2-one (Compound 177)

In Example 5, 10.32 g ($3.46 \times 10^{-2}$ mol) of 3-(benzoyloxy)-4,5-dihydroxy-2H-1-benzopyran-2-one was used in place of 3-(benzoyloxy)-4,7-(dihydroxy)-2H-1-benzopyran-2-one, and 4.90 g (yield=73%) of the desired compound 177 was obtained.

$^1$H-NMR (DMSO-d$_6$, δ-TMS) 9.22 (bs, 3H), 6.70~7.40 (m, 3H)

IR (KBr, cm$^{-1}$) 3300, 1680, 1650, 1610
Melting point: 255°~257° C.
Elemental analysis value: C$_9$H$_6$O$_5$
Theoretical value (%): C 51.44; H 2.88; O 45.68
Actual measured value (%): C 51.60; H 2.90; O 45.50

Example 178

3,5-(dihydroxy)-4-(acetoxy)-2H-1-benzopyran-2-one (Compound 178)

In Example 8, 2.69 g ($1.39 \times 10^{-2}$ mol) of 3,4,5-trihydroxy-2H-1-benzopyran-2-one was used in place of 3,4,7-trihydroxy-2H-1-benzopyran-2-one, acetylchloride was used in place of benzoylchloride, and 2.13 g (yield=65%) of the desired compound 178 was obtained.

$^1$H-NMR (DMSO-d$_6$, δ-TMS)
9.52 (bs, 2H), 6.70~7.40 (m, 3H), 1.93 (s, 3H)
IR(KBr, cm$^{-1}$)
3200, 1680, 1650, 1610
Elemental analysis value: C$_{11}$H$_8$O$_6$
Theoretical value (%): C 55.94; H 3.41; O 40.65
Actual measured value (%): C 55.84; H 3.55; O 40.61

Example 179

3,4,5-(triacetoxy)-2H-1-benzopyran-2-one (Compound 179)

In Example 8, 1.53 g ($7.88 \times 10^{-3}$ mol) of 3,4,5-trihydroxy-2H-1-benzopyran-2-one was used in place of 3,4,7-trihydroxy-2H-1-benzopyran-2-one, potassium carbonate was used in place of sodium bicarbonate, acetylchloride was used in place of benzoylchloride, and 1.67 g (yield=66%) of the desired compound 179 was obtained.

$^1$H-NMR (DMSO-d$_6$, δ-TMS)
6.70~7.40 (m, 3H), 1.93 (s, 3H), 1.82 (s, 3H), 1.80 (s, 3H)
IR (KBr, cm$^{-1}$) 1700, 1680, 1650, 1610, 1520
Elemental analysis value: C$_{15}$H$_{12}$O$_8$
Theoretical value (%): C 56.25; H 3.78; O 39.97
Actual measured value (%): C 56.32; H 3.62; O 40.06

Example 180

3-(benzoyloxy)-4-(acetoxy)-5-hydroxy-2H-1-benzopyran-2-one (Compound 180)

In Example 8, 2.03 g (6.81×10$^{-3}$ mol) of 3-(benzoyloxy)-4,5-(dihydroxy)-2H-1-benzopyran-2-one was used in place of 3,4,7-trihydroxy-2H-1-benzopyran-2-one, acetylchloride was used in place of benzoylchloride, and 1.74 g (yield=75%) of the desired compound 180 was obtained.

$^1$H-NMR (DMSO-d$_6$, δ-TMS) 9.59 (bs, 1H), 7.40~8.20 (m, 6H), 6.70~6.90 (m, 2H), 1.79 (s, 3H)
IR (KBr, cm$^{-1}$) 3150, 1740, 1690, 1630, 1610, 1580
Elemental analysis value: C$_{18}$H$_{12}$O$_7$
Theoretical value (%): C 63.53; H 3.55; O 32.91
Actual measured value (%): C 63.52; H 3.47; O 33.01

Example 181

3-(benzoyloxy)-4,5-(diacetoxy)-2H-1-benzopyran-2-one (Compound 181)

In Example 8, 1.77 g (5.93×10$^{-3}$ mol) of 3-(benzoyloxy)-4,5-(dihydroxy)-2H-1-benzopyran-2-one was used in place of 3,4,7-trihydroxy-2H-1-benzopyran-2-one, potassium carbonate was used in place of sodium bicarbonate, acetylchloride was used in place of benzoylchloride, and 1.59 g (yield=70%) of the desired compound 181 was obtained.

$^1$H-NMR (DMSO-d$_6$, δ-TMS) 7.40~8.20 (m, 6H), 6.70~6.90 (m, 2H), 1.82 (s, 3H), 1.79 (s, 3H)
IR (KBr, cm$^{-1}$) 1740, 1690, 1630, 1610, 1580
Elemental analysis value: C$_{20}$H$_{14}$O$_8$
Theoretical value (%): 62.83; H 3.69; O 33.48
Actual measured value C 62.94; H 3.66; O 33.40

Example 182

3-(isopropoxy)-4,5-(dihydroxy)-2H-1-benzopyran-2-one (Compound 182)

In Example 5, 1.95 g (7.01×10$^{-3}$ mol) of 3-(isopropoxy)-4-(acetoxy)-5-hydroxy-2H-1-benzopyran-2-one was used in place of 3-(benzoyloxy)-4,7-(dihydroxy)-2H-1-benzopyran-2-one, and 1.01 g (yield=61%) of the desired compound 182 was obtained.

$^1$H-NMR (DMSO-d$_6$, δ-TMS) 9.60 (bs, 2H), 6.70~7.40 (m, 3H), 3.95 (m, 1H), 1.18 (d, H, J=6.0Hz)
IR (KBr, cm$^{-1}$) 3300, 1680, 1650, 1610
Elemental analysis value: C$_{12}$H$_{12}$O$_5$
Theoretical value (%): C 62.90; H 4.87; O 32.23
Actual measured value (%): c 62.83; H 4.84; O 32.33

Example 183

3,5-(dihydroxy)-4-(decyloxy)-2H-1-benzopyran-2-one (Compound

In Example 8, 1.69 g (8.71×10$^{-3}$ mol) of 3,4,5-trihydroxy-2H-1-benzopyran-2-one was used in place of 3,4,7-trihydroxy-2H-1-benzopyran-2-one, decyl bromide was used in place of benzoyl chloride, and 2.22 g (yield=71%) of the desired compound 183 was obtained.

$^1$H-NMR (DMSO-d$_6$, δ-TMS) 9.98 (bs, 1H), 9.01 (bs, 1H), 6.70~7.40 (m, 3H), 3.40 (t, 2H, J=7.0 Hz), 1.22~1.70 (m, 16H), 0.90 (t, 3H, J=6.0Hz)
IR (KBr, cm$^{-1}$) 3200, 1740, 1690, 1630, 1610, 1580
Elemental analysis value: C$_{19}$H$_{26}$O$_5$
Theoretical value (%): C 68.24; H 7.84; O 23.92
Actual measured value (%): C 68.03; H 7.90; O 24.07

Example 184

3-(methoxy)-4-(decyloxy)-5-hydroxy-2H-1-benzopyran-2-one (Compound 184)

In Example 8, 2.75 g (7.67×10$^{-3}$ mol) of 3,5-(dihydroxy)-4-(decyloxy)-2H-1-benzopyran-2-one was used in place of 3,4,7-trihydroxy-2H-1-benzopyran-2-one, methyl iodide was used in place of benzoyl chloride, and 1.91 g (yield=67%) of the desired compound 184 was obtained.

$^1$H-NMR (DMSO-d$_6$, δ-TMS) 9.84 (bs, 1H), 6.70~7.40 (m,3H), 3.73 (s,3H), 3.40 (t, 2H, J=7.0 Hz), 1.22~1.70 (m, 16H), 0.90 (t, 3H, J=6.0Hz)
IR (KBr, cm$^{-1}$) 3200, 1740, 1690, 1630, 1610, 1580
Elemental analysis value: C$_{20}$H$_{26}$O$_5$
Theoretical value (%): C 69.34; H 7.57; O 23.09
Actual measured value (%): C 69.29; H 7.54; O 23.17

Example 185

3-(acetoxy)-4-(isopropoxy)-5-hydroxy-2H-1-benzopyran-2-one (Compound 185)

In Example 8, 2.01 g (8.51×10×10$^{-3}$ mol) of 3-(acetoxy)-4,5-(dihydroxy)-2H-1-benzopyran-2-one was used in place of 3,4,7-trihydroxy-2H-1-benzopyran-2-one, isopropyl bromide was used in place of benzoyl chloride, and 1.68 g (yield=71%) of the desired compound 185 was obtained.

$^1$H-NMR (DMSO-d$_6$, δ-TMS) 10. 02 (bs, 1H), 6.70~7.40 (m, 3H), 3.89 (m, 1H), 1.96 (s,3H), 1.12 (d, 6H, J=6.0Hz)
IR(KBr, cm$^{-1}$) 3200, 1680, 1650, 1610
Elemental analysis value: C$_{14}$H$_{14}$O$_6$
Theoretical value (%): C 60.43; H 5.07; O 34.50
Actual measured value C 60.46; H 5.11; O 34.43

Example 186

3-(decyloxy)-4-(benzoyloxy)-5-hydroxy-2H-1-benzopyran-2-one (Compound 186)

In Example 8, 2.05 g (5.72×10$^{-3}$ mol) of 3-(decyloxy)-4,5-(dihydroxy)-2H-1-benzopyran-2-one was used in place of 3,4,7-trihydroxy-2H-1-benzopyran-2-one, and 1.83 g (yield=69%) of the desired compound 186 was obtained.

$^1$H-NMR (DMSO-d$_6$, δ-TMS) 10.04 (bs, 1H), 7.40~8.20 (m, 6H), 6.70~6.90 (m, 2H), 3.44 (t, 2H, J=7.0Hz), 1.22~1.70 (m, 16H), 0.92 (t, 3H, J=6.0Hz)
IR(KBr , cm$^{-1}$) 3200, 1740, 1690, 1630, 1610, 1580
Elemental analysis value: C$_{26}$H$_{30}$O$_6$
Theoretical value (%): C 71.21; H 6.90; O 21.89
Actual measured value (%): C 71.19; H 6.93; O 21.88

Example 187

3-(geranyloxy)-4,5-(dihydroxy)-2H-1-benzopyran-2-one (Compound 187)

In Example 5, 1.80 g (4.83×10$^{-3}$ mol) of 3-(geranyloxy)-4-(acetoxy)-5-hydroxy-2H-1-benzopyran- 2-one was used in place of 3-(benzoyloxy)-4,7-(dihydroxy)-2H-1-benzopyran-2-one, and 1.01 g (yield=63%) of the desired compound 187 was obtained.

$^1$H-NMR (DMSO-d$_6$, δ-TMS) 9.44 (bs, 2H), 6.70~7.50 (m, 3H), 5.43 (bt, 1H, J=7.0Hz), 5.09 (bt, 1H, J=7.0Hz), 4.01 (d, 2H, J=7.0Hz), 1.95~2.20 (m, 4H), 1.55~1.85 (m, 9H)

IR (KBr, cm$^{-1}$) 3500, 1720, 1680, 1630, 1580
Elemental analysis value: C$_{19}$ H$_{22}$ O$_5$
Theoretical value (%): C 69.07; H 6.71; O 24.22
Actual measured value (%): C 69.11; H 6.69; O 24.20

Example 188

3,5-(dihydroxy)-4-(geranyloxy)-2H-1-benzopyran-2-one (Compound 188)

In Example 8, 2.50 g (1.29×10$^{-2}$ mol) of 3,4,5-trihydroxy-2H-1-benzopyran-2-one was used in place of 3,4,7-trihydroxy-2H-1-benzopyran-2-one, geranyl bromide was used in place of benzoyl chloride, and 2.55 g (yield=60%) of the desired compound 188 was obtained.

$^1$H-NMR (DMSO-d$_6$, δ-TMS) 10.06 (bs, 1H), 9.11 (bs, 1H), 6.70~7.40 (m, 3H), 5.41 (bt, 1H, J=7.0Hz), 5.11 (bt, 1H, J=7.0Hz), 4.01 (d, 2H, J=7.0Hz), 1.95~2.20 (m, 4H), 1.55~1.85 (m, 9H)

IR (KBr, cm$^{-1}$) 3200, 1720, 1680, 1630, 1580
Elemental analysis value: C$_{19}$ H$_{22}$ O$_5$
Theoretical value (%): C 69.07; H 6.71; O 24.22
Actual measured value (%): C 69.14; H 6.75; O 24.11

Example 189

3-(geranyloxy)-4-(acetoxy)-5-hydroxy-2H-1-benzopyran-2-one (Compound 18 9)

In Example 8, 1.64 g (4.96×10$^{-3}$ mol) of 3-(geranyloxy)-4,5-(dihydroxy)-2H-1-benzopyran-2-one was used in place of 3,4,7-trihydroxy-2H-1-benzopyran-2-one, acetyl chloride was used in place of benzoyl chloride, and 1.18 g (yield=64%) of the desired compound 189 was obtained.

$^1$H-NMR (DMSO-d$_6$, δ-TMS) 9.32 (bs, 1H), 6.70~7.50 (m, 3H), 5.42 (bt, 1H, J=7.0Hz), 5.03 (bt, 1H, J=7.0Hz), 4.03 (d, 2H, J=7.0Hz), 1.95~2.20 (m, 4H), 1.71 (S, 3H), 1.55~1.85 (m, 9H)

IR (KBr, cm$^{-1}$) 3300, 1710, 1660, 1630, 1580
Elemental analysis value: C$_{21}$ H$_{24}$ O$_6$
Theoretical value (%): C 67.73; H 6.50; O 25.78
Actual measured value (%): C 67.83; H 6.48; O 25.69

Example 190

3-(benzoyloxy)-4-(geranyloxy)-5-hydroxy-2H-1-benzopyran-2-one (Compound 190)

In Example 8, 1.50 g (5.03×10$^{-3}$ mol) of 3-(benzoyloxy)-4,5-(dihydroxy)-2H-1-benzopyran-2-one was used in place of 3,4,7-trihydroxy-2H-1-benzopyran-2-one, geranyl bromide was used in place of benzoyl chloride, and 1.31 g (yield=60%) of the desired compound 190 was obtained.

$^1$H-NMR (DMSO-d$_6$, δ-TMS) 9.46 (bs, 1H), 7.40~8.20 m, 6H), 6.70~6.90 (m,2H), 5.44 (bt, 1H, J=7.0Hz), 5.13 (bt, 1H, J=7.0Hz), 4.00 (d, 2H, J=7.0Hz), 1.95~2.20 (m, 4H), 1.55~1.85 (m, 9H)

IR (KBr, cm-1) 3200, 1 720, 1680, 1630, 1580
Elemental analysis value: C$_{26}$ H$_{26}$ O$_6$
Theoretical value (%) C 71.82; H 6.03; O 22.10
Actual measured value (%): C 71.80; H 6.14; O 22.06

Example 191

3-(geranyloxy)-4-(methoxy)-5-hydroxy-2H-1-benzopyran-2-one (Compound 191)

In Example 8, 1.53 g (7.35×10$^{-3}$ mol) of 3,5-(dihydroxy)-4-(methoxy)-2H-1-benzopyran-2-one was used in place of 3,4,7-trihydroxy-2H-1-benzopyran-2-one, geranyl bromide was used in place of benzoyl chloride, and 1.77 g (yield=70%) of the desired compound 191 was obtained. $^1$H-NMR (DMSO-d$_6$, δ-TMS) 9.88 (bs, 1H), 6.70~7.40 (m, 3H), 5.45 (bt, 1H, J=7.0Hz), 5.10 (bt, 1H, J=7.0Hz), 4.03 (d, 2H, J=7.0Hz), 3.71 (s,3H), 1.95~2.20 (m, 4H), 1.55~1.85 (m, 9H)

IR (KBr, cm$^{-1}$) 200, 1720, 1690, 1630, 1580, 1550
Elemental analysis value: C$_{20}$ H$_{24}$ O$_5$
Theoretical value (%): C 69.75; H 7.02; O 23.23
Actual measured value (%): C 69.78; H 7.09; O 23.13

Example 192

3-(isopropoxy)-4-(geranyloxy)-5-hydroxy-2H-1-benzopyran-2-one (Compound 192)

In Example 8, 1.52 g (4.60×10$^{-3}$ mol) of 3,5-(dihydroxy)-4-(geranyloxy)-2H-1-benzopyran-2-one was used in place of 3,4,7-trihydroxy-2H-1-benzopyran-2-one, isopropyl bromide was used in place of benzoyl chloride, and 1.01 g (yield=59%) of the desired compound 192 was obtained.

$^1$H-NMR (DMSO-d$_6$, δ-TMS) 9.38 (bs, 1H), 6.70~7.50 (m, 3H), 5.45 (bt, 1H, J=7.0Hz), 5.08 (bt, 1H, J=7.0Hz), 4.01 (d, 2H, J=7.0Hz), 3.49 (m, 1H), 1.95~2.20 (m, 4H), 1.55~1.85 (m, 9H), 1.13 (d, 6H, J=6.0Hz)

IR (KBr, cm$^{-1}$) 3200, 1710, 1690, 1630, 1580, 1550
Elemental analysis value: C$_{22}$ H$_{28}$ O$_5$
Theoretical value (%): C 70.94; H 7.52; O 21.48
Actual measured value (%): C 71.00; H 7.59; O 21.41

Example 193

3,4-(digeranyloxy)-5-hydroxy-2H-1-benzopyran-2-one (Compound

In Example 8, 1.55 g (4.69×10$^{-3}$ mol) of 3-(geranyloxy)-4,5-(dihydroxy)-2H-1-benzopyran-2-one was used in place of 3,4,7-trihydroxy-2H-1-benzopyran-2-one, geranyl bromide was used in place of benzoyl chloride, and 1.31 g (yield=60%) of the desired compound 193 was obtained.

$^1$H-NMR (DMSO-d$_6$, δ-TMS) 9.40 (bs, 1H), 6.70~7.60 (m, 3H), 5.10~5.50 (m, 4H), 4.03 (d, 2H, J=7.0Hz), 4.02 (d, 2H, J=6.0Hz), 1.95~2.20 (m, 8H), 1.55~1.85 (m, 18H)

IR (KBr, cm$^{-1}$) 3200, 1720, 1680, 1630, 1580, 1550
Elemental analysis value: C$_{29}$ H$_{38}$ O$_5$
Theoretical value (%): C 74.65; H 8.21; O 17.14
Actual measured value (%): C 74.77; H 8.17; O 17.06

Example 194

3-(benzoyloxy)-4-hydroxy-5-(methoxy)-2H-1-benzopyran-2-one (Compound 194)

In Example 4, 3.12 g (7.46×10$^{-3}$ mol) of methyl-β-oxo-2'-(phenylmethoxy)-6'-(methoxy)-2-(benzoyloxy)-benzene propanate was used in place of methyl-β-oxo-2',4'-bis(phenylmethoxy)-2-(benzoyloxy)benzenepropanate, and 1.58 g (yield=68%) of the desired compound 194 was obtained.

$^1$H-NMR (DMSO-d$_6$, δ-TMS) 9.31 (bs, 1H), 7.40~8.20 (m, 6H), 6.70~6.90 (m,2H), 3.76 (s, 3H)

IR (KBr, cm$^{-1}$) 3300, 1740, 1690, 1630, 1610, 1580
Elemental analysis value: $C_{17} H_{12} O_6$
Theoretical value (%): C 65.38; H 3.87; O 30.74
Actual measured value (%): C 65.44; H 3.78; O 30.78

Example 195

3,4-(dihydroxy)-5-(methoxy)-2H-1-benzopyran-2-one (Compound

In Example 5, 2.68 g ($8.58 \times 10^{-3}$ mol) of 3-(benzoyloxy)-4-hydroxy-5-(methoxy)-2H-1-benzopyran-2-one was used in place of 3-(benzoyloxy)-4,7-(dihydroxy)-2H-1-benzopyran-2-one, and 1.25 g (yield=70%) of the desired compound 195 was obtained.
$^1$H-NMR (DMSO-d$_6$, δ-TMS) 9.62 (bs, 2H), 6.70~7.40 (m, 3H), 3.78 (s, 3H)
IR (KBr, cm$^{-1}$) 3200, 1680, 1650, 1610
Elemental analysis value: $C_{10} H_8 O_5$
Theoretical value (%): C 57.69; H 3.87; O 38.43
Actual measured value (%): C 57.53; H 3.90; O 38.57

Example 196

3-hydroxy-4-(acetoxy)-5-(methoxy)-2H-1-benzopyran-2-one (Compound 196)

In Example 8, 1.99 g ($9.56 \times 10^{-3}$ mol) of 3,4-(dihydroxy)-5-(methoxy)-2H-1-benzopyran-2-one was used in place of 3,4,7-trihydroxy-2H-1-benzopyran-2-one, acetyl chloride was used in place of benzoyl chloride, and 1.48 g (yield=62%) of the desired compound 196 was obtained. H-NMR (DMSO-d$_6$, δ-TMS) 9.21 (bs, 1H), 6.70~7.40 (m,3H), 3.72 (s,3H), 1.86 (s,3H)
IR (KBr, cm$^{-1}$) 200, 1680, 1650, 1610
Elemental analysis value: $C_{12} H_{10} O_6$
Theoretical value (%): C 57.60; H 4.03; O 38.37
Actual measured value (%): C 57.49; H 4.14; O 38.37

Example 197

3-(acetoxy)-4-(benzoyloxy)-5-(methoxy)-2H-1-benzopyran-2-one (Compound 197)

In Example 8, 2.06 g ($8.23 \times 10^{-3}$ mol) of 3-(acetoxy)-4-hydroxy-5-(methoxy)-2H-1-benzopyran-2-one was used in place of 3,4,7-trihydroxy-2H-1-benzopyran-2-one, and 1.96 g (yield=70%) of the desired compound 197 was obtained. $^1$H-NMR (DMSO-d$_6$, δ-TMS) 7.40~8.20 (m, 6H), 6.70~6.90 (m, 2H), 3.78 (s,3H), 1.99 (s, 3H)
IR (KBr, cm$^{-1}$) 3200, 1680, 1650, 1610
Elemental analysis value: $C_{18} H_{12} O_7$
Theoretical value (%): C 63.53; H 3.55; O 32.91
Actual measured value (%): C 63.58; H 3.63; O 32.79

Example 198

3-(isopropoxy)-4-hydroxy-5-(methoxy)-2H-1-benzopyran-2-one (Compound 198)

In Example 5, 1.72 g ($5.88 \times 10^{-3}$ mol) of 3-(isopropoxy)-4-(acetoxy)-5-(methoxy)-2H-1-benzopyran-2-one was used in place of 3-(benzoyloxy)-4,7-(dihydroxy)-2H-1-benzopyran-2-one, and 1.02 g (yield=69%) of the desired compound 198 was obtained.
$^1$H-NMR (DMSO-d$_6$, δ-TMS) 9.24 (bs, 1H), 6.70~7.40 (m,3H), 3.79 (m, 1H), 3.72 (s, 3H), 1.16 (d, 6H, J=6.0Hz)
IR (KBr, cm$^{-1}$) 3200, 1680, 1650, 1610
Elemental analysis value: $C_{13} H_{14} O_5$
Theoretical value (%): C 62.39; H 5.64; O 31.97
Actual measured value (%): C 62.53; H 5.64; O 31.83

Example 199

3-hydroxy-4-(decyloxy)-5-(methoxy)-2H-1-benzopyran-2-one (Compound 199)

In Example 8, 1.28 g ($6.15 \times 10^{-3}$ mol) of 3,4-(dihydroxy)-5-(methoxy)-2H-1-benzopyran-2-one was used in place of 3,4,7-trihydroxy-2H-1-benzopyran-2-one, decyl bromide was used in place of benzoyl chloride, and 1.65 g (yield=72%) of the desired compound 199 was obtained.
$^1$H-NMR (DMSO-d$_6$, δ-TMS) 9.51 (bs, 1H), 6.70~7.40 (m, 3H), 3.79 (s,3H), 3.35 (t, 2H, J=7.0Hz), 1.20~1.70 (m, 16H), 0.93 (t, 3H, J=6.0Hz)
IR (KBr, cm$^{-1}$) 3200, 1670, 1650, 1610
Elemental analysis value: $C_{20} H_{26} O_5$
Theoretical value (%): C 69.34; H 7.57; O 23.09
Actual measured value (%): C 69.21; H 7.63; O 23.16

Example 200

3,5-(dimethoxy)-4-(isopropoxy)-2H-1-benzopyran-2-one (Compound 200)

In Example 8, 1.38 g ($5.51 \times 10^{-3}$ mol) of 3-hydroxy-4-(isopropoxy)-5-(methoxy)-2H-1-benzopyran-2-one was used in place of 3,4,7-trihydroxy-2H-1-benzopyran-2-one, methyl iodide was used in place of benzoyl chloride, and 1.11 g (yield=76%) of the desired compound 200 was obtained.
$^1$H-NMR (DMSO-d$_6$, δ-TMS) 6.70~7.40 (m, 3H), 3.80 (m, 1H), 3.75 (s, 3H), 3.69 (s, 3H), 1.17 (d, 6H, J=6.0Hz)
IR (KBr, cm$^{-1}$) 1680, 1650, 1610
Elemental analysis value: $C_{14} H_{16} O_5$
Theoretical value (%): C 63.62; H 6.10; O 30.27
Actual measured value (%): C 63.51; H 6.27; O 30.22

Example 201

3-(acetoxy)-4,5-(dimethoxy)-2H-1-benzopyran-2-one (Compound

In Example 8, 1.99 g ($7.95 \times 10^{-3}$ mol) of 3-(acetoxy)-4-hydroxy-5-(methoxy)-2H-1-benzopyran-2-one was used in place of 3,4,7-trihydroxy-2H-1-benzopyran-2-one, methyl iodide was used in place of benzoyl chloride, and 1.49 g (yield=71%) of the desired compound 201 was obtained.
$^1$H-NMR (DMSO-d$_6$, δ-TMS) 6.70~7.40 (m, 3H), 3.73 (s,3H), 3.69 (s,3H), 1.84 (s,3H)
IR (KBr, cm-1) 1750, 1 680, 1650, 1610
Elemental analysis value: $C_{13} H_{12} O_6$
Theoretical value (%): C 59.09; H 4.58; O 36.33
Actual measured value (%): C 58.94; H 4.63; O 36.43

Example 202

3-(decyloxy)-4-(benzoyloxy)-5-(methoxy)-2H-1-benzopyran-2-one (Compound 202)

In Example 8, 2.17 g ($6.95 \times 10^{-3}$ mol) of 3-hydroxy-4-(benzoyloxy)-5-(methoxy)-2H-1-benzopyran-2-one was used in place of 3,4,7-trihydroxy-2H-1-benzopyran-2-one, decyl bromide was used in place of benzoyl chloride, and 2.25 g (yield=68%) of the desired compound 202 was obtained.
$^1$H-NMR (DMSO-d$_6$, δ-TMS) 6.70~7.40 (m, 3H), 3.75 (s,3H), 3.32 (t, 2H, J=7.0Hz), 1.20~1.70 (m, 16H), 0.89 (t, 3H, J=6.0Hz)
IR (KBr, cm$^{-1}$) 1710, 1670, 1650, 1610

Elemental analysis value: $C_{27}H_{32}O_6$
Theoretical value (%): C 71.66; H 7.13; O 21.21
Actual measured value (%): C 71.52; H 7.12; O 21.36

Example 203

3-(geranyloxy)-4-hydroxy-5-(methoxy)-2H-1-benzopyran-2-one (Compound 203)

In Example 5, 2.01 g ($5.20 \times 10^{-3}$ mol) of 3-(geranyloxy)-4-(acetoxy)-5-(methoxy)-2H-1-benzopyran-2-one was used in place of 3-(benzoyloxy)-4,7-(dihydroxy)-2H-1-benzopyran-2-one, and 1.25 g (yield=70%) of the desired compound 203 was obtained.

$^1$H-NMR (DMSO-d$_6$, δ-TMS) 9.50 (bs, 1H), 6.70~7.40 (m, 3H), 5.43 (bt, 1H, J=7.0Hz), 5.09 (bt, 1H, J=7.0Hz), 4.01 (d, 2H, J=7.0Hz), 3.72 (s, 3H), 2.00~2.21 (m, 4H), 1.52~1.85 (m, 9H)
IR (KBr, cm$^{-1}$) 3200, 1720, 1680, 1630, 1580
Elemental analysis value: $C_{20}H_{24}O_5$
Theoretical value (%): C 69.75; H 7.02; O 23.23
Actual measured value (%): C 69.89; H 6.93; O 23.18

Example 204

3-hydroxy-4-(geranyloxy)-5-(methoxy)-2H-1-benzopyran-2-one (Compound 204)

In Example 8, 1.56 g ($7.49 \times 10^{-3}$ mol) of 3,4-(dihydroxy)-5-(methoxy)-2H-1-benzopyran-2-one was used in place of 3,4,7-trihydroxy-2H-1-benzopyran-2-one, geranyl bromide was used in place of benzoyl chloride, and 1.50 g (yield=58%) of the desired compound 204 was obtained.

$^1$H-NMR (DMSO-d$_6$, δ-TMS) 8.92 (bs, 1H), 6.70~7.40 (m, 3H), 5.45 (bt, 1H, J=7.0Hz), 5.08 (bt, 1H, J=7.0Hz), 4.03 (d, 2H, J=7.0Hz), 3.74 (s, 3H), 2.00~2.21 (m, 4H), 1.52~1.85 (m, 9H)
IR (KBr, cm$^{-1}$) 3200, 1730, 1670, 1630, 1580
Elemental analysis value: $C_{20}H_{24}O_5$
Theoretical value (%): C 69.75; H 7.02; O 23.23
Actual measured value (%): C 69.79; H 7.10; O 23.11

Example 205

3-(geranyloxy)-4-(benzoyloxy)-5-(methoxy)-2H-1-benzopyran-2-one (Compound 205)

In Example 8, 1.53 g ($4.90 \times 10^{-3}$ mol) of 3-hydroxy-4-(benzoyloxy)-5-(methoxy)-2H-1-benzopyran-2-one was used in place of 3,4,7-trihydroxy-2H-1-benzopyran-2-one, geranyl bromide was used in place of benzoyl chloride, and 1.41 (yield=64%) of the desired compound 205 was obtained.

$^1$H-NMR (DMSO-d$_6$, δ-TMS) 7.40~8.20 (m, 6H), 6.70~6.90 (m, 2H), 5.45 (bt, 1H, J=7.0Hz), 5.03 (bt, 1H, J=7.0Hz), 4.04 (d, 2H, J=7.0Hz), 3.72 (s, 3H), 2.00~2.21 (m, 4H), 1.52~1.85 (m, 9H)
IR (KBr, cm$^{-1}$) 1730, 1670, 1630, 1580, 1520
Elemental analysis value: $C_{27}H_{28}O_6$
Theoretical value (%): C 72.30; H 6.29; O 21.41
Actual measured value (%): C 72.31; H 6.25; O 21.44

Example 206

3-(acetoxy)-4-(geranyloxy)-5-(methoxy)-2H-1-benzopyran-2-one (Compound 206)

In Example 8, 1.50 g ($6.00 \times 10^{-3}$ mol) of 3-(acetoxy)-4-hydroxy-5-(methoxy)-2H-1-benzopyran-2-one was used in place of 3,4,7-trihydroxy-2H-1-benzopyran-2-one, geranyl bromide was used in place of benzoyl chloride, and 1.51 g (yield=65%) of the desired compound 206 was obtained.

$^1$H-NMR (DMSO-d$_6$, δ-TMS) 6.70~7.40 (m, 3H), 5.42 (bt, 1H, J=7.0Hz), 5.04 (bt, 1H, J=7.0Hz), 4.09 (d, 2H, J=7.0Hz), 3.70 (s, 3H), 2.00~2.21 (m, 4H), 1.76 (s, 3H), 1.52~1.85 (m, 9H)
IR (KBr, cm$^{-1}$) 1730, 1670, 1630, 1580, 1520
Elemental analysis value: $C_{22}H_{26}O_6$
Theoretical value (%): C 68.38; H 6.78; O 24.84
Actual measured value (%): C 68.30; H 6.76; O 24.94

Example 207

3-(geranyloxy)-4-(isopropoxy)-5-(methoxy)-2H-1-benzopyran-2-one (Compound 207)

In Example 8, 1.58 g ($4.59 \times 10^{-3}$ mol) of 3-(geranyloxy)-4-hydroxy-5-(methoxy)-2H-1-benzopyran-2-one was used in place of 3,4,7-trihydroxy-2H-1-benzopyran-2-one, isopropyl bromide was used in place of benzoyl chloride, and 1.06 g (yield=60%) of the desired compound 207 was obtained.

$^1$H-NMR (DMSO-d$_6$, δ-TMS) 6.70~7.40 (m, 3H), 5.42 (bt, 1H, J=7.0Hz), 5.04 (bt, 1H, J=7.0Hz), 4.09 (d, 2H, J=7.0Hz), 3.92 (m, 1H), 3.73 (s, 3H), 2.00~2.21 (m, 4H), 1.52~1.85 (m, 9H), 1.15 (d, 6H, J=6.0Hz)
IR (KBr, cm$^{-1}$) 1720, 1680, 1630, 1580, 1550
Elemental analysis value: $C_{22}H_{26}O_6$
Theoretical value (%): C 68.38; H 6.78; O 24.84
Actual measured value (%): C 68.34; H 6.76; O 24.90

Example 208

3,5-(dimethoxy)-4-(geranyloxy)-2H-1-benzopyran-2-one (Compound 208)

In Example 8, 1.58 g ($4.59 \times 10^{-3}$ mol) of 3-hydroxy-4-(geranyloxy)-5-(methoxy)-2H-1-benzopyran-2-one was used in place of 3,4,7-trihydroxy-2H-1-benzopyran-2-one, methyl iodide was used in place of benzoyl chloride, and 1.07 g (yield=65%) of the desired compound 208 was obtained.

$^1$H-NMR (DMSO-d$_6$, δ-TMS) 6.70~7.40 (m, 3H), 5.45 (bt, 1H, J=7.0Hz), 5.01 (bt, 1H, J=7.0 Hz), 4.06 (d, 2H, J=7.0Hz), 3.70 (s, 3H), 3.64 (s, 3H), 2.00~2.21 (m, 4H), 1.52~1.85 (m, 9H)
IR(KBr, cm$^{-1}$) 1730, 1670, 1630, 1580, 1520
Elemental analysis value: $C_{21}H_{26}O_5$
Theoretical value (%): C 70.37; H 7.31; O 22.32
Actual measured value (%): C 70.40; H 7.37; O 22.23

Example 209

3,4-(digeranyloxy)-5-(methoxy)-2H-1-benzopyran-2-one (Compound 209)

In Example 8, 1.58 g ($4.59 \times 10^{-3}$ mol) of 3-(geranyloxy)-4-hydroxy-5-(methoxy)-2H-1-benzopyran-2-one was used in place of 3,4,7-trihydroxy-2H-1-benzopyran-2-one, geranyl bromide was used in place of benzoyl chloride, and 1.43 g (yield=65%) of the desired compound 202 was obtained.

$^1$H-NMR (DMSO-d$_6$, δ-TMS) 6.70~7.40 (m, 3H), 5.10~5.50 (m, 4H), 4.07 (d, 2H, J=7.0Hz), 4.09 (d, 2H, J=6.0Hz), 3.81 (s, 3H), 1.95~2.20 (m, 8H), 1.55~1.85 (m, 18H)
IR (KBr, cm$^{-1}$) 1710, 1670, 1630, 1580, 1550
Elemental analysis value: $C_{30}H_{38}O_5$
Theoretical value (%): C 75.28; H 8.00; O 16.72
Actual measured value (%): C 75.07; H 8.15; O 16.78

Example 210

3-(benzoyloxy)-4-hydroxy-5-(isopropoxy)-2H-1-benzopyran-2-one (Compound 210)

In Example 4, 5.69 g ($1.27 \times 10^{-2}$ mol) of methyl-$\beta$-oxo-2'-(phenylmethoxy)-6'-(isopropoxy)-2-(benzoyloxy)benzene propanate was used in place of methyl-$\beta$-oxo-2',4'-bis(phenylmethoxy)-2-(benzoyloxy)benzenepropanate, and 3.47 g (yield=80%) of the desired compound 210 was obtained. $^1$H-NMR (DMSO-d$_6$, $\delta$-TMS) 9.31 (bs, 1H), 7.40~8.20 (m, 6H), 6.70~6.90 (m, 2H), 3.81 (m, 1H), 1.15 (d, 6H, J=6.0Hz)

IR(KBr, cm$^{-1}$) 3200, 1740, 1690, 1630, 1610, 1580
Elemental analysis value: C$_{19}$ H$_{16}$ O$_6$
Theoretical value (%): C 67.05; H 4.75; O 28.20
Actual measured value (%): C 67.00; H 4.69; O 28.31

Example 211

3,4-(dihydroxy)-5-(isopropoxy)-2H-1-benzopyran-2-one (Compound 211)

In Example 5, 2.08 g ($6.11 \times 10^{-3}$ mol) of 3-(benzoyloxy)-4-hydroxy-5-(isopropoxy)-2H-1-benzopyran-2-one was used in place of 3-(benzoyloxy)-4,7-(dihydroxy)-2H-1-benzopyran-2-one, and 0.94 g (yield=65%) of the desired compound 211 was obtained.

$^1$H-NMR (DMSO-d$_6$, $\delta$-TMS) 9.06 (bs, 1H), 8.99 (bs, 1H), 6.70~7.40 (m, 3H), 3.68 (m, 1H), 1.18 (d, 6H, J=6.0Hz)

IR (KBr, cm$^{-1}$) 3200, 1680, 1650, 1610
Elemental analysis value: C$_{12}$ H$_{12}$ O$_5$
Theoretical value (%): C 62.90; H 4.87; O 32.23
Actual measured value (%): C 62.84; H 4.99; O 32.17

Example 212

3-hydroxy-4-(acetoxy)-5-(isopropoxy)-2H-1-benzopyran-2-one (Compound 212)

In Example 8, 2.44 g ($1.03 \times 10^{-2}$ mol) of 3,4-(dihydroxy)-5-(isopropoxy)-2H-1-benzopyran-2-one was used in place of 3,4,7-trihydroxy-2H-1-benzopyran-2-one, acetyl chloride was used in place of benzoyl chloride, and 1.98 g (yield=69%) of the desired compound 212 was obtained.

$^1$H-NMR (DMSO-d$_6$, $\delta$-TMS) 9.31 (bs, 1H), 6.70~7.40 (m, 3H), 3.75 (m, 1H), 1.69 (s, 3H), 1.14 (d, 6H, J=6.0Hz)

IR (KBr, cm$^{-1}$) 3300, 1710, 1680, 1650, 1610
Elemental analysis value: C$_{14}$ H$_{14}$ O$_6$
Theoretical value 60.43; H 5.07; O 34.50
Actual measured value (%): C 60.26; H 5.23; O 34.51

Example 213

3,4-(diacetoxy)-5-(isopropoxy)-2H-1-benzopyran-2-one (Compound 2 t 3)

In Example 8, 2.61 g ($9.38 \times 10^{-3}$ mol) of 3-(acetoxy)-4-hydroxy-5-(isopropoxy)-2H-1-benzopyran-2-one was used in place of 3,4,7-trihydroxy-2H-1-benzopyran-2-one, acetyl chloride was used in place of benzoyl chloride, and 2.16 g (yield=72%) of the desired compound 213 was obtained.

$^1$H-NMR (DMSO-d$_6$, $\delta$-TMS) 6.70~7.40 (m, 3H), 3.75 (m, 1H), 1.69 (s, 3H), 1.65 (s, 3H), 1.11 (d, 6H, J=6.0Hz)

IR (KBr, cm$^{-1}$) 1750, 1710, 1680, 1650, 1610
Elemental analysis value: C$_{16}$ H$_{16}$ O$_7$ Theoretical value (%): C 60.00; H 5.04; O 34.96
Actual measured value (%): C 60.06; H 5.11; O 34.83

Example 214

3-(decyloxy)-4-hydroxy-5-(isopropoxy)-2H-1-benzopyran-2-one (Compound 214)

In Example 5, 2.03 g ($4.59 \times 10^{-3}$ mol) of 3-(decyloxy)-4-(acetoxy)-5-(isopropoxy)-2H-1-benzopyran-2-one was used in place of 3-(benzoyloxy)-4,7-(dihydroxy)-2H-1-benzopyran-2-one, and 1.43 g (yield=78%) of the desired compound 214 was obtained.

$^1$H-NMR (DMSO-d$_6$, $\delta$-TMS) 9.59 (bs, 1H), 6.70~7.40 (m,3H), 3.76 (m, 1H), 3.28 (t, 2H, J=7.0Hz), 1.20~1.70 (m, 16H), 1.15 (d, 6H, J=6.0Hz), 0.90 (t, 3H, J=6.0Hz)

IR (KBr, cm$^{-1}$) 3200, 1680, 1650, 1610
Elemental analysis value: C$_{22}$ H$_{32}$ O$_5$
Theoretical value (%): C 70.18; H 8.57; O 21.25
Actual measured value (%): C 70.11; H 8.55; O 21.34

Example 215

3-hydroxy-4,5-(diisopropoxy)-2H-1-benzopyran-2-one (Compound

In Example 8, 1.58 g ($6.69 \times 10^{-3}$ mol) of 3,4-(dihydroxy)-5-(isopropoxy)-2H-1-benzopyran-2-one was used in place of 3,4,7-trihydroxy-2H-1-benzopyran-2-one, isopropyl bromide was used in place of benzoyl chloride, and 1.15 g (yield=62%) of the desired compound 215 was obtained.

$^1$H-NMR (DMSO-d$_6$, $\delta$-TMS) 9.08 (bs, 1H), 6.70~7.40 (m,3H), 3.76 (m, 1H), 3.68 (m, 1H), 1.18 (d, 6H, J=6.0Hz), 1.15 (d, 6H, J=6.0Hz)

IR(KBr, cm$^{-1}$) 3200, 1680, 1650, 1610
Elemental analysis value: C$_{15}$ H$_{18}$ O$_5$
Theoretical value (%): C 64.73; H 6.52; O 28.75
Actual measured value (%): C 64.66; H 6.48; O 28.86

Example 216

3-(methoxy)-4-(decyloxy)-5-(isopropoxy)-2H-1-benzopyran-2-one (Compound 216)

In Example 8, 1.93 g ($4.82 \times 10^{-3}$ mol) of 3-hydroxy-4-(decyloxy)-5-(isopropoxy)-2H-1-benzopyran-2-one was used in place of 3,4,7-trihydroxy-2H-1-benzopyran-2-one, methyl iodide was used in place of benzoyl chloride, and 1.89 g (yield=59%) of the desired compound 216 was obtained.

$^1$H-NMR (DMSO-d6,$\delta$-TMS) 6.70~7.40 (m, 3H), 3.76 (m, 1H), 3.72 (s,3H), 3.36 (t, 2H, J=7.0Hz), 1.20~1.70 (m, 16H), 1.18 (d, 6H, J=6.0Hz), 0.88 (t, 3H, J=6.0Hz)

IR (KBr, cm$^{-1}$) 1680, 1650, 1610
Elemental analysis value: C$_{23}$ H$_{34}$ O$_5$
Theoretical value (%): C 70.74; H 8.78; O 20.49
Actual measured value (%): C 70.58; H 8.92; O 20.50

Example 217

3-(acetoxy)-4-(decyloxy)-5-(isopropoxy)-2H-1-benzopyran-2-one (Compound 217)

In Example 8, 1.36 g ($4.89 \times 10^{-3}$ mol) of 3-(acetoxy)-4-hydroxy-5-(isopropoxy)-2H-1-benzopyran-2-one was used in place of 3,4,7-trihydroxy-2H-1-benzopyran-2-one, decyl bromide was used in place of benzoyl chloride, and 1.45 g (yield=67%) of the desired compound 217 was obtained.

$^1$H-NMR (DMSO-d$_6$, $\delta$-TMS) 6.70~7.40 (m, 3H), 3.68 (m, 1H), 3.34 (t, 2H, J=7.0Hz), 1.85 (s, 3H), 1.20~1.70 (m, 16H), 1.15 (d, 6H, J=6.0Hz), 0.90 (t, 3H, J=6.0Hz)

IR (KBr, cm$^{-1}$) 1720, 1680, 1650, 1610

Elemental analysis value: $C_{24} H_{34} O_6$

Theoretical value (%): C 68.87; H 8.19; O 22.94

Actual measured value (%): C 68.71; H 8.24; O 23.05

Example 218

3-(decyloxy)-4-(benzoyloxy)-5-(isopropoxy)-2H-1-benzopyran-2-one (Compound 218)

In Example 8, 2.43 g (7.14×10$^{-3}$ mol) of 3-hydroxy-4-(benzoyloxy)-5-(isopropoxy)-2H-1-benzopyran-2-one was used in place of 3,4,7-trihydroxy-2H-1-benzopyran-2-one, decyl bromide was used in place of benzoyl chloride, and 2.63 g (yield=73%) of the desired compound 218 was obtained.

$^1$H-NMR (DMSO-d$_6$, δ-TMS) 7.40~8.20 (m, 6H), 6.70~6.90 (m, 2H), 3.81 (m, 1H), 3.36 (t, 2}t, J=7.0Hz), 1.20~1.70 (m, 16H), 1.15 (d, 6H, J=6.0Hz), 0.91 (t, 3H, J=6.0Hz)

IR (KBr, cm$^{-1}$) 1720, 1680, 1650, 1610

Elemental analysis value: $C_{29} H_{36} O_6$

Theoretical value (%): C 72.47; H 7.55; O 19.98

Actual measured value (%): C 72.53; H 7.42; O 20.05

Example 219

3-(geranyloxy)-4-hydroxy-5-(isopropoxy)-2H-1-benzopyran-2-one (Compound 219)

In Example 5, 2.00 g (4.83×10$^{-3}$ mol) of 3-(geranyloxy)-4-(acetoxy)-5-(isopropoxy)-2H-1-benzopyran-2-one was used in place of 3-(benzoyloxy)-4,7-(dihydroxy)-2H-1-benzopyran-2-one, and 1.08 g (yield=60%) of the desired compound 219 was obtained.

$^1$H-NMR (DMSO-d$_6$, δ-TMS) 9.35 (bs, 1H), 6.70~7.40 (m, 3H), 5.44 (bt, 1H, J=7.0Hz), 5.03 (bt, 1H, J=7.0Hz), 4.01 (d, 2H, J=7.0Hz), 3.50 (m, 1H), 2.00~2.21 (m, 4H), 1.52~1.85 (m, 9H), 1.12 (d, 6H, J=6.0Hz)

IR (KBr, cm$^{-1}$) 3200, 1720, 1680, 1630, 1580

Elemental analysis value: $C_{22} H_{28} O_5$

Theoretical value (%): C 70.94; H 7.58; O 21.48

Actual measured value (%): C 70.90; H 7.55; O 21.55

Example 220

3-hydroxy-4-(geranyloxy)-5-(isopropoxy)-2H-1-benzopyran-2-one (Compound 220)

In Example 8, 1.57 g (6.65×10$^{-3}$ mol) of 3,4-(dihydroxy)-5-(isopropoxy)-2H-1-benzopyran-2-one was used in place of 3,4,7-trihydroxy-2H-1-benzopyran-2-one, geranyl bromide was used in place of benzoyl chloride, and 1.46 g (yield=54%) of the desired compound 220 was obtained.

$^1$H-NMR (DMSO-d$_6$, δ-TMS) 9.02 (bs, 1H), 6.70~7.40 (m, 3H), 5.42 (bt, 1H, J=7.0Hz), 5.02 (bt, 1H, J=7.0Hz), 4.03 (d, 2H, J=7.0Hz), 3.50 (m, 1H), 2.00~2.21 (m, 4H), 1.52~1.85 (m, 9H), 1.11 (d, 6H, J=6.0Hz)

IR (KBr, cm$^{-1}$) 3200, 1720, 1670, 1630, 1580, 1520

Elemental analysis value: $C_{22} H_{28} O_5$

Theoretical value (%): C 70.94; H 7.58; O 21.48

Actual measured value (%): C 71.00; H 7.52; O 21.48

Example 221

3-(geranyloxy)-4,5-(diisopropoxy)-2H-1-benzopyran-2-one (Compound 221)

In Example 8, 1.53 g (4.11×10$^{-3}$ mol) of 3-(geranyloxy)-4-hydroxy-5-(isopropoxy)-2H-1-benzopyran-2-one was used in place of 3,4,7-trihydroxy-2H-1-benzopyran-2-one, isopropyl bromide was used in place of benzoyl chloride, and 1.19 g (yield=68%) of the desired compound 221 was obtained.

$^1$H-NMR (DMSO-d6,δ-TMS) 6.70~7.40 (m, 3H), 5.42 (bt, 1H, J=7.0Hz), 5.02 (bt, 1H, J=7.0Hz), 4.01 (d, 2H, J=7.0Hz), 3.40~3.60 (m, 2H), 2.00~2.21 (m, 4H), 1.52~1.85 (m, 9H), 1.12 (d, 6H, J=6.0Hz), 1.10 (d, 6H, J=6.0Hz)

IR (KBr, cm$^{-1}$) 1730, 1660, 1630, 1570, 1520

Elemental analysis value: $C_{25} H_{34} O_5$

Theoretical value (%): C 71.61; H 8.51; O 19.88

Actual measured value (%): C 71.53; H 8.56; O 19.91

Example 222

3-(methoxy)-4-(geranyloxy)-5-(isopropoxy)-2H-1-benzopyran-2-one (Compound 222)

In Example 8, 1.50 g (4.03×10$^{-3}$ mol) of 3-hydroxy-4-(geranyloxy)-5-(isopropoxy)-2H-1-benzopyran-2-one was used in place of 3,4,7-trihydroxy-2H-1-benzopyran-2-one, methyl iodide was used in place of benzoyl chloride, and 0.89 g (yield=57%) of the desired compound 222 was obtained.

$^1$H-NMR (DMSO-d$_6$, δ-TMS) 6.70~7.60 (m, 3H), 5.43 (bt, 1H, J=7.0Hz), 5.03 (bt, 1H, J=7.0Hz), 4.02 (d, 2H, J=7.0Hz), 3.71 (s,3H), 3.48 (m, 1H), 2.00~2.21 (m, 4H), 1.52~1.85 (m, 9H), 1.13 (d, 6H, J=6.0Hz)

IR (KBr, cm$^{-1}$) 1730, 1660, 1630, 1570, 1520

Elemental analysis value: $C_{23} H_{30} O_5$

Theoretical value (%): C 71.48; H 7.82; O 20.70

Actual measured value (%): C 71.39; H 7.91; O 20.70

Example 223

3,4-(digeranyloxy)-5-(isopropoxy)-2H-1-benzopyran-2-one (Compound 223)

In Example 8, 1.52 g (6.43×10$^{-3}$ mol) of 3,4-(dihydroxy)-5-(isopropoxy)-2H-1-benzopyran-2-one was used in place of 3,4,7-trihydroxy-2H-1-benzopyran-2-one, potassium carbonate was used in place of sodium bicarbonate, geranyl bromide was used in place of benzoyl chloride, and 1.96 g (yield=60%) of the desired compound 223 was obtained.

$^1$H-NMR (DMSO-d6,δ-TMS) 6.70~7 .60 (m, 3H), 5.10~5.50 (m, 4H), 4.08 (d, 2H, J=7.0Hz), 4.02 (d, 2H, J=7.0Hz), 3.42 (m, 1H), 1.90~2.20 (m, 8H), 1.50~1.90 (m, 18H), 1.12 (d, 6H, J=6.0Hz)

IR (KBr, cm$^{-1}$) 1720, 1680, 1630, 1570, 1520

Elemental analysis value: $C_{32} H_{44} O_5$

Theoretical value (%): C 75.55; H 8.72; O 15.73

Actual measured value (%): C 75.41; H 8.70; O 15.89

Example 224

3-(benzoyloxy)-4-(butoxy)-5-hydroxy-2H-1-benzopyran-2-one (Compound 224)

In Example 8, 2.30 g (7.71×10$^{-3}$ mol) of 3-(benzoyloxy)-4,5-(dihydroxy)-2H-1-benzopyran-2-one was used in place of 3,4,7-trihydroxy-2H-1-benzopyran-2-one, butyl bromide was used in place of benzoyl chloride, and 1.81 g (yield=68%) of the desired compound 224 was obtained.

$^1$H-NMR (DMSO-d$_6$, δ-TMS) 9.31 (bs, 1H), 7.40~8.20 (m, 6H), 6.70~6.90 (m, 2H), 3.23 (t, 2H, J=6.0Hz), 1.00~1.70 (m, 4H), 1.24 (s, 3H)
IR (KBr, cm$^{-1}$) 3250, 1740, 1690, 1630, 1610, 1580
Elemental analysis value: C$_{20}$ H$_{18}$ O$_6$
Theoretical value (%): C 67.79; H 5.12; O 27.09
Actual measured value (%): C 67.63; H 5.24; O 27.13

Example 225

3-(butoxy)-4-hydroxy-5-(methoxy)-2H-1-benzopyran-2-one (Compound 225)

In Example 5, 2.63 g (8.57×10$^{-3}$ mol) of 3-(butoxy)-4-(acetoxy)-5-(methoxy)-2H-1-benzopyran-2-one was used in place of 3-(benzoyloxy)-4,7-(dihydroxy)-2H-1-benzopyran-2-one, and 1.56 g (yield=69%) of the desired compound 225 was obtained.
$^1$H-NMR (DMSO-d$_6$, δ-TMS) 9.22 (bs, 1H), 6.70~7.40 (m,3H), 3.69 (s,3H), 3.21 (t, 2H, J=6.0Hz), 1.00~1.70 (m,4H), 1.12 (s,3H)
IR (KBr, cm$^{-1}$) 3300, 1680, 1650, 1610
Elemental analysis value: C$_{14}$ H$_{16}$ O$_5$
Theoretical value (%): C 63.62; H 6.10; O 30.27
Actual measured value (%): C 63.58; H 6.18; O 30.24

Example 226

3-(benzoyloxy)-4-hydroxy-5-(butoxy)-2H-1-benzopyran-2-one (Compound 226)

In Example 4, 2.69 g (5.96×10$^{-2}$ mol) of methyl-β-oxo-2'-(phenylmethoxy)-6'-(butoxy)-2-(benzoyloxy)-benzene propanate was used in place of methyl-β-oxo-2',4'-bis(phenylmethoxy)-2-(benzoyloxy)benzenepropanate, and 1.50 g (yield=73%) of the desired compound 226 was obtained.
$^1$H-NMR (DMSO-d$_6$, δ-TMS) 9.11 (bs, 1H), 7.40~8.20 (m, 6H), 6.70~6.90 (m, 2H), 3.13 (t, 2H, J=6.0Hz), 1.00~1.70 (m, 4H), 1.01 (s, 3H)
IR (KBr, cm$^{-1}$) 3300, 1740, 1690, 1630, 1610, 1580
Elemental analysis value: C$_{20}$ H$_{18}$ O$_6$
Theoretical value (%): C 67.79; H 5.12; O 27.09
Actual measured value (%): C 67.86; H 5.03; O 27.11

Example 227

3,4-(dihydroxy)-5-(butoxy)-2H-1-benzopyran-2-one (Compound

In Example 5, 1.58 g (4.58×10$^{-3}$ mol) of 3-(benzoyloxy)-4-hydroxy-5-(butoxy)-2H-1-benzopyran-2-one was used in place of 3-(benzoyloxy)-4,7-(dihydroxy)-2H-1-benzopyran-2-one, and 0.70 g (yield=63%) of the desired compound 227 was obtained.
$^1$H-NMR (DMSO-d$_6$, δ-TMS) 9.21 (bs, 1H), 8.96 (bs, 1H), 6.70~7.40 (m, 3H), 3.18 (t, H, J=6.0Hz), 1.00~1.70 (m, 4H), 0.98 (s, 3H)
IR (KBr, cm$^{-1}$) 3300, 1680, 1650, 1610
Elemental analysis value: C$_{13}$ H$_{14}$ O$_5$
Theoretical value (%): C 62.39; H 5.64; O 31.97
Actual measured value (%): C 62.20; H 5.73; O 32.07

Example 228

3-(benzoyloxy)-4-(methoxy)-5-(butoxy)-2H-1-benzopyran-2-one (Compound 228)

In Example 8, 2.51 g (7.27×10$^{-3}$ mol) of 3-(benzoyloxy)-4-hydroxy-5-(butoxy)-2H-1-benzopyran-2-one was used in place of 3,4,7-trihydroxy-2H-1-benzopyran-2-one, methyliodide was used in place of benzoyl chloride, and 1.59 g (yield=61%) of the desired compound 228 was obtained.
$^1$H-NMR (DMSO-d$_6$, δ-TMS) 7.20~8.20 (m, 6H), 6.70~6.90 (m, 2H), 3 . 73 (s, 3H) , 3.12 (t, 2H, J=6.0Hz), 1.00~1.70 (m, 4H), 0.99 (s,3H)
IR (KBr, cm$^{-1}$) 1740, 1690, 1630, 1610, 1580
Elemental analysis value: C$_{21}$ H$_{20}$ O$_6$
Theoretical value (%): C 68.47; H 5.47; O 26.06
Actual measured value (%): C 68.51; H 5.31; O 26.18

Example 229

3-(benzoyloxy)-4-hydroxy-5-(decyloxy)-2H-1-benzopyran-2-one (Compound 229)

In Example 4, 6.27 g (1.10×10$^{-2}$ mol) of methyl-β-oxo-2'-(phenylmethoxy)-6'-(decyloxy)-2-(benzoyloxy)-benzene propanate was used in place of methyl-β-oxo-2',4'-bis(phenylmethoxy)-2-(benzoyloxy)benzenepropanate, and 4.07 g (yield=80%) of the desired compound 229 was obtained.
$^1$H-NMR (DMSO-d$_6$, δ-TMS) 9.35 (bs, 1H) , 7.40~8.20 (m, 6H), 6.70~6.90 (m, 2H), 3.32 (m, 2H, J=7.0Hz), 1.20~1.70 (m, 16H), 0.88 (t, 3H, J=6.0Hz)
IR (KBr, cm$^{-1}$) 3200, 1740, 1690, 1630, 1610, 1580
Elemental analysis value: C$_{26}$ H$_{30}$ O$_6$
Theoretical value (%): C 71.21; H 6.90; O 21.89
Actual measured value (%): C 71.27; H 6.88; O 21.85

Example 230

3,4-(dihydroxy)-5-(decyloxy)-2H-1-benzopyran-2-one (Compound 230)

In Example 5, 2.33 g (5.04×10$^{-3}$ mol) of 3-(benzoyloxy)-4-hydroxy-5-(decyloxy)-2H-1-benzopyran-2-one was used in place of 3-(benzoyloxy)-4,7-(dihydroxy)-2H-1-benzopyran-2-one, and 1.08 g (yield=60%) of the desired compound 230 was obtained.
$^1$H-NMR (DMSO-d$_6$,δ-TMS) 9.49 (bs, 1H), 8.99 (bs, 1H), 6.70~7.40 (m, 3H), 3.38 (d, H, J=7.0Hz), 1.21~1.70 (m, 16H), 0.86 (t, 3H, J=6.0Hz)
IR (KBr, cm$^{-1}$) 3200, 1680, 1650, 1610
Elemental analysis value: C$_{19}$ H$_{26}$ O$_5$
Theoretical value (%): C 68.24; H 7.84; O 23.92
Actual measured value (%): C 68.23; H 7.81; O 23.96

Example 231

3-hydroxy-4-(acetoxy)-5-(decyloxy)-2H-1-benzopyran-2-one (Compound 231)

In Example 8, 1.23 g (3.43×10$^{-3}$ mol) of 3,4-(dihydroxy)-5-(decyloxy)-2H-1-benzopyran-2-one was used in place of 3,4,7-trihydroxy-2H-1-benzopyran-2-one, acetyl chloride was used in place of benzoyl chloride, and 0.89 g (yield=61%) of the desired compound 231 was obtained.
$^1$H-NMR (DMSO-d$_6$,δ-TMS) 9.21 (bs, 1H), 6.70~7.40 (m,3H), 3.40 (d, 2H, J=7 . 0Hz), 1.81 (s, 3H), 1.21~1.70 (m, 16H), 0.82 (t, 3H, J=6.0Hz)
IR (KBr, cm$^{-1}$) 3200, 1680, 1650, 1610
Elemental analysis value: C$_{21}$ H$_{28}$ O$_6$
Theoretical value (%): C 67.00; H 7.50; O 25.50
Actual measured value (%): C 66.94; H 7.47; O 25.59

Example 232

3-(acetoxy)-4-(benzoyloxy)-5-(decyloxy)-2H-1-benzopyran-2-one (Compound 232)

In Example 8, 2.15 g (5.37×10$^{-3}$ mol) of 3-(acetoxy)-4-hydroxy-5-(decyloxy)-2H-1-benzopyran-2-one was used in place of 3,4,7-trihydroxy-2H-1-benzopyran-2-one, and 1.92 g (yield=71%) of the desired compound 232 was obtained.

$^1$H-NMR (DMSO-d$_6$, δ-TMS) 7.40~8.20 (m, 6H), 6.70~6.90 (m, 2H), 3.36 (m, 2H, J=7.0Hz), 1.79 (s,3H), 1.20~1.70 (m, 16H), 0.90 (t, 3H, J=6.0Hz)

IR (KBr, cm$^{-1}$) 1740, 1690, 1630, 1610, 1580

Elemental analysis value: C$_{28}$ H$_{32}$ O$_7$

Theoretical value (%): C 69.98; H 6.71; O 23.31

Actual measured value (%): C 69.94; H 6.78; O 23.28

Example 233

3-(isopropoxy)-4-hydroxy-5-(decyloxy)-2H-1-benzopyran-2-one (Compound 233)

In Example 5, 1.67 g (3.77×10$^{-3}$ mol) of 3-(isopropoxy)-4-(acetoxy)-5-(decyloxy)-2H-1-benzopyran-2-one was used in place of 3-(benzoyloxy)-4,7-(dihydroxy)-2H-1-benzopyran-2-one, and 1.10 g (yield=73%) of the desired compound 233 was obtained.

$^1$H-NMR (DMSO-d$_6$,δ-TMS) 9.92 (bs, 1H), 6.70~7.40 (m, 3H), 3.89 (m, 1H), 3.36 (d, H, J=7.0Hz), 1.21~1.70 (m, 16H), 1.12 (d, 6H, J=6.0Hz), 0.85 (t, 3H, J=6.0Hz)

IR (KBr, cm$^{-1}$) 200, 1680, 1650, 1610

Elemental analysis value: C$_{22}$ H$_{32}$ O$_5$

Theoretical value (%): C 70.18; H 8.57; O 21.25

Actual measured value (%): C 70.27; H 8.59; O 21.14

Example 234

3-hydroxy-4-(butoxy)-5-(decyloxy)-2H-1-benzopyran-2-one (Compound 234)

In Example 8, 1.37 g (3.82×10$^{-2}$ mol) of 3,4-(dihydroxy)-5-(decyloxy)-2H-1-benzopyran-2-one was used in place of 3,4,7-trihydroxy-2H-1-benzopyran-2-one, butyl bromide was used in place of benzoyl chloride, and 0.88 g (yield=57%) of the desired compound 234 was obtained.

$^1$H-NMR (DMSO-d$_6$, δ-TMS) 9.13 (bs, 1H), 6.70~7.40 (m, 3H), 3.48 (d, 2H, J=7.0Hz), 3.20 (t, 2H, J=6.0Hz), 1.00~1.70 (m, 20H), 0.96 (t, 3H, J=6.0Hz), 0.81 (t, 3H, J=6.0Hz)

IR (KBr, cm$^{-1}$) 3200, 1680, 1650, 1610

Elemental analysis value: C$_{23}$ H$_{34}$ O$_5$

Theoretical value (%): C 70.74; H 8.78; O 20.49

Actual measured value (%): C 70.63; H 8.85; O 20.52

Example 235

3-(acetoxy)-4-(isopropoxy)-5-(decyloxy)-2H-1-benzopyran-2-one (Compound 235)

In Example 8, 2.00 g (4.99×10$^{-3}$ mol) of 3-(acetoxy)-4-hydroxy-5-(decyloxy)-2H-1-benzopyran-2-one was used in place of 3,4,7-trihydroxy-2H-1-benzopyran-2-one, isopropyl bromide was used in place of benzoyl chloride, and 1.59 g (yield=72%) of the desired compound 235 was obtained.

$^1$H-NMR (DMSO-d$_6$,δ-TMS) 6.70~7.40 (m, 3H), 3.80 (m, 1H), 3.39 (d, 2H, J=7.0Hz), 1.81 (s, 3H), 1.21~1.70 (m, 16H), 1.11 (d, 6H, J=6.0Hz), 0.84 (t, 3H, J=6.0Hz)

IR (KBr, cm$^{-1}$) 1740, 1680, 1650, 1610

Elemental analysis value: C$_{24}$ H$_{34}$ O$_6$

Theoretical value (%): C 69.21; H 7.74; O 23.05

Actual measured value (%): C 69.35; H 7.80; O 22.85

Example 236

3-(methoxy)-4-(benzoyloxy)-5-(decyloxy)-2H-1-benzopyran-2-one (Compound 236)

In Example 8, 1.39 g (3.73×10$^{-3}$ mol) of 3-(methoxy)-4-hydroxy-5-(decyloxy)-2H-1-benzopyran-2-one was used in place of 3,4,7-trihydroxy-2H-1-benzopyran-2-one, and 1.24 g (yield=70%) of the desired compound 236 was obtained.

$^1$H-NMR (DMSO-d$_6$,δ-TMS) 7.40~8.20 (m, 6H), 6.70~6.90 (m, 2H), 3.68 (s, 3H), 3.35 (m, 2H, J=7.0Hz), 1.20~1.70 (m, 16H), 0.87 (t, 3H, J=6.0Hz)

IR (KBr, cm$^{-1}$) 1740, 1690, 1630, 1620, 1580

Elemental analysis value: C$_{27}$ H$_{32}$ O$_6$

Theoretical value (%): C 71.66; H 7.13; O 21.21

Actual measured value (%): C 71.65; H 7.15; O 21.20

Example 237

3-(geranyloxy)-4-hydroxy-5-(decyloxy)-2H-1-benzopyran-2-one (Compound 237)

In Example 5, 2.11 g (3.93×10$^{-3}$ mol) of 3-(geranyloxy)-4-(acetoxy)-5-(decyloxy)-2H-1-benzopyran-2-one was used in place of 3-(benzoyloxy)-4,7-(dihydroxy)-2H-1-benzopyran-2-one, and 1.07 g (yield=55%) of the desired compound 237 was obtained.

$^1$H-NMR (DMSO-d$_6$, δ-TMS) 9.79 (bs, 1H), 6.70~7.40 (m, 3H), 5.43 (bt, 1H, J=7.0Hz), 5.07 (bt, 1H, J=7.0Hz), 4.01 (d, 2H, J=7.0Hz), 3.35 (t, 2H, J=7.0Hz), 2.00~2.21 (m, 4H), 1.22~1.85 (m, 25H), 0.84 (t, 3H, J=6.0Hz)

IR (KBr, cm$^{-1}$) 3200, 1720, 1680, 1630, 1580

Elemental analysis value: C$_{29}$ H$_{42}$ O$_5$

Theoretical value (%): C 74.01; H 9.00; O 17.00

Actual measured value (%): C 74.12; H 8.90; O 16.98

Example 238

3-hydroxy-4-(geranyloxy)-5-(decyloxy)-2H-1-benzopyran-2-one (Compound 238)

In Example 8, 1.52 g (4.24×10$^{-3}$ mol) of 3,4-(dihydroxy)-5-(decyloxy)-2 H-1-benzopyran-2-one was used in place of 3,4,7-trihydroxy- 2H-1-benzopyran-2-one, geranyl bromide was used in place of benzoyl chloride, and 1.30 g (yield=62%) of the desired compound 238 was obtained.

$^1$H-NMR (DMSO-d$_6$,δ-TMS) 9.04 (bs, 1H), 6.70~7.60 (m, 3H), 5.42 (bt, 1H, J=7.0Hz), 5.02 (bt, 1H, J=7.0Hz), 4.01 (d, 2H, J=7.0Hz), 3.32 (t, 2H, J=7.0Hz), 2.00~2.20 (m, 4H), 1.24~1.85 (m, 25H), 0.83 (t, 3H, J=6.0Hz)

IR (KBr, cm$^{-1}$) 3200, 1700, 1670, 1620, 1580

Elemental analysis value: C$_{22}$ H$_{32}$ O$_5$

Theoretical value (%): C 74.01; H 9.00; O 17.00

Actual measured value (%): C 74.10; H 8.93; O 16.97

Example 239

3-(geranyloxy)-4-(acetoxy)-5-(decyloxy)-2H-1-benzopyran-2-one (Compound 239)

In Example 8, 1.50 g (3.74×10$^{-3}$ mol) of 3-hydroxy-4-(acetoxy)-5-(decyloxy)-2H-1-benzopyran-2-one was used in place of 3,4,7-trihydroxy-2H-1-benzopyran- 2-one, geranyl bromide was used in place of benzoyl chloride, and 1.13 g (yield=56%) of the desired compound 239 was obtained.

$^1$H-NMR (DMSO-d$_6$, δ-TMS) 6.70~7.60 (m,3H), 5.44 (bt, 1H, J=7.0Hz), 5.01 (bt, 1H, J=7.0Hz), 4.02 (d, 2H, J=7.0Hz), 3.35 (t, 2H, J=7.0Hz), 2.00~2.20 (m, 4H), 1.86 (s,3H), 1.24~1.85 (m, 25H), 0.81 (t, H, J=6.0Hz)

IR (KBr, cm$^{-1}$) 1720, 1670, 1630, 1580, 1530
Elemental analysis value: C$_{31}$ H$_{44}$ O$_6$
Theoretical value (%): C 72.62; H 8.65; O 18.73
Actual measured value (%): C 72.70; H 8.61; O 18.69

Example 240

3-(benzoyloxy)-4-(geranyloxy)-5-(decyloxy)-2H-1-benzopyran-2-one (Compound 240)

In Example 8, 1.55 g (3.35×10$^{-3}$ mol) of 3-(benzoyloxy)-4-hydroxy-5-(decyloxy)-2H-1-benzopyran-2-one was used in place of 3,4,7-trihydroxy-2H-1-benzopyran-2-one, geranyl bromide was used in place of benzoyl chloride, and 1.22 g (yield=61%) of the desired compound 240 was obtained.

$^1$H-NMR (DMSO-d$_6$, δ-TMS) 7.40~8.20 (m, 6H), 6.70~7.40 (m, 2H), 5.44 (bt, 1H, J=7.0Hz), 5.02 (bt, 1H, J=7.0Hz), 4.01 (d, 2H, J=7.0Hz), 3.35 (t, 2H, J=7.0Hz), 2.00~2.20 (m, 4H), 1.24~1.85 (m, 25H), 0.82 (t, 3H, J=6.0Hz)

IR (KBr, cm$^{-1}$) 1720, 1670, 1650, 1630, 1580, 1530
Elemental analysis value: C$_{36}$ H$_{46}$ O$_6$
Theoretical value (%): C 75.23; H 8.07; O 16.70
Actual measured value (%): C 75.22; H 8.01; O 16.77

Example 241

3-(geranyloxy)-4-(methoxy)-5-(decyloxy)-2H-1-benzopyran-2-one (Compound 241)

In Example 8, 1.51 g (4.05×10$^{-3}$ mol) of 3-hydroxy-4-(methoxy)-5-(decyloxy)-2H-1-benzopyran-2-one was used in place of 3,4,7-trihydroxy-2H-1-benzopyran-2-one, geranyl bromide was used in place of benzoyl chloride, and 1.13 g (yield=55%) of the desired compound 241 was obtained.

$^1$H-NMR (DMSO-d$_6$,δ-TMS) 6.70~7.60 (m, 3H), 5.42 (bt, 1H, J=7.0Hz), 5.01 (bt, 1H, J=7.0Hz), 4.02 (d, 2H, J=7.0Hz), 3.69 (s, 3H), 3.32 (t, 2H, J=7.0Hz), 2.00~2.20 (m, 4H), 1.24~1.85 (m, 25H), 0.83 (t, 3H, J=6.0Hz)

IR (KBr, cm$^{-1}$) 1720, 1670, 1630, 1580, 1530
Elemental analysis value: C$_{30}$ H$_{44}$ O$_5$
Theoretical value (%): C 74.34; H 9.15 O 16.51
Actual measured value (%): C 74.26; H 9.18; O 16.53

Example 242

3-(isopropoxy)-4-(geranyloxy)-5-(decyloxy)-2H-1-benzopyran-2-one (Compound 242)

In Example 8, 1.57 g (3.92×10$^{-3}$ mol) of 3-(isopropoxy)-4-hydroxy-5-(decyloxy)-2H-1-benzopyran-2-one was used in place of 3,4,7-trihydroxy-2H-1-benzopyran-2-one, geranyl bromide was used in place of benzoyl chloride, and 1.33g (yield=63%) of the desired compound 242 was obtained.

$^1$H-NMR (DMSO-d6,δ-TMS) 6.70~7.40 (m, 3H), 5.44 (bt, 1H, J=7.0Hz), 5.02 (bt, 1H, J=7.0Hz), 4.02 (d, 2H, J=7.0Hz), 3.50 (m, 1H), 3.32 (t, 2H, J=7.0Hz), 2.00~2.20 (m, 4H), 1.24~1.85 (m, 25H), 1.12 (d, 6H, J=6.0Hz), 0.81 (t, 3H, J=6.0Hz)

IR (KBr, cm$^{-1}$) 1720, 1670, 1620, 1550, 1520

Elemental analysis value: C$_{32}$ H$_{48}$ O$_5$
Theoretical value (%): C 74.96; H 9.44; O 15.60
Actual measured value (%): C 74.96; H 9.39; O 15.65

Example 243

3,4-(digeranyloxy)-5-(decyloxy)-2H-1-benzopyran-2-one (Compound 243)

In Example 8, 1.50 g (4.18×10$^{-3}$ mol) of 3,4-(dihydroxy)-5-(decyloxy)-2H-t-benzopyran-2-one was used in place of 3,4,7-trihydroxy-2H-1-benzopyran-2-one, potassium carbonate was used in place of sodium bicarbonate, geranyl bromide was used in place of benzoyl chloride, and 1.40 g (yield=53%) of the desired compound 243 was obtained.

$^1$H-NMR (DMSO-d$_6$, δ-TMS) 6.70~7.50 (m, 3H), 5.00~5.50 (m, 4H), 4.03 (d, 2H, J=7.0Hz), 4.01 (d, 2H, J=7.0Hz), 3.32 (t, 2H, J=7.0Hz), 2.00~2.20 (m, 8H), 1.24~1.85 (m, 34H), 0.82 (t, 3H, J=6.0Hz)

IR (KBr, cm$^{-1}$) 1700, 1670, 1620, 1550, 1520
Elemental analysis value: C$_{39}$ H$_{58}$ O$_5$
Theoretical value (%): C 77.18; H 9.63; O 13.18
Actual measured value (%): C 77.22; H 9.52; O 13.26

Example 244

3-(benzoyloxy)-4-hydroxy-5-(geranyloxy)-2H-1-benzopyran-2-one (Compound 244)

In Example 4, 4.50 g (8.32×10$^{-3}$ mol) of methyl-β-oxo-2'-(phenylmethoxy)-6'-(geranyloxy)-2-(benzoyloxy)benzene propanate was used in place of methyl-β-oxo-2',4'-bis(phenylmethoxy)-2-(benzoyloxy)benzenepropanate, and 2.50 g (yield=69%) of the desired compound 244 was obtained.

$^1$H-NMR (DMSO-d$_6$, δ-TMS) 9.34 (bs, 1H), 7.40~8.20 (m, 6H), 6.70~6.90 (m, 2H), 5.45 (bt, 1H, J=7.0Hz), 5.02 (bt, 1H, J=7.0Hz), 4.01 (bt, 2H, J=7.0 Hz), 2.00~2.20 (m, 4H), 1.55~1.85 (m, 9H)

IR (KBr, cm$^{-1}$) 3350, 1720, 1680, 1630, 1580, 1520
Elemental analysis value: C$_{26}$ H$_{26}$ O$_6$
Theoretical value (%): C 71.87; H 6.03; O 22.10
Actual measured value (%): C 71.88; H 6.10; O 22.02

Example 245

3,4-(dihydroxy)-5-(geranyloxy)-2H-1-benzopyran-2-one (Compound 245)

In Example 5, 5.00 g (1.15×10$^{-2}$ mol) of 3-(benzoyloxy)-4-hydroxy-5-(geranyloxy)-2H-1-benzopyran-2-one was used in place of 3-(benzoyloxy)-4,7-(dihydroxy)-2H-1-benzopyran-2-one, and 2.32 g (yield=61%) of the desired compound 245 was obtained.

$^1$H-NMR (DMSO-d$_6$, δ-TMS) 9.02 (bs, 2H), 9.00 (bs, 1H), 6.70~7.40 (m, 3H), 5.43 (bt, H, J=7.0Hz), 5.03 (bt, 1H, J=7.0Hz), 4.01 (d, 2H, J=7.0Hz), 2.00~2.21 (m, 4H), 1.55~1.85 (m, 9H)

IR (KBr, cm$^{-1}$) 3550, 3200, 1720, 1680, 1630, 1580
Elemental analysis value: C$_{19}$ H$_{22}$ O$_5$
Theoretical value (%): C 69.07; H 6.71; O 24.22
Actual measured value (%): C 69.15; H 6.73; O 24.12

Example 246

3-hydroxy-4-(acetoxy)-5-(geranyloxy)-2H-1-benzopyran-2-one (Compound 246)

In Example 8, 1.52 g (4.60×10$^{-3}$ mol) of 3,4-(dihydroxy)-5-(geranyloxy)-2H-1-benzopyran-2-one was used in place of 3,4,7-trihydroxy-2H-1-benzopyran- 2-one, acetyl chloride was used in place of benzoyl chloride, and 0.94 g (yield=55%) of the desired compound 246 was obtained.

$^1$H-NMR (DMSO-d6,δ-TMS) 8.99 (bs, 1H), 6.70~7.40 (m,3H), 5.46 (bt, 1H, J=7.0Hz), 5.01 (bt, 1H, J=7.0Hz), 4.04 (d, 2H, J=7.0Hz), 2.00~2.21 (m, 4H), 1.86 (s,3H), 1.55~1.85 (m, 9H)

IR (KBr, cm$^{-1}$) 3550, 3200, 1720, 1680, 1630, 1580
Elemental analysis value: $C_{21}H_{24}O_6$
Theoretical value (%): C 67.73; H 6.50; O 25.78
Actual measured value (%): C 67.66; H 6.59; O 25.75

Example 247

3-(benzoyloxy)-4-(acetoxy)-5-(geranyloxy)-2H-1-benzopyran-2-one (Compound 247)

In Example 8, 1.50 g ($3.45\times10^{-3}$ mol) of 3-(benzoyloxy)-4-hydroxy-5-(geranyloxy)-2H-1-benzopyran-2-one was used in place of 3,4,7-trihydroxy-2H-1-benzopyran-2-one, acetyl chloride was used in place of benzoyl chloride, and 0.90 g (yield=55%) of the desired compound 247 was obtained.

$^1$H-NMR (DMSO-d$_6$, δ-TMS) 7.40~8.20 (m, 6H), 6.70~6.90 (m, 2H), 5.46 (bt, 1H, J=7.0Hz), 5.03 (bt, 1H, J=7.0Hz), 4.04 (d, 2H, J=7.0Hz), 2.00~2.21 (m, 4H), 1.73 (s, 3H), 1.55~1.85 (m, 9H)

IR (KBr, cm$^{-1}$) 1720, 1680, 1630, 1580, 1520
Elemental analysis value: $C_{28}H_{28}O_7$
Theoretical value (%): C 70.57; H 5.92; O 23.50
Actual measured value (%): C 70.51; H 6.10; O 23.39

Example 248

3-(methoxy)-4-hydroxy-5-(geranyloxy)-2H-1-benzopyran-2-one (Compound 248)

In Example 5, 1.60 g ($4.14\times10^{-3}$ mol) of 3-(methoxy)-4-(acetoxy)-5-(geranyloxy)-2H-1-benzopyran-2-one was used in place of 3-(benzoyloxy)-4,7-(dihydroxy)-2H-1-benzopyran-2-one, and 0.83 g (yield=58%) of the desired compound 248 was obtained.

$^1$H-NMR (DMSO-d$_6$, δ-TMS) 9.31 (bs, 1H), 6.70~7.40 (m, 3H), 5.46 {bt, 1H, J=7.0Hz), 5.03 (bt, 1H, J=7.0Hz), 4.00 (d, 2H, J=7.0Hz), 3.7 6 (s, 3H), 2.00~2.21 (m, 4H), 1.55~1.85 (m, 9H)

IR (KBr, cm$^{-1}$) 3200, 1720, 1680, 1630, 1580
Elemental analysis value: $C_{20}H_{24}O_5$
Theoretical value (%): C 69.75; H 7.02; O 23.23
Actual measured value (%): C 69.63; H 7.06; O 23.31

Example 249

3-hydroxy-4-(isopropoxy)-5-(geranyloxy)-2H-1-benzopyran-2-one (Compound 24 9)

In Example 8, 1.51 g ($4.57\times10^{-3}$ mol) of 3,4-(dihydroxy)-5-(geranyloxy)-2H-1-benzopyran-2-one was used in place of 3,4,7-trihydroxy-2H-1-benzopyran-2-one, isopropyl bromide was used in place of benzoyl chloride, and 0.97 g (yield=57%) of the desired compound 249 was obtained.

$^1$H-NMR (DMSO-d$_6$, δ-TMS) 9.12 (bs, 1H), 6.70~7.60 (m, 3H), 5.43 (bt, 1H, J=7.0Hz), 5.07 (bt, 1H, J=7.0Hz), 4.02 (d, 2H, J=7.0Hz), 3.45 (m, 1H), 2.00~2.21 (m, 4H), 1.55~1.85 (m, 9H), 1.12 (d, 6H, J=6.0Hz)

IR (KBr, cm$^{-1}$) 3200, 1720, 1680, 1630, 1580
Elemental analysis value: $C_{22}H_{28}O_5$
Theoretical value (%): C 70.94; H 7.58; O 21.48
Actual measured value (%): C 71.03; H 7.51; O 21.46

Example 250

3-(decyloxy)-4-(isopropoxy)-5-(geranyloxy)-2H-1-benzopyran-2-one (Compound 250)

In Example 8, 1.50 g ($4.03\times10^{-3}$ mol) of 3-hydroxy-4-(isopropoxy)-5-(geranyloxy)-2H-1-benzopyran-2-one was used in place of 3,4,7-trihydroxy-2H-1-benzopyran-2-one, decyl bromide was used in place of benzoyl chloride, and 1.30 g (yield=60%) of the desired compound 250 was obtained.

$^1$H-NMR (DMSO-d6,δ-TMS) 6.70~7.40 (m, 3H), 5.43 (bt, 1H, J=7.0Hz), 5.02 (bt, 1H, J=7.0Hz), 4.01 (d, 2H, J=7.0Hz), 3.47 (m, 1H), 3.33 (t, 2H, J=7.0Hz), 2.00~2.21 (m, 4H), 1.22~1.85 (m, 25H), 1.12 (d, 6H, J=6.0Hz), 0.81 (t, 3H, J=6.0Hz)

IR (KBr, cm$^{-1}$) 1720, 1680, 1630, 1580, 1530
Elemental analysis value: $C_{32}H_{48}O_5$
Theoretical value (%): C 74.96; H 9.44; O 15.60
Actual measured value (%): C 74.91; H 9.41; O 15.68

Example 251

3-(benzoyloxy)-4-(isopropoxy)-5-(geranyloxy)-2H-1-benzopyran-2-one (Compound 251)

In Example 8, 1.53 g ($3.52\times10^{-3}$ mol) of 3-(benzoyloxy)-4-hydroxy-5-(geranyloxy)-2H-1-benzopyran-2-one was used in place of 3,4,7-trihydroxy-2H-1-benzopyran-2-one, isopropyl bromide was used in place of benzoyl chloride, and 0.90 g (yield=57%) of the desired compound 251 was obtained.

$^1$H-NMR (DMSO-d$_6$, δ-TMS) 7.40~8.20 (m, 6H), 6.70~6.90 (m, 2H), 5.43 (bt, 1H, J=7.0Hz), 5.04 (bt, 1H, J=7.0Hz), 4.01 (bt, 2H, J=7.0Hz), 3.46 (m, 1H), 2.00~2.20 (m, 4H), 1.55~1.85 (m, 9H), 1.12 (d, 6H, J=6.0Hz)

IR (KBr, cm$^{-1}$) 1720, 1680, 1630, 1580, 1520
Elemental analysis value: $C_{29}H_{32}O_6$
Theoretical value (%): C 73.09; H 6.77; O 20.14
Actual measured value (%): C 73.18; H 6.79; O 20.03

Example 252

3-(methoxy)-4-(acetoxy)-5-(geranyloxy)-2H-1-benzopyran-2-one (Compound 252)

In Example 8, 1.50 g ($4.03\times10^{-3}$ mol) of 3-hydroxy-4-(acetoxy)-5-(geranyloxy)-2H-1-benzopyran-2-one was used in place of 3,4,7-trihydroxy-2H-1-benzopyran-2-one, methyl iodide was used in place of benzoyl chloride, and 0.92 g (yield=59%) of the desired compound 252 was obtained.

$^1$H-NMR (DMSO-d6,δ-TMS) 6.70~7.40 (m, 3H), 5.43 (bt, 1H, J=7.0Hz), 5 . 03 (bt, 1H, J=7.0Hz), 4.01 (d, 2H, J=7.0Hz), 3.65 (s,3H), 2.00~2.21 (m, 4H), 1.87 (s, 3H), 1.55~1.85 (m, 9H)

IR (KBr, cm$^{-1}$) 1720, 1680, 1630, 1580, 1520
Elemental analysis value: $C_{22}H_{26}O_6$
Theoretical value (%): C 68.38; H 6.78; O 24.84
Actual measured value (%): C 68.27; H 6.74; O 24.99

Example 253

3,5-(digeranyloxy)-4-hydroxy-2H-1-benzopyran-2-one (Compound 253)

In Example 5, 2.00 g ($3.93\times10^{-3}$ mol) of 3,5-(digeranyloxy)-4-(acetoxy)-2H-1-benzopyran-2-one was used in place of 3-(benzoyloxy)-4,7-(dihydroxy)-2H-1-benzopyran-2-one, and 0.95 g (yield=52%) of the desired compound 253 was obtained.

$^1$H-NMR (DMSO-d$_6$, δ-TMS) 9.13 (bs, 1H), 6.70~7.40 (m, 3H), 5.00~5.50 (m, 4H), 4.03 (d, 2H, J=7.0Hz), 4.01 (d, 2H, J=7.0Hz), 2.00~2.21 (m, 8H), 1.55~1.85 (m, 18H)

IR (KBr, cm$^{-1}$) 3200, 1720, 1680, 1630, 1580
Elemental analysis value: C$_{29}$H$_{38}$O$_5$
Theoretical value C 74.65; H 8.21; O 17.14
Actual measured value (%): C 74.67; H 8.24; O 17.09

Example 254

3-hydroxy-4,5-(digeranyloxy)-2H-1-benzopyran-2-one (Compound 254)

In Example 8, 1.50 g (4.54×10$^{-3}$ mol) of 3,4-(dihydroxy)-5-(geranyloxy)-2H-1-benzopyran-2-one was used in place of 3,4,7-trihydroxy-2H-1-benzopyran-2-one, geranyl bromide was used in place of benzoyl chloride, and 1.14 g (yield=54%) of the desired compound 254 was obtained.

$^1$H-NMR (DMSO-d$_6$, δ-TMS) 9.04 (bs, 1H), 6.70~7.40 (m, 3H), 5.00~5.50 (m, 4H), 4.01 (d, 2 H, J=7.0Hz), 4.00 (d, 2H, J=7.0Hz), 2.00~2.20 (m,8H), 1.55~1.85 (m, 18H)

IR (KBr, cm$^{-1}$) 3550, 3200, 1700, 1670, 1620, 1580
Elemental analysis value: C$_{29}$H$_{38}$O$_5$
Theoretical value (%): C 74.65; H 8.21; O 17.14
Actual measured value (%): C 74.56; H 8.25; O 17.19

Example 255

3,5-(digeranyloxy)-4-(acetoxy)-2H-1-benzopyran-2-one (Compound 255)

In Example 8, 1.53 g (4.11×10$^{-3}$ mot) of 3-hydroxy-4-(acetoxy)-5-(geranyloxy)-2H-1-benzopyran-2-one was used in place of 3,4,7-trihydroxy-2H-1-benzopyran-2-one, geranyl bromide was used in place of benzoyl chloride, and 1.23 g (yield=60%) of the desired compound 255 was obtained.

$^1$H-NMR (DMSO-d6,δ-TMS) 6.70~7.40 (m, 3H), 5.00~5.50 (m, 4H), 4.04 (d, 2H, J=7.0Hz), 4.01 (d, 2H, J=7.0Hz), 2.00~2.20 (m, 8H), 1.83 (s, 3H), 1.55~1.85 (m, 18H)

IR (KBr, cm$^{-1}$) 1720, 1670, 1630, 1580, 1530
Elemental analysis value: C$_{31}$H$_{40}$O$_6$
Theoretical value (%): C 73.20; H 7.93; O 18.87
Actual measured value (%): C 73.21; H 8.04; O 18.75

Example 256

3-(benzoyloxy)-4,5-(digeranyloxy)-2H-1-benzopyran-2-one (Compound 256)

In Example 8, 1.49 g (3.43×10$^{-3}$ mol) of 3-(benzoyloxy)-4-hydroxy-5-(geranyloxy)-2H-1-benzopyran-2-one was used in place of 3,4,7-trihydroxy-2H-1-benzopyran-2-one, geranyl bromide was used in place of benzoyl chloride, and 1.10 g (yield=56%) of the desired compound 256 was obtained.

$^1$H-NMR (DMSO-d$_6$, δ-TMS) 7.40~8.20 (m, 6H), 6.70~6.90 (m, 2H), 5.00~5.50 (m, 4H), 4.01 (d, 2H, J=7.0Hz), 4.00 (d, 2H, J=7.0Hz), 2.00~2.20 (m, 8H), 1.55~1.85 (m, 18H)

IR (KBr, cm$^{-1}$) 1720, 1670, 1650, 1630, 1580, 1530
Elemental analysis value: C$_{36}$H$_{42}$O$_6$
Theoretical value (%): C 75.76; H 7.42; O 16.82
Actual measured value (%): C 75.73; H 7.49; O 16.78

Example 257

3,5-(digeranyloxy)-4-(methoxy)-2H-1-benzopyran-2-one (Compound 257)

In Example 8, 1.50 g (3.21×10$^{-3}$ mol) of 3,5-(digeranyloxy)-4-hydroxy-2H-1-benzopyran-2-one was used in place of 3,4,7-trihydroxy-2H-1-benzopyran-2-one, methyl iodide was used in place of benzoyl chloride, and 0.94 g (yield=61%) of the desired compound 257 was obtained.

$^1$H-NMR (DMSO-d$_6$, δ-TMS) 6.70~7.40 (m, 3H), 5.03 (d, 2H, J=7.0Hz), 4.02 (d, 2H, J=7.0Hz), 3.66 (s, 3H), 2.00~2.20 (m, 8H), 1.55~1.85 (m, 18H)

IR (KBr, cm$^{-1}$) 1720, 1670, 1630, 1580, 1530
Elemental analysis value: C$_{30}$H$_{40}$O$_5$
Theoretical value (%): C 74.97; H 8.39; O 16.65
Actual measured value (%): C 75.04; H 8.32; O 16.64

Example 258

3-(isopropoxy)-4,5-(digeranyloxy)-2H-1-benzopyran-2-one (Compound 258)

In Example 8, 1.50 g (3.21×10$^{-3}$ mol) of 3-hydroxy-4,5-(digeranyloxy)-2H-1-benzopyran-2-one was used in place of 3,4,7-trihydroxy-2H-1-benzopyran-2-one, isopropyl bromide was used in place of benzoyl chloride, and 0.85 g (yield=52%) of the desired compound 258 was obtained.

$^1$H-NMR (DMSO-d$_6$, δ-TMS) 6.70~7.40 (m, 3H), 5.00~5.50 (m, 4H), 4.02 (d, 2H, J=7.0Hz), 4.01 (d, 2H, J=7.0Hz), 3.50 (m, 1H), 3.32 (t, 2H, J=7.0Hz), 2.00~2.20 (m, 8H), 1.55~1.85 (m, 18H), i. 12 (d, 6H, J=6.0Hz)

IR (KBr, cm$^{-1}$) 1700, 1670, 1620, 1550, 1520
Elemental analysis value: C$_{32}$H$_{44}$O$_5$
Theoretical value (%): C 75.55; H 8.72; O 15.73
Actual measured value (%): C 75.48; H 8.80; O 15.72

Example 259

1-[2',5'-bis(phenylmethoxy)phenyl]ethanone (Compound 259)

15 g (9.86×10$^{-2}$ mol) of 2',5'-dihydroxyacetophenone was dissolved in 150 ml of DMF, into which 32.71 g (2.37×10$^1$ mol) of potassium carbonate and 29.96 g (2.37×10$^{-1}$ mol) of benzylchloride were added, and the mixture was refluxed for three hours. Following this, water was added and extraction was carried out with benzene. After removal of the solvent under reduced pressure, recrystallization of the residue was carried out using ethyl acetate/n-hexane, and 28.11 g (yield=87.6%) of the desired compound 259 was obtained.

$^1$H-NMR (CDCl$_3$, δ-TMS) 7.30~7.60 (m, 13H), 5.10 (s,2H), 5.01 (s,2H), 2.58 (s, 3H)

Example 260

Methyl-β-oxo-2',5'-bis(phenylmethoxy)benzenepropanate (Compound 260)

4.12 g (1.03×10$^{-1}$ mol) of 60% sodium hydride was suspended in 77.35 g (8.59×10$^{-1}$ mol) of dimethyl carbonate, into which 28.11 g (8.59×10~2 mol) of 1-[2',5'-bis(phenylmethoxy)phenyl]ethanone was added and the mixture was heated at 70~75° C for one hour. Following this, water and 6N hydrochloric acid were added, the pH was adjusted to 8, and extraction was carried out with methylene chloride. After removal of the solvent under reduced pressure, the residue was purified by means of silica gel column chromatography, and 30.34 g (yield=90.5%) of the desired compound 260 was obtained.

¹H-NMR (CDCl₃, δ-TMS) 6.80~7.80 (m, 13H), 5.10 (s,2H), 5.03 (s,2H), 3.95 (s, 2H), 3.55 (s, 3H)

Example 261

Methyl-β-oxo-2',5'-bis(phenylmethoxy)-2-(benzoyloxy) benzenepropanate (Compound 261)

3.73 g (9.33×10⁻² mol) of 60% sodium hydride was suspended in 40 ml of benzene, and a 100 ml benzene solution containing 30.34 g (7.77×10⁻² mol) of methyl-β-oxo-2',4'-bis(phenylmethoxy)benzenepropanate was added drop by drop at room temperature. After agitating for one hour at room temperature, the mixture was cooled in an ice bath, a 100 ml benzene solution containing 18.82 g (7.77×10⁻² mol) of dibenzoyl peroxide was added drop by drop, and the resulting mixture was agitated at room temperature for three hours. Water was then added, and after the benzene layer separated, the water layer was extracted with methylene chloride, after which, the aforementioned benzene layer and the organic layer were removed under reduced pressure. The residue was purified by means of silica gel column chromatography, and 36.81 g (yield=92.8%) of the desired compound 261 was obtained.

¹H-NMR (CDCl₃, δ-TMS)
6.80~7.80 (m, 13H), 5.09 (s, 2H), 5.03 (s, 2H), 3.88 (s, 1H), 3.60 (s, 3H)

Example 262

3-(benzoyloxy)-4, 6-(dihydroxy)-2H-1-benzopyran-2-one (Compound 262)

300 ml of ethanol was added to 36.81 g (7.21×10⁻² mol) of methyl-β-oxo-2',5'-bis(phenylmethoxy)-2-(benzoyloxy)benzenepropanate, to which 3.7 g of 10% palladium-carbon was further added. After the mixture was refluxed under hydrogen atmosphere for 4 hours, the catalyst was removed by filtration, and the filtrate was concentrated under reduced pressure. 150 ml of 35% hydrochloric acid and 150 ml of methanol were then added to the residue, and the mixture was refluxed for 30 minutes. Following this, the methanol was removed under reduced pressure, and the precipitate crystals were collected, washed and dried under reduced pressure to produce 18.00 g (yield=83.7%) of the desired compound 262.

¹H-NMR (DMSO-d₆, δ-TMS)
9.88 (bs, 2H), 7.05~8.15 (m, 8H)
IR (KBr, cm⁻¹) 3300, 1730, 1690, 1630, 1580
Melting Point: 258°~261° C.
Elemental analysis value: $C_{16}H_{10}O_6$
Theoretical value (%): C 64.43; H 3.38; O 32.19
Actual measured value (%): C 64.43; H 3.32; O 32.25

Example 263

3,4,6-trihydroxy-2H-1-benzopyran-2-one (Compound 263)

Under argon atmosphere, 160 ml of dehydrated methanol was added to 7.11 g (2.38×10⁻² mol) of 3-(benzoyloxy)-4,6-(dihydroxy)-2H-1-benzopyran-2-one, and the mixture was agitated and cooled in an ice bath. 43 ml of a dehydrated methanol solution containing 3.86 g (7.15×10⁻² mol) of sodium methoxide was then added drop by drop, and the mixture was agitated for 2 hours at room temperature. The mixture was then cooled in an ice bath and 24.39 g of Amberlyst 15 was added, following which agitation of the mixture was performed again for 2 hours at room temperature. After the Amberlyst 15 was removed by filtration, the filtrate was concentrated under reduced pressure, to produce 4.46 g of a crude product. This was then recrystallized using tetrahydrofuran/n-hexane to produce 3.86 g (yield=83.4%) of the desired compound 263.

¹H-NMR (DMSO-d₆, δ-TMS)
11.03 (bs,1H), 9.64 (bs, 1H), 9.11 (bs, 1H), 6.80~7.20 (m, 3H)
IR (KBr, cm⁻¹)
3400, 3300, 1670, 1640, 1580
Melting Point: 260°~262° C.
Elemental analysis value: $C_9H_6O_5$
Theoretical value (%): C 51.44; H 2.88; O 45.68
Actual measured value (%): C 51.48; H 2.89; O 45.63

Example 264

3-(acetoxy)-4,6-(dihydroxy)-2H-1-benzopyran-2-one (Compound 264)

In Example 4, 6.00 g (1.38×10⁻² mol) of methyl-β-oxo-2',5'-bis(phenylmethoxy)-2-(acetoxy)benzenepropanate was used in place of methyl-β-oxo-2',4'-bis(phenylmethoxy)-2-(benzoyloxy)benzenepropanate, and 2.05 g (yield=62.9%) of the desired compound 264 was obtained.

¹H-NMR (DMSO-d₆, δ-TMS) 9.89 (bs, 2H), 6.80~7.20 (m, 3H), 1.66 (s,3H)
IR (KBr, cm⁻¹) 3550, 3200, 1720, 1670, 1630
Elemental analysis value: $C_{11}H_8O_6$
Theoretical value (%): C 55.94; H 3.41; O 40.65
Actual measured value (%): C 55.96; H 3.40; O 40.64

Example 265

3-(methoxy)-4,6-(dihydroxy)-2H-1-benzopyran-2-one (Compound 265)

In Example 5, 1.50 g (6.00×10⁻³ mol) of 3-(methoxy)-4-(acetoxy)-6-hydroxy-2H-1-benzopyran-2-one was used in place of 3-(benzoyloxy)-4,7-(dihydroxy)-2H-1-benzopyran-2-one, and 0.74 g (yield=59.9%) of the desired compound 265 was obtained.

¹H-NMR (DMSO-d₆, δ-TMS) 9.87 (bs, 2H), 6.80~7.20 (m, 3H), 3.55 (s, 3H)
IR(KBr, cm⁻¹) 3400, 3200, 1670, 1630
Elemental analysis value: $C_{10}H_8O_5$
Theoretical value (%): C 57.69; H 3.87; O 38.43
Actual measured value (%): C 57.72; H 3.87; O 38.41

Example 266

3-(decyloxy)-4, 6-(dihydroxy)-2H-1-benzopyran-2-one (Compound 266)

In Example 5, 1.50 g (3.98×10⁻³ mol) of 3-(decyloxy)-4-(acetoxy)-6-hydroxy-2H-1-benzopyran-2-one was used in place of 3-(benzoyloxy)-4,7-(dihydroxy)-2H-1-benzopyran-2-one, and 0.84 g (yield=63.1%) of the desired compound 266 was obtained.

¹H-NMR (DMSO-d₆, δ-TMS) 9.85 (bs,2H), 6.80~7.20 (m,3H), 3.36 (t, 2H, J=7.0Hz), 1.24~1.70 (m, 16H), 0.82 (t, 3H, J=6.0Hz)
IR (KBr, cm⁻¹) 3400, 3200, 1680, 1620
Elemental analysis value: $C_{19}H_{25}O_5$
Theoretical value (%): C 68.24; H 7.84; O 23.92
Actual measured value (%): C 68.23; H 7.81; O 23.96

Example 267

3,6-(dihydroxy)-4-(methoxy-2H-1-benzopyran-2-one (Compound 267)

In Example 8, 2.50 g 1.29×10$^{-2}$ mol) of 3,4,6-(trihydroxy)-2H-1-benzopyran-2-one was used in place of 3,4,7-trihydroxy-2H-1-benzopyran-2-one, methyl iodide was used in place of benzoyl chloride, and 1.49 g (yield=55.7%) of the desired compound 267 was obtained.

$^1$-NMR (DMSO-d$_6$, δ-TMS) 10.26 (bs,1H), 9.56 (bs,1H), 6.80~7.20 (m, 3H), 3.51 (s, 3H)
IR (KBr, cm$^{-1}$) 3400, 3200, 1670, 1630
Elemental analysis value: C$_{10}$ H$_8$ O$_5$
Theoretical value (%): C 57.69; H 3.87; O 38.43
Actual measured value (%): C 57.75; H 3.81; O 38.44

Example 268

3,6-(dihydroxy)-4-(decyloxy)-2H-1-benzopyran-2-one (Compound 268

In Example 8, 2.50 g (1.29×10$^{-2}$ mol) of 3,4,6-(trihydroxy)-2H-1-benzopyran-2-one was used in place of 3,4,7-trihydroxy-2H-1-benzopyran-2-one, decyl bromide was used in place of benzoyl chloride, and 2.32 g (yield=53.9%) of the desired compound 268 was obtained.

$^1$H-NMR (DMSO-d$_6$, δ-TMS) 10.33 (bs, 1H), 9.77 (bs, 1H), 6.80~7.20 (m, 3H), 3.38 (t, 2H, J=7.0Hz), 1.24~1.70 (m, 16H), 0.85 (t, 3H, J=6.0Hz)
IR (KBr, cm$^{-1}$) 3550, 3200, 1670, 1620
Elemental analysis value: C$_{19}$ H$_{25}$ O$_5$
Theoretical value (%): C 68.24; H 7.84; O 23.92
Actual measured value (%): C 68.20; H 7.89; O 23.91

Example 269

4,6-(dihydroxy)-3-(geranyloxy)-2H-1-benzopyran-2-one (Compound 269)

In Example 5, 1.40 g (3.51×10$^{-3}$ mol) of 4,6-(diacetoxy)-3-(geranyloxy)-2H-1-benzopyran-2-one was used in place of 3-(benzoyloxy)-4, 7-(dihydroxy)-2H-1-benzopyran-2-one, and 0.94 g (yield=81.0%) of the desired compound 269 was obtained.

$^1$H-NMR (DMSO-d$_6$,δ-TMS) 10.22 (bs,1H), 9.65 (bs, 1H), 6.80~7.20 (m, 3H), 5.44 (bt, 1H, J=7.0Hz), 5.10 (bt, 1H, J=7.0Hz), 4.02 (d, 2H, J=7.0Hz), 1.95~2.20 (m, 4H), 1.55~1.85 (m, 9H)
IR(KBr, cm$^{-1}$) 550, 3300, 1670, 1620
Elemental analysis value: C$_{19}$ H$_{22}$ O$_5$
Theoretical value (%): C 69.07; H 6.71; O 24.22
Actual measured value (%): C 69.10; H 6.71; O 24.19

Example 270

3-(methoxy)-4-hydroxy-6-(acetoxy)-2H-1-benzopyran-2-one (Compound 270)

In Example 8, 3.31 g (1.59×10$^{-2}$ mol) of 3-(methoxy)-4,6-(dihydroxy)-2H-1-benzopyran-2-one was used in place of 3,4,7-trihydroxy-2H-1-benzopyran-2-one, acetyl chloride was used in place of benzoyl chloride, and 2.61 g (yield=65.6%) of the desired compound 270 was obtained.

$^1$H-NMR (DMSO-d$_6$, δ-TMS) 9.94 (bs, 1H), 6.80~7.20 (m, 3H), 3.55 (s,3H), 1.77 (s, 3H)
IR (KBr, cm$^{-1}$) 3300, 1670, 1630
Elemental analysis value: C$_{12}$ H$_{10}$ O$_6$
Theoretical value (%): C 57.60; H 4.03; O 38.37
Actual measured value (%): C 57.66; H 4.01; O 38.33

Example 271

3-(geranyloxy)-4-hydroxy-6-(acetoxy)-2H-1-benzopyran-2-one (Compound 271)

In Example 8, 2.67 g (8.08×10$^{-3}$ mol) of 3-(geranyloxy)-4,6-(dihydroxy)-2H-1-benzopyran-2-one was used in place of 3,4,7-trihydroxy-2H-1-benzopyran-2-one, acetyl chloride was used in place of benzoyl chloride, and 1.05 g (yield=34.9%) of the desired compound 271 was obtained.

$^1$H-NMR (DMSO-d$_6$, δ-TMS) 9.98 (bs, 1H), 6.80~7.20 (m, 3H), 5.46 (bt, 1H, J=7.0Hz), 5.02 (bt, 1H, J=7.0Hz), 4.01 (d, 2H, J=7.0Hz), 2.00~2.21 (m, 4H), 1.55 (s, 3H), 1.53~1.85 (m, 9H)
IR (KBr, cm$^{-1}$) 3550, 3200, 1730, 1670, 1630
Elemental analysis value: C$_{21}$ H$_{24}$ O$_6$
Theoretical value (%): C 67.73; H 6.50; O 25.78
Actual measured value (%): C 67.72; H 6.53; O 25.75

Example 272

3,4-(dihydroxy)-6-(methoxy)-2H-1-benzopyran-2-one (Compound 272)

In Example 5, 2.37 g (7.58×10$^{-3}$ mol) of 3-(benzoyloxy)-4-hydroxy- 6-(methoxy)-2H- 1-benzopyran-2-one was used in place of 3-(benzoyloxy)-4,7-(dihydroxy)-2H-1-benzopyran-2-one, and 1.26 g (yield=79.9%) of the desired compound 272 was obtained.

$^1$H-NMR (DMSO-d$_6$, δ-TMS) 0.89 (bs,1H), 9.91 (bs, 1H), 6.80~7.20 (m, 3H), 3.25 (s, 3H)
IR (KBr, cm$^{-1}$) 3300, 1700, 1670, 1620
Elemental analysis value: C$_{10}$ H$_8$ O$_5$
Theoretical value (%): C 57.69; H 3.87; O 38.43
Actual measured value (%): C 57.66; H 3.92; O 38.42

Example 273

3,4-(dihydroxy)-6-(decyloxy)-2H-1-benzopyran-2-one (Compound 273)

In Example 5, 2.65 g (5.73×10$^{-3}$ mol) of 3-(benzoyloxy)-4-hydroxy-6-(decyloxy)-2H-1-benzopyran-2-one was used in place of 3-(benzoyloxy)-4,7-(dihydroxy)-2H-1-benzopyran-2-one, and 1.34 g (yield=69.9%) of the desired compound 273 was obtained.

$^1$H-NMR (DMSO-d$_6$, δ-TMS) 10.80 (bs, 1H), 9.88 (bs, 1H), 6.80~7.20 (m, 3H), 3.33 (t, H, J=7.0Hz), 1.24~1.70 (m, 16H), 0.82 (t, 3H, J=6.0Hz)
IR (KBr, cm$^{-1}$) 3400, 1700, 1670, 1620
Elemental analysis value: C$_{19}$ H$_{26}$ O$_5$
Theoretical value (%): C 68.24; H 7.84; O 23.92
Actual measured value (%): C 68.22; H 7.90; O 28.88

Example 274

3-(decyl)-4-(hydroxy)-6-(methoxy)-2H-1-benzopyran-2-one (Compound 274)

In Example 5, 2.00 g (5.12×10$^{-3}$ mol) of 3-(decyloxy)-4-(acetoxy)-6-(methoxy)-2H-1-benzopyran-2-one was used in place of 3-(benzoyloxy)-4,7-(dihydroxy)-2H-1-benzopyran-2-one, and 1.28 g (yield=72.0%) of the desired compound 274 was obtained.

$^1$H-NMR (DMSO-d$_6$, δ-TMS) 9.70 (bs, 1H), 6.80~7.20 (m,3H), 3.40 (s,3H), 3.31 (t, 2H, J=7.0Hz), 1.24~1.70 (m, 16H), 0.79 (t, 3H, J=6.0Hz)
IR (KBr, cm$^{-1}$) 3300, 1680, 1620, 1530

Elemental analysis value: $C_{20} H_{28} O_5$
Theoretical value (%): C 68.94; H 8.10; O 22.96
Actual measured value (%): C 68.99; H 8.03; O 22.98

Example 275

3-(methoxy)-4-(hydroxy)-6-(decyloxy)-2H-1-benzopyran-2-one (Compound 275)

In Example 5, 2.20 g ($5.63 \times 10^{-3}$ mol) of 3-(methoxy)-4-(acetoxy)-6-(decyloxy)-2H-1-benzopyran-2-one was used in place of 3-(benzoyloxy)-4,7-(dihydroxy)-2H-1-benzopyran-2-one, and 1.35 g (yield=68.9%) of the desired compound 275 was obtained.

$^1$H-NMR (DMSO-$d_6$, $\delta$-TMS) 9.78 (bs, 1H), 6.80~7.20 (m,3H), 3.36 (s,3H), 3.28 (t, 2H, J=7.0Hz), 1.24~1.70 (m, 16H), 0.82 (t, 3H, J=6.0Hz)
IR (KBr, $cm^{-1}$) 3200, 1670, 1620, 1580
Elemental analysis value: $C_{20} H_{28} O_5$
Theoretical value (%): C 68.94; H 8.10; O 22.96
Actual measured value (%): C 68.89; H 8.11; O 23.00

Example 276

3-(hydroxy)-4-(decyloxy)-6-(methoxy)-2H-1-benzopyran-2-one (Compound 276)

In Example 8, 3.00 g ($1.44 \times 10^{-2}$ mol) of 3,4-(dihydroxy)-6-(methoxy)-2H-1-benzopyran-2-one was used in place of 3,4,7-trihydroxy-2H-1-benzopyran-2-one, decyl bromide was used in place of benzoyl chloride, and 2.63 g (yield=52.3%) of the desired compound 276 was obtained.

$^1$H-NMR (DMSO-$d_6$, $\delta$-TMS) 9.26 (bs, 1H), 6.80~7.20 (m,3H), 3.51 (s,3H), 3.11 (t, 2H, J=7.0Hz), 1.24~1.70 (m, 16H), 0.80 (t, 3H, J=6.0Hz)
IR (KBr, $cm^{-1}$) 3550, 1660, 1630, 1580
Elemental analysis value: $C_{20} H_{28} O_5$
Theoretical value (%): C 68.94; H 8.10; O 22.96
Actual measured value (%): C 68.99; H 8.09; O 22.92

Example 277

3-(hydroxy)-4-(methoxy)-6-(decyloxy)-2H-1-benzopyran-2-one (Compound 277)

In Example 8, 2.56 g ($7.66 \times 10^{-3}$ mol) of 3,4-(dihydroxy)-6-(decyloxy)-2H-1-benzopyran-2-one was used in place of 3,4,7-trihydroxy-2H-1-benzopyran-2-one, methyl iodide was used in place of benzoyl chloride, and 1.16 g (yield=43.3%) of the desired compound 277 was obtained.

$^1$H-NMR (DMSO-$d_6$, $\delta$-TMS) 9.10 (bs, 1tl), 6.80~7.20 (m, 3H), 3.81 (s, 3H), 3.14 (t, H, J=7.0Hz), 1.24~1.70 (m, 16H), 0.76 (t, 3H, J=6.0Hz)
IR (KBr, $cm^{-1}$) 3200, 1670, 1620, 1580
Elemental analysis value: $C_{20} H_{28} O_5$
Theoretical value (%): C 68.94; H 8.10; O 22.96
Actual measured value (%): C 68.96; H 8.10; O 22.94

Example 278

3-(acetoxy)-4-(hydroxy)-6-(methoxy)-2H-1-benzopyran-2-one (Compound 278)

In Example 4, 3.00 g ($8.42 \times 10^{-3}$ mol) of methyl-$\beta$-oxo-2'-(phenylmethoxy)-5'-(methoxy)-2-(acetoxy)benzenepropanate was used in place of methyl-$\beta$-oxo-2',4'-bis(phenylmethoxy)-2-(benzoyloxy)benzenepropanate, and 1.20 g (yield=56.9%) of the desired compound 278 was obtained.

$^1$H-NMR (DMSO-$d_6$, $\delta$-TMS) 9.29 (bs, 1H), 6.80~7.20 (m,3H), 3.11 (s, 3H), 1.76 (s, 3H)
IR(KBr, $cm^{-1}$) 3400, 3200, 1710, 1680, 1630
Elemental analysis value: $C_{12} H_{10} O_6$
Theoretical value (%): C 57.60; H 4.03; O 38.37
Actual measured value (%): C 57.54; H 4.09; O 38.37

Example 279

3-(acetoxy)-4-(hydroxy)-6-(decyloxy)-2H-1-benzopyran-2-one (Compound 279)

In Example 4, 3.50 g ($7.02 \times 10^{-3}$ mol) of methyl-$\beta$-oxo-2'-(phenylmethoxy)-5'-(decyloxy)-2-(acetoxy)benzenepropanate was used in place of methyl-$\beta$-oxo-2',4'-bis(phenylmethoxy)-2-(benzoyloxy)benzenepropanate, and 1.38 g (yield=52.4%) of the desired compound 279 was obtained.

$^1$H-NMR (DMSO-$d_6$, $\delta$-TMS) 9.22 (bs, 1H), 6.80~7.20 (m,3H), 3.39 (t, 2H, J=7.0Hz), 1.66 (s, 3H), 1.24~1.70 (m, 16H), 0.81 (t, 3H, J=6.0Hz)
IR (KBr, $cm^{-1}$) 3200, 1720, 1670, 1620
Elemental analysis value: $C_{21} H_{28} O_6$
Theoretical value (%): C 67.00; H 7.50; O 25.50
Actual measured value (%): C 66.96; H 7.56; O 25.48

Example 280

3,4-(dihydroxy)-6-(geranyloxy)-2H-1-benzopyran-2-one (Compound 280)

In Example 5, 4.00 g ($9.17 \times 10^{-3}$ mol) of 3-(benzoyloxy)-4-(hydroxy)-6-(geranyloxy)-2H-1-benzopyran-2-one was used in place of 3-(benzoyloxy)-4,7-(dihydroxy)-2H-1-benzopyran-2-one, and 1.69 g (yield=55.7%) of the desired compound 280 was obtained.

$^1$H-NMR (DMSO-$d_6$, $\delta$-TMS) 9.83 (bs, 1H), 9.22 (bs, 1H), 6.80~7.20 (m, 3H), 5.40 (bt, 1H, J=7.0Hz), 5.00 (bs, 1H, J=7.0Hz), 4.03 (d, 2H, J=7.0Hz), 2.00~2.22 (m, 4H), 1.54~1.85 (m, 9H)
IR (KBr, $cm^{-1}$) 3550, 3200, 1670, 1620
Elemental analysis value: $C_{19} H_{22} O_5$
Theoretical value (%): C 69.07; H 6.71; O 24.22
Actual measured value (%): C 69.02; H 6.70; O 24.28

Example 281

Mouse Acute Toxicity Assay

The present Example was carried out in order to confirm the safety of the novel compound according to the present invention. In the following the assay method used will be explained.

Assay method: After ICR-type male mice (body weight=20~25 g) were fasted for 16 hours, each substance to be tested was forcibly administered orally at 1000 mg/kg and 2000 mg/kg to groups of five mice, using a esophageal sound. After administration, the mice were kept in cages for seven days, following which observations were made on the general conditions and existence of dead animals. From the survival ratio of the mice at the end of the observation, the lethal dose 50 ($LD_{50}$) was estimated.

The results of the mouse acute toxicity assay are recorded in Tables 1 and 2.

TABLE 1

| Mouse acute toxicity assay | |
| --- | --- |
| Compound No. | $LD_{50}$ (mg/kg) |
| 4~5 | >2000 |
| 7~18 | >2000 |
| 19~26 | >1000 |
| 27~36 | >2000 |
| 37~43 | >1000 |

TABLE 1-continued

Mouse acute toxicity assay

| Compound No. | LD$_{50}$ (mg/kg) |
|---|---|
| 44~53 | >2000 |
| 54~57 | >1000 |
| 58~66 | >2000 |
| 67~88 | >1000 |
| 92~102 | >2000 |
| 103~109 | >1000 |
| 110~120 | >2000 |
| 121~126 | >1000 |
| 127~137 | >2000 |
| 138~142 | >1000 |
| 143~150 | >2000 |

TABLE 2

| Compound No. | LD$_{50}$ (mg/kg) |
|---|---|
| 151~172 | >1000 |
| 176~186 | >2000 |
| 187~193 | >1000 |
| 194~202 | >2000 |
| 203~209 | >1000 |
| 210~219 | >2000 |
| 220~223 | >1000 |
| 224~236 | >2000 |
| 237~258 | >1000 |
| 262~268 | >2000 |
| 269 | >1000 |
| 270 | >2000 |
| 271 | >1000 |
| 272~279 | >2000 |
| 280 | >1000 |

In all of the compounds, deaths were not observed at oral administrations of 1000 mg/kg or 2000 mg/kg, thus the LD$_{50}$ levels were estimated to be 1000 mg/kg or greater, or mg/kg or greater respectively.

Consequently, it is clear from the above results that the compounds according to the present invention are extremely safe compounds all possessing an extremely low toxicity.

Example 282

Anti-allergic Action Confirmation Assay (Guinea Pig Homogeneous Skin Passive Anaphylaxis Assay)

In order to confirm the anti-allergic action of the compounds according to the present invention, as an anti-allergic action confirmation assay, the widely used Guinea Pig Homogeneous Skin Passive Anaphylaxis Assay (PCA Reaction Assay; Passive Cutaneous Anaphylaxis Reaction Assay) was carried out. The assay method used will be explained in the following.

Assay method: Hartley-type male guinea pigs (body weight: 250~300 g) were sensitized by the following procedure; a mixture of 2 μg of egg albumin (OVA) and 5 μg of aluminium hydroxide gel was administered intraperitoneally 3 times every 2 weeks, and the anti-OVA blood serum was manufactured.

The anti-blood serum obtained was then diluted 120 times using physiological saline solution, and then to groups each containing 6 shaved guinea pigs, was injected at a quantity of 0.05 ml respectively, into two positions in the back portion, inside the skin of each animal.

After the 48th hour of sensitization, 10 mg/kg of the test substance to be tested was orally administered, following which a mixture of 2 mg OVA and 5 mg of Evans Blue was administered by intraveneous injection into the hind leg, triggering the anaphylaxis reaction.

As the positive control, Tranilast, a well known anti-allergic agent, was used, and in the same manner as the substances to be tested, 100 mg/kg of it was orally administered after the 48th hour of sensitization.

30 minutes after triggering the reaction, the animals were bled to death under ether anesthesia, and their back portion skins were peeled off. The long and short diameters of pigment leakage spots on the interior surface of the skins were measured, and the product of these (mm$^2$) were entered into formula 1 as "pigment leakage amount", from which the allergic reaction inhibitory index wins calculated.

$$I = \frac{A - B}{C} \times 100 \quad \text{(Formula 1)}$$

In formula 1:
I: Allergic reaction inhibitory index (%)
A: Pigment leakage amount of solvent control group
B: Pigment leakage amount of test substance group
C: Pigment leakage amount of solvent control group Tables 3~17 show the results of the anti-allergic action confirmation assay.

TABLE 3

Anti-allergic action confirmation assay

| Compound No. | Allergic reaction inhibitory index (%) |
|---|---|
| 4 | 43 |
| 5 | 68 |
| 7 | 48 |
| 8 | 40 |
| 9 | 39 |
| 10 | 30 |
| 11 | 31 |
| 12 | 30 |
| 13 | 32 |
| 14 | 47 |
| 15 | 41 |
| 16 | 40 |
| 17 | 31 |
| 18 | 30 |
| 19 | 42 |
| 20 | 30 |
| 21 | 33 |
| 22 | 31 |

TABLE 4

| Compound No. | Allergic reaction inhibitory index (%) |
|---|---|
| 23 | 30 |
| 24 | 33 |
| 25 | 32 |
| 26 | 30 |
| 27 | 40 |
| 28 | 53 |
| 29 | 46 |
| 30 | 31 |
| 31 | 38 |
| 32 | 33 |
| 33 | 33 |
| 34 | 39 |
| 35 | 30 |
| 36 | 30 |
| 37 | 40 |
| 38 | 31 |
| 39 | 30 |
| 40 | 34 |

TABLE 5

| Compound No. | Allergic reaction inhibitory index (%) |
|---|---|
| 41 | 30 |
| 42 | 33 |
| 43 | 30 |
| 44 | 37 |
| 45 | 58 |
| 46 | 34 |
| 47 | 31 |
| 48 | 42 |
| 49 | 36 |
| 50 | 33 |
| 51 | 30 |
| 52 | 32 |
| 53 | 38 |
| 54 | 32 |
| 55 | 33 |
| 56 | 31 |
| 57 | 30 |
| 58 | 38 |

TABLE 6

| Compound No. | Allergic reaction inhibitory index (%) |
|---|---|
| 59 | 47 |
| 60 | 35 |
| 61 | 30 |
| 62 | 43 |
| 63 | 37 |
| 64 | 30 |
| 65 | 32 |
| 66 | 30 |
| 67 | 39 |
| 68 | 32 |
| 69 | 33 |
| 70 | 30 |
| 71 | 30 |
| 72 | 34 |
| 73 | 30 |
| 74 | 34 |
| 75 | 45 |
| 76 | 32 |

TABLE 7

| Compound No. | Allergic reaction inhibitory index (%) |
|---|---|
| 77 | 31 |
| 78 | 37 |
| 79 | 32 |
| 80 | 30 |
| 81 | 31 |
| 82 | 30 |
| 83 | 34 |
| 84 | 30 |
| 85 | 33 |
| 86 | 30 |
| 87 | 31 |
| 88 | 30 |
| 92 | 33 |
| 93 | 42 |
| 94 | 36 |
| 95 | 30 |
| 96 | 32 |
| 97 | 34 |

TABLE 8

| Compound No. | Allergic reaction inhibitory index (%) |
|---|---|
| 98 | 31 |
| 99 | 33 |
| 100 | 30 |
| 101 | 30 |
| 102 | 35 |
| 103 | 30 |

TABLE 8-continued

| Compound No. | Allergic reaction inhibitory index (%) |
|---|---|
| 104 | 32 |
| 105 | 30 |
| 106 | 31 |
| 107 | 33 |
| 108 | 32 |
| 109 | 34 |
| 110 | 31 |
| 111 | 38 |
| 112 | 32 |
| 113 | 30 |
| 114 | 31 |
| 115 | 33 |

TABLE 9

| Compound No. | Allergic reaction inhibitory index (%) |
|---|---|
| 116 | 34 |
| 117 | 32 |
| 118 | 32 |
| 119 | 30 |
| 120 | 33 |
| 121 | 30 |
| 122 | 30 |
| 123 | 34 |
| 124 | 33 |
| 125 | 31 |
| 126 | 30 |
| 127 | 34 |
| 128 | 40 |
| 129 | 36 |
| 130 | 39 |
| 131 | 31 |
| 132 | 32 |
| 133 | 36 |

TABLE 10

| Compound No. | Allergic reaction inhibitory index (%) |
|---|---|
| 134 | 30 |
| 135 | 30 |
| 136 | 33 |
| 137 | 32 |
| 138 | 35 |
| 139 | 33 |
| 140 | 30 |
| 141 | 32 |
| 142 | 31 |
| 143 | 30 |
| 144 | 34 |
| 145 | 32 |
| 146 | 30 |
| 147 | 30 |
| 148 | 31 |
| 149 | 33 |
| 150 | 34 |
| 151 | 34 |

TABLE 11

| Compound No. | Allergic reaction inhibitory index (%) |
|---|---|
| 152 | 31 |
| 153 | 30 |
| 154 | 31 |
| 155 | 30 |
| 156 | 32 |
| 157 | 30 |
| 158 | 30 |
| 159 | 36 |
| 160 | 34 |
| 161 | 31 |
| 162 | 31 |
| 163 | 32 |

TABLE 11-continued

| Compound No. | Allergic reaction inhibitory index (%) |
|---|---|
| 164 | 33 |
| 165 | 30 |
| 166 | 30 |
| 167 | 30 |
| 168 | 34 |
| 169 | 30 |

TABLE 12

| Compound No. | Allergic reaction inhibitory index (%) |
|---|---|
| 170 | 31 |
| 171 | 33 |
| 172 | 30 |
| 176 | 34 |
| 177 | 37 |
| 178 | 30 |
| 179 | 32 |
| 180 | 30 |
| 181 | 33 |
| 182 | 31 |
| 183 | 30 |
| 184 | 33 |
| 185 | 30 |
| 186 | 32 |
| 187 | 30 |
| 188 | 32 |
| 189 | 30 |
| 190 | 31 |

TABLE 13

| Compound No. | Allergic reaction inhibitory index (%) |
|---|---|
| 191 | 30 |
| 192 | 37 |
| 193 | 30 |
| 194 | 46 |
| 195 | 55 |
| 196 | 33 |
| 197 | 32 |
| 198 | 40 |
| 199 | 32 |
| 200 | 30 |
| 201 | 31 |
| 202 | 30 |
| 203 | 41 |
| 204 | 30 |
| 205 | 31 |
| 206 | 32 |
| 207 | 33 |
| 208 | 32 |

TABLE 14

| Compound No. | Allergic reaction inhibitory index (%) |
|---|---|
| 209 | 33 |
| 210 | 40 |
| 211 | 52 |
| 212 | 37 |
| 213 | 33 |
| 214 | 38 |
| 215 | 34 |
| 216 | 34 |
| 217 | 30 |
| 218 | 31 |
| 219 | 36 |
| 220 | 30 |
| 221 | 33 |
| 222 | 32 |
| 223 | 33 |
| 224 | 30 |
| 224 | 35 |

TABLE 14-continued

| Compound No. | Allergic reaction inhibitory index (%) |
|---|---|
| 226 | 33 |

TABLE 15

| Compound No. | Allergic reaction inhibitory index (%) |
|---|---|
| 227 | 50 |
| 228 | 34 |
| 229 | 37 |
| 230 | 43 |
| 231 | 31 |
| 232 | 32 |
| 233 | 39 |
| 234 | 33 |
| 235 | 30 |
| 236 | 31 |
| 237 | 34 |
| 238 | 33 |
| 239 | 31 |
| 240 | 30 |
| 241 | 32 |
| 242 | 30 |
| 243 | 31 |
| 244 | 33 |

TABLE 16

| Compound No. | Allergic reaction inhibitory index (%) |
|---|---|
| 245 | 37 |
| 246 | 30 |
| 247 | 34 |
| 248 | 35 |
| 249 | 32 |
| 250 | 31 |
| 251 | 30 |
| 252 | 32 |
| 253 | 33 |
| 254 | 30 |
| 255 | 33 |
| 256 | 30 |
| 257 | 31 |
| 258 | 32 |
| 262 | 30 |
| 263 | 42 |
| 264 | 36 |
| 265 | 37 |

TABLE 17

| Compound No. | Allergic reaction inhibitory index (%) |
|---|---|
| 266 | 33 |
| 267 | 34 |
| 268 | 33 |
| 269 | 33 |
| 270 | 35 |
| 271 | 33 |
| 272 | 30 |
| 273 | 30 |
| 274 | 35 |
| 275 | 36 |
| 276 | 34 |
| 277 | 35 |
| 278 | 36 |
| 279 | 30 |
| 280 | 35 |
| Tranilast | 52 |

All of the compounds of the present invention, when compared with Tranilast, the welt-known anti-allergic agent which was used as a positive control agent, exhibited superior anti-allergic action.

Additionally, when the positive control agent Tranilast was administered in an amount of 100 mg/kg, 10 times the dosage amount of the compounds according to the present invention, it was observed that the Tranilast's anti-allergic action was approximately equal to or less than the anti-allergic action exhibited by the compounds of the present invention. As well since in male mice the $LD_{50}$ of Tranilast was 780 mg/kg, it was not judged to be an agent possessing a very broad safety range.

It is obvious from the above results that the compounds of the present invention display superior anti-allergic action at a dosage amount of 10 mg/kg, 1/10 the dosage amount of the Tranilast. In addition, the $LD_{50}$ in mice was 1000~2000 mg/kg or greater, thus demonstrating that the compounds of the present invention are effective anti-allergic agents possessing an extremely broad safety range.

Examples 283~308

| (5% powder) | |
|---|---|
| Compound 5 | 50 |
| Lactose | 950 |
| | 1000 mg |

Inside a mortar, after crystals of compound 5 were ground, lactose was added and sufficiently mixed while grinding with a pestle to produce a 5% powder. Using the same procedure, powders of compounds 4 and 7~30 were also manufactured.

Examples 309~334

| (10% powder) | |
|---|---|
| Compound 31 | 100 |
| Lactose | 900 |
| | 1000 mg |

Inside a mortar, after crystals of compound 31 were ground, lactose was added and sufficiently mixed while grinding with a pestle to produce a 10% powder. Using the same procedure, powders of compounds 32~56 were also manufactured.

Examples 335~366

| (10% granule) | |
|---|---|
| Compound 57 | 300 |
| Lactose | 2000 |
| Starch | 670 |
| Gelatin | 30 |
| | 3000 mg |

Inside a mortar, compound 57 was mixed with an equivalent weight of starch and then ground. To this lactose and the remaining portion of starch was added and mixed. Separately, 1 ml of purified water was added to 30 mg of gelatin, and the mixture was dissolved by heating. After cooling, 1 ml of ethanol was added while stirring, and a gelatin-like liquid was prepared. This gelatin-like liquid was then added to the previously prepared mixture and granulated. After granulating, this mixture was dried and graded.

Using the same procedure, granules of compounds 58~88 were manufactured.

Examples 367~392

| (5 mg pills) | |
|---|---|
| Compound 93 | 5 |
| Lactose | 62 |
| Starch | 30 |
| Talc | 2 |
| Magnesium stearate | 1 |
| | 100 mg/pill |

In a mortar, pills were manufactured using a compound containing 20 times the amount of the above mentioned composition. Namely, after 100 mg of compound 93 crystals were ground, lactose and starch were added and mixed. 10% starch paste was then added to the aforementioned mixture, and the mixture was granulated. After drying, talc and magnesium stearate were mixed in, and pills were formed using conventional methods.

Using the same procedure, 5 mg pills of compounds 92 and 94~117 were also manufactured.

Examples 393~418

| (25 mg pills) | |
|---|---|
| Compound 118 | 25 |
| Lactose | 120 |
| Starch | 52 |
| Talc | 2 |
| Magnesium stearate | 1 |
| | 200 mg/pill |

In a mortar, 25 mg pills were formed using a compound containing 10 times the amount of the above mentioned composition in the same manner as in Examples 367~392, ie. by mixing, kneading, granulating followed by pill formation.

Using the same procedure, 25 mg pills for compounds 1191[143 were also manufactured.

Examples 419~447

| (25 mg pills) | |
|---|---|
| Compound 144 | 25 |
| Lactose | 122 |
| Carboxy methyl starch | 50 |
| Talc | 2 |
| Magnesium stearate | 1 |
| | 200 mg/pill |

Inside a mortar, 25 mg pills were manufactured using a compound containing 10 times the amount of each of the above mentioned composition. Namely, inside a mortar, 250 mg of compound 144 crystals were ground, to which lactose was added and sufficiently mixed. An adequate amount of purified water was added to the carboxy methyl starch, and then this was poured into the previously prepared mixture, kneaded and granulated. After drying, talc and magnesium stearate were mixed in, and using conventional methods pills were formed.

Using the same procedure, 25 mg pills of compounds 145~172 were also manufactured.

Examples 448~473

| (20 mg pills) | |
|---|---|
| Compound 177 | 20 |

| -continued | |
|---|---|
| 6% hydroxypropyl cellulose lactose | 75 |
| Talc stearate | 2 |
| Potato starch | 3 |
| | 100 mg/pill |

20 mg pills were manufactured using a compound containing 10 times the amount of each of the above mentioned composition. Namely, 6 g of hydroxypropyl cellulose was dissolved in an adequate amount of ethanol, into which 94 g of lactose was poured, and the mixture was kneaded. After drying slightly, a number 20 sifter was used to sift out the mixture.

After allowing to sit overnight, the mixture was graded in a number 60 sifter, forming a 6% hydroxypropyl lactose. Magnesium stearate and talc, in a 1:4 ratio, were additionally mixed, forming a talc stearate. Finally, compound 177, the 6% hydroxypropyl lactose, the talc stearate and the potato starch were mixed throughly, and using conventional methods pills were formed.

Using the same procedure, 20 mg pills for compounds 176 and 178~201 were also manufactured.

Example 474~499

| (5 mg pills) | |
|---|---|
| Compound 202 | 5 |
| Lactose | 35 |
| 3% hydroxypropyl lactose | 30 |
| Crystal cellulose | 20 |
| Potato starch | 8 |
| Talc stearate | 2 |
| | 100 mg/pill |

Inside a mortar, 5 mg pills were manufactured using a compound containing 20 times the amount of the above mentioned composition. Namely compound 202 was ground, following which lactose was added and mixed in little by little. To this, 3% hydroxypropyl lactose and talc stearate, prepared using the same procedure as in Examples 448~473, in addition to crystal cellulose and potato starch were added and mixed uniformly. Following which, formation of the pills was carried out using conventional methods.

Using the same procedure, 5 mg pills of compounds 203~227 were also manufactured.

Example 500~530

| (25 mg capsules) | |
|---|---|
| Compound 228 | 25 |
| Lactose | 53 |
| Starch | 20 |
| Magnesium stearate | 2 |
| | 100 mg |

In a mortar, after crystals of compound 228 were thoroughly ground, starch, lactose and magnesium stearate were added, mixed sufficiently, and packed in capsules.

Using the same procedure, 25 mg capsules of compounds 229~258 were also manufactured.

Example 531~549

| (10 mg capsules) | |
|---|---|
| Compound 263 | 300 |
| Lactose | 2000 |
| Starch | 670 |
| Gelatin | 30 |
| | 3000 mg |

Using the same procedure as in Examples 335~366, granules of compound 263 were prepared and 100 mg granules were each packed into capsules.

Using the same procedure, 10 mg capsules of compounds and 264~280 were also manufactured.

Possibilities of Industrial Use

The benzopyran derivative novel action supplied according to the present invention is useful in medical treatment against diseases, caused by self-immune disorders, allergies and shock.

What is claimed is:

1. General Formula (I):

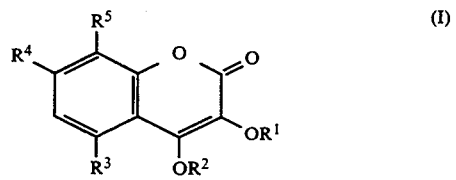

A benzopyran derivative or its physiologically acceptable salts, said benzopyran derivative being represented by general formula (I) wherein $R^1$ is a hydrogen atom; $R^2$ is a straight chain or branched alkyl, acyl, or alkenyl group having 3~12 carbon atoms; one of $R^3$, $R^4$, $R^5$ is a hydroxyl group or a protected hydroxyl group and the others are hydrogen atoms.

2. A benzopyran derivative or its physiologically acceptable salts according to claim 1 wherein in general formula (I) $R^1$ is a hydrogen atom; and $R^2$ is an acyl group selected from the group consisting of an aroyl group and an alkanoyl group.

3. A benzopyran derivative or its physiologically acceptable salts according to claim 1 wherein in general formula (I) $R^1$ is a hydrogen atom; and $R^2$ is a straight chain or branched alkyl group having 3~12 carbon atoms.

4. A benzopyran derivative or its physiologically acceptable salts according to claim 1 wherein in general formula (I) $R^1$ is a hydrogen atom; and $R^2$ is a straight chain or branched alkenyl group having 2~10 carbon atoms.

5. A benzopyran derivative or its physiologically acceptable salts according to claim 2 wherein in general formula (I) $R^1$ is a hydrogen atom; and $R^2$ is an aroyl group.

6. A benzopyran derivative or its physiologically acceptable salts according to claim 2 wherein in general formula (I) $R^1$ is a hydrogen atom; and $R^2$ is an alkanoyl group.

7. A benzopyran derivative or its physiologically acceptable salts according to claim 1 wherein in general formula (I) one of $R^3$, $R^4$ or $R^5$ is a hydroxyl group and the others are hydrogen atoms.

8. A benzopyran derivative or its physiologically acceptable salts according to claim 1 wherein in general formula (I) one of $R^3$, $R^4$ or $R^5$ is a protected hydroxyl group, and the others are hydrogen atoms.

9. A benzopyran derivative or its physiologically acceptable salts according to claim 1 wherein in general formula (I) one of $R^3$, $R^4$ or $R^5$ is a hydroxyl group protected by an acyl group selected from the group consisting of an aroyl group and an alkanoyl group, and the others are hydrogen atoms.

10. A benzopyran derivative or its physiologically acceptable salts according to claim 1 wherein in general formula (I) one of $R^3$, $R^4$ or $R^5$ is a hydroxyl group protected by an aroyl group, and the others are hydrogen atoms.

11. A benzopyran derivative or its physiologically acceptable salts according to claim 1 wherein in general formula (I) one of $R^3$, $R^4$ or $R^5$ is a hydroxyl group protected by an alkanoyl group, and the others are hydrogen atoms.

12. A benzopyran derivative or its physiologically acceptable salts according to claim 1 wherein in general formula (I) one of $R^3$, $R^4$ or $R^5$ is a hydroxyl group protected by a straight chain or branched alkyl group having 1~10 carbon atoms, and the others are hydrogen atoms.

13. A benzopyran derivative or its physiologically acceptable salts according to claim 1 wherein in general formula (I) one of $R^3$, $R^4$ or $R^5$ is a hydroxyl group protected by a straight chain or branched alkenyl group having 2~20 carbon atoms, and the others are hydrogen atoms.

14. A benzopyran derivative or its physiologically acceptable salts according to claim 1 wherein in general formula (I) $R^3$ is a hydroxyl group; and $R^4$ and $R^5$ are hydrogen atoms.

15. A benzopyran derivative or its physiologically acceptable salts according to claim 1 wherein in general formula (I) $R^4$ is a hydroxyl group; and $R^3$ and $R^5$ are hydrogen atoms.

16. A benzopyran derivative or its physiologically acceptable salts according to claim 1 wherein in general formula (I) $R^5$ is a hydroxyl group; and $R^3$ and $R^4$ are hydrogen atoms.

17. A benzopyran derivative or its physiologically acceptable salts according to claim 1 wherein in general formula (I) $R^3$ is a hydroxyl group protected by an acyl group selected from the group consisting of an aroyl group and an alkanoyl group; and $R^4$ and $R^5$ are hydrogen atoms.

18. A benzopyran derivative or its physiologically acceptable salts according to claim 1 wherein in general formula (I) $R^3$ is a hydroxyl group protected by an aroyl group; and $R^4$ and $R^5$ are hydrogen atoms.

19. A benzopyran derivative or its physiologically acceptable salts according to claim 1 wherein in general formula (I) $R^3$ is a hydroxyl group protected by an alkanoyl group; and $R^4$ and $R^5$ are hydrogen atoms.

20. A benzopyran derivative or its physiologically acceptable salts according to claim 1 wherein in general formula (I) $R^4$ is a hydroxyl group protected by an acyl group selected from the group consisting of an aroyl group and an alkanoyl group; and $R^3$ and $R^5$ are hydrogen atoms.

21. A benzopyran derivative or its physiologically acceptable salts according to claim 1 wherein in general formula (I) $R^4$ is a hydroxyl group protected by an aroyl group; and $R^3$ and $R^5$ are hydrogen atoms.

22. A benzopyran derivative or its physiologically acceptable salts according to claim 1 wherein in general formula (I) $R^4$ is a hydroxyl group protected by an alkanoyl group; and $R^3$ and $R^5$ are hydrogen atoms.

23. A benzopyran derivative or its physiologically acceptable salts according to claim 1 wherein in general formula (I) $R^5$ is a hydroxyl group protected by an acyl group selected from the group consisting of an aroyl group and an alkanoyl group; and $R^3$ and $R^4$ are hydrogen atoms.

24. A benzopyran derivative or its physiologically acceptable salts according to claim 1 wherein in general formula (I) $R^5$ is a hydroxyl group protected by an aroyl group; and $R^3$ and $R^4$ are hydrogen atoms.

25. A benzopyran derivative or its physiologically acceptable salts according to claim 1 wherein in general formula (I) $R^5$ is a hydroxyl group protected by an alkanoyl group; and $R^3$ and $R^4$ are hydrogen atoms.

26. A benzopyran derivative or its physiologically acceptable salts according to claim 1 wherein in general formula (I) $R^3$ is a hydroxyl group protected by a straight chain or branched alkyl group having 1~10 carbon atoms; and $R^4$ and $R^5$ are hydrogen atoms.

27. A benzopyran derivative or its physiologically acceptable salts according to claim 1 wherein in general formula (I) $R^4$ is a hydroxyl group protected by a straight chain or branched alkyl group having 1~10 carbon atoms; and $R^3$ and $R^5$ are hydrogen atoms.

28. A benzopyran derivative or its physiologically acceptable salts according to claim 1 wherein in general formula (I) $R^5$ is a hydroxyl group protected by a straight chain or branched alkyl group having 1~10 carbon atoms; and $R^3$ and $R^4$ are hydrogen atoms.

29. A benzopyran derivative or its physiologically acceptable salts according to claim 1 wherein in general formula (I) $R^3$ is a hydroxyl group protected by a straight chain or branched alkenyl group having 2~10 carbon atoms; and $R^4$ and $R^5$ are hydrogen atoms.

30. A benzopyran derivative or its physiologically acceptable salts according to claim 1 wherein in general formula (I) $R^4$ is a hydroxyl group protected by a straight chain or branched alkenyl group having 2~10 carbon atoms; and $R^3$ and $R^5$ are hydrogen atoms.

31. A benzopyran derivative or its physiologically acceptable salts according to claim 1 wherein in general formula (I) $R^5$ is a hydroxyl group protected by a straight chain or branched alkenyl group having 2~10 carbon atoms; and $R^3$ and $R^4$ are hydrogen atoms.

32. General Formula (I):

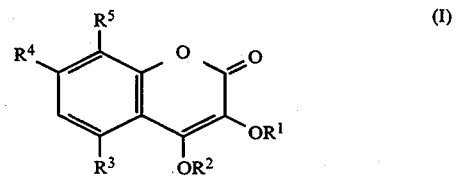

A benzopyran derivative or its physiologically acceptable salts, said benzopyran derivative being represented by general formula (I) wherein $R^1$ is a hydrogen atom; $R^2$ is a methyl group; $R^3$ is a hydroxyl group or a protected hydroxyl group; and $R^4$ and $R^5$ are hydrogen atoms.

33. General Formula (I):

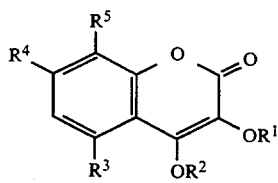

(I)

A benzopyran derivative or its physiologically acceptable salts, said benzopyran derivative being represented by general formula (I) wherein $R^1$ is a hydrogen atom; $R^2$ is a methyl group; $R^3$ and $R^5$ are hydrogen atoms; and $R^4$ is a hydroxyl group or a protected hydroxyl group.

34. General Formula (I):

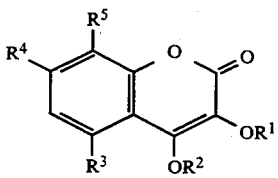

(I)

A benzopyran derivative or its physiologically acceptable salts, said benzopyran derivative being represented by general formula (I) wherein $R^1$ is a straight chain or branched alkyl, acyl, or alkenyl group having 2~12 carbon atoms; $R^2$ is a hydrogen atom; one of $R^3$, $R^4$, $R^5$ is a hydroxyl group or a protected hydroxyl group and the others are hydrogen atoms.

35. A benzopyran derivative or its physiologically acceptable salts according to claim 34 wherein in general formula (I) $R^2$ is a hydrogen atom; and $R^1$ is an acyl group selected from the group consisting of an aroyl group and an alkanoyl group.

36. A benzopyran derivative or its physiologically acceptable salts according to claim 34 wherein in general formula (I) $R^1$ is a straight chain or branched alkyl group having 2~12 carbon atoms; and $R^2$ is a hydrogen atom.

37. A benzopyran derivative or its physiologically acceptable salts according to claim 34 wherein in general formula (I) $R^2$ is a hydrogen atom; and $R^1$ a straight chain or branched alkenyl group having 2~10 carbon atoms.

38. A benzopyran derivative or its physiologically acceptable salts according to claim 35 wherein in general formula (I) $R^1$ is an aroyl group; and $R^2$ is a hydrogen atom.

39. A benzopyran derivative or its physiologically acceptable salts according to claim 35 wherein in general formula (I) $R^1$ is an alkanoyl group; and $R^2$ is a hydrogen atom.

40. A benzopyran derivative or its physiologically acceptable salts according to claim 34 wherein in general formula (I) one of $R^3$, $R^4$ or $R^5$ is a hydroxyl group and the others are hydrogen atoms.

41. A benzopyran derivative or its physiologically acceptable salts according to claim 34 wherein in general formula (I) one of $R^3$, $R^4$ or $R^5$ is a protected hydroxyl group and the others are hydrogen atoms.

42. A benzopyran derivative or its physiologically acceptable salts according to claim 34 wherein in general formula (I) one of $R^3$, $R^4$ or $R^5$ is a hydroxyl group protected by an acyl group selected from the group consisting of an aroyl group and an alkanoyl group, and the others are hydrogen atoms.

43. A benzopyran derivative or its physiologically acceptable salts according to claim 34 wherein in general formula (I) one of $R^3$, $R^4$ or $R^5$ is a hydroxyl group protected by an aroyl group, and the others are hydrogen atoms.

44. A benzopyran derivative or its physiologically acceptable salts according to claim 34 wherein in general formula (I) one of $R^3$, R4or $R^5$ is a hydroxyl group protected by an alkanoyl group, and the others are hydrogen atoms.

45. A benzopyran derivative or its physiologically acceptable salts according to claim 34 wherein in general formula (I) one of $R^3$, $R^4$ or $R^5$ is a hydroxyl group protected by a straight chain or branched alkyl group having 1~10 carbon atoms, and the others are hydrogen atoms.

46. A benzopyran derivative or its physiologically acceptable salts according to claim 34 wherein in general formula (I) one of $R^3$, $R^4$ or $R^5$ is a hydroxyl group protected by a straight chain or branched alkenyl group having 2~10 carbon atoms, and the others are hydrogen atoms.

47. A benzopyran derivative or its physiologically acceptable salts according to claim 34 wherein in general formula (I) $R^3$ is a hydroxyl group; and $R^4$ and $R^5$ are hydrogen atoms.

48. A benzopyran derivative or its physiologically acceptable salts according to claim 34 wherein in general formula (I) $R^4$ is a hydroxyl group; and $R^3$ and $R^5$ are hydrogen atoms.

49. A benzopyran derivative or its physiologically acceptable salts according to claim 34 wherein in general formula (I) $R^5$ is a hydroxyl group; and $R^3$ and $R^4$ are hydrogen atoms.

50. A benzopyran derivative or its physiologically acceptable salts according to claim 34 wherein in general formula (I) $R^3$ is a hydroxyl group protected by an acyl group selected from the group consisting of an aroyl group and an alkanoyl group; and $R^4$ and $R^5$ are hydrogen atoms.

51. A benzopyran derivative or its physiologically acceptable salts according to claim 34 wherein in general formula (I) $R^3$ is a hydroxyl group protected by an aroyl group; and $R^4$ and $R^5$ are hydrogen atoms.

52. A benzopyran derivative or its physiologically acceptable salts according to claim 34 wherein in general formula (I) $R^3$ is a hydroxyl group protected by an alkanoyl group; and $R^4$ and $R^5$ are hydrogen atoms.

53. A benzopyran derivative or its physiologically acceptable salts according to claim 34 wherein in general formula (I) $R^4$ is a hydroxyl group protected by an acyl group selected from the group consisting of an aroyl group and an alkanoyl group; and $R^3$ and $R^5$ are hydrogen atoms.

54. A benzopyran derivative or its physiologically acceptable salts according to claim 34 wherein in general formula (I) $R^4$ is a hydroxyl group protected by an aroyl group; and $R^3$ and $R^5$ are hydrogen atoms.

55. A benzopyran derivative or its physiologically acceptable salts according to claim 34 wherein in general formula (I) $R^4$ is a hydroxyl group protected by an alkanoyl group; and $R^3$ and $R^5$ are hydrogen atoms.

56. A benzopyran derivative or its physiologically acceptable salts according to claim 34 wherein in general formula (I) $R^5$ is a hydroxyl group protected by an acyl group selected from the group consisting of an aroyl group and an alkanoyl group; and $R^3$ and $R^4$ are hydrogen atoms.

57. A benzopyran derivative or its physiologically acceptable salts according to claim 34 wherein in general formula (I) $R^5$ is a hydroxyl group protected by an aroyl group; and $R^3$ and $R^4$ are hydrogen atoms.

58. A benzopyran derivative or its physiologically acceptable salts according to claim 34 wherein in general formula (I) $R^5$ is a hydroxyl group protected by an alkanoyl group; and $R^3$ and $R^4$ are hydrogen atoms.

59. A benzopyran derivative or its physiologically acceptable salts according to claim 34 wherein in general formula (I) $R^3$ is a hydroxyl group protected by a straight chain or branched alkyl group having 1~10 carbon atoms; and $R^4$ and $R^5$ are hydrogen atoms.

60. A benzopyran derivative or its physiologically acceptable salts according to claim 34 wherein in general formula (I) $R^4$ is a hydroxyl group protected by a straight chain or branched alkyl group having 1~10 carbon atoms; and $R^3$ and $R^5$ are hydrogen atoms.

61. A benzopyran derivative or its physiologically acceptable salts according to claim 34 wherein in general formula (I) $R^5$ is a hydroxyl group protected by a straight chain or branched alkyl group having 1~10 carbon atoms; and $R^3$ and $R^4$ are hydrogen atoms.

62. A benzopyran derivative or its physiologically acceptable salts according to claim 34 wherein in general formula (I) $R^3$ is a hydroxyl group protected by a straight chain or branched alkenyl group having 2~10 carbon atoms; and $R^4$ and $R^5$ are hydrogen atoms.

63. A benzopyran derivative or its physiologically acceptable salts according to claim 34 wherein in general formula (I) $R^4$ is a hydroxyl group protected by a straight chain or branched alkenyl group having 2~10 carbon atoms; and $R^3$ and $R^5$ are hydrogen atoms.

64. A benzopyran derivative or its physiologically acceptable salts according to claim 34 wherein in general formula (I) $R^5$ is a hydroxyl group protected by a straight chain or branched alkenyl group having 2~10 carbon atoms; and $R^3$ and $R^4$ are hydrogen atoms.

65. General Formula (I):

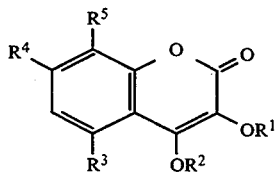

A benzopyran derivative or its physiologically acceptable salts, said benzopyran derivative being represented by general formula (I) wherein $R^1$ is a methyl group; $R^2$ is a hydrogen atom; $R^3$ is a hydroxyl group; and $R^4$ and $R^5$ are hydrogen atoms.

66. General Formula (I):

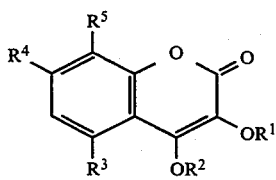

A benzopyran derivative or its physiologically acceptable salts, said benzopyran derivative being represented by general formula (I) wherein $R^1$ is a methyl group; $R^2$, $R^3$ and $R^4$ are hydrogen atoms; and $R^5$ is a hydroxyl group or a protected hydroxyl group.

67. General Formula (I):

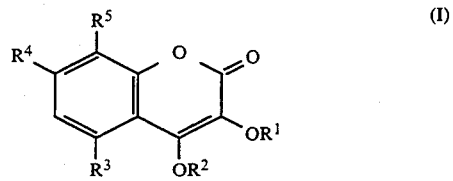

A benzopyran derivative or its physiologically acceptable salts, said benzopyran derivative being represented by general formula (I) wherein $R^1$ is a straight chain on branched alkyl, acyl, or alkenyl group having 2~12 carbon atoms; $R^2$ is a straight chain on branched alkyl, acyl, or alkenyl group having 3~12 carbon atoms; one of $R^3$, $R^4$, $R^5$ is a hydroxyl group or a protected hydroxyl group and the others are hydrogen atoms.

68. A benzopyran derivative or its physiologically acceptable salts according to claim 67 wherein in general formula (I) $R^1$ is an acyl group selected from the group consisting of an aroyl group, an alkanoyl group, and a straight chain or branched alkyl group having 2~12 carbon atoms; and $R^2$ is an acyl group selected from the group consisting of an aroyl group and an alkanoyl group, or a straight chain or branched alkyl group having 3~12 carbon atoms.

69. A benzopyran derivative or its physiologically acceptable salts according to claim 67 wherein in general formula (I) $R^1$ and $R^2$ are each respectively an acyl group selected from the group consisting of an aroyl group and an alkanoyl group, or a straight chain or branched alkenyl group having 2~10 carbon atoms.

70. A benzopyran derivative or its physiologically acceptable salts according to claim 67 wherein in general formula (I) $R^1$ is a straight chain or branched alkyl group having 2~12 carbon atoms, or a straight chain or branched alkenyl group having 2~12 carbon atoms; and $R^2$ is a straight chain or branched alkyl group having 3~12 carbon atoms, or a straight chain or branched alkenyl group having 2~10 carbon atoms.

71. A benzopyran derivative or its physiologically acceptable salts according to claim 68 wherein in general formula (I) $R^1$ and $R^2$ are acyl groups selected from the group consisting of an aroyl group and an alkanoyl group.

72. A benzopyran derivative or its physiologically acceptable salts according to claim 68 wherein in general formula (I) $R^1$ and $R^2$ are aroyl groups.

73. A benzopyran derivative or its physiologically acceptable salts according to claim 68 wherein in general formula (I) $R^1$ and $R^2$ are alkanoyl groups.

74. A benzopyran derivative or its physiologically acceptable salts according to claim 68 wherein in general formula (I) $R^1$ is an acyl group selected from the group consisting of an aroyl group and an alkanoyl group; and $R^2$ is a straight chain or branched alkyl group having 3~12 carbon atoms.

75. A benzopyran derivative or its physiologically acceptable salts according to claim 68 wherein in general formula (I) $R^1$ is an aroyl group; and $R^2$ is a straight chain or branched alkyl group having 3~12 carbon atoms.

76. A benzopyran derivative or its physiologically acceptable salts according to claim 68 wherein in general formula (I) $R^1$ is an alkanoyl group; and $R^2$ is a straight chain or branched alkyl group having 3~12 carbon atoms.

77. A benzopyran derivative or its physiologically acceptable salts according to claim 68 wherein in general formula (I) $R^1$ is a straight chain or branched alkyl group having 2~12 carbon atoms; and $R^2$ is an acyl group selected from the group consisting of an aroyl group and an alkanoyl group.

78. A benzopyran derivative or its physiologically acceptable salts according to claim 68 wherein in general formula (I) $R^1$ is a straight chain or branched alkyl group having 2~12 carbon atoms; and $R^2$ is an aroyl group.

79. A benzopyran derivative or its physiologically acceptable salts according to claim 68 wherein in general formula (I) $R^1$ is a straight chain or branched alkyl group having 2~12 carbon atoms; and $R^2$ is an alkanoyl group.

80. A benzopyran derivative or its physiologically acceptable salts according to claim 68 wherein in general formula (I) $R^1$ is a straight chain or branched alkyl group having 2~12 carbon atoms; and $R^2$ is a straight chain or branched alkyl group having 3~12 carbon atoms.

81. A benzopyran derivative or its physiologically acceptable salts according to claim 69 wherein in general formula (I) $R^1$ is an acyl group selected from the group consisting of an aroyl group and an alkanoyl group; and $R^2$ is a straight chain or branched alkenyl group having 2~10 carbon atoms.

82. A benzopyran derivative or its physiologically acceptable salts according to claim 69 wherein in general formula (I) $R^1$ is an aroyl group; and $R^2$ is a straight chain or branched alkenyl group having 2~10 carbon atoms.

83. A benzopyran derivative or its physiologically acceptable salts according to claim 69 wherein in general formula (I) $R^1$ is an alkanoyl group; and $R^2$ is a straight chain or branched alkenyl group having 2~10 carbon atoms.

84. A benzopyran derivative or its physiologically acceptable salts according to claim 69 wherein in general formula (I) $R^1$ is a straight chain or branched alkenyl group having 2~10 carbon atoms; and $R^2$ is an acyl group selected from the group consisting of an aroyl group and an alkanoyl group.

85. A benzopyran derivative or its physiologically acceptable salts according to claim 69 wherein in general formula (I) $R^1$ is a straight chain or branched alkenyl group having 2~10 carbon atoms; and $R^2$ is an aroyl group.

86. A benzopyran derivative or its physiologically acceptable salts according to claim 69 wherein in general formula (I) $R^1$ is a straight chain or branched alkenyl group having 2~10 carbon atoms; and $R^2$ is an alkanoyl group.

87. A benzopyran derivative or its physiologically acceptable salts according to claim 69 wherein in general formula (I) $R^1$ and $R^2$ are straight chain or branched alkenyl group having 2~10 carbon atoms.

88. A benzopyran derivative or its physiologically acceptable salts according to claim 70 wherein in general formula (I) $R^1$ is a straight chain or branched alkyl group having 2~12 carbon atoms; and $R^2$ is a straight chain or branched alkenyl group having 2~10 carbon atoms.

89. A benzopyran derivative or its physiologically acceptable salts according to claim 70 wherein in general formula (I) $R^1$ is a straight chain or branched alkenyl group having 2~10 carbon atoms; and $R^2$ is a straight chain or branched alkyl group having 3~12 carbon atoms.

90. A benzopyran derivative or its physiologically acceptable salts according to claim 67 wherein in general formula (I) one of $R^3$, $R^4$ or $R^5$ is a hydroxyl group, and the others are hydrogen atoms.

91. A benzopyran derivative or its physiologically acceptable salts according to claim 67 wherein in general formula (I) one of $R^3$, $R^4$ or $R^5$ is a protected hydroxyl group and the others are hydrogen atoms.

92. A benzopyran derivative or its physiologically acceptable salts according to claim 67 wherein in general formula (I) one of $R^3$, $R^4$ or $R^5$ is a hydroxyl group protected by an acyl group selected from the group consisting of an aroyl group and an alkanoyl group, and the others are hydrogen atoms.

93. A benzopyran derivative or its physiologically acceptable salts according to claim 67 wherein in general formula (I) one of $R^3$, $R^4$ or $R^5$ is a hydroxyl group protected by an aroyl group, and the others are hydrogen atoms.

94. A benzopyran derivative or its physiologically acceptable salts according to claim 67 wherein in general formula (I) one of $R^3$, $R^4$ or $R^5$ is a hydroxyl group protected by an alkanoyl group, and the others are hydrogen atoms.

95. A benzopyran derivative or its physiologically acceptable salts according to claim 67 wherein in general formula (I) one of $R^3$, $R^4$ or $R^5$ is a hydroxyl group protected by a straight chain or branched alkyl group having 1~10 carbon atoms, and the others are hydrogen atoms.

96. A benzopyran derivative or its physiologically acceptable salts according to claim 67 wherein in general formula (I) one of $R^3$, $R^4$ or $R^5$ is a hydroxyl group protected by a straight chain or branched alkenyl group having 2~10 carbon atoms, and the others are hydrogen atoms.

97. A benzopyran derivative or its physiologically acceptable salts according to claim 67 wherein in general formula (I) $R^3$ is a hydroxyl group; and $R^4$ and $R^5$ are hydrogen atoms.

98. A benzopyran derivative or its physiologically acceptable salts according to claim 67 wherein in general formula (I) $R^4$ is a hydroxyl group; and $R^3$ and $R^5$ are hydrogen atoms.

99. A benzopyran derivative or its physiologically acceptable salts according to claim 67 wherein in general formula (I) $R^5$ is a hydroxyl group; and $R^3$ and $R^4$ are hydrogen atoms.

100. A benzopyran derivative or its physiologically acceptable salts according to claim 67 wherein in general formula (I) $R^3$ is a hydroxyl group protected by an acyl group selected from the group consisting of an aroyl group and an alkanoyl group; and $R^4$ and $R^5$ are hydrogen atoms.

101. A benzopyran derivative or its physiologically acceptable salts according to claim 67 wherein in general formula (I) $R^3$ is a hydroxyl group protected by an aroyl group; and $R^4$ and $R^5$ are hydrogen atoms.

102. A benzopyran derivative or its physiologically acceptable salts according to claim 67 wherein in general formula (I) $R^3$ is a hydroxyl group protected by an alkanoyl group; and $R^4$ and $R^5$ are hydrogen atoms.

103. A benzopyran derivative or its physiologically acceptable salts according to claim 67 wherein in general formula (I) $R^4$ is a hydroxyl group protected by an acyl group selected from the group consisting of an aroyl group and an alkanoyl group; and $R^3$ and $R^5$ are hydrogen atoms.

104. A benzopyran derivative or its physiologically acceptable salts according to claim 67 wherein in general formula (I) $R^4$ is a hydroxyl group protected by an aroyl group; and $R^3$ and $R^5$ are hydrogen atoms.

105. A benzopyran derivative or its physiologically acceptable salts according to claim 67 wherein in general formula (I) $R^4$ is a hydroxyl group protected by an alkanoyl group; and $R^3$ and $R^5$ are hydrogen atoms.

106. A benzopyran derivative or its physiologically acceptable salts according to claim 67 wherein in general formula (I) $R^5$ is a hydroxyl group protected by an acyl group selected from the group consisting of an aroyl group and an alkanoyl group; and $R^3$ and $R^4$ are hydrogen atoms.

107. A benzopyran derivative or its physiologically acceptable salts according to claim 67 wherein in general formula (I) $R^5$ is a hydroxyl group protected by an aroyl group; and $R^3$ and $R^4$ are hydrogen atoms.

108. A benzopyran derivative or its physiologically acceptable salts according to claim 67 wherein in general formula (I) $R^5$ is a hydroxyl group protected by an alkanoyl group; and $R^3$ and $R^4$ are hydrogen atoms.

109. A benzopyran derivative or its physiologically acceptable salts according to claim 67 wherein in general formula (I) $R^3$ is a hydroxyl group protected by a straight chain or branched alkyl group having 1~10 carbon atoms; and $R^4$ and $R^5$ are hydrogen atoms.

110. A benzopyran derivative or its physiologically acceptable salts according to claim 67 wherein in general formula (I) $R^4$ is a hydroxyl group protected by a straight chain or branched alkyl group having 1~10 carbon atoms; and $R^3$ and $R^5$ are hydrogen atoms.

111. A benzopyran derivative or its physiologically acceptable salts according to claim 67 wherein in general formula (I) $R^5$ is a hydroxyl group protected by a straight chain or branched alkyl group having 1~10 carbon atoms; and $R^3$ and $R^4$ are hydrogen atoms.

112. A benzopyran derivative or its physiologically acceptable salts according to claim 67 wherein in general formula (I) $R^3$ is a hydroxyl group protected by a straight chain or branched alkenyl group having 2~10 carbon atoms; and $R^4$ and $R^5$ are hydrogen atoms.

113. A benzopyran derivative or its physiologically acceptable salts according to claim 67 wherein in general formula (I) $R^4$ is a hydroxyl group protected by a straight chain or branched alkenyl group having 2~10 carbon atoms; and $R^3$ and $R^5$ are hydrogen atoms.

114. A benzopyran derivative or its physiologically acceptable salts according to claim 67 wherein in general formula (I) $R^5$ is a hydroxyl group protected by a straight chain or branched alkenyl group having 2~10 carbon atoms; and $R^3$ and $R^4$ are hydrogen atoms.

115. General Formula (I):

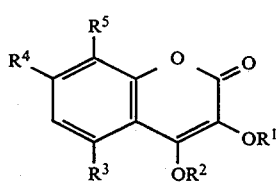

A benzopyran derivative or its physiologically acceptable salts, said benzopyran derivative being represented by general formula (I) wherein $R^1$ is a methyl group, $R_2$ is a straight chain or branched alkyl group having 3~12 carbon atoms; one of $R^3$, $R^4$ or $^5$ is a hydroxyl group or a protected hydroxyl group, and the others are hydrogen atoms.

116. General Formula (I):

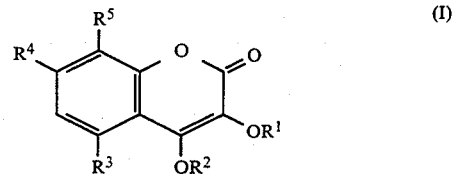

A benzopyran derivative or its physiologically acceptable salts, said benzopyran derivative being represented by general formula (I) wherein $R^1$ is a methyl group, $R^2$ is an aroyl group; one of $R^3$, $R^4$ or $R^5$ is a hydroxyl group or a protected hydroxyl group and the others are hydrogen atoms.

117. General Formula (I):

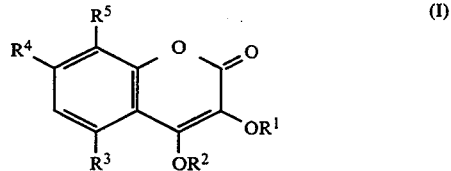

A benzopyran derivative or its physiologically acceptable salts, said benzopyran derivative being represented by general formula (I) wherein $R^1$ is a methyl group, $R^2$ is an alkenyl group having 2~10 carbon atoms; one of $R^3$, $R^4$ or $R^5$ is a hydroxyl group or a protected hydroxyl group, and the others are hydrogen atoms.

118. General Formula (I):

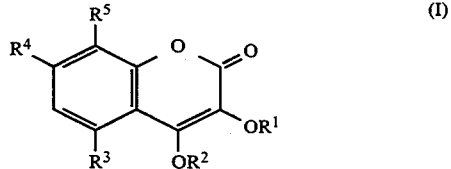

A benzopyran derivative or its physiologically acceptable salts, said benzopyran derivative being represented by general formula (I) wherein $R^1$ is a straight chain or branched alkyl group having 2~12 carbon atoms; $R^2$ is a methyl group or an ethyl group; one of $R^3$, $R^4$ or $R^5$ is a hydroxyl group or a protected hydroxyl group, and the others are hydrogen atoms.

119. General Formula (I):

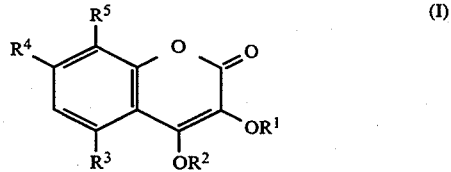

A benzopyran derivative or its physiologically acceptable salts, said benzopyran derivative being represented by general formula (I) wherein $R^1$ is an aroyl group or an alkanoyl group; $R^2$ is a methyl group or an ethyl group; one of $R^3$, $R^4$ or $R^5$ is a hydroxyl group or a protected hydroxyl group, and the others are hydrogen atoms.

120. General Formula (I):

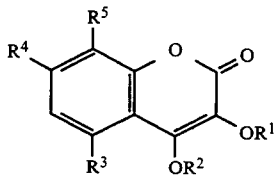

A benzopyran derivative or its physiologically acceptable salts, said benzopyran derivative being represented by general formula (I) wherein $R^1$ is an alkenyl group having 2~10 carbon atoms; $R^2$ is a methyl group or an ethyl group, one of $R^3$, $R^4$ or $R^5$ is a hydroxyl group or a protected hydroxyl group, and the others are hydrogen atoms.

121. General Formula (I):

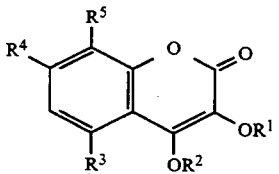

A benzopyran derivative or its physiologically acceptable salts, said benzopyran derivative being represented by general formula (I) wherein $R^1$ is a methyl group; $R^2$ is an alkanoyl group; $R^3$ is a hydroxyl group; and $R^4$ and $R^5$ are hydrogen atoms.

122. General Formula (I):

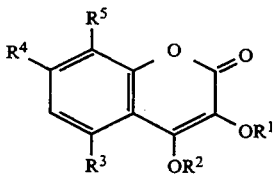

A benzopyran derivative or its physiologically acceptable salts, said benzopyran derivative being represented by general formula (I) wherein $R^1$ is a methyl group; $R^2$ is an alkanoyl group; $R^3$ and $R^4$ are hydrogen atoms, and $R^5$ is a hydroxyl group or a protected hydroxyl group.

123. General Formula (I):

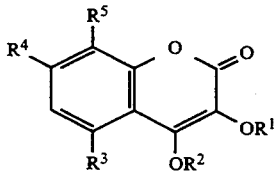

A benzopyran derivative or its physiologically acceptable salts, said benzopyran derivative being represented by general formula (I) wherein $R^1$ is a hydrogen atom, or a straight chain or branched alkyl, acyl, or alkenyl group having 2~12 carbon atoms; $R^2$ is a hydrogen atom, or a straight chain or branched alkyl, acyl, or alkenyl group having 3~12 carbon atoms; $R^3$ is a hydroxyl group or a protected hydroxyl group; and both $R^4$ and $R^5$ are hydrogen atoms.

124. A benzopyran derivative or its physiologically acceptable salts according to claim 123 wherein in general formula (I) $R^1$ and $R^2$ are each respectively a hydrogen atom, or an acyl group selected from the group consisting of an aroyl group and an alkanoyl group; $R^3$ is a hydroxyl group or a protected hydroxyl group; and both $R^4$ and $R^5$ are hydrogen atoms.

125. A benzopyran derivative or its physiologically acceptable salts according to claim 123 wherein in general formula (I) $R^1$ is a hydrogen atom, or a straight chain or branched alkyl group having 2~12 carbon atoms; and $R^2$ is a hydrogen atom, or a straight chain or branched alkyl group having 3~12 carbon atoms; $R^3$ is a hydroxyl group or a protected hydroxyl group; and both $R^4$ and $R^5$ are hydrogen atoms.

126. A benzopyran derivative or its physiologically acceptable salts according to claim 123 wherein in general formula (I) $R^1$ and $R^2$ are each respectively a hydrogen atom, or a straight chain or branched alkenyl group having 2~10 carbon atoms; $R^3$ is a hydroxyl group or a protected hydroxyl group; and both $R^4$ and $R^5$ are hydrogen atoms.

127. A benzopyran derivative or its physiologically acceptable salts according to claim 124 wherein in general formula (I) $R^1$ and $R^2$ are hydrogen atoms; $R^3$ is a hydroxyl group or a hydroxyl protected group; and both $R^4$ and $R^5$ are hydrogen atoms.

128. General Formula (I):

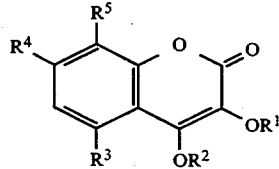

A benzopyran derivative or its physiologically acceptable salts, said benzopyran derivative being represented by general formula (I) wherein $R^1$ is a hydrogen atom, or a straight chain or branched alkyl, acyl, or alkenyl group having 2~12 carbon atoms; $R^2$ is a hydrogen atom, or a straight chain or branched alkyl, acyl, or alkenyl group having 3~12 carbon atoms; $R^4$ is a hydroxyl group; and both $R^3$ and $R^5$ are hydrogen atoms.

129. A benzopyran derivative or its physiologically acceptable salts according to claim 128 wherein in general formula (I) $R^1$ and $R^2$ are each respectively a hydrogen atom, or an acyl group selected from the group consisting of an aroyl group and an alkanoyl group; $R^4$ is a hydroxyl group; and both $R^3$ and $R^5$ are hydrogen atoms.

130. A benzopyran derivative or its physiologically acceptable salts according to claim 128 wherein in general formula (I) $R^1$ is a hydrogen atom, or a straight chain or branched alkyl group having 2~12 carbon atoms; and $R^2$ is a hydrogen atom, or a straight chain or branched alkyl group having 3~12 carbon atoms; $R^4$ is a hydroxyl group; and both $R^3$ and $R^5$ are hydrogen atoms.

131. A benzopyran derivative or its physiologically acceptable salts according to claim 128 wherein in general formula (I) $R^1$ and $R^2$ are each respectively a hydrogen atom, or a straight chain or branched alkenyl group having 2~10 carbon atoms; $R^4$ is a hydroxyl group; and both $R^3$ and $R^5$ are hydrogen atoms.

132. A benzopyran derivative or its physiologically acceptable salts according to claim 129 wherein in general formula (I) $R^1$ and $R^2$ are hydrogen atoms; $R^4$ is a hydroxyl group; and both $R^4$ and $R^5$ are hydrogen atoms.

133. General Formula (I):

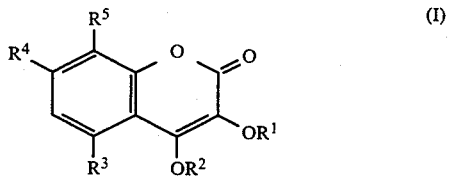

A benzopyran derivative or its physiologically acceptable salts, said benzopyran derivative being represented by general formula (I) wherein $R^1$ is a hydrogen atom, or a straight chain or branched alkyl acyl, or alkenyl group having 2~12 carbon atoms; $R^2$ is a hydrogen atom, or a straight chain or branched alkyl, acyl, or alkenyl group having 3~12 carbon atoms; $R^5$ is a hydroxyl group or a protected hydroxyl group; and both $R^3$ and $R^4$ are hydrogen atoms.

134. A benzopyran derivative or its physiologically acceptable salts according to claim 133 wherein in general formula (I) $R^1$ and $R^2$ are each respectively a hydrogen atom, or an acyl group selected from the group consisting of an aroyl group and an alkanoyl group; $R^5$ is a hydroxyl group or a protected hydroxyl group; and both $R^3$ and $R^4$ are hydrogen atoms.

135. A benzopyran derivative or its physiologically acceptable salts according to claim 133 wherein in general formula (I) $R^1$ is a hydrogen atom, or a straight chain or branched alkyl group having 2~12 carbon atoms; $R^2$ is a hydrogen atom, or a straight chain or branched alkyl group having 3~12 carbon atoms; $R^5$ is a hydroxyl group or a protected hydroxyl group; and both $R^3$ and $R^4$ are hydrogen atoms.

136. A benzopyran derivative or its physiologically acceptable salts according to claim 133 wherein in general formula (I) $R^1$ and $R^2$ are each respectively a hydrogen atom, or a straight chain or branched alkenyl group having 2~10 carbon atoms; $R^5$ is a hydroxyl group or a protected hydroxyl group; and both $R^3$ and $R^4$ are hydrogen atoms.

137. A benzopyran derivative or its physiologically acceptable salts according to claim 134 wherein in general formula (I) $R^1$ and $R^2$ are hydrogen atoms; $R^5$ is a hydroxyl group or a protected hydroxyl group; and both $R^3$ and $R^4$ are hydrogen atoms.

138. An anti-allergic agent comprising as its active ingredient a benzopyran derivative or its physiologically acceptable salts according to any one of claims 1, 34, 67, 123, 128, and 133.

139. General Formula (II):

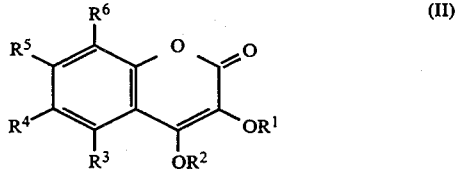

An anti-allergic agent comprising as its active ingredient a benzopyran derivative or its physiologically acceptable salts, said benzopyran derivative being represented by general formula (II) wherein $R^1$ is a hydrogen atom; $R^2$ is an acyl group, an alkyl group, or an alkenyl group; one of $R^3$, $R^4$, $R^5$ or $R^6$ is a hydroxyl group or a protected hydroxyl group, and the others are hydrogen atoms.

140. An anti-allergic agent comprising as its active ingredient a benzopyran derivative or its physiologically acceptable salts according to claim 139 wherein in general formula (II) $R_4$ is a hydroxyl group or a protected hydroxyl group; $R_1$ is a hydrogen atom; and $R^2$ is an acyl group selected from the group consisting of an aroyl group and an alkanoyl group.

141. An anti-allergic agent comprising as its active ingredient a benzopyran derivative or its physiologically acceptable salts according to claim 139 wherein in general formula (II) $R_4$ is a hydroxyl group or a protected hydroxyl group; $R_1$ is a hydrogen atom; and $R^2$ is a straight chain or branched alkyl group having 1~12 carbon atoms.

142. An anti-allergic agent comprising as its active ingredient a benzopyran derivative or its physiologically acceptable salts according to claim 139 wherein in general formula (II) $R_4$ is a hydroxyl group or a protected hydroxyl group; $R_1$ is a hydrogen atom; and $R^2$ is a straight chain or branched alkenyl group having 2~10 carbon atoms.

143. An anti-allergic agent comprising as its active ingredient a benzopyran derivative or its physiologically acceptable salts according to claim 139 wherein in general formula (II) $R_4$ is a hydroxyl group or a protected hydroxyl group; $R_1$ is a hydrogen atom; and $R_2$ is an acyl group selected from the group consisting of an aroyl group and an alkanoyl group.

144. An anti-allergic agent comprising as its active ingredient a benzopyran derivative or its physiologically acceptable salts according to claim 139 wherein in general formula (II) $R_4$ is a hydroxyl group or a protected hydroxyl group; $R_1$ is a hydrogen atom; and $R_2$ is an aroyl group.

145. An anti-allergic agent comprising as its active ingredient a benzopyran derivative or its physiologically acceptable salts according to claim 139 wherein in general formula (II) $R_4$ is a hydroxyl group or a protected hydroxyl group; $R_1$ is a hydrogen atom; and $R_2$ is an alkanoyl group.

146. General Formula (II):

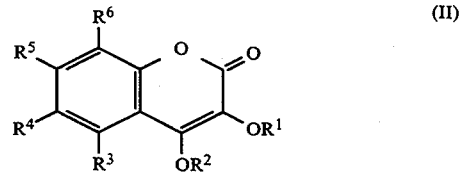

An anti-allergic agent comprising as its active ingredient a benzopyran derivative or its physiologically acceptable salts, said benzopyran derivative being represented by general formula (II) wherein $R^2$ is a hydrogen atom; $R^1$ is an acyl group, an alkyl group, or an alkenyl group; one of $R^3$, $R^4$, $R^5$ or $R^6$ is a hydroxyl group or a protected hydroxyl group, and the others are hydrogen atoms.

147. An anti-allergic agent comprising as its active ingredient a benzopyran derivative or its physiologically acceptable salts according to claim 146 wherein in general formula (II) $R_4$ is a hydroxyl group or a protected hydroxyl group; $R^2$ is a hydrogen atom; and $R^1$ is a straight chain or branched alkyl group having 1~12 carbon atoms.

148. An anti-allergic agent comprising as its active ingredient a benzopyran derivative or its physiologically acceptable salts according to claim 146 wherein in general formula (II) $R_4$ is a hydroxyl group or a protected hydroxyl group; $R_2$ is a hydrogen atom; and $R_1$ is a straight chain or branched alkenyl group having 2~10 carbon atoms.

149. An anti-allergic agent comprising as its active ingredient a benzopyran derivative or its physiologically acceptable salts according to claim 146 wherein in general formula (II) $R_4$ is a hydroxyl group or a protected hydroxyl group; $R_1$ is an acyl group selected from the group consisting of an aroyl group and an alkanoyl group; and $R^2$ is a hydrogen atom.

150. An anti-allergic agent comprising as its active ingredient a benzopyran derivative or its physiologically acceptable salts according to claim 140 wherein in general formula (II) $R_4$ is a hydroxyl group or a protected hydroxyl group; $R_1$ is an aroyl group; and $R_2$ is a hydrogen atom.

151. An anti-allergic agent comprising as its active ingredient a benzopyran derivative or its physiologically acceptable salts according to claim 146 wherein in general formula (II) $R_4$ is a hydroxyl group or a protected hydroxyl group; $R_1$ is an alkanoyl group; and $R_2$ is a hydrogen atom.

152. General Formula (II):

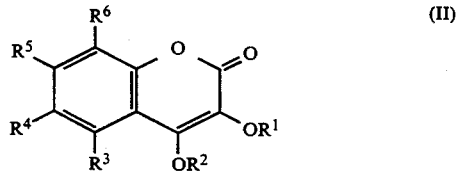

An anti-allergic agent comprising as its active ingredient a benzopyran derivative or its physiologically acceptable salts, said benzopyran derivative being represented by general formula (II) wherein $R^1$ and $R^2$ are each respectively an acyl group, an alkyl group, or an alkenyl group; one of $R^3$, $R^4$, $R^5$, or $R^6$ is a hydroxyl group or a protected hydroxyl group, and the others are hydrogen atoms.

153. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ and $R^2$ are each respectively an acyl group selected from the group consisting of an aroyl group and an alkanoyl group, or a straight chain or branched alkyl group having 1~12 carbon atoms.

154. An anti-allergic agent comprising as its active ingredient a benzopyran derivative or its physiologically acceptable salts according to claim 153 wherein in general formula (II) $R^4$ is a hydroxyl group or a protected hydroxyl group; $R^1$ and $R^2$ are each respectively an acyl group selected from the group consisting of an aroyl group and an alkanoyl group, or a straight chain or branched alkenyl group having 2~10 carbon atoms.

155. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ and $R^2$ are each respectively a straight chain or branched alkyl group having 1~12 carbon atoms, or a straight chain or branched alkenyl group having 2~10 carbon atoms.

156. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ and $R^2$ are acyl groups selected from the group consisting of an aroyl group and an alkanoyl group.

157. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ and $R^2$ are aroyl groups.

158. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ and $R^2$ are alkanoyl groups.

159. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is an acyl group selected from the group consisting of an aroyl group and an alkanoyl group; and $R^2$ is a straight chain or branched alkyl group having 1~12 carbon atoms.

160. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is an aroyl group; and $R^2$ is a straight chain or branched alkyl group having 1~12 carbon atoms.

161. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is an alkanoyl group; and $R^2$ is a straight chain or branched alkyl group having 1~12 carbon atoms.

162. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkyl group having 1~12 carbon atoms; and $R^2$ is an acyl group selected from the group consisting of an aroyl group and an alkanoyl group.

163. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkyl group having 1~12 carbon atoms; and $R^2$ is an aroyl group.

164. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkyl group having 1~12 carbon atoms; and $R^2$ is an alkanoyl group.

165. An anti-allergic agent comprising as its active ingredient a benzopyran derivative or its physiologically acceptable salts according to claim 152 wherein in general formula (II) $R^4$ is a hydroxyl group or a protected hydroxyl group; and $R^1$ and $R^2$ are straight chain or branched alkyl group having 1~12 carbon atoms.

166. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is an acyl group selected from the group selected from the group consisting of an aroyl group and an alkanoyl group; and $R^2$ is a straight chain or branched alkenyl group having 2~10 carbon atoms.

167. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is an aroyl group; and $R^2$ is a straight chain or branched alkenyl group having 2~10 carbon atoms.

168. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is an alkanoyl group; and $R^2$ is a straight chain or branched alkenyl group having 2~10 carbon atoms.

169. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkenyl group having 2~10 carbon atoms; and $R^2$ is an acyl group selected from the group consisting of an aroyl group and an alkanoyl group.

170. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkenyl group having 2~10 carbon atoms; and $R^2$ is an aroyl group.

171. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkenyl group having 2~10 carbon atoms; and $R^2$ is an alkanoyl group.

172. An anti-allergic agent comprising as its active ingredient a benzopyran derivative or its physiologically acceptable salts according to claim 152 wherein in general formula (II) $R^4$ is a hydroxyl group or a protected hydroxyl group; and $R^1$ and $R^2$ are straight chain or branched alkenyl groups having 2~10 carbon atoms.

173. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkyl group having 1~12 carbon atoms; and $R^2$ is a straight chain or branched alkenyl group having 2~10 carbon atoms.

174. An anti-allergic agent comprising as its active ingredient a benzopyran derivative or its physiologically acceptable salts according to claim 152 wherein in general formula (II) $R^4$ is a hydroxyl group or a protected hydroxyl group; $R^1$ is a straight chain or branched alkenyl group having 2~10 carbon atoms; and $R^2$ is a straight chain or branched alkyl group having 1~12 carbon atoms.

175. General Formula (II):

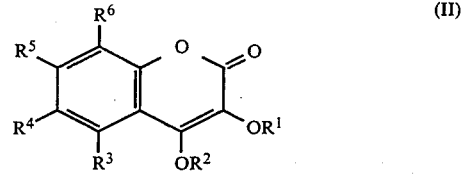

An anti-allergic agent comprising as its active ingredient a benzopyran derivative or its physiologically acceptable salts, said benzopyran derivative being represented by general formula (II) wherein $R^1$ and $R^2$ are each respectively a hydrogen atom, an acyl group, an alkyl group, or an alkenyl group; $R^3$ is a hydroxyl group or a protected hydroxyl group; $R^4$, $R^5$ and $R^6$ are hydrogen atoms.

176. General Formula (II):

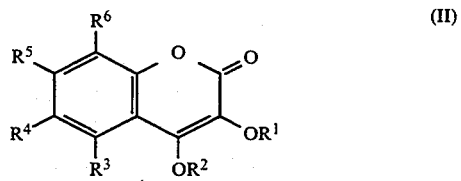

An anti-allergic agent comprising as its active ingredient a benzopyran derivative or its physiologically acceptable salts, said benzopyran derivative being represented by general formula (II) wherein $R^1$ and $R^2$ are each respectively a hydrogen atom, an acyl group, an alkyl group, or an alkenyl group; $R^4$ is a hydroxyl group; $R^3$, $R^5$, and $R^6$ are hydrogen atoms.

177. An anti-allergic agent comprising as its active ingredient a benzopyran derivative or its physiologically acceptable salts according to claim 176 wherein in general formula (II) $R^4$ is a hydroxyl group; $R^1$ and $R^2$ are hydrogen atoms.

178. General Formula (II):

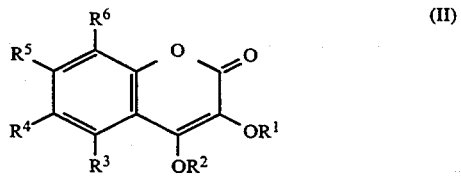

An anti-allergic agent comprising as its active ingredient a benzopyran derivative or its physiologically acceptable salts, said benzopyran derivative being represented by general formula (II) wherein $R^1$ and $R^2$ are each respectively a hydrogen atom, an acyl group, an alkyl group, or an alkenyl group; $R^5$ is a hydroxyl group; $R^3$, $R^4$ and $R^6$ are hydrogen atoms.

179. General Formula (II):

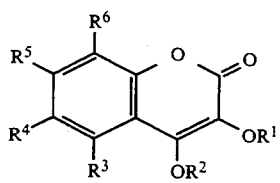

(II)

An anti-allergic agent comprising as its active ingredient a benzopyran derivative or its physiologically acceptable salts said benzopyran derivative being represented by general formula (II) wherein $R^1$ and $R^2$ are each respectively a hydrogen atom, an acyl group, an alkyl group, or an alkenyl group; $R^6$ is a hydroxyl group or a hydroxyl protected group; $R^3$, $R^4$ and $R^5$ are hydrogen atoms.

180. General Formula (II):

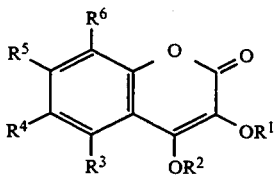

(II)

An anti-allergic composition comprising an effective and non-toxic amount of a benzopyran derivative or its physiologically acceptable salts, said benzopyran derivative being represented by general formula (II) wherein $R^1$ is a hydrogen atom; $R^2$ is an acyl group, an alkyl group, or an alkenyl group; and one of $R^3$, $R^4$, $R^5$ or $R^6$ is a hydroxyl group or a protected hydroxyl group, and the others are hydrogen atoms, which is formed by adding physiologically acceptable additives selected from the group consisting of excipients, bonding agents, lubricants, disintegrators, preservatives, isotonic agents, stabilizing agents, dispersing agents, anti-oxidative agents, coloring agents, sweetening agents and buffering agents.

181. General Formula (II):

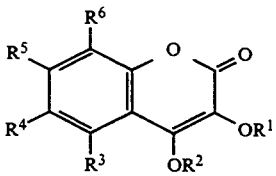

(II)

An anti-allergic composition comprising an effective and non-toxic amount of a benzopyran derivative or its physiologically acceptable salts, said benzopyran derivative being represented by general formula (II) wherein $R^2$ is a hydrogen atom; $R^1$ is an acyl group, an alkyl group, or an alkenyl group; one of $R^3$, $R^4$, $R^5$ or $R^6$ is a hydroxyl group or a protected hydroxyl group, and the others are hydrogen atoms, which is formed by adding physiologically acceptable additives selected from the group consisting of excipients, bonding agents, lubricants, disintegrators, preservatives, isotonic agents, stabilizing agents, dispersing agents, anti-oxidative agents, coloring agents, sweetening agents and buffering agents.

182. General Formula (II):

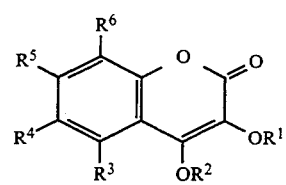

(II)

An anti-allergic composition comprising an effective and non-toxic amount of a benzopyran derivative or its physiologically acceptable salts, said benzopyran derivative being represented by general formula (II) wherein $R^1$ and $R^2$ are each respectively an acyl group, an alkyl group, or an alkenyl group; one of $R^3$, $R^4$, $R^5$ or $R^6$ is a hydroxyl group or a protected hydroxyl group, and the others are hydrogen atoms, which is formed by adding to the benzopyran derivative or its physiologically acceptable salts physiologically acceptable additives selected from the group consisting of excipients, bonding agents, lubricants, disintegrators, preservatives, isotonic agents, stabilizing agents, dispersing agents, anti-oxidative agents, coloring agents, sweetening agents and buffering agents.

183. General Formula (II):

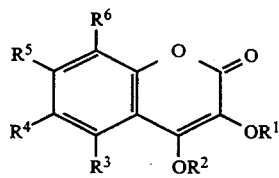

(II)

An anti-allergic composition comprising an effective and non-toxic amount of a benzopyran derivative or its physiologically acceptable salts, said benzopyran derivative being represented by general formula (II) wherein $R^1$ and $R^2$ are each respectively a hydrogen atom, an acyl group, an alkyl group, or an alkenyl group; $R^3$ is a hydroxyl group or a protected hydroxyl group; $R^4$, $R^5$, and $R^6$ are hydrogen atoms, which is formed by adding to the benzopyran derivative or its physiologically acceptable salts physiologically acceptable additives selected from the group consisting of excipients, bonding agents, lubricants, disintegrators, preservatives, isotonic agents, stabilizing agents, dispersing agents, anti-oxidative agents, coloring agents, sweetening agents and buffering agents.

184. General Formula (II):

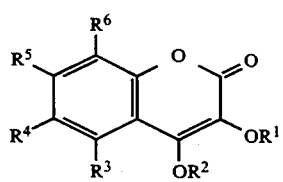

(II)

An anti-allergic composition comprising an effective and non-toxic amount of a benzopyran derivative or its physiologically acceptable salts, said benzopyran derivative being represented by general formula (II) wherein $R^1$ and $R^2$ are each respectively a hydrogen atom, an acyl group, an alkyl group, or an alkenyl group; $R^4$ is a hydroxyl group; $R^3$, $R^5$ and $R^6$ are hydrogen atoms, which is formed by adding to the benzopyran derivative or its physiologically acceptable salts physiologically acceptable additives selected from the group consisting of excipients, bonding agents, lubricants, disintegrators, preservatives, isotonic agents, stabilizing agents, dispersing agents, anti-oxidative agents, coloring agents, sweetening agents and buffering agents.

185. General Formula (II):

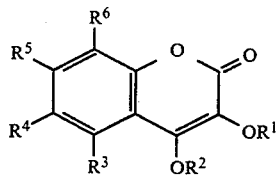

(II)

An anti-allergic composition comprising an effective and non-toxic amount of a benzopyran derivative or its physiologically acceptable salts, said benzopyran derivative being represented by general formula (II) wherein $R^1$ and $R^2$ are each respectively a hydrogen atom, an acyl group, an alkyl group, or an alkenyl group; and $R^5$ is a hydroxyl group; $R^3$, $R^4$ and $R^6$ are hydrogen atoms, which is formed by adding to the benzopyran derivative or its physiologically acceptable salts physiologically acceptable additives selected from the group consisting of excipients, bonding agents, lubricants, disintegrators, preservatives, isotonic agents, stabilizing agents, dispersing agents, anti-oxidative agents, coloring agents, sweetening agents and buffering agents.

186. General Formula (II):

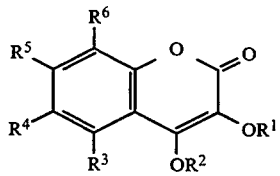

(II)

An anti-allergic composition comprising an effective and non-toxic amount of a benzopyran derivative or its physiologically acceptable salts, said benzopyran derivative being represented by general formula (II) wherein $R^1$ and $R^2$ are each respectively a hydrogen atom, an acyl group, an alkyl group, or an alkenyl group; $R^6$ is a hydroxyl group or a protected hydroxyl group; $R^3$, $R^4$, and $R^5$ are hydrogen atoms, which is formed by adding to the benzopyran derivative or its physiologically acceptable salts physiologically acceptable additives selected from the group consisting of excipients, bonding agents, lubricants, disintegrators, preservatives, isotonic agents, stabilizing agents, dispersing agents, anti-oxidative agents, coloring agents, sweetening agents and buffering agents.

187. General Formula (II):

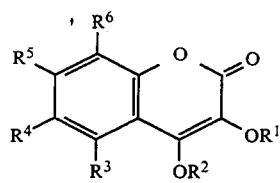

(II)

A medical treatment process for allergic diseases comprising administering an effective and non-toxic amount of a benzopyran derivative or its physiologically salts, said benzopyran derivative being represented by general formula (II) wherein $R^1$ and $R^2$ are each respectively a hydrogen atom, an acyl group, an alkyl group, or an alkenyl groups; one of $R^3$, $R^4$, $R^5$ or $R^6$ is a hydroxyl group or a protected hydroxyl group, and the others are hydrogen atoms.

188. A medical treatment process for allergic diseases according to claim 186 wherein the administration method is oral.

189. A medical treatment process for allergic diseases according to claim 186 wherein the administration method is non-oral.

190. General Formula (I):

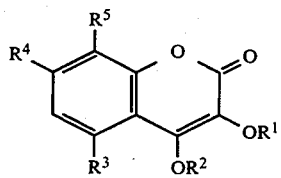

(I)

A benzopyran derivative or its physiologically acceptable salts, said benzopyran derivative being represented by general formula (I) wherein $R^1$, $R^2$, $R^3$, and $R_5$ are hydrogen atoms; and $R^4$ is one selected from the group consisting of an acetoxy group, a hexenyloxy group, a geranyloxy group, and a decyloxy group.

191. A benzopyran derivative selected from the group consisting of 3,4-(hydroxy)-7-(acetoxy)-2H-1-benzopyran -2-one and its physiologically acceptable salts.

192. A benzopyran derivative selected from the group consisting of 3,4-(dihydroxy)-7-(3-hexenyloxy)-2H-1-benzopyran-2-one and its physiologically acceptable salts.

193. A benzopyran derivative selected from the group consisting of 3,4-(dihydroxy)-7-(geranyloxy)-2-H-1-benzopyran-2-one and its physiologically acceptable salts.

194. A benzopyran derivative selected from the group consisting of 3,4-(dihydroxy)-7-(decyloxy)-2H-1-benzopyran-2-one and its physiologically acceptable salts.

* * * * *

UNITED STATES PATENT AND TRADEMARK OFFICE
CERTIFICATE OF CORRECTION

PATENT NO. : 5,428,059
DATED : June 27, 1995
INVENTOR(S) : TAKAGAKI et al.

It is certified that error appears in the above-indentified patent and that said Letters Patent is hereby corrected as shown below:

Column 148, line 2, "$R^3$, $R^4$ or $^5$" should be --$R^3$, $R^4$ or $R^5$--.

Signed and Sealed this

Seventeenth Day of October, 1995

Attest:

BRUCE LEHMAN

Attesting Officer  Commissioner of Patents and Trademarks